United States Patent
Patel et al.

(10) Patent No.: US 11,565,041 B2
(45) Date of Patent: Jan. 31, 2023

(54) AMBULATORY MEDICAMENT DEVICE WITH POWER SAVING MODE

(71) Applicant: Beta Bionics, Inc., Irvine, CA (US)

(72) Inventors: Himanshu Patel, Rancho Santa Margarita, CA (US); Justin P. Brown, Tustin, CA (US)

(73) Assignee: Beta Bionics, Inc., Concord, MA (US)

( * ) Notice: Subject to any disclaimer, the term of this patent is extended or adjusted under 35 U.S.C. 154(b) by 0 days.

(21) Appl. No.: 17/685,170

(22) Filed: Mar. 2, 2022

(65) Prior Publication Data
US 2022/0265928 A1    Aug. 25, 2022

Related U.S. Application Data

(63) Continuation of application No. PCT/US2021/064228, filed on Dec. 17, 2021, which
(Continued)

(51) Int. Cl.
*A61M 5/172* (2006.01)
*A61M 5/168* (2006.01)
(Continued)

(52) U.S. Cl.
CPC ......... *A61M 5/16831* (2013.01); *A61B 5/002* (2013.01); *A61B 5/0004* (2013.01);
(Continued)

(58) Field of Classification Search
CPC .............. A61B 5/14532; A61B 5/7435; A61B 5/7455; A61B 5/746; A61B 5/7475;
(Continued)

(56) References Cited

U.S. PATENT DOCUMENTS

| | | |
|---|---|---|
| 6,650,951 B1 | 11/2003 | Jones et al. |
| 6,744,350 B2 | 6/2004 | Blomquist |
| 6,852,104 B2 | 2/2005 | Blomquist |
| 7,806,854 B2 | 10/2010 | Damiano et al. |
| 8,192,394 B2 | 6/2012 | Estes |

(Continued)

FOREIGN PATENT DOCUMENTS

CN      103793048      5/2014

OTHER PUBLICATIONS

Hein, Jun. 17, 2016, iOS 10's 'Raise to Wake' only works on new iPhones, https://www.cultofmac.com/433989/ios-10s-raise-to-wake-only-workers-on-new-iphones, 6 pp.
(Continued)

*Primary Examiner* — Jason E Flick
(74) *Attorney, Agent, or Firm* — Knobbe Martens Olson & Bear LLP

(57) ABSTRACT

Ambulatory medicament devices that provide therapy to a subject, such as blood glucose control, are disclosed. Disclosed systems and methods can implement one or more features that improve the user experience, by modifying delivery of therapy to a subject after determining that a possible occlusion exists in a medicament delivery system, monitoring the status of an ambulatory medical device and the health condition of a subject that receives therapy from the ambulatory medical device and annunciating alarm condition when necessary, selectively muting alarm annunciations while a Do Not Disturb mode is activated, implementing various power saving modes to save power, controlling operation of the device and medicament delivery based on the user gesture controls, and controlling medicament delivery based on a condition of the ambulatory medicament device.

30 Claims, 69 Drawing Sheets

Related U.S. Application Data is a continuation-in-part of application No. PCT/US2021/072742, filed on Dec. 3, 2021.

(60) Provisional application No. 63/128,428, filed on Dec. 21, 2020, provisional application No. 63/167,563, filed on Mar. 29, 2021, provisional application No. 63/216,177, filed on Jun. 29, 2021, provisional application No. 63/239,365, filed on Aug. 31, 2021, provisional application No. 63/169,112, filed on Mar. 31, 2021, provisional application No. 63/151,565, filed on Feb. 19, 2021, provisional application No. 63/261,290, filed on Sep. 16, 2021, provisional application No. 63/152,744, filed on Feb. 23, 2021, provisional application No. 63/157,541, filed on Mar. 5, 2021, provisional application No. 63/152,716, filed on Feb. 23, 2021, provisional application No. 63/168,203, filed on Mar. 30, 2021, provisional application No. 63/212,521, filed on Jun. 18, 2021, provisional application No. 63/139,210, filed on Jan. 19, 2021, provisional application No. 63/238,670, filed on Aug. 30, 2021, provisional application No. 63/276,481, filed on Nov. 5, 2021, provisional application No. 63/215,857, filed on Jun. 28, 2021, provisional application No. 63/183,900, filed on May 4, 2021, provisional application No. 63/249,975, filed on Sep. 29, 2021, provisional application No. 63/194,126, filed on May 27, 2021, provisional application No. 63/263,602, filed on Nov. 5, 2021, provisional application No. 63/264,645, filed on Nov. 29, 2021, provisional application No. 63/122,427, filed on Dec. 7, 2020.

(51) Int. Cl.

| | | |
|---|---|---|
| *G06F 3/041* | (2006.01) | |
| *A61M 5/142* | (2006.01) | |
| *G06F 3/04883* | (2022.01) | |
| *G06F 3/16* | (2006.01) | |
| *A61B 5/00* | (2006.01) | |
| *A61B 5/145* | (2006.01) | |
| *G08B 21/02* | (2006.01) | |
| *G08B 21/18* | (2006.01) | |
| *G08B 23/00* | (2006.01) | |
| *G08B 25/01* | (2006.01) | |

(52) U.S. Cl.
CPC ........ *A61B 5/14532* (2013.01); *A61B 5/7405* (2013.01); *A61B 5/746* (2013.01); *A61B 5/7435* (2013.01); *A61B 5/7455* (2013.01); *A61B 5/7475* (2013.01); *A61M 5/14244* (2013.01); *A61M 5/16877* (2013.01); *A61M 5/1723* (2013.01); *G06F 3/04166* (2019.05); *G06F 3/04883* (2013.01); *G06F 3/16* (2013.01); *G08B 21/02* (2013.01); *G08B 21/182* (2013.01); *G08B 23/00* (2013.01); *G08B 25/016* (2013.01); *A61B 2560/0209* (2013.01); *A61M 2005/14208* (2013.01); *A61M 2005/16863* (2013.01); *A61M 2205/18* (2013.01); *A61M 2205/3331* (2013.01); *A61M 2205/502* (2013.01); *A61M 2205/505* (2013.01); *A61M 2205/8212* (2013.01); *A61M 2230/201* (2013.01); *A61M 2230/63* (2013.01); *G06F 2203/04808* (2013.01)

(58) Field of Classification Search
CPC .............. A61B 2560/0209; A61B 5/74; A61B 2560/00; A61B 2560/02; A61B 2560/0204; A61M 5/14244; A61M 5/1723; A61M 2205/18; A61M 2205/502; A61M 2205/505; A61M 2205/8212; A61M 2230/201; A61M 2230/63; A61M 5/14; G08B 23/00; G06F 2203/04808; G06F 3/00; G06F 3/01; G06F 3/048; G06F 3/0487; G06F 3/0488; Y02D 10/00
See application file for complete search history.

(56) References Cited

U.S. PATENT DOCUMENTS

| | | |
|---|---|---|
| 8,823,528 B2 | 9/2014 | Blomquist |
| 8,936,573 B2 | 1/2015 | Blomquist |
| 9,078,971 B2 | 7/2015 | Scarpaci |
| 9,114,210 B2 | 8/2015 | Estes |
| 9,421,329 B2 | 8/2016 | Kruse |
| 9,731,072 B2 | 8/2017 | Estes |
| 9,833,570 B2 | 12/2017 | El-Khatib et al. |
| 9,844,627 B2 | 12/2017 | Estes |
| 9,940,441 B2 | 4/2018 | Walsh |
| 9,959,746 B1 | 5/2018 | Krishnamoorthy et al. |
| 10,052,049 B2 | 8/2018 | Blomquist et al. |
| 10,543,313 B2 | 1/2020 | Damiano et al. |
| 10,561,789 B2 | 2/2020 | Mastrototaro et al. |
| 10,842,934 B2 | 11/2020 | El-Khatib et al. |
| 11,135,363 B2 | 10/2021 | Rosinko et al. |
| 11,135,364 B2 | 10/2021 | Rosinko et al. |
| 11,135,366 B2 | 10/2021 | Rosinko et al. |
| 2003/0065308 A1 | 4/2003 | Lebel |
| 2004/0176984 A1 | 9/2004 | White |
| 2008/0033360 A1 | 2/2008 | Evans et al. |
| 2008/0125700 A1 | 5/2008 | Moberg |
| 2008/0159737 A1 | 7/2008 | Noble |
| 2008/0167641 A1 | 7/2008 | Hansen et al. |
| 2008/0300572 A1 | 12/2008 | Rankers |
| 2009/0005724 A1 | 1/2009 | Regittnig |
| 2011/0040247 A1 | 2/2011 | Mandro |
| 2012/0232520 A1 | 9/2012 | Sloan |
| 2013/0191513 A1 | 7/2013 | Kamen |
| 2014/0024907 A1 | 1/2014 | Howell et al. |
| 2014/0046260 A1 | 2/2014 | Kamen et al. |
| 2014/0276409 A1 | 9/2014 | Rosinko et al. |
| 2014/0282003 A1 | 9/2014 | Gruber et al. |
| 2014/0288947 A1 | 9/2014 | Simpson |
| 2015/0106121 A1 | 4/2015 | Muhsin |
| 2016/0030669 A1 | 2/2016 | Harris |
| 2016/0175520 A1 | 6/2016 | Palerm |
| 2017/0100538 A1 | 4/2017 | Mhatre et al. |
| 2017/0102846 A1 | 4/2017 | Ebler et al. |
| 2017/0161439 A1 | 6/2017 | Raduchel et al. |
| 2017/0286614 A1 | 10/2017 | Morris |
| 2017/0296056 A1 | 10/2017 | Hresko |
| 2017/0311903 A1 | 11/2017 | Davis |
| 2019/0009019 A1 | 1/2019 | Shor |
| 2019/0099551 A1* | 4/2019 | Yodfat ................ A61M 5/1407 |
| 2019/0147721 A1 | 5/2019 | Avitan |
| 2019/0344009 A1 | 11/2019 | Damiano et al. |
| 2020/0203012 A1* | 6/2020 | Kamath ................ A61B 5/002 |
| 2020/0274782 A1 | 8/2020 | Balaiah et al. |
| 2020/0306445 A1 | 10/2020 | Michaud |
| 2021/0030949 A1 | 2/2021 | Damiano |
| 2022/0077705 A1 | 3/2022 | Takahashi et al. |
| 2022/0080118 A1 | 3/2022 | Rosinko |
| 2022/0080119 A1 | 3/2022 | Rosinko |
| 2022/0080120 A1 | 3/2022 | Rosinko |
| 2022/0184300 A1 | 6/2022 | Lim |
| 2022/0184308 A1 | 6/2022 | Patel et al. |
| 2022/0184309 A1 | 6/2022 | Rosinko et al. |
| 2022/0193340 A1 | 6/2022 | Patel |

OTHER PUBLICATIONS

Hoskins, Oct. 2, 2018, iLet "Bionic Pancreas" making progress with gen 4 device, Healthline, https"//www.healthline.com/diabetesmine/beta-bionics-ilet-update#1, 15 pp.

(56) References Cited

OTHER PUBLICATIONS

Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.
Krugman, Aug. 25, 2018, iLet Bionic Pancreas Interface, sarakrugman.com/ilet-interface, 3 pp.
Senior Tech Club, Aug. 16, 2018, Sleep and Shutdown—How To Know The Difference On Your Iphone, https://www.seniortechclub.com/tech-recipe/sleep-shutdown-iphone-100, 8 pp.
International Search Report and Written Opinion dated Apr. 8, 2022 in application No. PCT/US2021/064228.

\* cited by examiner

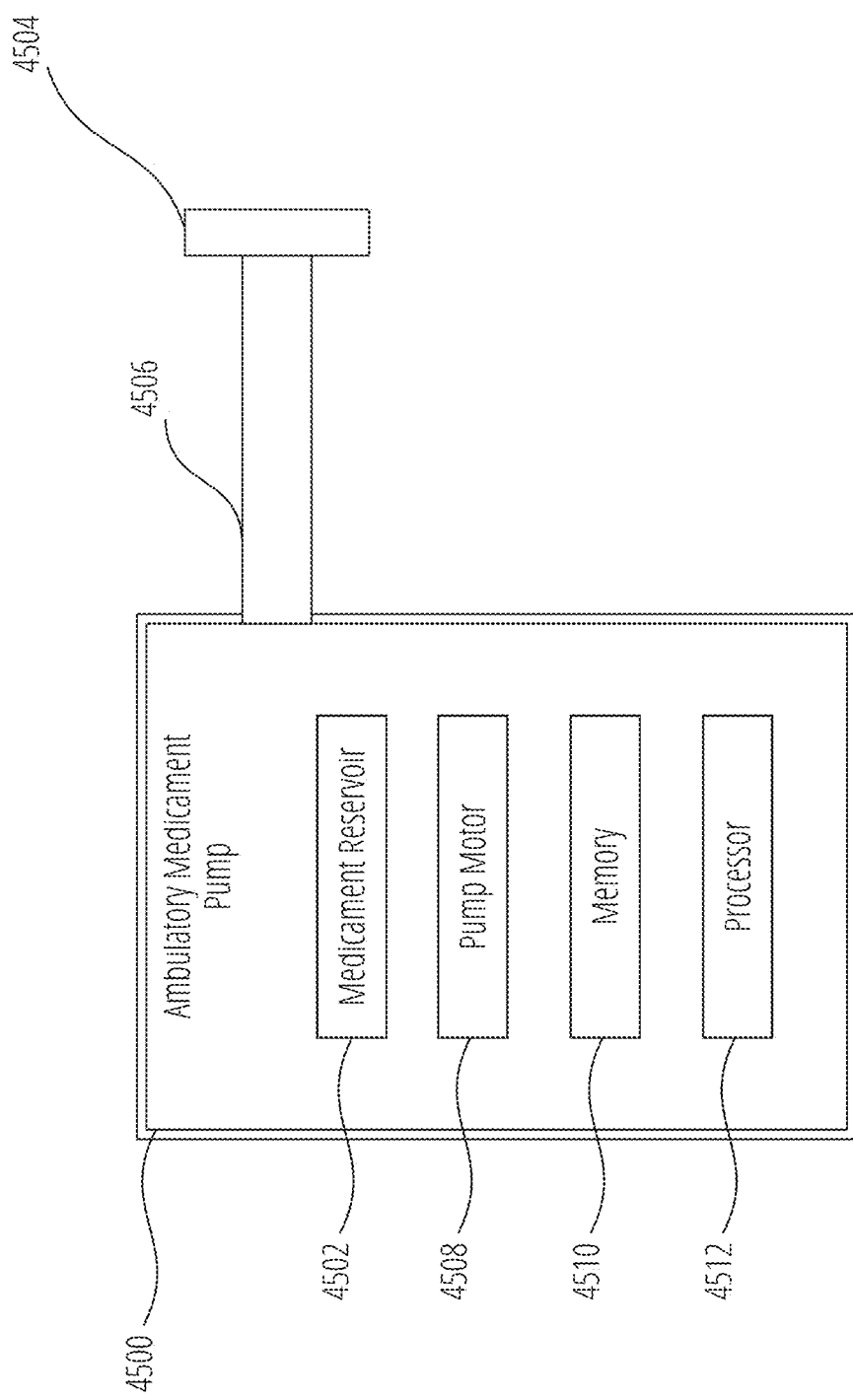

AMBULATORY MEDICAMENT DEVICE WITH POWER SAVING MODE

INCORPORATION BY REFERENCE

This application is a continuation of PCT Application No. PCT/US2021/0064228, filed Dec. 17, 2021, which claims priority to U.S. Provisional Patent Application No. 63/128,428, filed Dec. 21, 2020; 63/167,563, filed Mar. 29, 2021; 63/216,177, filed Jun. 29, 2021; 63/239,365, filed Aug. 31, 2021; 63/169,112, filed Mar. 31, 2021; 63/151,565, filed Feb. 19, 2021; 63/261,290, filed Sep. 16, 2021; 63/152,744, filed Feb. 23, 2021; 63/157,541, filed Mar. 5, 2021; 63/152,716, filed Feb. 23, 2021; 63/168,203, filed Mar. 30, 2021; 63/212,521, filed Jun. 18, 2021; 63/139,210, filed Jan. 19, 2021; 63/238,670, filed Aug. 30, 2021; 63/2plurality76,481, filed Nov. 5, 2021; 63/215,857, filed Jun. 28, 2021; 63/183,900, filed May 4, 2021; 63/249,975, filed Sep. 29, 2021; 63/194,126, filed May 27, 2021; 63/263,602, filed Nov. 5, 2021; and 63/264,645, filed Nov. 29, 2021. PCT Application No. PCT/US2021/0064228 claims priority to PCT Application No. PCT/US2021/072742, filed Dec. 3, 2021, which claims priority to U.S. Provisional Application No. 63/122,427, filed Dec. 7, 2020. The entire contents of each application referenced in this paragraph are hereby incorporated by reference herein for all purposes and made part of this specification. Any and all applications for which a foreign or domestic priority claim is identified in the Application Data Sheet as filed with the present application are hereby incorporated by reference under 37 CFR 1.57.

BACKGROUND

Technical Field

This disclosure relates to glucose control systems, including medical devices that provide glucose control therapy to a subject, glucose level control systems, and ambulatory medicament pumps that deliver medicament to the subject to control blood glucose level in the subject.

Description of Related Art

Sustained delivery, pump driven medicament injection devices generally include a delivery cannula mounted in a subcutaneous manner through the skin of the subject at an infusion site. The pump draws medicine from a reservoir and delivers it to the subject via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a subject while others are configured to deliver multiple medicaments to a subject.

SUMMARY

Blood glucose control systems and ambulatory medical devices that provide therapy to a subject, such as blood glucose control, are disclosed. Disclosed systems and devices can implement one or more features that improve the user experience, such as software update techniques that avoid interrupting delivery of therapy, gesture-based control of therapy delivery, automatic resumption of therapy after a user-initiated pause, improved alarm management, display of autonomously calculated dosing recommendations, wide area network connectivity, and security features.

BRIEF DESCRIPTION OF THE DRAWINGS

The systems, methods, and devices of this disclosure each have several innovative aspects, no single one of which is solely responsible for all of the desirable attributes disclosed herein. Details of one or more implementations of the subject matter described in this specification are set forth in the accompanying drawings and the description below. The drawings are provided to illustrate certain aspects of the subject matter described herein and not to limit the scope thereof.

FIG. 45A is a schematic illustrating an example ambulatory medicament pump that is configured to maintain delivery of therapy to a subject after determining that a possible occlusion exists in a medicament delivery system.

DETAILED DESCRIPTION

Figure 1A:
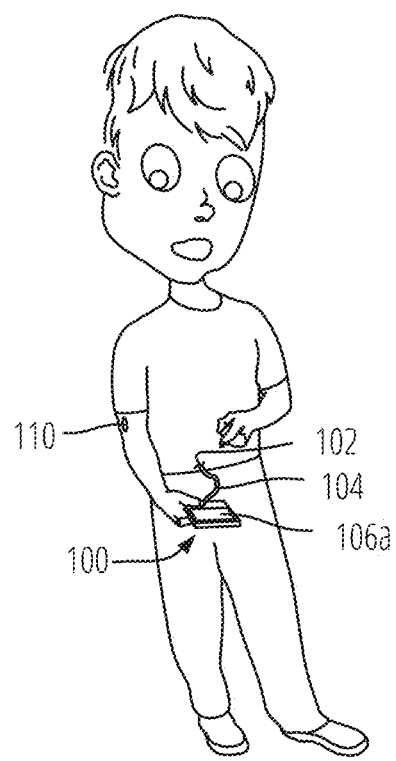
FIG. 1A illustrates an example blood glucose control system that provides blood glucose control via an ambulatory medicament pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a patient. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A glucose level control system can operate in conjunction with an infusion system to infuse one or more medicaments, including at least one glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Further, certain embodiments disclosed herein relate to a glucose level control system that is capable of supporting different operating modes associated with different adaptation ranges used to generate dose control signals for delivering medicament to a subject. The different adaptation ranges may be associated with a value or a change in value of one or more control parameters used by a control algorithm that controls the administering of medicament to a subject. In some non-limiting examples, the control parameter may be associated with the quantity of medicament, a delivery rate of medicament, a step-size or graduation used to modify the quantity of medicament between administrations of the medicament, a timing of supplying medicament to the subject, a glucose absorption rate, a time until the concentration of insulin in blood plasma for a subject reaches half of the maximum concentration, a time until the concentration of insulin in blood plasma for a subject reaches a maximum concentration, or any other control parameter that can impact a timing or quantity of medicament (e.g., insulin or counter-regulatory agent) supplied or administered to a subject.

Advantageously, in certain embodiments, supporting different operating modes enables a user (e.g., a healthcare provider, parent, guardian, the subject receiving treatment, etc.) to modify the operating mode of an ambulatory medicament device. In some cases, the operating mode may be modified automatically. Moreover, modifying the operating mode enables different dosing modes to be supported. Advantageously, supporting different dosing modes enables an ambulatory medicament device to be used by different types of subjects, and/or a subject under different conditions (e.g., when exercising, before, during, or after puberty, under different health conditions, etc.).

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Some embodiments described herein pertain to medicament infusion systems for one or more medicaments. Some embodiments pertain to methods of using infusion systems for infusing one or more medicaments (e.g., pharmaceutical, hormone, etc.) to a subject. Some embodiments pertain to methods of managing access to one or more therapy settings of a medicament infusion system. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. An infusion system may include a user interface that allow modifying one or more control parameters that control medicament delivery to a subject. An infusion system may include a wireless transceiver that allows data communication between the infusion system and one or more electronic devices.

Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Blood Glucose Control System Overview

A blood glucose control system (BGCS) is used to control blood glucose level in a subject. Blood glucose control systems can include a controller configured to generate dose control signals for one or more glucose control agents that can be infused into the subject. Glucose control agents include regulatory agents that tend to decrease blood glucose level, such as insulin and insulin analogs, and counter-regulatory agents that tend to increase blood glucose level, such as glucagon or dextrose. A blood glucose control system configured to be used with two or more glucose control agents can generate a dose control signal for each of the agents. In some embodiments, a blood glucose control system can generate a dose control signal for an agent even though the agent may not be available for dosing via a medicament pump connected to the subject.

Glucose control agents can be delivered to a subject via subcutaneous injection, via intravenous injection, or via another suitable delivery method. In the case of blood glucose control therapy via an ambulatory medicament pump, subcutaneous injection is most common. An ambulatory medicament pump 100 is a type of ambulatory medical device, which is sometimes referred to herein as an ambulatory device, an ambulatory medicament device, ambulatory medical device, a mobile ambulatory device, or an AMD. Ambulatory medical devices include ambulatory medicament pumps and other devices configured to be carried by a subject and to deliver therapy to the subject. It should be understood that one or more of the embodiments described herein with respect to one AMD may be applicable to one or more of the other AMDs described herein.

In some embodiments, the AMD can be a portable or wearable device (e.g., an insulin or bi-hormonal medicament pump) that provides life-saving treatment to a subject by delivering one or more medicaments (e.g., insulin and/or glucagon) to a subject. Some AMDs may continuously monitor the health condition of a subject (e.g., blood glucose level) using a sensor (e.g., a blood glucose level sensor that can measure values corresponding to the blood glucose level) and deliver therapy (e.g., one or more medicaments) to the subject based on the condition of the subject. Certain ambulatory medicament devices may be worn by subjects constantly (e.g., all day), or for a large portion of the day (e.g., during waking hours, during sleep hours, when not swimming, etc.) to enable continuous monitoring of the health condition of the subject and to deliver medicament as. In some embodiments, an AMD may be an ambulatory medicament device such as a medicament delivery pump. In some examples, an AMD may be a device that provides therapy in the form of electrical stimulation based on a health condition of a subject (e.g., heart rhythm or brain activity) determined using signals received from one or more sensors (e.g., heartbeat monitor or electrodes monitoring activity of the brain). An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Figure 1B:
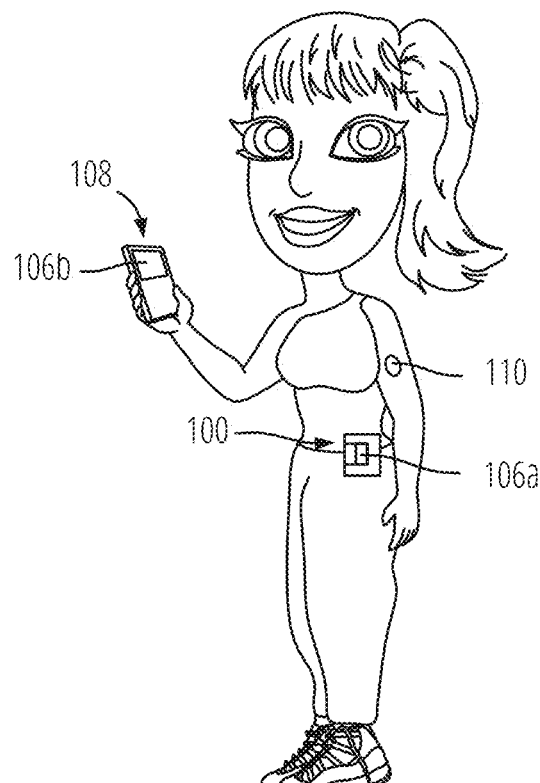
FIG. 1B illustrates another example blood glucose control system that provides blood glucose control via an ambulatory medicament pump.
Figure 1C:
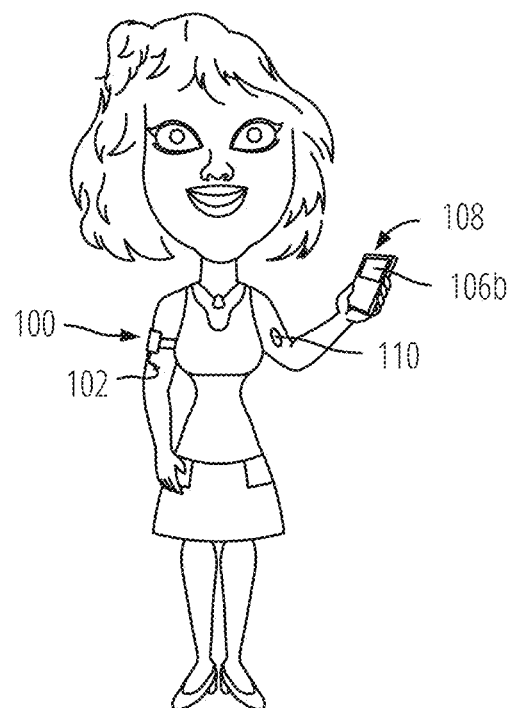
FIG. 1C illustrates a further example blood glucose control system that provides blood glucose control via an ambulatory medicament pump.

FIG. 1A-FIG. 1C show examples of blood glucose control systems that provide blood glucose control via an ambulatory medical device or AMD, such as a medicament pump connected to a subject. In FIG. 1A, the AMD 100 (medicament pump) is connected to an infusion site 102 using an infusion set 104. The AMD 100 (medicament pump) has integrated pump controls 106a that permit a user to view pump data and change therapy settings via user interaction with the pump controls 106a. A glucose level sensor 110 generates a glucose level signal that is received by the blood glucose control system.

In FIG. 1B, the medicament pump 100 communicates with an external electronic device 108 (such as, for example, a smartphone or another remote device) via a wireless data connection. At least some of the pump controls 106a and 106b can be manipulated via user interaction with user interface elements of the external electronic device 108. The glucose level sensor 110 can also communicate with the AMD 100 (medicament pump) via a wireless data connection.

In FIG. 1C, the AMD 100 (medicament pump) includes an integrated cannula that inserts into the infusion site 102 without a separate infusion set. At least some of the pump controls 106b can be manipulated via user interaction with user interface elements of an external electronic device 108. In some instances, pump controls can be manipulated via user interaction with user interface elements generated by a remote computing environment (not shown), such as, for example, a cloud computing service, that connects to the AMD 100 (medicament pump) via a direct or indirect electronic data connection.

Glucose control systems typically include a user interface configured to provide one or more of therapy information, glucose level information, and/or therapy control elements capable of changing therapy settings via user interaction with interface controls. For example, the user can provide an indication of the amount of the manual bolus of medicament from an electronic device remote from the medicament pump. The user interface can be implemented via an electronic device that includes a display and one or more buttons, switches, dials, capacitive touch interfaces, or touchscreen interfaces. In some embodiments, at least a portion of the user interface is integrated with an ambulatory medicament pump that can be tethered to a body of a subject via an infusion set configured to facilitate subcutaneous injection of one or more glucose control agents. In certain embodiments, at least a portion of the user interface is implemented via an electronic device separate from the ambulatory medicament pump, such as a smartphone. In some embodiments, to protect patient privacy, the device screen may include a filter configured to have a predetermined viewing angle range such that information cannot be seen on the touchscreen when viewed from an angle outside of the predetermined viewing angle range.

Figure 2A:
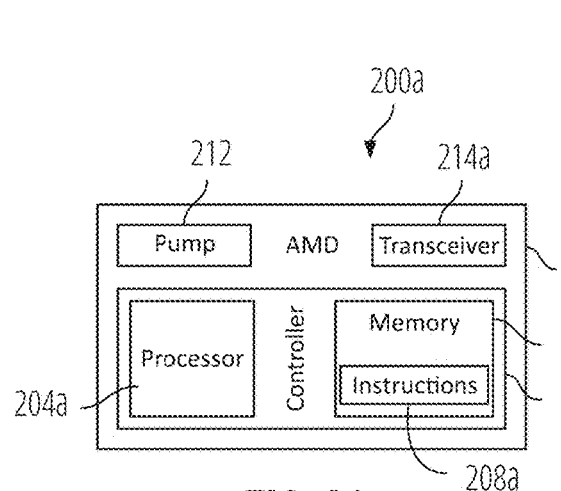
FIG. 2A shows a block diagram of an example blood glucose control system.

FIG. 2A-FIG. 2D illustrate block diagrams showing example configurations of a glucose control system 200a/200b/200c/200d. As shown in FIG. 2A, a glucose control system 200a can include a controller 202a having an electronic processor 204a and a memory 210a that stores instructions 208a executable by the electronic or hardware processor 204a. The controller 202a can include a touchscreen controller. The controller 202a and a pump 212 can be integrated into an ambulatory medical device (AMD) 100. The AMD 100 can have one or more pumps 212. The pump 212 can be a regulatory agent pump and/or counter-regulatory agent pump. The AMD 100 can have one or more pumps 212. The AMD 100 can include a transceiver or wireless electronic communications interface 214a for wireless digital data communications with external electronic devices. When the instructions 208a stored in memory 210a are executed by the electronic processor 204a, the controller 202a can implement at least a portion of a control algorithm that generates dose control signals for one or more glucose control agents based on time-varying glucose levels of the subject (e.g., received from a glucose level sensor 110 that is in communication with the AMD 100, e.g., a medicament pump) and one or more control parameters. The dose control signals, when delivered to the pump 212, result in dosing operations that control the blood glucose of a subject. The pump 212 may be controlled by a pump controller. The pump controller receives the dose control signals and controls the operation of the pump 212 based on the received dose control signals. In some embodiments the pump controller may be integrated with the pump.

Figure 2B:
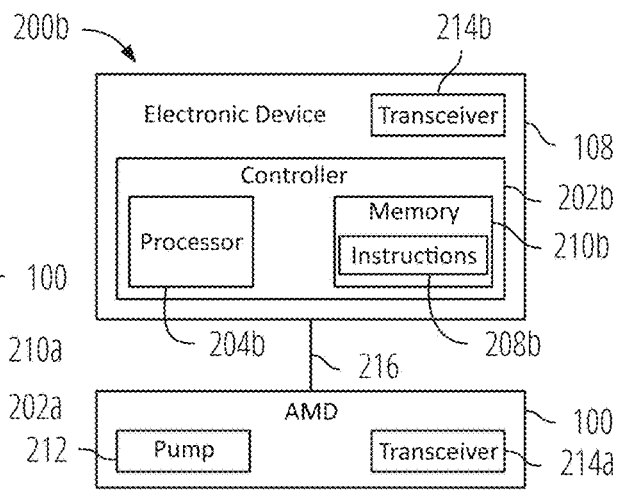
FIG. 2B shows a block diagram of another example blood glucose control system.

As shown in FIG. 2B, a glucose control system 200b can operate at least partially via execution of instructions 208b by an electronic or hardware processor 204b of an external electronic device 108 separate from the AMD 100. The external electronic device 108 can include a transceiver 214b capable of establishing a wireless digital data connection to the AMD 100, and a controller 202b can implement at least a portion of a control algorithm via execution of instructions 208b stored in memory 210b. When the instructions 208b stored in memory 210b are executed by the electronic processor 204b, the controller 202b can implement at least a portion of a control algorithm that generates dose control signals for one or more glucose control agents based on time-varying glucose levels of the subject and one or more control parameters. The dose control signals, when delivered to the pump 212 (e.g., pump controller of the pump 212), may result in dosing operations that control the blood glucose of a subject. In some embodiments, the dose control signals are transmitted from the device transceiver 214b to the AMD transceiver 214a over a short-range wireless data connection 216. The AMD 100 may receive the dose control signals and pass them to the pump 212 (e.g., pump controller of the pump 212) for dosing operations.

Figure 2C:
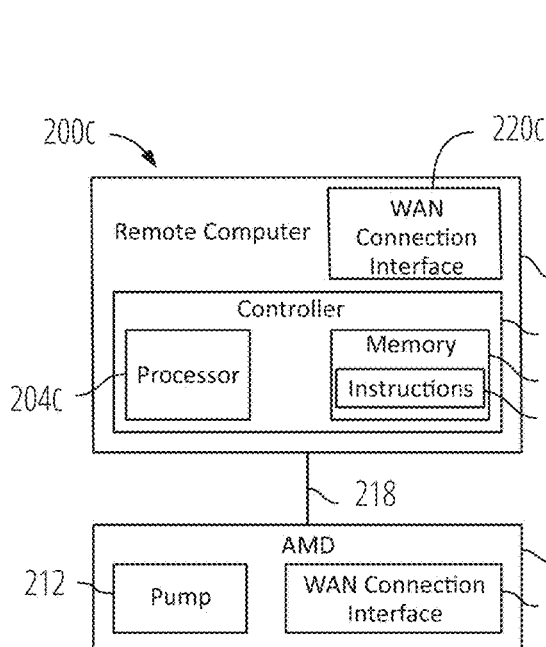
FIG. 2C shows a block diagram of another example blood glucose control system.

As shown in FIG. 2C, a glucose control system 200c can operate at least partially via execution of instructions 208c on an electronic processor or hardware 204c integrated with a remote computer or device 206, such as, for example, a cloud service. When the instructions 208c stored in memory 210c are executed by the electronic processor 204c, the controller 202c can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the remote computer WAN connection interface 220c to the AMD WAN connection interface 220a over an end-to-end wireless data connection 218. The AMD 100 receives the dose control signals and passes them to the pump 212 for dosing operations.

Figure 2D:
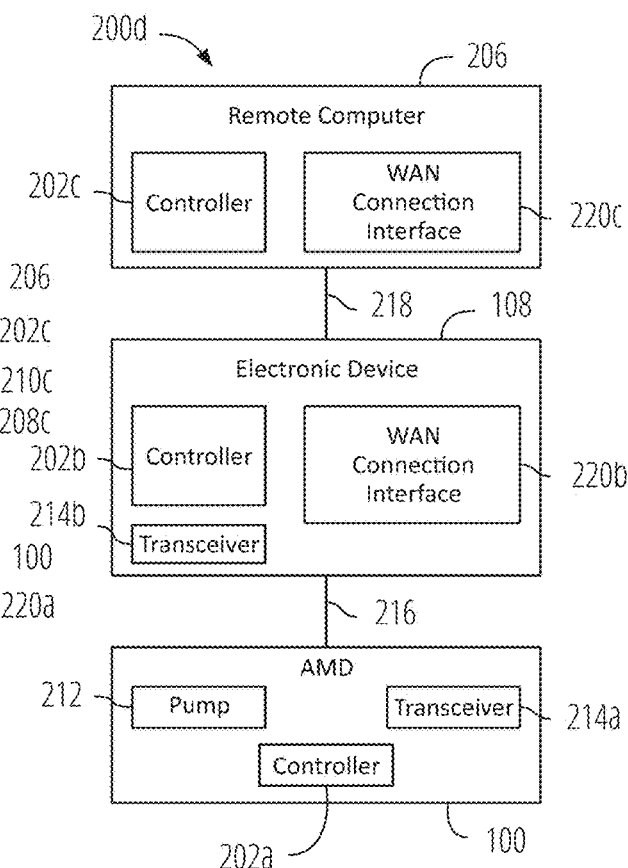
FIG. 2D shows a block diagram of another example blood glucose control system.

As shown in FIG. 2D, a glucose control system 200d can have two or more controllers 202a, 202b, 202c that cooperate to generate a dose control signal for dosing operations by the pump 212. In some examples, any one or any combination of controllers 202a, 202b, 202c can include the touchscreen controller. A remote computer 206 can transmit or receive data or instructions passed through a WAN connection interface 220c via an end-to-end wireless data connection 218 to a WAN connection interface 220b of an external electronic device 108. The external electronic device 108 can transmit or receive data or instructions passed through a transceiver 214b via a short-range wireless data connection 216 to a transceiver 214a of an AMD 100. In some embodiments, the electronic device can be omitted, and the controllers 202a, 202c of the AMD 100 and the remote computer 206 cooperate to generate dose control signals that are passed to the pump 212. In such embodiments, the AMD 100 may have its own WAN connection interface 220a to support a direct end-to-end wireless data connection to the remote computer 206.

Figure 3:
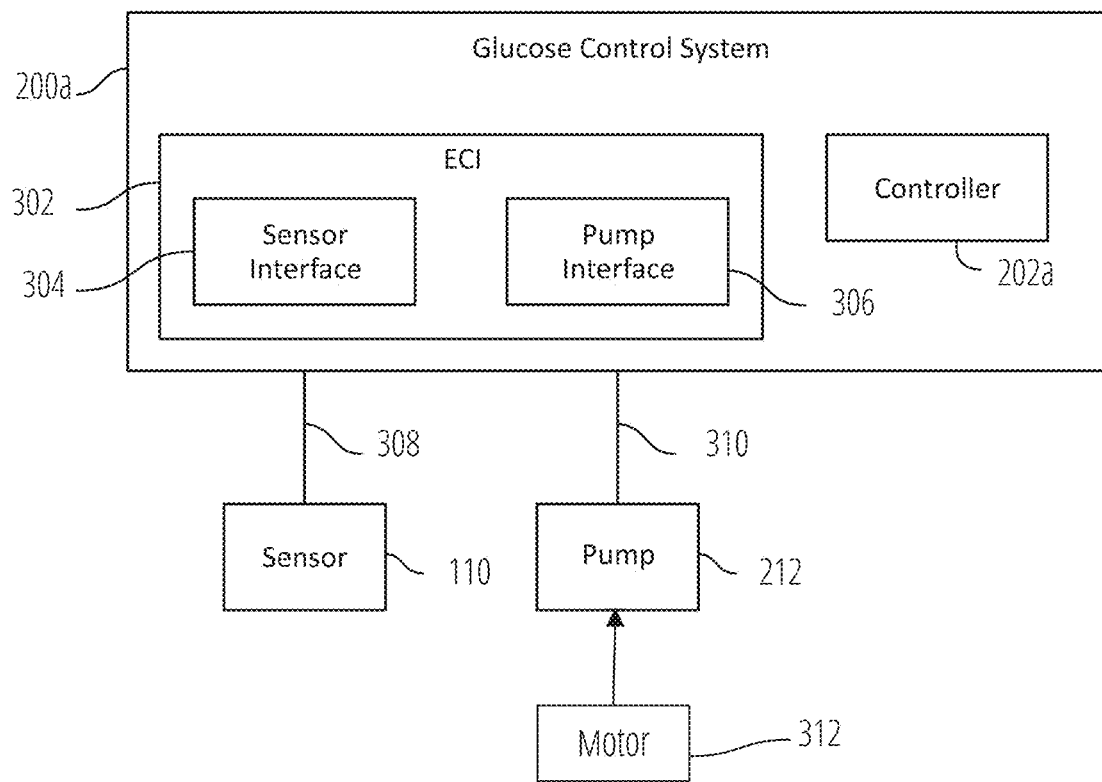
FIG. 3 is a schematic of an example glucose control system that includes an electronic communications interface.

As shown in FIG. 3, in some embodiments, the glucose control system 200a includes circuitry that implements an electronic communications interface (ECI) 302 configured to send and receive electronic data from one or more electronic devices. The ECI includes a sensor interface or glucose sensor interface 304 configured to receive a glucose level signal from a glucose level sensor 110 such as a continuous glucose monitor (CGM). Some CGMs generate the glucose level signal at fixed or periodic measurement intervals, such as five-minute intervals. The glucose level sensor 110 can be operatively connected to a subject in order to generate a glucose level signal that corresponds to a blood glucose estimate or measurement of the subject. The glucose level signal can be used by the controller 202a to generate a dose control signal. The dose control signal can be provided to a pump 212 via a delivery device interface or pump interface 306. In some embodiments, the sensor interface 304 connects to the glucose level sensor 110 via a short-range wireless connection 308. In some embodiments, the pump interface 306 connects to the pump 212 via a short-range wireless connection 310. In other embodiments, the pump interface 306 connects to the pump 212 via a local data bus, such as when the controller 202a, the ECI 302, and the pump 212 are integrated into an AMD 100. In addition, the pump 212 may be connected to a pump motor 312.

The controller can be configured to generate the dose control signal using a control algorithm that generates at least one of a basal dose, a correction dose, and/or a meal dose. Examples of control algorithms that can be used to generate these doses are disclosed in U.S. Patent Application Publication Nos. 2008/0208113, 2013/0245547, 2016/0331898, and 2018/0220942 (referenced herein as the "Controller Disclosures"), the entire contents of which are incorporated by reference herein and made a part of this specification. The correction dose can include regulatory or counter-regulatory agent and can be generated using a model-predictive control (MPC) algorithm such as the one disclosed in the Controller Disclosures. The basal dose can include regulatory agent and can be generated using a basal control algorithm such as disclosed in the Controller Disclosures. The meal dose can include regulatory agent and can be generated using a meal control algorithm such as disclosed in the Controller Disclosures. Additional aspects and improvements for at least some of these controllers are disclosed herein. The dose control signal can be transmitted to a pump interface 306 via the ECI 302 or can be transmitted to the pump interface 306 via an electrical conductor when the controller 202a is integrated in the same housing as the pump interface 306.

Figure 4A:
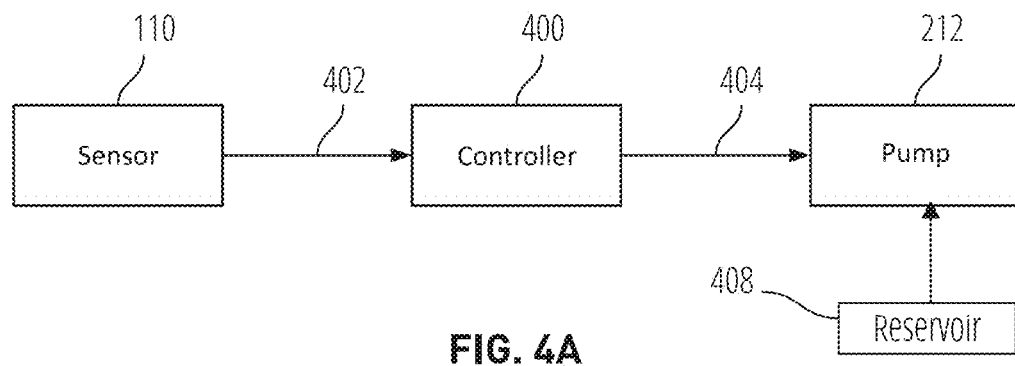
FIG. 4A shows a block diagram of an example blood glucose control system in online operation mode.

As shown in FIG. 4A, the ambulatory medicament pump 212 can include one or more medicament cartridges or can have an integrated reservoir 408 of medicament. The reservoir 408 may be integrated with the pump 212. A medicament stored in the reservoir 408 can be delivered to the subject by operation of the pump 212. In various embodiments, the operation of the pump 212 can be controlled by a controller 400. As shown in FIG. 4A, the controller 400 can be configured to operate in "online mode" during time periods when the controller receives a glucose level signal 402 from a glucose level sensor 110. In online mode, the control algorithm generates a dose control signal 404 that implements regular correction doses based on values of the glucose level signal 402 and control parameters of the control algorithm. The pump 212 is configured to deliver at least correction doses and basal doses to the subject without substantial user intervention while the controller 400 remains in online mode.

Figure 4B:
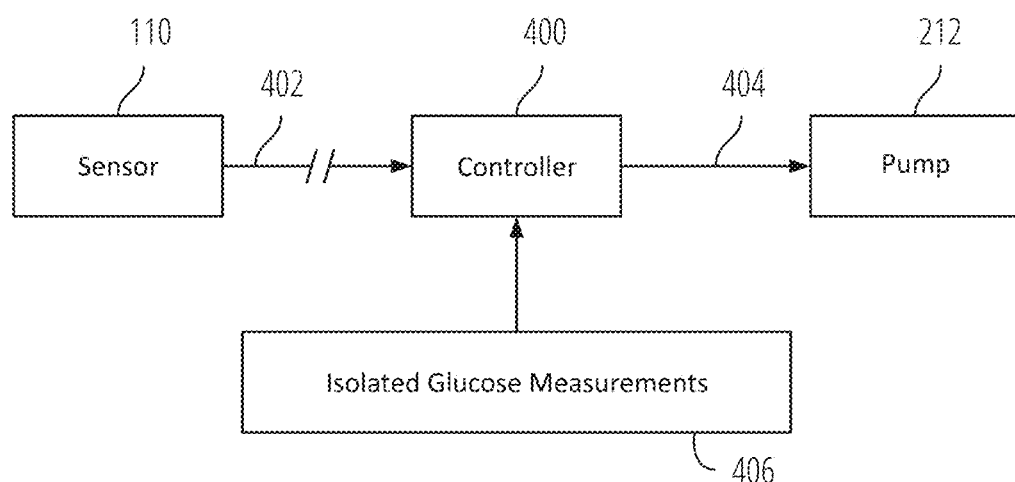
FIG. 4B shows a block diagram of an example blood glucose control system in offline operation mode.

As shown in FIG. 4B, the controller 400 can be configured to operate in "offline mode" during time periods when the controller does not receive a glucose level signal 402 from a sensor 110, at least during periods when the glucose level signal 402 is expected but not received. In offline mode, the control algorithm generates a dose control signal 404 that implements correction doses in response to isolated glucose measurements 406 (such as, for example, measurements obtained from the subject using glucose test strips) and based on control parameters of the control algorithm. The pump 212 is configured to deliver basal doses to the subject without substantial user intervention and can deliver correction doses to the subject in response to isolated glucose measurements 406 while the controller 400 remains in offline mode.

Example Ambulatory Medical Device (AMD)

In some embodiments, the ambulatory medicament device (AMD) can be a portable or wearable device (e.g., an insulin or bi-hormonal medicament pump) such as an ambulatory medicament pump (AMP) that provides life-saving treatment to a subject by delivering one or more medicaments (e.g., insulin and/or glucagon) to a subject. Some AMDs may continuously monitor the health condition of a subject (e.g., blood glucose level) using a sensor (e.g., a blood glucose level sensor that can measure values corresponding to the blood glucose level) and deliver therapy such as one or more medicaments to the subject based on the health condition of the subject. For example, an ambulatory medicament pump (e.g., an insulin pump or a bi-hormonal pump) may monitor the blood glucose level in a subject using a Continuous Glucose Monitor (CGM) and adjust the dose or frequency of the medicament delivery (e.g., insulin or glucagon) accordingly. Certain ambulatory medicament devices may be worn by subjects constantly (e.g., all day), or for a large portion of the day (e.g., during waking hours, during sleep hours, when not swimming, etc.) to enable continuous monitoring of the health condition of the subject and to deliver medicament as desired. In some embodiments, the AMD may be an ambulatory medicament device such as a medicament delivery pump. In some examples, the AMD may be a device that provides therapy in the form of electrical stimulation based on a health condition of a subject (e.g., heart rhythm or brain activity) determined using signals received from one or more sensors (e.g., heartbeat monitor or electrodes monitoring activity of the brain).

Figure 5A:
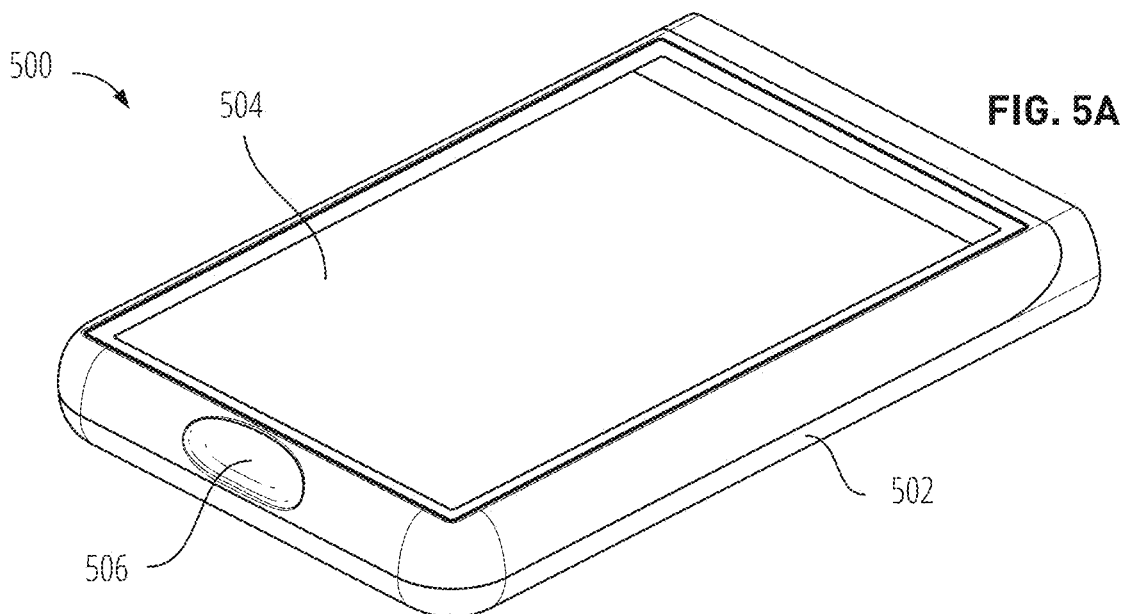
FIG. 5A illustrates a perspective view of an example ambulatory medical device.
Figure 5B:
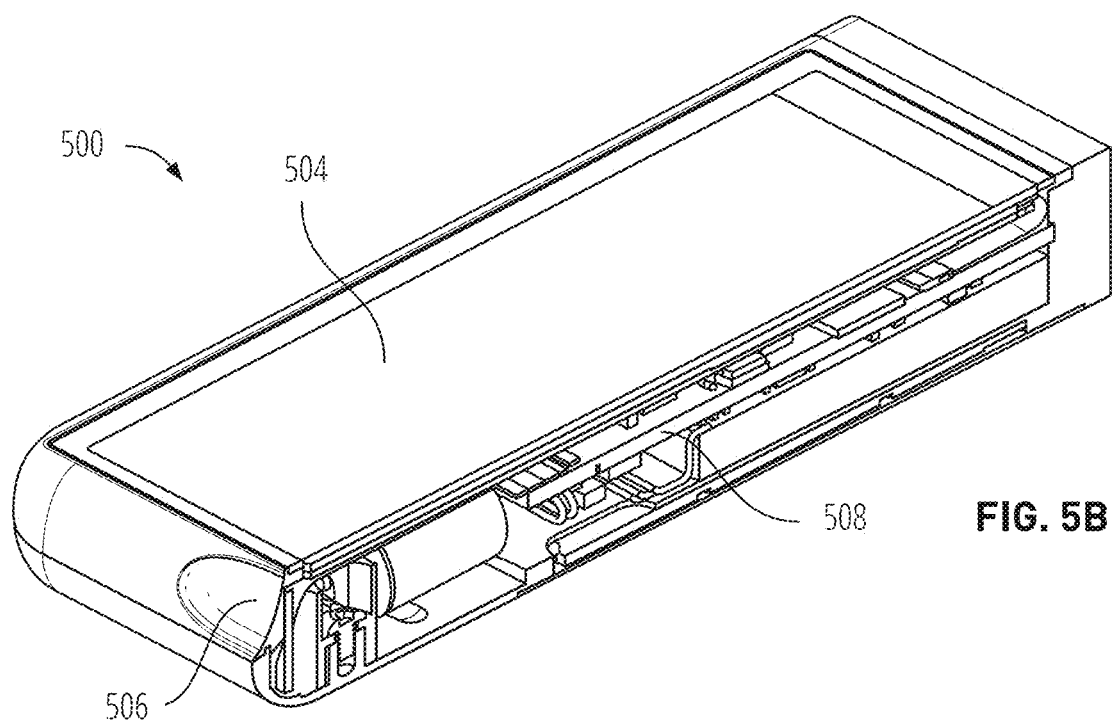
FIG. 5B illustrates a cross sectional view of the ambulatory medical device shown in FIG. 5A.

FIG. 5A illustrates a three-dimensional (3D) view of an example ambulatory medical device 500 (e.g., an ambulatory medical delivery pump such as an insulin pump) including a housing 502 with a wake button 506 and a touchscreen display 504. FIG. 5B is an illustration of a cross sectional view of the ambulatory medical device 500 shown in FIG. 5A. In this example, all the electronic modules 508 are included inside the housing 502, for example, as a single integrated electronic board. The wake button 506 may be any type of button (e.g., capacitive, inductive, resistive, mechanical) that registers an input generated by user interaction with the wake button 506 to generate a wake signal. In some embodiments, the wake signal is generated by a sensor (e.g., a biometric sensor such as a fingerprint reader or a retinal scanner, an optical or RF proximity sensor, and the like). In various embodiments, the wake signal may be generated by user interaction with the touch screen display 504 or with an alphanumeric pad (not shown).

The wake button 506 may be located at one edge of the AMD, more specifically, at a lower surface of the AMD for the user to conveniently interact (e.g., touch or tap) while holding or carrying the AMD. In some embodiments, there may be more than one wake button 506.

In certain embodiments, a user may wake the AMD from a sleep state or unlock the AMD by interacting with the touch screen display 504 having via a wake interface. When the AMD is in a sleep state or other state/mode, the touchscreen controller may not receive user interaction or user interaction signals corresponding to user interaction (e.g., via an accelerometer or other motion sensors). As discussed herein, motion or motion detection may include all types of user gesture control inputs discussed herein, including tapping the AMD (including on the touchscreen), touching or other gesturing on the touchscreen of the AMD, shaking the AMD, moving of the AMD, or motioning proximate the AMD such as handwaving or other body part moving near, proximate, or in front of a motion sensor (e.g., a camera) of the AMD.

In certain cases, a single tap such as on the back of the AMD or anywhere on the AMD can correspond to wake touchscreen and/or snooze alarm control inputs as discussed. Other tapping for user gesture control inputs can include multi-tap such as double or triple tapping anywhere on the AMD, including the back of the AMD can correspond to wake AMD, unlock AMD, quick meal announcement (e.g., for bolus administration), confirmation of control inputs (such as when AMD is unlocked), and/or alarm acknowledgement control inputs as discussed herein. In some cases, multi-location-tap for gesture control inputs can be utilized for additional user gesture control inputs. For example, the AMD can generate a user interface with two dots on touchscreen; the two dots can be tapped or touched simultaneously, sequentially, or multi-tap to provide control inputs for various actions and functions as discussed herein. In some cases, the AMD can implement specific timing between taps or touches or other gesture controls to register the control inputs as valid. For example, there can be 100 to 600 milliseconds timing between taps. The timing between taps can be adjusted by the user.

In some embodiments, the user may wake the AMD by touching the wake button 506 as the wake interface. In some cases, the wake button 506 may be incorporated into the alphanumeric pad. In some cases, the wake interface 3220 may be any one or more keys of the alphanumeric pad. In some cases, the wake interface may be a capacitive button that detects a change in capacitance. In some cases, a wake interface may have a computing component for interpreting and executing instructions from the signal processing component. Thus, the wake interface can follow a program that is dictated by the signal processing component. In some cases, a wake interface can include one or more additional user interfaces mentioned above that are configured to generate and provide a wake input (or wake signal) to the CCM when detecting a pre-set user interaction. Alternatively, or in addition, the wake interface can be any type of wake interface element of the AMD that a user can interact with to wake at least a feature (e.g., a touchscreen interface) of the AMD. In some cases, the wake interface element can be a physical button (e.g., a push button, a slide button, etc.), a capacitive element, a resistive element, or an inductive element. In some cases, the wake interface element can be or can include a biometric element, such as a fingerprint reader, an iris scanner, a face detection scanner, etc. In some cases, the AMD may wake in response to detection of a particular movement or motion. In some cases, the AMD may wake in response to detection of a particular movement or motion. For example, a determination that the ambulatory medicament device is being moved with a particular motion or within a line of sight or a visual range of a user may cause the AMD to awaken or cause the AMD to awake the touchscreen interface of the AMD. The AMD may determine that the AMD is being moved within a line of sight of the user based on the type of motion and/or the detection of a user's eyes via, for example, an iris scanner or a camera.

In some examples, a wake signal may be generated based on facial recognition or other biometric indicia. In some examples, the wake signal may be generated by a wireless signal such as a signal generated by an RFID system or Bluetooth signals received from an electronic device or by detection of movement using one or more motion sensors such as an accelerometer.

The wake button 506, if touched, pressed, or held for a certain period of time, may generate a wake signal that activates the touchscreen display 504. In some examples, touches on the touchscreen display 504 are not registered until the wake button activates the touchscreen display. In some such examples, the AMD remains locked from accepting at least certain types of user interaction or settings modification until a gesture (such as, for example, any of the gesture interactions described with reference to any of the embodiments disclosed herein) is received after the touchscreen display 504 is activated by the wake button 506.

In some examples, after the touchscreen display 504 has been activated by the wake signal, a passcode may be required to unlock the touchscreen display.

Figure 6:
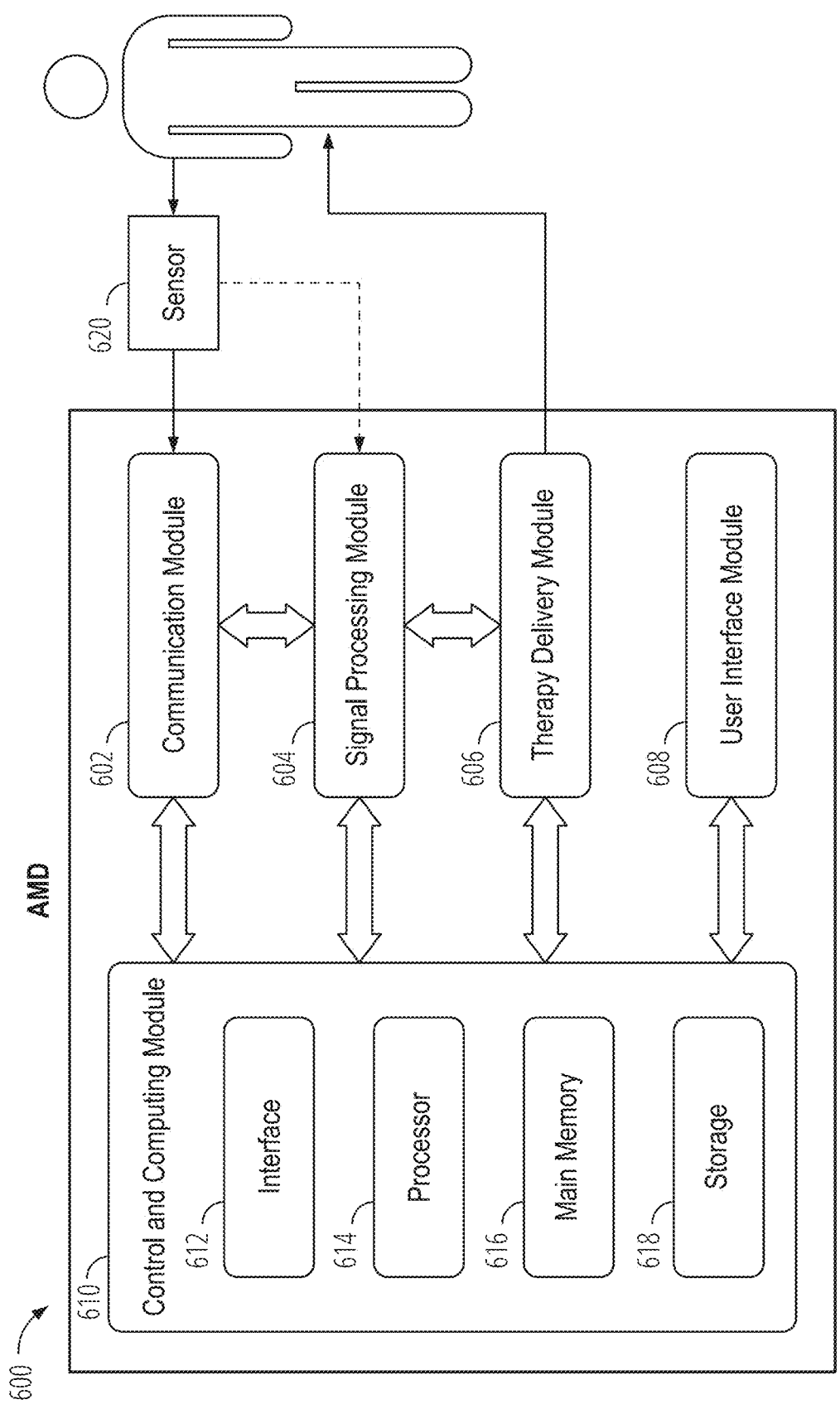
FIG. 6 illustrates different modules that may be included in an example ambulatory medical device.

FIG. 6 illustrates different modules that may be included in an example ambulatory medical device 600. In some examples, all these modules may be integrated together inside a single housing (as shown in FIG. 5B). In some other examples, one or more modules may be individual modules contained in separate housings that communicate with the main unit via a wired or wireless communication links (e.g., Bluetooth). The modules included in the AMD may include a communication module 602, signal processing module 604, a therapy delivery module 606, a user interface module 608, and a control and computing module 610.

The control and computing module 610 may include one or more processors 614, a main memory 616, a storage 618 that may include one or more non-transitory memories and an interface 612 that enables data and signal communication among the components within the control and computing module 610 as well as communication between the control and computing module and all other modules of the AMD. The main memory and the storage each may be divided into two or more memory locations or segments. The main memory 616 may communicate with the other components of the control and computing module 610 as well as other modules through the interface 612. Instructions may be transmitted to the main memory (e.g., from the storage) and the processor 614 executes instructions that are communicated to the processor through the main memory 616. The storage 618 may store data while the control and computing module 610 is powered or unpowered. The storage 618 may exchange data with the main memory directly or through the interface 612. The main memory 616 can be any type of memory that can store instructions and communicate them to the processor 614 and receive executed instructions from the processor 614. Types of main memory include but are not limited to random access memory ("RAM") and read-only memory ("ROM"). The processor 614 may be any type of general-purpose central processing unit ("CPU"). In some embodiments, the control and computing module may include more than one processor of any type including, but not limited to complex programmable logic devices ("CPLDs"), field programmable gate arrays ("FPGAs"), application-specific integrated circuits ("ASICs") or the like. The storage 618 can be any type of computer storage that can receive data, store data, and transmit data to the main memory 616 and possibly other modules of AMD. Types of storage 618 that can be used in the control and computing module 610 include, but are not limited to, magnetic disk memory, optical disk memory, flash memory and the like. The interface 612 may include data transfer buses and electronic circuits configured to support data exchange among different components within the control and computing module 610. In some examples, the interface 612 may also support data and signal exchange among other modules as well as data exchange between any of the modules and the control and computing module 610.

The signal processing module 604 may include a plurality of interconnected electronic modules for signal conditioning and signal conversion (e.g., A-to-D and D-to-A conversion) configured to support communication and data exchange between different modules. For example, the signal processing module 604 may convert an analog signal received from the communication module 602 and convert it to a digital signal that can be transmitted to the control and computing module 610 (e.g., via the interface 612). As another example, the signal processing module may receive a digital control signal from the control and computing module 610 and convert it to an analog signal that can be transmitted to the therapy delivery module 606, for example, to control one or more pumps.

The therapy delivery module 606 may include one or more infusion pumps configured to deliver one or more medicaments to a subject. The medicaments may be stored in one or more medicament cartridges housed in the therapy delivery module 606. In some examples, the therapy delivery module may include electronic and mechanical components configured to control the infusion pumps based on the signals received from control and computing module 610 (e.g., via the signal processing module 604).

The user interface module 608 may include a display to show various information about the AMD, medicament type and delivery schedule, software status, and the like. Graphic images and text may be shown by any display technology including, but not limited to OLED, LCD, or e-ink. In some embodiments, the AMD, may include a user interface (e.g., an alphanumeric pad) that lets a user enter information or interact with the AMD to modify the settings of the AMD, respond to request for certain actions (i.e., installing a software) and the like. The alphanumeric pad may include a multitude of keys with numerical, alphabetical, and symbol characters. Keys of the alphanumeric pad may be capacitive or mechanical. The user may be a subject receiving medicament or therapy, or may be another user, such as a clinician or healthcare provider, or a parent or guardian of the subject. In some other embodiments, the AMD may include a touchscreen display that produces output and also accepts input enabling a two-way interaction between the user and the AMD. The touchscreen display may be any input surface that shows graphic images and text and also registers the position of touches on the input surface. The touchscreen display may accept input via capacitive touch, resistive touch, or other touch technology. The input surface of the touchscreen display can register the position of touches on the surface. In some examples, the touchscreen display can register multiple touches at once. In some embodiments, the alphanumeric pad is displayed on the touchscreen display. The touchscreen may present one or more user-interface screens to a user enabling the user to modify one or more therapy settings of the ambulatory medicament device.

The communication module 602, may include one or more wireless transceivers, one or more antennas and plurality of electronic modules. Each transceiver may be configured to receive or transmit different types of signals based on different wireless standards via the antenna (e.g., an antenna chip). The transceiver may support communication using a low power wide area network (LPWAN) communication standard. In some examples, the transceiver may support communication with wide area networks such as a cellular network transceiver that enables 3G, 4G, 4G-LTE, or 5G. Further, the transceiver may support communication via a Narrowband Long-Term Evolution (NB-LTE), a Narrowband Internet-of-Things (NB-IoT), or a Long-Term Evolution Machine Type Communication (LTE-MTC) communication connection with the wireless wide area network. In yet other cases, the transceiver may support Wi-Fi® communication. In some examples, the transceiver may be capable of down-converting and up-converting a baseband or data signal from and to a carrier signal. In some examples, the communication module may wirelessly exchange data between other components of the ambulatory medical system (e.g., a sensor), a mobile device (e.g., smart phone), a Wi-Fi network, WLAN, a wireless router, a cellular tower, a Bluetooth device, and the like. The antenna chip may be capable of sending and receiving various types of wireless signals including, but not limited to, Bluetooth, LTE, or 3G. In some examples, the communication module may support direct communication between the AMD and a server or a cloud network. In some other examples the AMD may communicate with an intermediary device (e.g., a smart phone). In some embodiments, the AMD may include an eSIM card that stores all of the information necessary to identify and authenticate a mobile subscriber. The eSIM card may allow the ambulatory device to transmit data on a very inexpensive IOT device basis. In other embodiments, the ambulatory medical device may be configured to transmit data in a narrowband communication protocol such as 2G or EDGE. Using the cellular connection, the ambulatory medical device may be paired with the mobile device at inception and permit real-time data access to the ambulatory medical device by a healthcare provider. In certain implementations, the ambulatory medical device may include a geolocation receiver or transceiver, such as a global positioning system (GPS) receiver.

Example Operation of the AMD

In some embodiments, the AMD may continuously, periodically, or intermittently receive information about one or more parameters that are correlated with a health condition of a subject (e.g., glucose level, glucose trend, heart rate, body movement indicia, etc.). This information may be encoded to a signal provided to AMD by a subject sensor 620 (e.g., a wearable sensor that measured an analyte in the interstitial fluid) that is connected to the ambulatory medical device 600 main unit via a wired or wireless link (e.g., Bluetooth). In some cases, the subject sensor 620 can be any sensor that generates a signal or status value associated with one or more physiological indicators (or parameters) of a subject (e.g., heart rate, blood pressure, body temperature, level of blood sugar, serum levels of various hormones or other analytes). In some such examples, the subject sensor can be a continuous glucose monitoring sensor (CGS). In some examples, the signal sent by the sensor may be received by the communication module 602 and transmitted to a signal processing module 604 that converts the signal to a machine-readable signal (e.g., a digital signal). The signal processed by the signal processing module 604 may be transmitted to the control and computing module 610 where it is analyzed to determine whether medicament should be delivered to the subject. If it is determined that medicament is needed, the control and computing module the volume of the medicament may calculate required dosage based on the information received from the subject sensor 620 and send a signal to the therapy module (e.g., via the signal processing module) to initiate the medicament delivery process to the subject.

All the procedures within the control and computing module 610 are executed by the processor 614 (or a plurality of processors) based on instructions provided by one or more software applications installed in one of the memories (e.g., the main memory) of control and computing module 610. These procedures include, but are not limited to, determining the need for delivering medicament, determining the type of medicament and the required dose, determining the rate of delivery during a therapy session, providing information (e.g., device status, next delivery time, level of certain analytes in the subject's blood and the like) via the user interface module 608, processing the information received from a subject sensor 620 via the user interface module 608, and the like. In some embodiments, a first software application may control the AMD and may be installed on the main memory 616 while a second software application (e.g., different version) may be stored in the storage 618. In some examples, the first and second software applications may be both installed in the main memory 616 but in different locations or segments. In these examples, if needed, the control of the device can be switched from the first software application to the second software application.

In some embodiments, the ambulatory medical device 600 may deliver multiple types of therapies that are selectable by a user or the control and computing module 610. For example, the ambulatory medical device 600 may deliver the therapy of infusing insulin into a user and may also deliver the therapy of infusing glucagon into a user. In some examples, the user interface may include an option for the user to select an infusion of insulin, glucagon, or both insulin and glucagon. In other embodiments, other hormones, liquids, or therapies may be delivered. In some examples, the software application executed by the control and computing module 610, may determine the type of hormone that needs to be delivered, at least partly based on the information received from the subject sensor 620.

Communication and Networking

Figure 7:
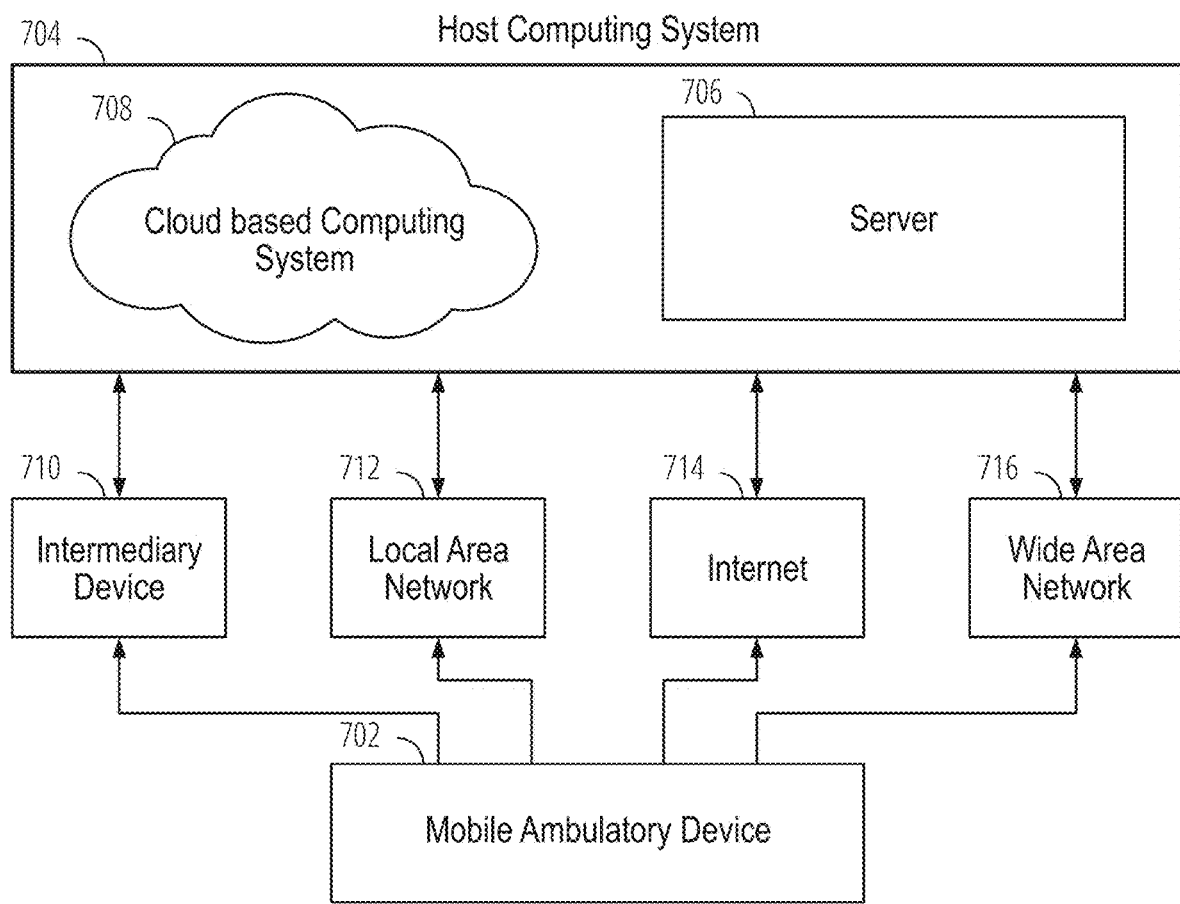
FIG. 7 illustrates various methods and links that AMD may establish a connection with a host computing system.

FIG. 7 illustrates various methods and links that an ambulatory medical device (e.g., the AMD 702) may use to establish a connection with a host computing system 704 in order to obtain an application update. The host computing system 704 may be a server 706 or a computing system within a cloud-based computing system 708 or other networked computing environment. The host computing system 704 may be part of a data center (e.g., the data center of a health care provider).

To obtain the application update, the AMD 702 may establish a connection (e.g., using its communication module) with the host computing system through an intermediary device 710, such as a desktop computer, a mobile device (e.g., a smart phone, a laptop, and the like). In some examples, the intermediary device 710 can be an electronic device of a user or the subject (e.g., a computer in a clinic, a subject's home computer, a smartphone, etc.) that has obtained a copy of the application update from the host computing system directly or via internet 714. In some other examples the AMD 702 may communicate with the host computing system 704 through a local area network 712 through a Wi-Fi connection. Alternatively, or in addition, the AMD 702 may establish a connection to the host computing system 704 via a wide area network 716. Moreover, the communication connection established between the AMD 702 and the cloud computing service may be encrypted.

In some embodiments, the AMD 702 may establish a direct end-to-end connection over a wide area network 716 (e.g., a cellular network) with the host computing system 704. The method may include receiving a public key from the AMD 702. The public key and a private key stored in the host computing system 704 can be used to permit the host computing system 704 to decrypt data communications transmitted by the AMD 702. In some implementations, establishing the direct end-to-end data connection includes receiving a device identifier associated with the AMD 702. The device identifier may be a unique identifier specific to the AMD 702. Further, establishing the direct end-to-end data connection may include determining that the AMD 702 is permitted to communicate with the computing system based at least in part on the device identifier. The device identifier may be initially provided to the networked-computing environment prior to provisioning of the AMD 702 to the subject. For example, the device identifier may be initially provided to the networked-computing environment as part of a manufacturing process for manufacturing the AMD 702. The device identifier may include or may be based on one or more of an Internet Protocol (IP) address, a Media Access Control (MAC) address, a serial number, or a subject identifier of a subject that receives therapy from the AMD 702. In some cases, the subject or a user establishes or initiates establishing the direct end-to-end data connection with the computing system. In other cases, the direct end-to-end data connection may be initiated or established without action by the subject or the user. For example, the direct end-to-end data connection may occur automatically at particular times or when the AMD 702 is in particular locations. This automatic connection may occur using information supplied to the AMD 702 at a time of manufacture, shipment, sale, or prescription to the subject. In some cases, the wide area network may include, or may communicate with, the internet 714.

In some embodiments, the ambulatory medical device (e.g., AMD 702) may be configured to communicate via the wide local area network 712 during manufacture or prior to being provisioned to the subject. For example, a manufacturer can register the ambulatory medical device with a wireless wide-area network provider (e.g., T-Mobile or Verizon) and provide an International Mobile Equipment Identity (IMEI) number or serial number for the ambulatory medical device to the network provider. Moreover, any fees can be negotiated or paid between the manufacturer and the network provider or between the subject's health insurance and the network provider. Thus, the subject's ambulatory medical device may be configured to communicate via the network of the network provider without any action by the subject.

In some other examples, the ambulatory medical device may be pre-registered or authenticated with a computing network of the cloud services provider as part of the manufacturing process or before the ambulatory medical device is provided to the subject. This enables the ambulatory medical device to communicate over the wide area network with the computing system of the cloud services provider from day one without any or with minimal configuration by the subject. In some cases, a user, such as a healthcare provider may register or associate the ambulatory medical device with the subject at the computing network of the cloud services provider.

To enhance security, the ambulatory medical device may use a whitelist that identifies via a unique identifier (e.g., via an IP address, a MAC address, or a URL) permitted cloud servers or computing system of the cloud computing system. Further, the cloud computing service may have a whitelist that uses unique identifiers to specify ambulatory medical devices and/or other computing systems (e.g., remote display systems) that are permitted to communicate with the cloud computing system.

To enhance security, the ambulatory medical device may use a whitelist that identifies via a unique identifier (e.g., via an IP address, a MAC address, or a URL) permitted cloud servers or computing system of the cloud computing system. Further, the cloud computing service may have a whitelist that uses unique identifiers to specify ambulatory medical devices and/or other computing systems (e.g., remote display systems) that are permitted to communicate with the cloud computing system. The whitelist may be stored in a memory of the ambulatory medical device. Further, the whitelist may be configured during manufacture of the ambulatory medical device. For example, the whitelist may be configured with connection information to establish communication with one or more computing systems of a networked-computing environment. Further, the ambulatory medical device may be configured to execute the specific computer-executable instructions to at least obtain an address of the computing system from the whitelist and to establish a direct end-to-end data connection to the computing system of the networked-computing environment via a wireless wide area network using the address. Moreover, the ambulatory medical device may be configured to execute the specific computer-executable instructions to at least receive a public key from the computing system of the networked-computing environment.

Software Update of Ambulatory Medical Device

It is often the case that a computer application is updated after it is released. In some cases, the application is updated to patch bugs or vulnerabilities. In other cases, the application is updated or replaced with a new version to introduce new features or improve existing features. Regardless of the reason, it is often the case that an application is shutdown or is not executing while the application is updated. For most applications, there is minimal to no harm in shutting down or not executing an application while it is updated or otherwise replaced. For example, it is inconsequential that a video game, word processing, or edutainment application is not executing while it is updated.

However, it can be inconvenient, harmful, or, in some cases, life-threatening to cause an application on an ambulatory medical device to cease executing while it is updated or replaced by a new version of the application. If a subject or subject that is receiving therapy from the ambulatory medical device enters a state where therapy is desired or needed while an application or control software of the ambulatory medical device is being updated or replaced, harm may occur to the subject. For example, suppose the ambulatory medical device is an insulin pump, such as those that may be used by a type-1 diabetic. If the insulin pump becomes inoperative due to a software update process occurring at a time when a subject's blood glucose level exceeds a set-point or target range, the user may not receive a necessary insulin bolus from the ambulatory medical device. Thus, it is desirable to modify reduce or eliminate disruption to subject care or therapy when updating applications, such as control software, of an ambulatory medical device.

In some embodiments, an ambulatory medical device includes a computer-implemented method of updating an application executing on the ambulatory medical device without interrupting, or while causing minimal interruption, to therapy provided by the ambulatory medical device to a subject or subject. The method may generally be performed by a hardware processor, (e.g., a controller, and the like), included in an ambulatory medical device and based on a set of instructions that may be stored, for example, in a non-transitory memory of the AMD. The application update may be a new version of the application, a replacement or substitute application, or an application patch. In some examples, the application may be an older version of the application that has been used by instances of the ambulatory medical device for more than a threshold period of time and has experienced less than a threshold number of faults. The application update may be stored in one or more host computing systems. The application update may be pushed to the host computing systems by a company that manages or manufactured the ambulatory medical device or other software company that is authorized by the manufacturer or licensee of the device.

Figure 8:
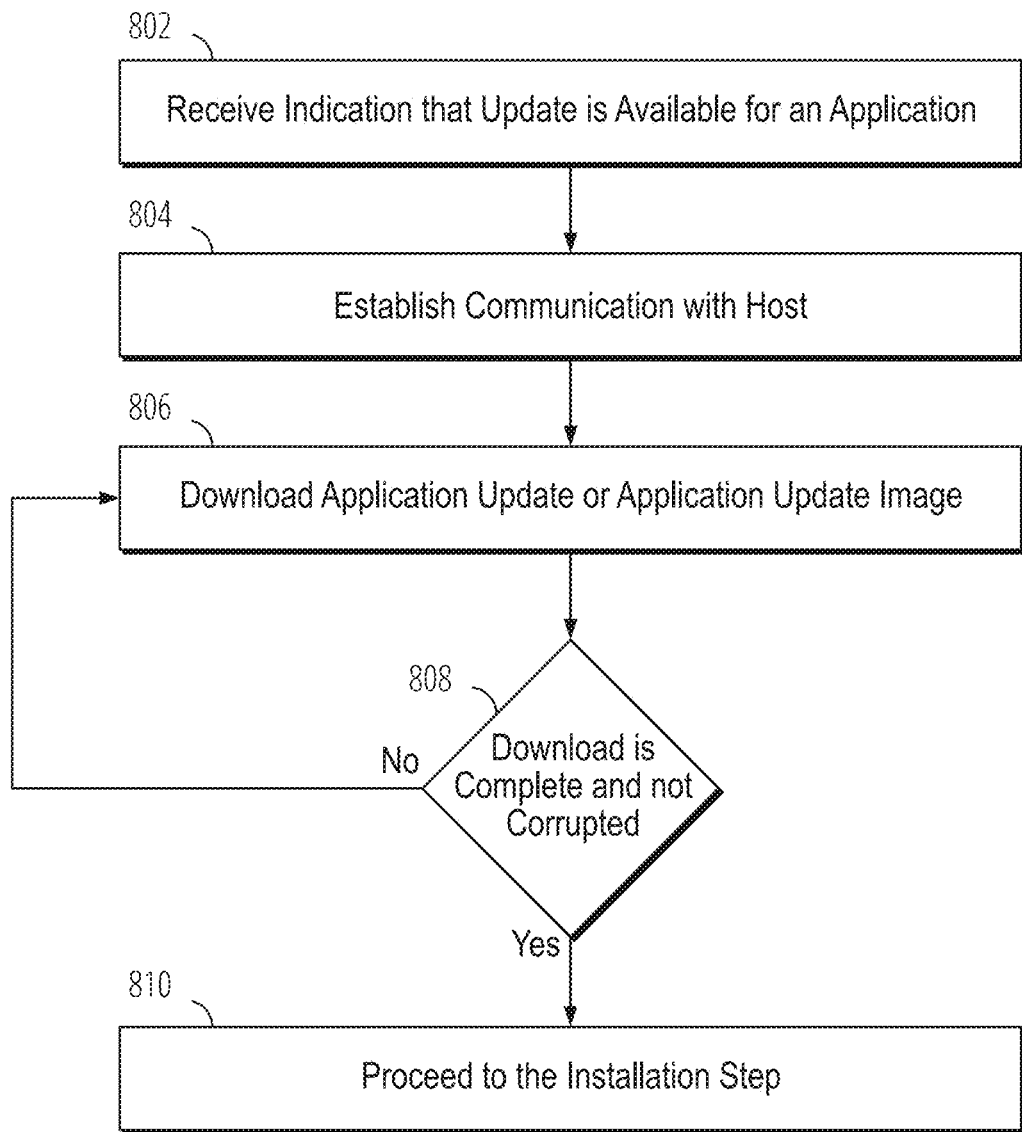
FIG. 8 is a flow diagram showing an example of a computer-implemented method that may be used by an AMD in order to detect and download an application update.

FIG. 8 is a flow diagram showing an example of a computer-implemented method that may be used by the AMD in order to detect and download an application update from a host computing system or other computer readable media in which a copy of the application update is stored. In certain aspects, an ambulatory medical device, such as a medicament delivery device or a medicament pump may receive an indication that an update is available for an application (block 802), such as control software or other software that controls or facilitates the operation of the ambulatory medical device. The software update may include a binary executable file for various processors of the ambulatory medical device. In some embodiments, the indication may be a determination made by a software or hardware module included in an ambulatory medical device of AMD. For example, the AMD may access a particular host computing system (e.g., using its communication module) to determine whether an update is available, based on set of update trigger conditions stored in a memory of AMD. The set of update trigger conditions may be defined/changed by a user and/or received by AMD from a host computing system. For example, a trigger condition may push the AMD to periodically search for an update at time intervals set by the user or received from a host computing system. Alternatively, or in addition, in response to a trigger (such as a user command, the replacement of medicament within the ambulatory medical device, the connecting to a particular network, or the connecting to a network using a particular communication transceiver (e.g., Wi-Fi) or the like), the ambulatory medical device may access a particular host computing system to determine whether an update is available to an application installed on the AMD. The software to be updated on the AMD may be currently executing on the ambulatory medical device or may be executed in future.

In some embodiments, the indication may a query received from the host computing system that may access the AMD to read and compare the software versions and the hardware configuration (and warranty) to determine the eligibility of the ambulatory medical device for a software upgrade. The serial number, the model number, and/or the software version may be used to determine software upgrade eligibility. In some embodiments, the eligibility may be determined based on the geoposition of the device and/or whether the device is connected to a local area network (such as for example, a Wi-Fi network) or a wide area network (such as, for example, a cellular network). In various embodiments, the ambulatory medical device may have an antenna that provides the device with GPS, text or picture messaging, telephone calling, and data transfer capabilities. Software update may be provided on a limited release with test groups of varying sizes, e.g., 1-100 or 1-1000 or 1-10000. There may be a phase rollout of the software updates. In some embodiments, the AMD may respond to an upgrade eligibility request with a version of the first software or a model identification information of the ambulatory medical device or a manufacturing date of the ambulatory medical device.

If it is determined that an update is available to the application executing on the ambulatory medical device, the ambulatory medical device may establish a connection 804 to a host computing system that hosts the update to the application. Such connection may be established via one or more links or methods discussed above with reference to FIG. 7.

Once a connection is established, at block 806, the ambulatory medical device may download the application update or application update from the host computing system over the connection. In some examples, the ambulatory medical device may download an image of the application update from the host computing system. While the application update is being downloaded, an existing version of the application on the ambulatory medical device may continue to execute. Thus, there is little or no interruption to therapy provided by the ambulatory medical device while the application update is being obtained by the ambulatory medical device.

Once the application update is obtained, the ambulatory medical device (e.g., using its control and computing module) may perform one or more operations to confirm that the application update was successfully downloaded from the application host system and that the download was not corrupted 808. For example, the ambulatory medical device may calculate a hash or checksum value from the downloaded application update. This hash or checksum value may be compared with one received from the application host system. If the calculated hash or checksum value matches the received hash or checksum value, then it may be determined that the download is both complete and not corrupt. Further, the ambulatory medical device may use the checksum, a tag, a payload size, or any other method to confirm that the download of the application update is complete and not corrupt. If it is determined that the download is corrupt 808, the AMD discards the corrupt copy and downloads another copy of the update 806. If it is determined that the download is complete and not corrupt, the AMD may proceed to the installation step 810 wherein the application update may be installed on the AMD without interrupting the ongoing or upcoming therapy sessions.

Figure 9:
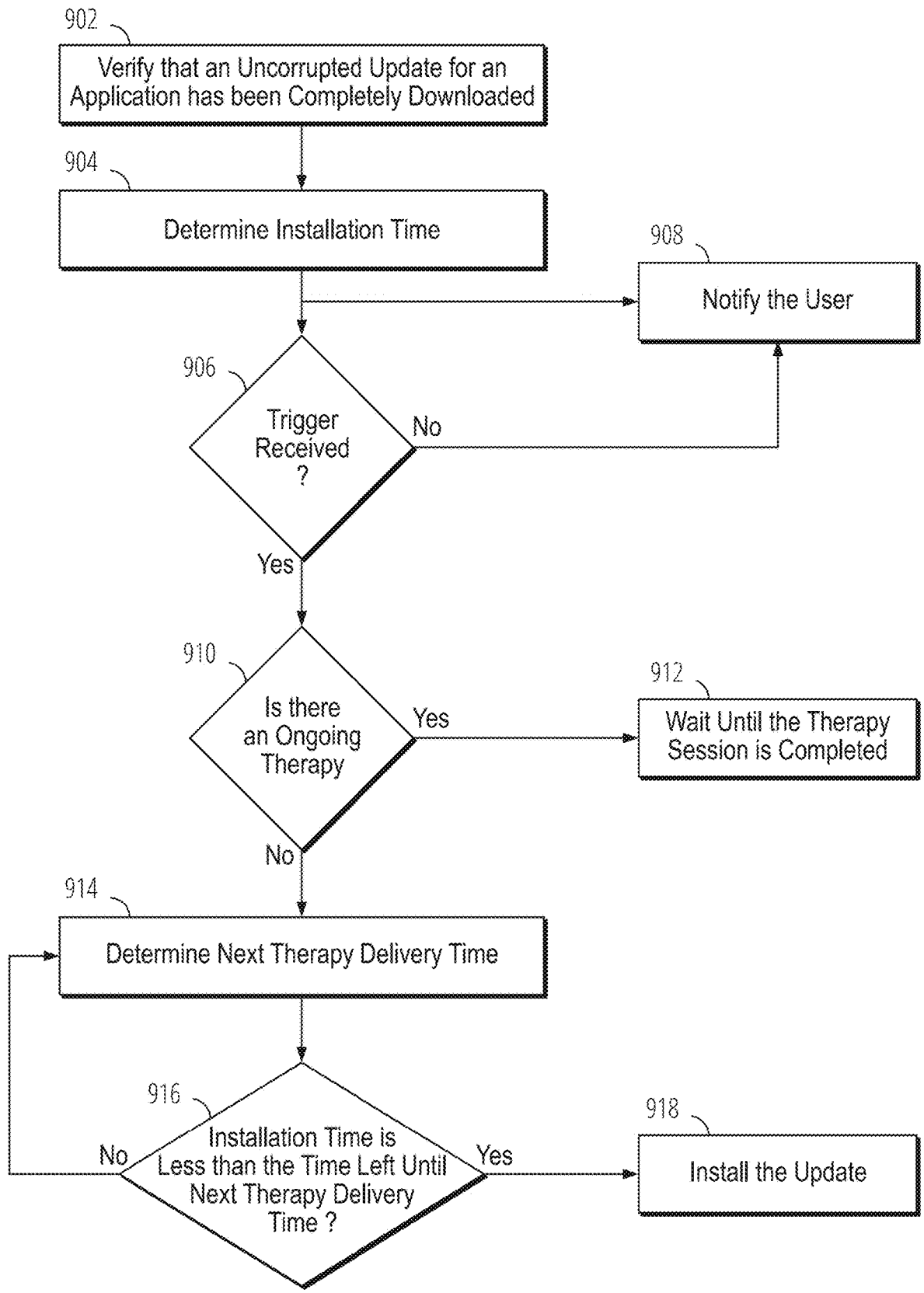
FIG. 9 is a flow diagram showing an example of a computer-implemented method that may be used by an AMD to install a down-loaded application update without interrupting the therapy provided to a subject.
Figure 10:
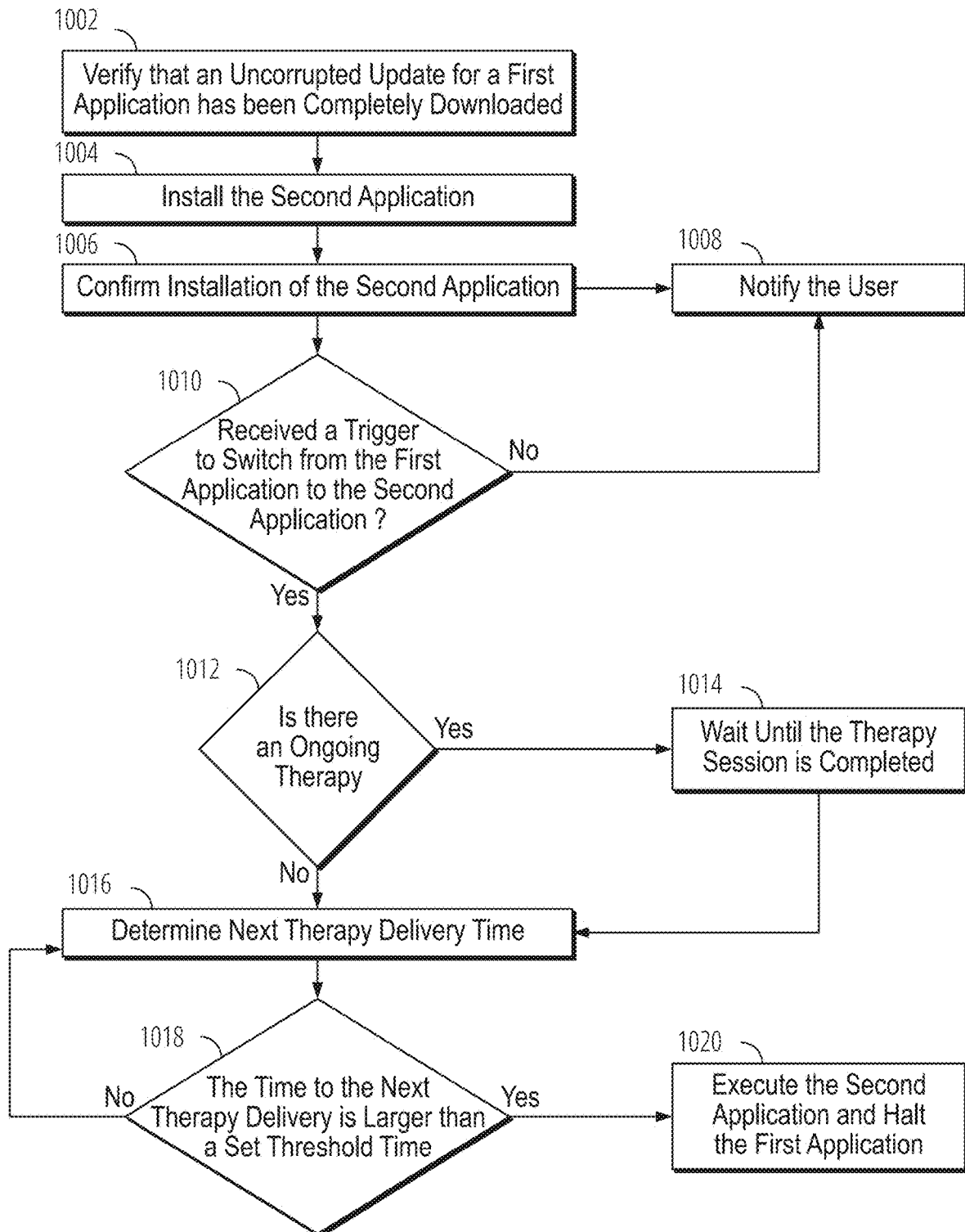
FIG. 10 is a flow diagram showing an example of a computer-implemented method that may be used by an AMD to install a second update downloaded from a host computing system and switch control of the AMD from a first application to the second application without interrupting the therapy provided to a subject.
Figure 11:
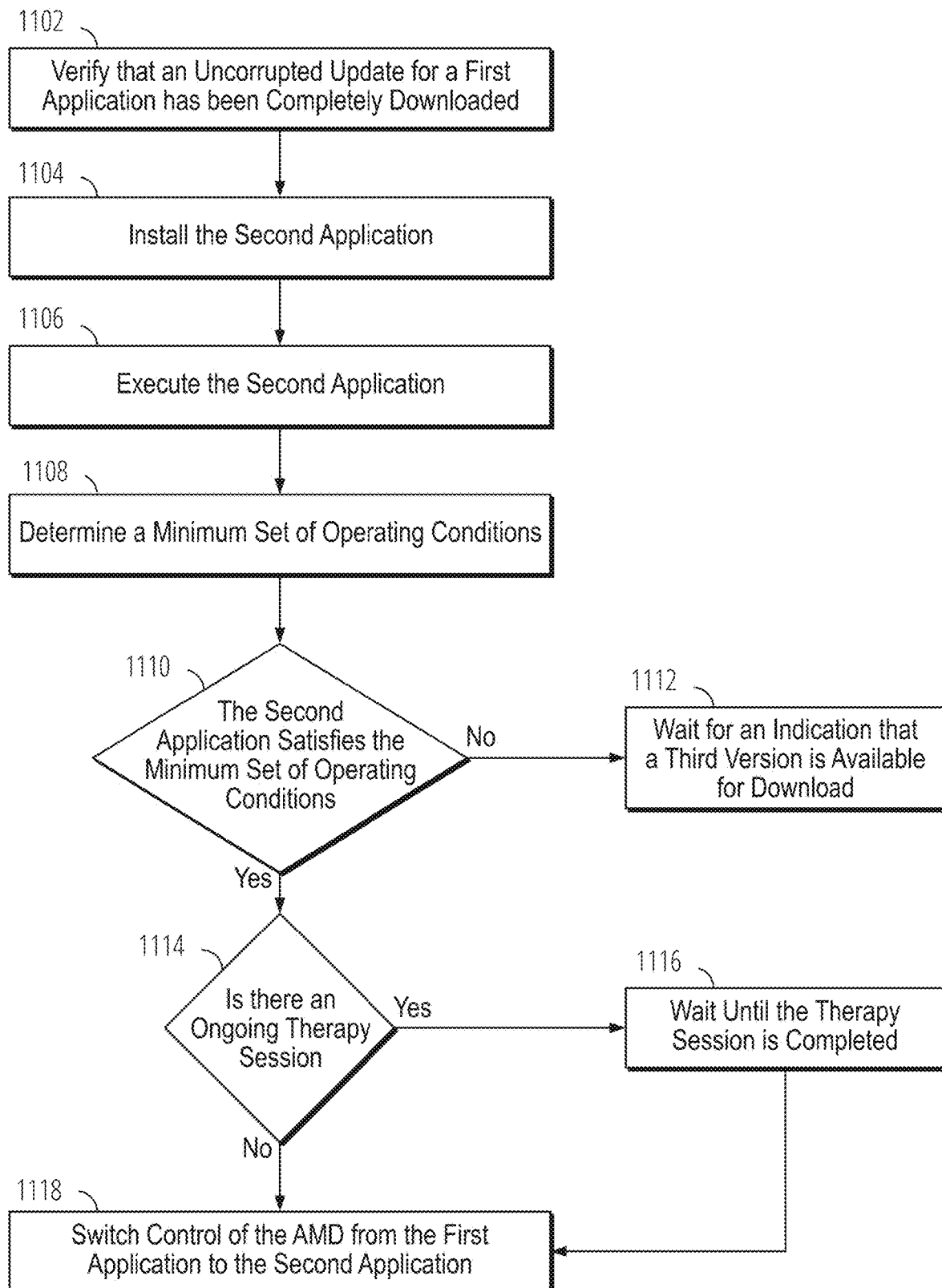
FIG. 11 is a flow diagram showing an example of a computer-implemented method that may be used by an AMD to install a second application downloaded from a host computing system, verify and switch control of the AMD from a first application to the second application without interrupting the therapy provided to a subject, when the second application satisfies a minimum set of operation conditions.

FIG. 9-FIG. 11 are flow diagrams illustrating examples of computer-implemented methods that may be used by the AMD to install a downloaded application update without disrupting the therapy provided to a subject.

In the example method illustrated in FIG. 9, if it is verified that an uncorrupted copy of the update for an application is successfully downloaded 902 (e.g., using the procedure described above with reference to FIG. 8), the control and computing module 610 (CCM 610) of the AMD may determine the amount of time required to install the application update 904 and wait for a trigger signal 906 to initiate installation process. In some examples, the CCM may notify to the user 908 through a user interface (e.g., a touchscreen display), that an update is ready for installation. The notification may include the installation time and information about the update. In such examples, if a trigger is not received, CCM may send one or more notifications to the user indicating that a new update is ready for installation. In some examples, the trigger may be the confirmation that the application was successfully downloaded. Alternatively, or in addition, the trigger may be a user command received based on an interaction by a user or subject with a user interface that is part of or that communicates with the ambulatory medical device.

The installation time may be determined by the CCM based on data or metadata provided with the downloaded application update. For example, the application update may include a file (e.g., a text file or configuration file) that includes the install time. The installation time may be determined by the manufacturer of the ambulatory medical device or the publisher of the application update. For example, the developer of the software update may average the install time across several test devices to determine the install time metadata that is provided with the software update. General purpose computers have a wide variety of configurations and the performance of a general-purpose computer may vary depending on the applications executing at a particular time. Thus, the determination of install time for an application based on the measurement of install time on a test device is typically unreliable. However, as an ambulatory medical device is often a special-purpose device that is designed to perform a specific function (e.g., provide insulin to a subject), an install time determined during testing by a manufacturer may in many cases be a reliable determination of install time on an ambulatory medical device of a subject. Alternatively, or in addition, to determining the install time based on testing by a manufacturer, the install time of an application update may be determined or estimated based on a size of the application update. In some cases, the provided or estimated install time may include a buffer. In other words, an additional amount of time may be added to the install time to account for variances in operating condition of the ambulatory medical device or inaccuracies in the estimated install time.

If a trigger is received 906, the CCM may check for any ongoing therapy session 910. If the no therapy is currently being administered, the CCM determines the next therapy time 914 (or the time left until the next therapy session). If therapy is currently being administered the installation will be delayed 912 until the therapy session is compete. Once the current therapy session is complete, the CCM may determine the time remaining until next therapy session 914 (e.g., during which medicament, such as insulin is delivered to a subject).

In some cases, the determination of the next time that therapy is to be delivered may be an estimate based on historical delivery of therapy, a present condition of the subject (e.g., when a glucose level is of a subject is at the center of a desired range, the next therapy delivery time may be estimated to be further off than when the glucose level is at the edge of the desired range), and/or an indication provided by a user or subject (e.g., an indication that the user is planning to have a meal, to exercise, or to go to sleep). Alternatively, or in addition, the determination of the next time that therapy is to be delivered may be based on a scheduled delivery of therapy (e.g., every 5 minutes or every hour).

As previously described, it is desirable to prevent disruption to therapy during the application update process. Thus, after the next therapy time is determined 914, the estimated install time may be compared 916 to the determined or estimated next therapy delivery time to determine whether the installation of the application update can be completed before the next therapy delivery to the subject. If it is determined that the time left until the next therapy session is sufficiently longer than the determined time for completing the installation, installation of the application updated may be initiated 918. In some examples, the determined time to the next therapy session has to be longer than the determined installation time by a threshold value. Such threshold value may be different for different application updates and/or the type of next therapy session. If it is determined that the application installation cannot be completed before the next therapy delivery (or the time left until the next therapy is not larger than that estimated installation time by a threshold value), the installation of the application may be delayed, regardless of receipt of the trigger. In this case, the CCM may wait for the next therapy to be completed and then determine a new therapy time 914. This process may be repeated until CCM determines that the update can be installed without interrupting an expected or scheduled therapy by the ambulatory medical device. In some examples, a new determination may be made before completion of the next therapy, to determine whether installation may be completed prior to a subsequent therapy time after the next therapy time.

In some cases, a time when the application can be installed without interrupting therapy may not be identified. In some such cases, a user (e.g., a clinician or other medical provider, or a subject) may be provided with an alert that an application update is available and/or that the application update cannot be installed without interrupting therapy. The user may be provided with an option as to whether to permit the update and/or when to install the application update. The option may include presenting the user with the estimated install time enabling the user to schedule the application update at a time when interruptions to therapy may be minimal or when an alternative source of therapy (e.g., injection therapy) can be utilized.

In some embodiments, once it is verified that an uncorrupted copy of the update for an application is successfully downloaded 902, the AMD's control and computing module (CCM) may notify the user and wait for a trigger signal before determining the installation time. Once the trigger has been received, the CCM initiates the installation process of the downloaded copy of the application update without interrupting therapy provided by the ambulatory medical device to the subject. In such embodiments, the application update may be installed in a different memory location than the memory location where the original application is installed and executed.

FIG. 10 is flow diagram illustrating an example of a computer-implemented method that may be used by the AMD in order to install a second application that is an update to a first application executing on the ambulatory medical device, without disrupting the therapy provided to a subject. In this example, once the control and computing module 610 (CCM 610) of the AMD verifies that an uncorrupted copy of the second application is successfully downloaded 1002 (e.g., using the procedure described above with reference to FIG. 8), the CCM may initiate the installation process of the second application 1004 without interrupting the execution of the first application. The CCM may confirm 1006 the successful installation of the second application and wait for a trigger signal 1010 to initiate the execution of the second application in place of the first application. In some examples, the installation of the second application may be confirmed by sending a notification the user 1008 via a user interface of the AMD. In some examples, the CCM may determine the amount of time required for switching the control of AMD to from the first application to the second application. The notification may include information about the update and the time required for switching between the applications. In some examples, the trigger may be a user command received based on an interaction by a user or subject with a user interface that is part of or that communicates with the ambulatory medical device. In such examples, if a trigger is not received the AMD may send one or more notifications to the user indicating that a new update is ready for installation. If a trigger is received, the CCM may check for any ongoing therapy session 1012. If the no therapy is currently being administered, the CCM determines the next therapy time 1016 (or the time left until the next therapy session). If therapy is currently being administered the installation will be delayed 1014 until the therapy session is compete. Once the current therapy session is complete, the CCM may determine the time remaining until next therapy session 1016. The estimated next therapy delivery time may be compared to a set threshold time to determine whether the switching from the first application to the second application can be performed without interfering with the next therapy session. If it is determined that the time left until the next therapy session is longer than the set threshold time 1018, the execution of the second application will be initiated and the execution of the first application will be halted 1020. In some examples, the set threshold time may be determined by the CCM at least partly based on the time required to execute of the second application and halt the first application. In some other examples, the set threshold time may be received from a host computing system.

In some embodiments, the performance of an application update may be tested before switching control of the AMD to the application update. FIG. 11 illustrate an example method that may be used by such embodiment. First the AMD verifies that an uncorrupted copy of the update for a first application is successfully downloaded 1102 (e.g., using the procedure described above with reference to FIG. 8). Next the AMD may install 1104 and execute 1106 the downloaded copy of the second application without interrupting the execution of the first application and therefore the therapy that might be provided by the ambulatory medical device to the subject. In some examples, the second application update may be installed to a separate portion (e.g., a separate execution space or separate memory) from the portion where the first application is installed and is being executed. The Control and computing module 610 (CCM 610) of the AMD may determine a minimum set of operating conditions 1108 and then determine whether the minimum set of operating conditions are satisfied by the second application 1110. In some cases, the minimum set of operating conditions may relate to maintaining therapy provided by the ambulatory medical device to the subject. If at block 1110 it is determined that the minimum set of operating conditions are not satisfied by the second application, the AMD may wait for an indication that a third application is available 1112 and repeat the procedure described above to evaluate the performance of the third application. If it is determined that the minimum set of operating conditions are satisfied by the second application, the AMD may check for an ongoing therapy session 1114. If it is determined that currently no therapy is provided to a subject, CCM may switch the control of the ambulatory medical device from the first application to the second application 1118. If currently therapy is provided to a subject, the CCM may wait until the therapy session is competed 1116 and then switch the control of the AMD from the first application to the second application.

In some cases, the ambulatory medical device may be updated (or downgraded) to add (or remove) features from the ambulatory medical device. For example, the ambulatory medical device may initially provide only insulin therapy. At some point in time, the ambulatory medical device may be upgraded to include bi-hormonal control (e.g., to provide both insulin therapy and counter-regulatory agent (e.g., Glucagon) therapy). The upgrade may be based on newly available features and/or based on a decision by a user to purchase or otherwise obtain additional features. Similarly, a user may opt to downgrade therapy from bi-hormonal to insulin-only therapy. Alternatively, the upgrade or downgrade may be made based on the availability of medicament. In some examples, a first update can be a first application version including a first feature set (e.g., providing insulin therapy) and a second update can be a second application version including a second feature set (e.g., provide both insulin therapy and Glucagon therapy). In some such examples the first feature set may include a subset of the second feature set. In some other examples, the first feature set may include a partially overlapping set of features with the second feature set.

In some examples a computer-implemented method that may be used by the AMD in order to detect, download and install an update to an application executing on the ambulatory medical device wherein the application includes one of a first application version including a first feature set or a second application version including a second feature set. In some examples, the first feature set may include partially overlapping set of features with the second feature set. In some other examples, the first feature set may include partially overlapping set of features with the second feature set. The AMD may receive an indication of availability of the application update, download the application update and verify that an uncorrupted image of the application update is successfully downloaded (e.g., using the procedure described above with reference to FIG. 8). Next, the control and computing module (CCM 610) of the AMD may initiate the installation process of the application update image without interrupting the execution of the application. In some examples, the indication received by the AMD 802 (with reference to FIG. 8), may include information about application update being an update to the first application version or to the second application version. In some such examples, the CCM 610 may determine the version of the application update and download the application update image based on the determined version.

In some embodiments, any downloaded application update may be installed to a separate portion (e.g., a separate execution space or separate memory) from a currently executing version of the application. Once installation of the application is complete and the application is verified as being successfully installed, the active version of the application can be switched. For example, control of the ambulatory medical device can be provided to the updated application, the previously executing application can be ceased or halted. The old application can then be removed or kept as backup. Determining when to switch which version of the application is active may follow a similar process as previously described for identifying a next therapy delivery time and selecting a time to switch active versions of the application when there will not be an interruption to the therapy provided by the ambulatory medical device.

In some embodiments, the ambulatory medical device may be configured to store multiple instances of an application (e.g., ambulatory medical device control software). For example, the ambulatory medical device may have a current, or first, version of the application that it is installed in a first memory location (e.g., in the main memory 616) and is executing to, for example, control therapy provided by a subject. Further, the ambulatory medical device may include an updated, or second version of the application installed in a second memory location (e.g., in the main memory 616). The update of the second version may have been downloaded and installed (e.g., in a prior to detection of the fault). In such embodiments, when a fault is detected during execution of the first version of the application, the ambulatory medical device may initiate the execution of the second version of the application and then switch control of the AMD to the second version of the application to maintain therapy to the subject.

Figure 12:
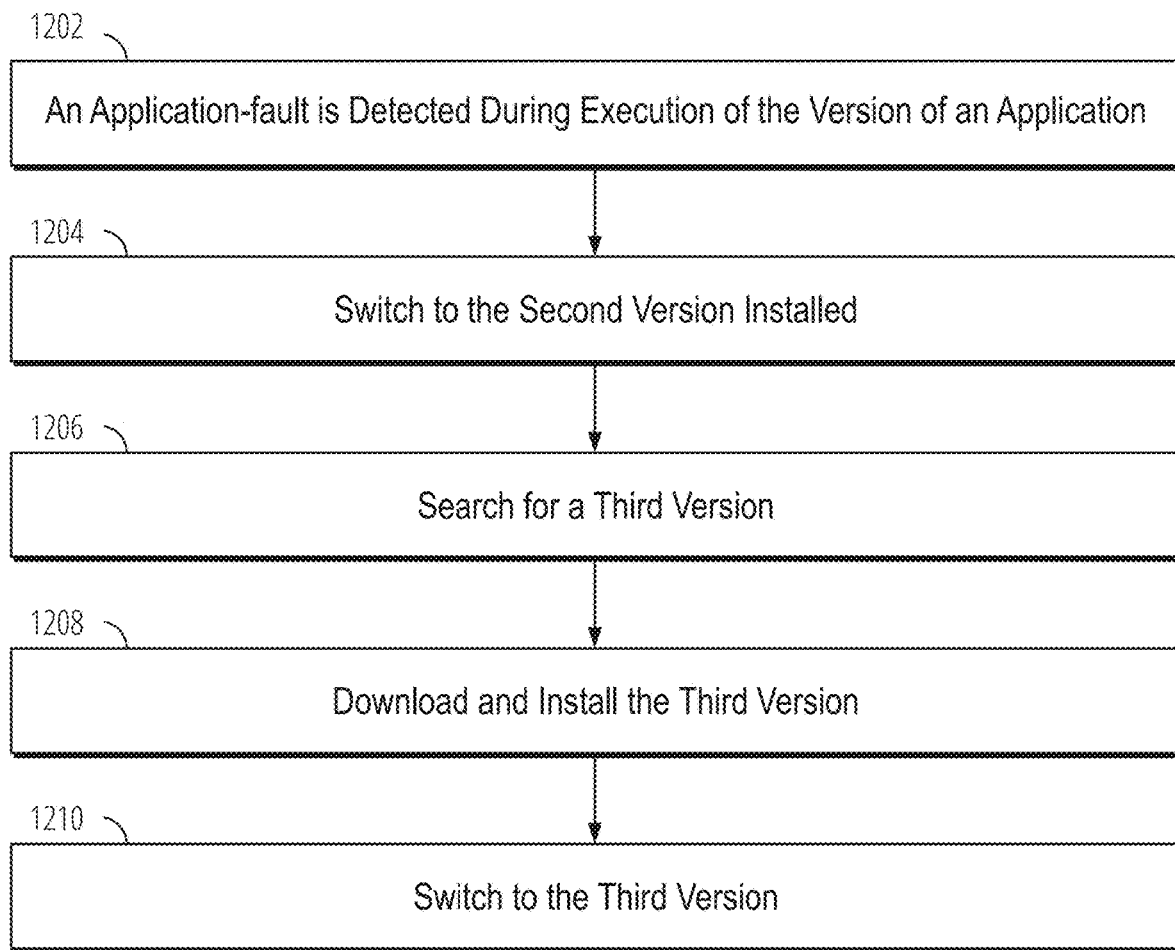
FIG. 12 is a flow diagram showing an example of a computer-implemented method that may be used to respond to detection of an application fault during the execution of a first version of an application and switching control of the AMD to a second version an application installed on the AMD.

In some examples, the second version of the application installed on the AMD may be a version older than the first version, or version that may not have track a record of stability and reliability. FIG. 12 is a flow diagram for such examples. Once an application-fault is detected during execution of the first version 1202, the control and computing module 610 (CCM) of the AMD may switch the control of the AMD to the second version of the application 1204 while establishing a connection with a host computing system configured to host a third update and download the third update 1206. The third version of the application may be a new version, a version prior to the first version, an update to the first application that addresses the detected application-fault or an older version that satisfies the conditions to be classified as a "safe version" (e.g., less than a threshold number or rate of faults over a minimum period of time). The second version (installed in the device) may control the AMD while the third version is being downloaded and installed 1208 without interrupting the therapy. Once the download of the third version is complete, the CCM may initiate the installation process of the downloaded copy of the third application and switch control of the ambulatory medical device form the second application to the third application 1210 without interrupting therapy provided by the ambulatory medical device to the subject In yet other embodiments, a "safe version" of the application may have been installed on the ambulatory medical device prior to detection of a fault. The safe version of the application may include a version of the application that has been used by instances of the ambulatory medical device for more than a threshold period of time and has experienced less than a threshold number of faults. For example, the safe version of the application may be a two-year old version of the application that has demonstrably had less than a threshold number of faults occur over the period of two years. This safe version of the application may have less features than the first or second version of the application. However, when a fault is detected during execution of the first or second version of the application, the ambulatory medical device may switch control of the device to the safe version of the application to maintain therapy to the subject.

In some cases, if there is an issue installing an updated version of the application, the ambulatory medical device may revert to the current version or a safe version installed on the AMD.

In some other examples, the AMD may be triggered to establish a connection with the host computing system and search for the second version once a fault is detected during execution of the first version. In these examples, the ambulatory medical device may revert to the safe version (installed in the device) while downloading and installing the second version without interrupting the therapy.

Figure 13:
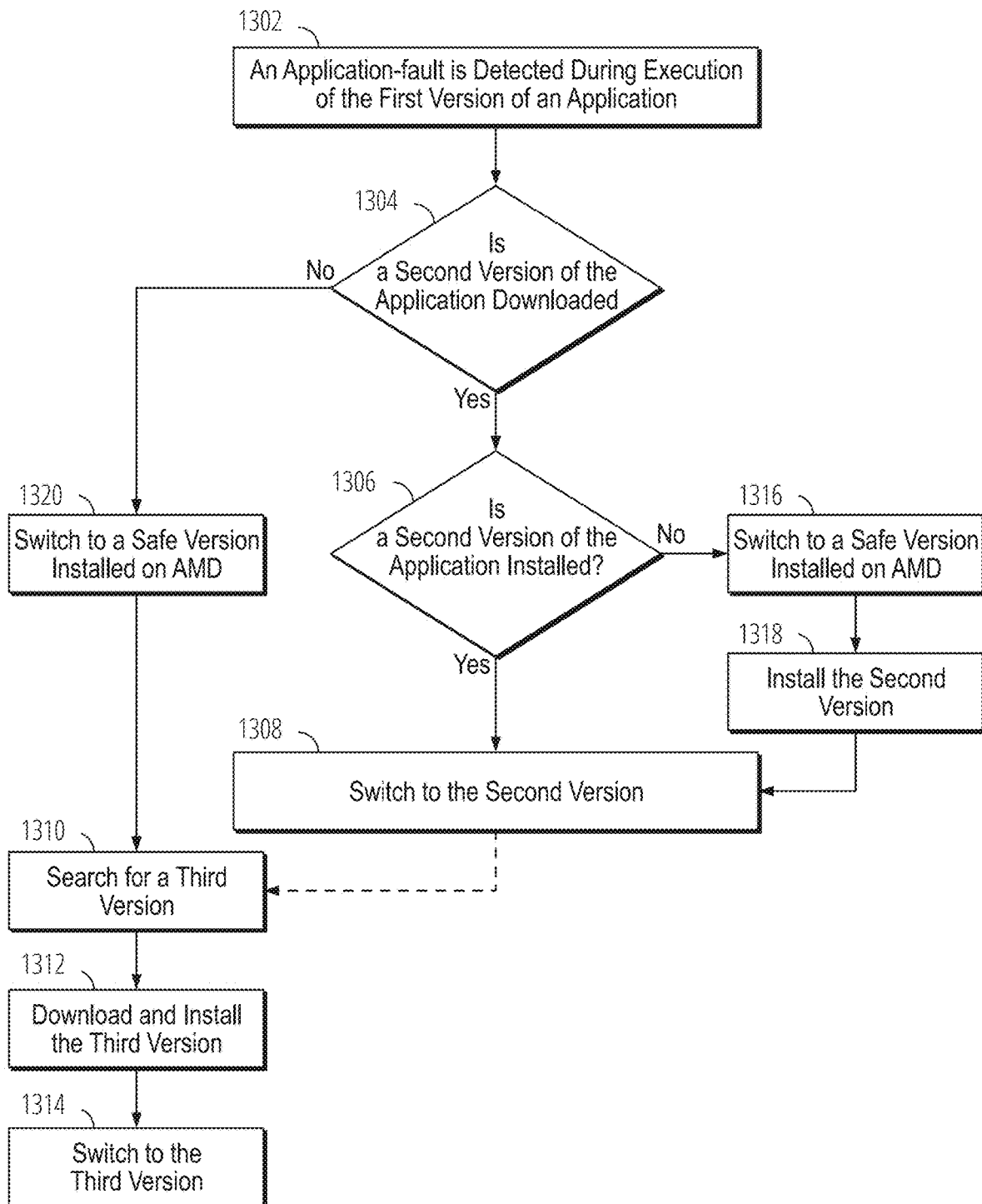
FIG. 13 is a flow diagram showing an example of a computer-implemented method that may be used to respond to detection of an application fault during the execution of a first version of an application and switching control of the AMD to a second version an application installed on the AMD and/or downloading a third version of the application.

FIG. 13 is a flow diagram illustrating yet another example of a method of responding to a fault detection by the AMD. In this example, once an application-fault is detected during execution of the first version of an application 1302, the control and computing module 610 (CCM 610) of the AMD may look for a second version of the application 1304 in the main memory or the storage. If it is determined that the second version has been already downloaded, the CCM will determine 1306 whether the second version of the application is installed in a memory location and is ready to be executed. If it is determined that the second version of the application is installed, the control of the AMD will be switched to the second version of the application 1308. With reference to block 1306, if CCM determines that the second version exists in the memory, but it is not installed, it will switch the control of the AMD to a safe version that may be already installed 1316 and then initiates the installation 1318 of the second version. Once the installation of the second version is complete, the CCM may switch control of the AMD from the safe version of the application to the second version of the application. In some embodiments, after the control of the AMD is switched to the second version of the application, the CCM may search for a third version of the application 1310 that may be an update to the previously downloaded second version. If a third version is found, the CCM may download and install the third version 1312 and switch the control of the AMD to the third version 1314. With reference to block 1304, if the CCM cannot find a second version of the application in a memory or storage location, it will switch the control of the AMD to a safe version of the application 1320 that may be installed in a memory location (e.g., in the main memory or in the storage) and then search for a third version of the application 1310. If a third version is found, the system may download and install the third version 1312 and switch the control of the device to the third version 1314.

In some embodiments, when an application-fault of an application executing on the ambulatory medical device is detected, the AMD may transmit an indication of the application-fault to the host computing system of a manufacturer or maintenance service of the ambulatory medical device. In some other embodiments, the AMD may notify the user when an application-fault occurs through a user interface of the AMD or user interface communicating with the AMD.

Direct Network-Connected Medical Device Communication and Remote Viewing

An ambulatory medical device, such as an ambulatory medicament device (e.g., blood glucose control system (e.g., an insulin pump or a bi-hormonal pump that includes insulin and a counter-regulatory agent), a pacemaker, or any type of medical device that may be connected to a subject to provide therapy to the subject, can generate a significant amount of data related to therapy provided to a subject (therapy data). This therapy data may be useful for the subject, a healthcare provider, or other users (e.g., parent or guardian) to actively manage the subject's health condition. For example, the therapy data may be useful to determine whether a modification to therapy may be desirable or to confirm that intended therapy is being delivered at the right time. In other examples the data may be used to generate an alerts about the health condition of the subject when therapy data indicates that immediate attention is needed with regards to subject' health condition.

Various aspects of accessing the therapy data or other types of data stored in a memory of the AMD needs proper management in order to provide uninterrupted, secure, and easy access to authorized users. As described above, the procedures and task performed by an AMD, including those associated with data transfer management, may be associated with certain computer-executable instructions stored and executed by the control and computing module 610 of the AMD 600. As such, different AMD configurations used for various data transfer management tasks, may be configurations of the control and computing module 610 of the AMD 600.

Accessing the data in the ambulatory medical device can be problematic in some cases. For example, accessing the data may require a user to connect the ambulatory medical device to a computer to upload the data. This places a burden on the user to remember to connect the ambulatory medical device. Further, during the period when the device is connected to the computer, the subject may not be receiving therapy from the ambulatory medical device. In some cases, the subject may not be capable of connecting the device to the computer (e.g., when the AMD is not within range of the local device) and may not have someone available to assist the subject. Thus, a direct end-to-end connection to a computing system that (e.g., computing system of a healthcare provider) can safely share data (e.g., therapy data) with authorized users may facilitate data management and access.

Figure 14:
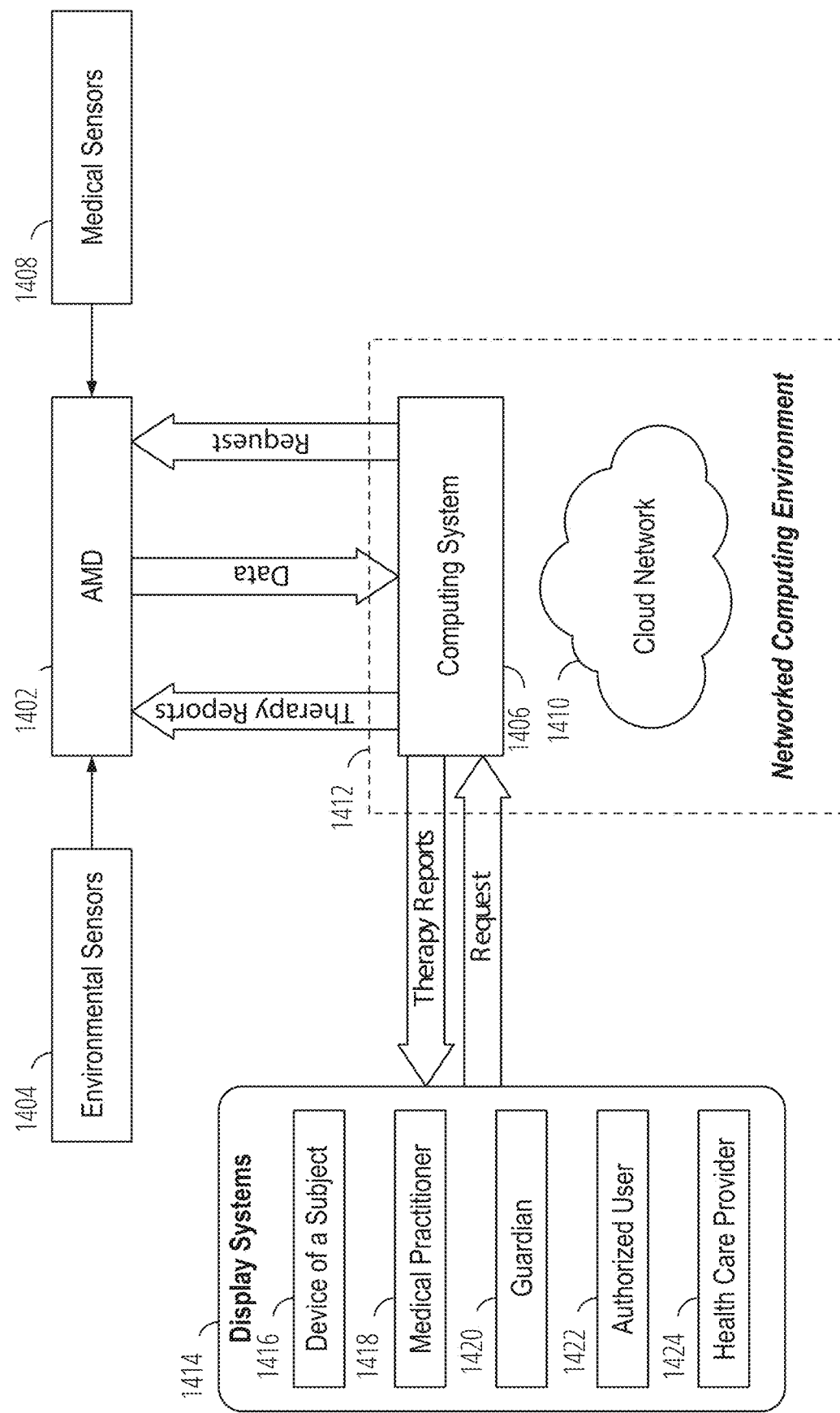
FIG. 14 is a block diagram, illustrating an example network configuration wherein the AMD is directly connected to a computing system and the computing system shares the therapy reports with one or more display systems and the AMD.

FIG. 14 is a block diagram illustrating an example network configuration wherein the AMD 1402 is directly connected to a computing system 1406. In some cases, the AMD 1402 may receive data from one or more environmental sensors 1404 and/or one or more medical sensors 1408 (e.g., a glucose sensor operatively connected to a subject. The computing system 1406 may be part of networked computing environment 1412 (e.g., a data center, networked computing system), or cloud network 1410 or cloud computing system of a cloud service provider. The computing system may include one or more non-transitional memories and one or more hardware processors configured to execute the computer-executable instructions stored in one or more non-transitional memories. In some such examples, the procedures performed by the computing system may be associated with the execution of certain computer-executable instructions stored in a memory of the computing system by a hardware processor of the computing system.

In some examples, the direct end-to-end data connection may be supported by one or more transceivers in AMD's communication module 602. For examples, a direct connection may be established between the AMD 1402 and the computing system 1406 over a wide area network (e.g., a cellular network) without using an intermediary system using various wireless standards and technologies (e.g., 4G, 5G and the like). In some examples, the transceiver may support communication via communication standards, including but not limited to, low power wide area network (LPWAN), Narrowband Long-Term Evolution (NB-LTE), Narrowband Internet-of-Things (NB-IoT), or Long-Term Evolution Machine Type Communication (LTE-MTC). In some cases, the transceiver is always on, and in other cases, the transceiver may be activated when a data transfer is scheduled, requested, or activated. In some cases, the capability of the ambulatory medical device 1402 to communicate with the computing system may be activated during manufacture or before providing the device to a subject.

In some cases, the subject or a user establishes or initiates establishing the direct end-to-end data connection with the computing system. For example, the subject may interact with a user interface to cause the ambulatory medical device to communicate with the cloud computing service. In other cases, the direct end-to-end data connection may be initiated or established without action by the subject or the user. For example, the direct end-to-end data connection may occur automatically at particular times or when the ambulatory medical device is in particular locations. This automatic connection may occur using information supplied to the ambulatory medical device at a time of manufacture, shipment, sale, or prescription to the subject. Further, in some cases, the ambulatory medical device can communicate with the computing system without having access to a Wi-Fi network or a local area network (LAN). For example, the ambulatory medical device may communicate using a cellular or other wide area network. Further, in some cases, the interaction by the user with the ambulatory medical device may be relatively minimal or simple compared to traditional network communication. For example, a user may push a single button (e.g., an "upload" button) to trigger establishing of a connection with the cloud computing service and causing data to be provided from the ambulatory medical device to the cloud computing service.

In some cases, the ambulatory medical device may be turned on and paired with the wireless wide area network (e.g., a cellular network) at the time of manufacture, or prior to being provided to a subject. Further, the ambulatory medical device may be authenticated with the networked-computing environment as part of the manufacturing process Further, establishing the direct end-to-end data connection may include determining that the ambulatory medical device is permitted to communicate with the computing system based at least in part on the device identifier.

In some implementations, establishing the direct end-to-end data connection may include determining that the ambulatory medical device is permitted to communicate with the computing system based at least in part on a device identifier associated with the ambulatory medical device. The device identifier may be a unique identifier specific to the ambulatory medical device. The device identifier may include or may be based on one or more of an Internet Protocol (IP) address, a Media Access Control (MAC) address, a serial number, or a subject identifier of a subject that receives therapy from the ambulatory medical device.

Further, establishing the direct end-to-end data connection may include determining that the ambulatory medical device is permitted to communicate with the computing system based at least in part on the device identifier. The device identifier may be initially provided to the networked-computing environment prior to provisioning of the ambulatory medical device to the subject. For example, the device identifier may be initially provided to the networked-computing environment as part of a manufacturing process for manufacturing the ambulatory medical device. The request may include a device identifier associated with the ambulatory medical device.

The ambulatory medical device may be configured to at least identify a computing system 1406 of a networked computing environment 1412 based on a whitelist of one or more approved computing systems. The whitelist may be stored in a memory of the AMD 1402 (e.g., a memory in the control and computing module of the AMD). Further, the whitelist may be configured during manufacture of the ambulatory medical device. For example, the whitelist may be configured with connection information to establish communication with one or more computing systems of a networked-computing environment. Further, the ambulatory medical device may be configured to at least obtain an address of the computing system from the whitelist and to establish a direct end-to-end data connection to the computing system of the networked-computing environment via a wireless wide area network using the address. The whitelist may include unique identifiers, such as MAC addresses or static IP addresses that are associated with computing systems of the cloud services provider.

To enhance security, the ambulatory medical device may use a whitelist that identifies via a unique identifier (e.g., via an IP address, a MAC address, or a URL) permitted cloud servers or computing systems in networked computing environment. Further, the cloud computing service may have a whitelist that uses unique identifiers to specify ambulatory medical devices and/or other computing systems (e.g., remote display systems) that are permitted to communicate with the cloud computing system.

When the AMD communicates data over a network, there is a risk of a data breach. Thus, to improve security, all communication between the ambulatory medical device and the computing may be based on a secure data transmission method. For example, the ambulatory medical device may encrypt all data using an asymmetric key.

In some examples, the therapy data may be encrypted before being transferred to the computing system. In these examples, AMD may have a public key and a private key stored in one of its memories permitting the AMD to encrypt data communications transmitted by the ambulatory medical device to the computing system. In these examples, AMD may transmit the public key along with the therapy data to the computing system. The public key provided by the AMD and a private key stored on the computing system may permit the computing system to decrypt the data received from the ambulatory medical device. In some such cases, the public key may timeout and a new public key may be obtained from the ambulatory medical device to facilitate decrypting subsequent communications from the ambulatory medical device. In some cases, the public key may be associated with a time-to-live (TTL) value. In some such cases, the public key may timeout and a new public key may be obtained from the ambulatory medical device to facilitate decrypting subsequent communications from the ambulatory medical device.

Moreover, the secure data transmission may include generating a shared secret based at least in part on the public key and the private key. In some such cases, decrypting the encrypted data includes using the shared secret to decrypt the encrypted data. In some examples, shared secret may be established using public key exchange algorithm (e.g., Diffie-Hellman key exchange algorithm).

In some cases, the computing system may be configured to transfer the data after receiving a request to transfer data stored on the ambulatory medical device to the computing system over the direct end-to-end data connection via the wireless wide area network. Responsive to receiving the request to transfer data stored on the ambulatory medical device to the computing system, the computing system may be configured to receive, via the direct end-to-end data connection.

Once a connection is established and the therapy data is transferred to the computing system, the computing system may analyze the therapy data received from the ambulatory medical device and generate a therapy report. Further, the computing system may detect an alarm condition, based on therapy data analysis, and generate an alarm that may be provided to the subject, authorized user (e.g., healthcare provider). In some cases, the therapy data may trigger an automatic response by the computing system. For example, the AMD may determine that a medicament or another disposable is running low based on the received data and may automatically reorder the medicament or the disposable.

In some cases, the computing system may periodically receive data from the ambulatory medical device based on a regular schedule. Alternatively, or in addition, the data may be received in response to a command or when the ambulatory medical device determines it is within a certain location. For example, when the ambulatory medical device determines it is within a subject's home or at a healthcare provider's office based on a local area network connection or based on a geolocation system (e.g., a global positioning system (GPS)). In some implementations, additional encrypted data is received from the ambulatory medical device on an intermittent basis. Alternatively, or in addition, additional encrypted data is received from the ambulatory medical device on a continuous basis for at least a time period. The ambulatory medical device may be configured to transmit data as it is generated, or shortly thereafter, (e.g., in real or near real-time (e.g., within a few millisecond, seconds, or minutes of the data being generated)), or in bulk at specified periods of time. Transmitting the data in bulk at particular time periods may extend battery life, but may provide for less up-to-date analysis. Data can be made available on-demand by keeping the transceiver always on, but this may consume more power. Thus, the scheduling of data transfer may be balanced based on different considerations, such as: (1) power consumption and (2) need to share information with authorized users or systems.

In some cases, the computing system may be used as a backup for the ambulatory medical device. For example, the ambulatory medical device can backup data to the computing system every night, when it is charging, or when it is in proximity to home or a physician's office (e.g., when subject is in waiting room, the device may upload data that the physician can then access). Moreover, if the ambulatory medical device is replaced (e.g., for a new model or to replace a damaged device), the device can automatically synchronize with the computing system to obtain subject-specific configuration or therapy control data.

Therapy Data and Therapy Report

In some examples, the therapy data may include dose or dosage data corresponding to one or more doses of medicament provided by the ambulatory medical device to the subject. Further, the therapy data may include subject data corresponding to a medical or physiological state of the subject as determined by the ambulatory medical device.

In other examples, the data provided to computing system may include any type of data that may be measured or obtained by the ambulatory medical device and may include a record of therapy provided by the ambulatory medical device. For example, the data may include a time that therapy was provided, an amount of medicament provided as part of the therapy, a measure of one or more vital signs of the subject, a measure of blood glucose levels at different times for the subject, a location of the subject, and the like.

In some cases, the therapy data may be used to track the use of disposables, such as insulin or other medicament, or insulin pump site kits. In some cases, the computing system may automatically order or reorder disposables at a particular time based on tracking the use of the disposable. Alternatively, or in addition, the reordering of the disposables may be initiated or performed from the ambulatory medical device (e.g., via a wireless wide area network or via a local connection through a separate electronic device).

In some cases, the data transferred to the computing systems may include operation data corresponding to operation of the ambulatory medical device. Alternatively, or in addition, the data may further include error data corresponding to an error in operation of the ambulatory medical device.

In some examples, the data, therapy data and/or the therapy report may be stored in a memory of the computing system and/or at a storage of the networked-computing environment.

In some cases, the method may include converting the therapy data from one format to another format. For example, the method may include converting the therapy data from a format used to store and/or present data on ambulatory medical device to a format that can be stored or processed on the computing system. In some cases, the therapy data is converted from a machine-readable format to a human-readable format. The data may be stored in a more easily interpreted format that can be understood by different types of users. For example, the data may be presented in one format for a healthcare provider (e.g., sensor readings), a simplified format for a subject or parent of a subject, other data formats for displaying data to different types of users.

In some examples, the therapy data collected from different AMDs associated with plurality of subjects may be aggregated for a group of subjects based on their association with an institution or organization (e.g., a clinic, an insurance company, and the like)

In some other examples, a therapy report based at least in part on the therapy data may be generated by the computing system. The therapy report may include time-series therapy data relating to the therapy delivered by the ambulatory medical device over a particular time period.

In some examples, the therapy report may be sent to AMD wherein the subject can see the report via a user interface (e.g., a touchscreen display).

In some cases, the ambulatory device data and/or data generated by the computing system based on the ambulatory device data can be viewed on a secondary display system from the computing system. For example, a clinician or parent can access the data from their personal device. The communication between the computing systems and the viewing device may be encrypted. Moreover, permission for sharing of end user data with a 'follower' (e.g., family member) or clinician may be granted or controlled by the end user (e.g., the subject or a guardian).

An association between a subject, a clinic, and/or an ambulatory medical device may be performed by association of a device serial number of the ambulatory medical device with the subject and/or clinic. Further, a user (e.g., a subject, clinician, or parent) can access therapeutic recommendations through the cloud in case either the ambulatory medical device (e.g., an insulin pump) or the CGM sensor fails to function.

With reference to FIG. 14, in some cases, the computing system may be configured to at least receive a request from one or more display systems 1414 that are separate from the networked computing environment to access the therapy report, therapy data or other data received by or stored in the AMD. In some cases, the display system may be a computing system of a medical practitioner 1418 (e.g., such as a doctor, nurse, . . . ), a guardian of the subject 1420 (e.g., subject's parents), a health care service provider 1424 an authorized user 1422 (e.g., a user authorized by the subject such as spouse, relative, friend, and the like), or a device of the subject 1416 (e.g., cell phone, personal computer, tablet and the like).

In some examples, the display system can be a therapy data management system that analyses a therapy data associated with a specific type health problem (e.g., data associated with managing diabetes) and provides useful information to the subject or an authorized user to monitor and manage the corresponding ailment.

The request may include an account identifier associated with a user that generated the request. In some examples, the account identifier may include a unique identifier associated with the subject. Alternatively, or in addition, the account identifier includes a unique identifier associated with a user that is authorized to access the therapy report. The user may or may not be the subject. In some aspects of the present disclosure, the method may further include associating the therapy data with the account identifier at a storage of the networked-computing environment. Further, the computing system may be configured to determine whether an account associated with the account identifier is permitted to view the therapy report. In some examples, account permissions may be granted and/or modified by the subject. For example, the subject can access an account at a networked computing environment 1412, for example, a cloud service provider associated with the subject, and provide one or more identifiers associated with one or more other users to give them permission to access the subject's therapy data or report stored on the computing system.

Responsive to determining that the account is permitted to view the therapy report, the hardware processor may be configured to transmit the therapy report to the display system over an encrypted communication channel.

In some cases, the method may include receiving an identity or identification information of one or more users that are authorized to access therapy data stored at the networked-computing environment. For example, a user or subject may authorize a clinician or other healthcare provider, a parent or guardian, or other users that the subject desires to have access to the therapy data. The identity information of the one or more users may include any type of information that may identify the user or enable the user to be authenticated. For example, the identity information may include a name, unique identifier (e.g., social security number), an email, an address, a phone number, account information for the user at the networked-computing environment, or any other identifying information.

Figure 15:
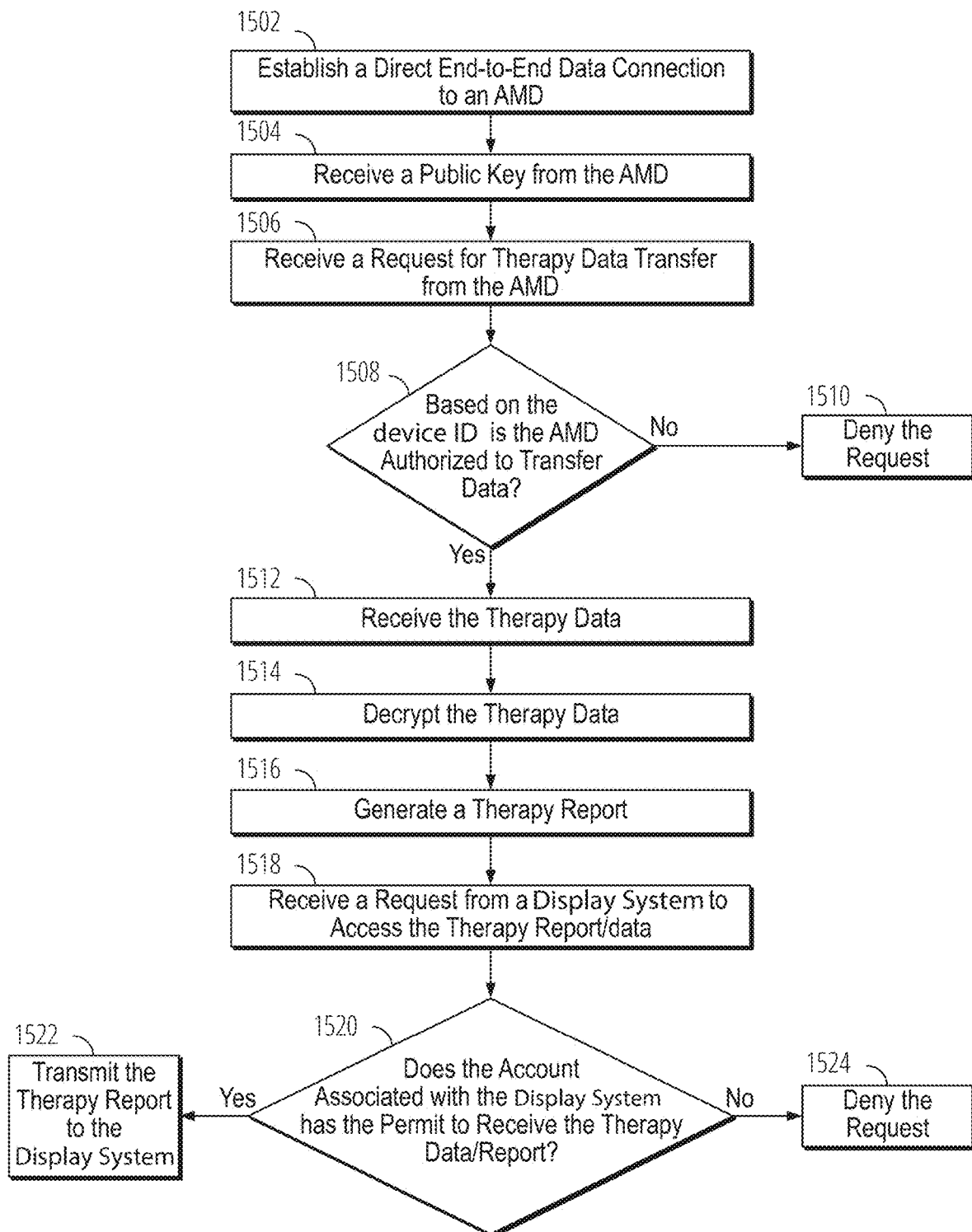
FIG. 15 is a flow diagram illustrating an example method that may be used by a computing system, to generate and share a therapy report based on encrypted therapy data received from an AMD.

FIG. 15 is a flow diagram that illustrates an example method that may be used by computing system 1406, to generate and share a therapy report based on encrypted therapy data received from an AMD 1402. In some examples, the AMD 1402 may generate the encrypted therapy data using a public key and a private key. The method may include establishing a direct end-to-end data connection 1502 to an ambulatory medical device, for example, via a wireless wide area network (WAN) using a Narrowband Long-Term Evolution (NB-LTE) transceiver included in the AMD 1402. Once a direct end-to-end data connection between the AMD 1402 and the computing system 1406 is established, the computing system may receive a public key 1504 (e.g., associated with encrypted data), from the AMD 1402 over the established connection. Next, the computing system may receive a request from the AMD 1506 to transfer data (e.g., therapy data) stored on the AMD 1402 to the computing system 1406 over the direct end-to-end data connection. In some examples, the computing system 1406 may use the device ID associated with the AMD 1402 to determine whether the AMD 1402 is authorized to transfer data to the computing system 1508. If, based on the device ID, it is determined that the AMD 1402 is authorized to transfer data to the computing system, the encrypted therapy data may be transferred 1512 to the computing system. If, based on the device ID, it is determined that the AMD 1402 is not authorized to transfer data to the computing system, the request may be denied 1510. The computing system may decrypt the encrypted therapy data 1514 using a private key (e.g., stored in a memory of the computing system) and a public key received from the AMD 1402. In some examples, the therapy data may be used to generate a therapy report 1516. In some examples, the decrypted therapy data and/or therapy report may be stored in a memory of the computing system 1406.

The example method may further include receiving a request from a display system 1414 that is separate from the networked computing environment, to access the therapy report 1518. The request may include an account identifier associated with a user that generated the request. The method may include determining using the account identifier to determine whether the account associated with the account identifier is permitted to view the therapy report 1520. In the computing system determines that the account associated with the received account identifier does not have the required permission, the request will be denied 1524. Responsive to determining that the account is permitted to view the therapy report, the method may include transmitting the therapy report to the display system 1522 over an encrypted communication channel.

In certain implementations, the method may further include determining that the therapy data or other data received from the AMD satisfy an alert threshold condition. In these implementations, when the computing system determines that the therapy data or other data received from the AMD satisfy an alert threshold condition, the computing system may send an alert to one or more display systems designated to receive alerts from the computing system.

In some examples, alert threshold condition may be associated with the health condition of the subject. For example, alert threshold condition may include subject's blood sugar level is above or below a set value (hyperglycemia or hypoglycemia). In some other examples the alert threshold condition may be associated with the operation of the AMD. For example, alert threshold condition may include the rate of therapy (e.g., the rate at which insulin is provided to a subject) being above or below a set value.

In some other examples, alert threshold condition may be associated with the temporal behavior of therapy data over a period of time. For example, the alert threshold condition may include the fluctuations or variations of the subject's blood sugar level being above a set value.

In some examples, the alert threshold condition may be defined or set by health provider. In some such examples, the health provider may change one or more alert threshold conditions based on the health condition of the subject.

Figure 16:
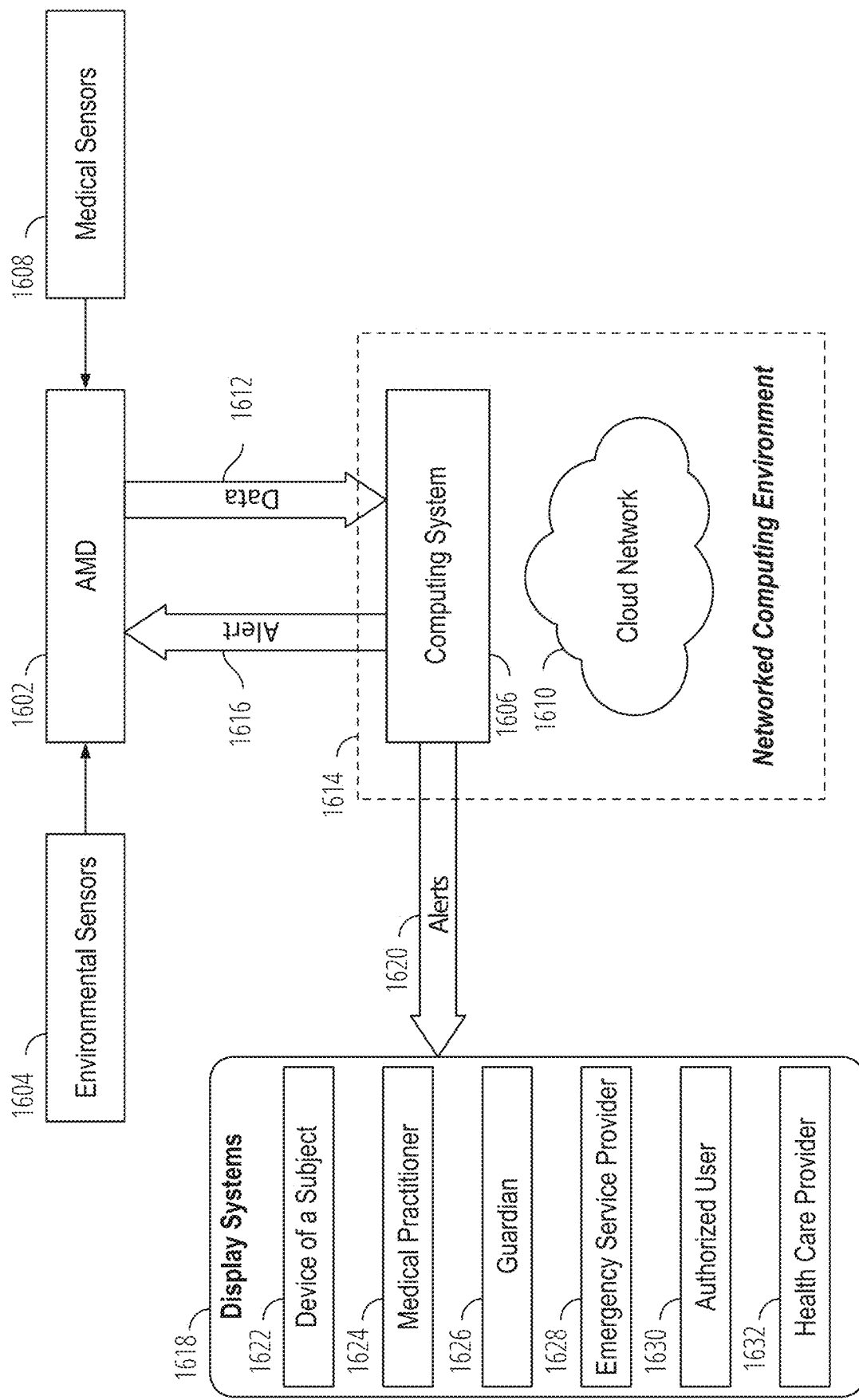
FIG. 16 is a block diagram, illustrating an example network and data flow configuration wherein the AMD is directly connected to a computing system and the computing system generates and sends alerts to one or more display systems and the AMD.

FIG. 16 is block diagram, illustrating an example network and data flow configuration where an AMD 1602, which is directly connected to a computing system 1606 (e.g., computing system within a cloud network 1610), may generate and send alerts 1616 (e.g., alert messages, alert signals, and the like) upon determining that data 1612 received from the AMD satisfies a threshold condition. The computing system 1606 may be part of networked computing environment 1614 (e.g., a data center, networked computing system), or cloud network 1610 or cloud computing system of a cloud service provider. The computing system may include one or more non-transitional memories and one or more hardware processors configured to execute the computer-executable instructions stored in one or more non-transitional memories. The AMD may receive data from one or more medical sensors 1608 (e.g., analyte sensor, temperature sensor, heartbeat sensor, and the like) and/or one or more environmental sensors (e.g., geolocation receiver, motions sensor, accelerometer, and the like). These sensors may be included in the AMD unit or may be connected to the AMD via a wired or wireless link.

In some cases, the display systems receiving the alert 1620, may be display systems that have already received therapy reports from the computing system 1606. In other examples, a group of display systems may be selected and authorized by the subject, who is receiving therapy from the AMD, to receive alerts 1620. The display systems that may receive alerts 1620 from the AMD may include: a medical practitioner 1624 (e.g., such as a doctor, nurse, etc.), a guardian of the subject 1626 (e.g., subject's parents), an emergency service provider 1628, an authorized user 1630 (e.g., a user authorized by the subject such as spouse, relative, friend, and the like), a health care healthcare provider 1632, or a device of a subject 1622 (e.g., cell phone, personal computer, tablet and the like). In some examples, when it is determined that received data 1612 the AMD satisfies a threshold condition, in addition to sending a alerts to one or more display systems 1618, the computing system 1606 may send an alert 1616 to the AMD 1602.

In some examples, the AMD 1602 may be configured to establish a connection to support continuous data transfer to the computing system 1606 for a given period of time (e.g., provided to the AMD by the subject), in order to capture any data that is generated over that period and satisfies an alert threshold condition. For example, the subject may request a continuous connection between AMD and the computing system when going for hike alone to make sure that if his/her health condition deteriorate during the hike, an alert is sent to authorized display systems.

In some examples, a geolocation sensor (e.g., a Global Positioning System (GPS) receiver) and/or a proximity sensor can be used to enable location-activated features such as automatic upload of data at certain locations.

In some cases, the ambulatory medical device may include or be connected to an accelerometer or a geolocation system. This velocity of the ambulatory medical device may be determined based at least in part on the accelerometer or geolocation system. Using the data obtained 1612 from the ambulatory medical device 1602 including the location and/or velocity information, the computing system 1606 can provide intelligent alerts. For example, if the data indicates that a user is travelling at a high rate of speed (e.g., likely in a car) and the user's blood glucose level is low (e.g., below 55 mg/dl), the computing system may automatically alert emergency service provider 1628 that a subject is at risk of hypoglycemia and may be driving. Further, the computing system can provide a location of the subject to the emergency service provider 1628.

In some examples, the computing system can generate alerts based on a trend of the aggregated therapy data or based on therapy data that is an outlier to the aggregate therapy data or an outlier to a time-based average of the therapy data.

Further, the geolocation sensor and/or a motion sensor (e.g., an accelerometer) can be used to detect velocity of a subject to enable intelligent motion-sensitive alerts. For example, if the subject is moving at 60 mph and experiences low blood glucose, the system may enable a set of driving alerts and schedule possibly therapy in the future. The driving alerts may inform the subject to pull over immediately due to a risk of a hypoglycemic event. Further, an emergency responder may be informed of a subject location using based on information obtained from the geolocation sensor. If the subject is moving at 6-7 mph, exercise alerts may be enabled to, for example, alert the user to pause exercising and attend to low blood sugar. If the subject hasn't moved for 3 hours and has low blood sugar, the system can enable automatic notification to and emergency service provider 1628. Further, a determination of the subject's motion can be used to automatically adjust setpoint (e.g., raise setpoint during exercise). The activity level of the subject can be sensed and use to improve alerts and therapy.

Additionally, the cloud server can send a text message or call to a follower's and/or end user's phone or smart device in case the therapy data satisfies an alert threshold. These messages may be provided from the cloud computing system to a third-party device in case roaming or disabling of the data plan on the ambulatory medical device occurs (e.g., no TCP/IP available). Further, the cloud computing service may send a text message or call 911 in case of a detected emergency. The cloud server can track, for example, via GPS, the end user's most recent location and share that information with a follower and/or emergency personnel. Moreover, the cloud computing system may enable an end user to order and re-order medical supplies directly from the viewing device.

Moreover, the computing system can generate notifications (e.g., generate a message when there is a risk of hypoglycemia). Further, more detailed processing in the cloud can result in improved recommendations (e.g., Tmax, setpoint, or other control parameters)

Figure 17:
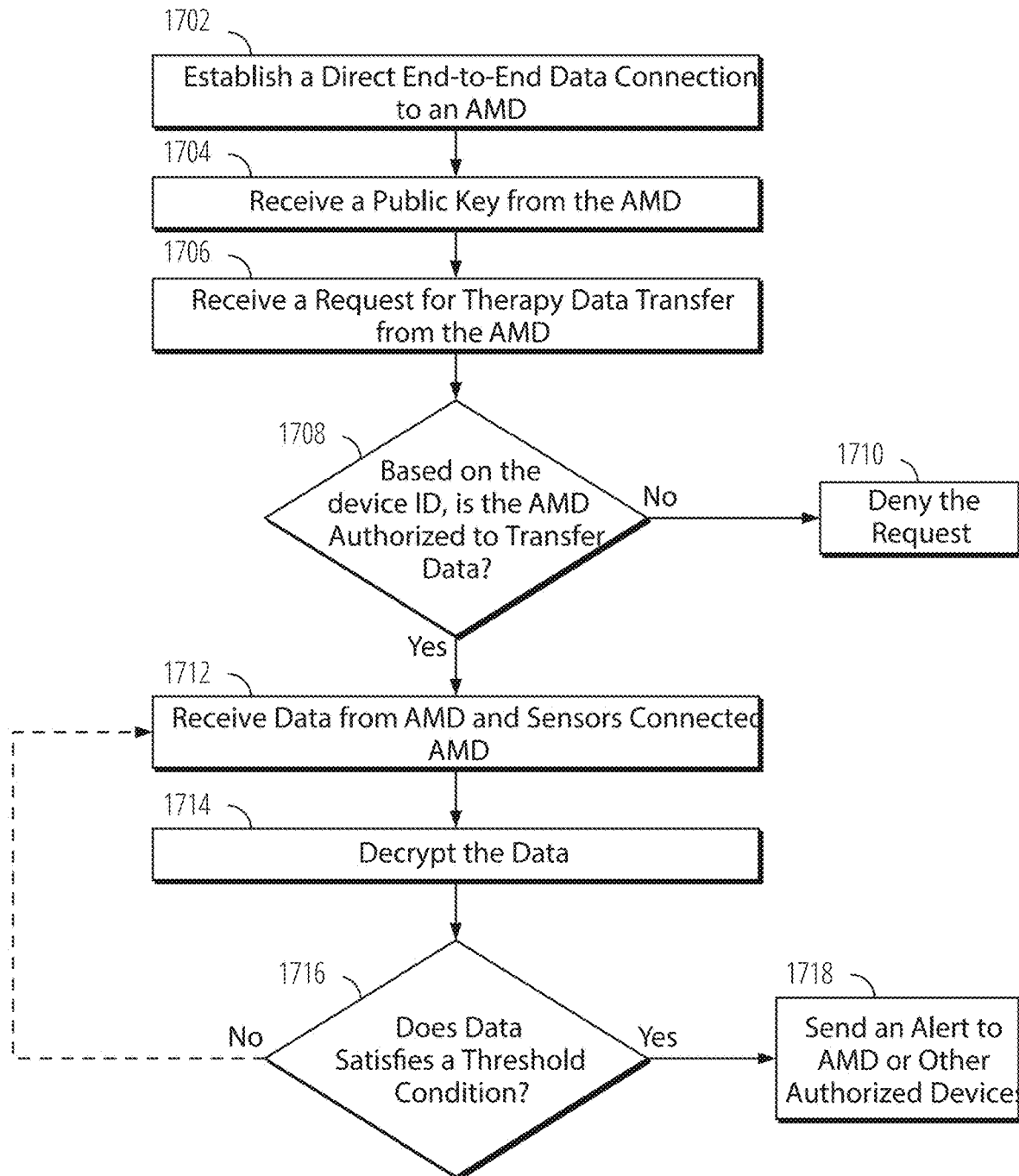
FIG. 17 is a flow diagram illustrating an example method that may be used by a computing system, to generate and send an alert to one or more authorized devices.

FIG. 17 is a flow diagram illustrating an example method that may be used by computing system 1606, to generate and send alerts (e.g., alert messages, alert signals, and the like) to one or more authorized devices and to the AMD. The method may include establishing a direct end-to-end data connection 1702 to an ambulatory medical device, for example, via a wireless wide area network (WAN) using a Narrowband Long-Term Evolution (NB-LTE) transceiver included in the AMD 1602. In some examples, the direct end-to-end connection may be established for a given period of time set by the subject or an authorized user (e.g., a guardian of the subject). Once a direct end-to-end data connection between the AMD 1602 and the computing system 1606 is established, the computing system may receive a public key 1704, from the AMD 1602 over the established connection. Next, at block 1706, the computing system may receive a request from the AMD 1602 to transfer data (e.g., therapy data, medical sensor data or environmental sensor data) generated by the AMD 1602 to the computing system 1606 over the direct end-to-end data connection. In some cases, the request may include a time period during which AMD continuously transmits any data generated by the AMD 1602 or obtained from one or more sensors (e.g., environmental sensors 1604 or medical sensors 1608), to the computing system 1606. In some such cases, the time period for continuous data transfer from the AMD 1602 to the computing system 1606, may be provided by the subject or a guardian of the subject to the AMD. At the decision block 1708, the computing system 1606 may use the device ID associated with the AMD 1602 to determine whether the AMD 1602 is authorized to transfer data to the computing system 1606. If the computing system 1606 determines that the AMD 1602 is authorized to transfer data to the computing system 1606 (e.g., based on the device ID), at block 1712, the encrypted therapy data may be transferred to the computing system 1606. If, at the decision block 1708 the computing system 1606 determines that the AMD 1602 is not authorized to transfer data to the computing system, the process may move to block 1710 and the request may be denied. At block 1714, the computing system 1606 may decrypt the received data using a private key (e.g., stored in a memory of the computing system 1606) and a public key received from the AMD 1602. At the decision block 1716 the computing system 1606 may determine whether the received data (e.g., therapy data, medical sensor data or the environmental sensor data), satisfies a threshold condition. In some cases, the threshold condition may be provided to the AMD by the subject or an authorized user (e.g., a guardian of the subject). In some other examples, the threshold condition may be provided by a healthcare provider. In some such examples, the threshold condition may be stored in a memory of the AMD. If at the decision block 1716 the computing system 1606 determines that the data satisfies a threshold condition, an alert may be generated and sent 1718 to one or more display systems 1618 that are authorized (e.g., by the subject or a guardian of the subject) to receive alerts. In some examples, the subject or the guardian may authorize one or more display systems 1618 to receive alerts by providing the account IDs of the one or more displays systems to the computing system 1606 or the networked computing environment 1614.

Preventing Inadvertent Therapy Changes

As described above, the ambulatory medicament device may include a user interface (e.g., touchscreen interface or a non-touchscreen interface) that may present one or more user-interface screens to a user enabling the user to modify one or more therapy settings of the ambulatory medicament device, such as a quantity of medicament delivered when a condition is met or the condition that triggers the delivery of medicament to a subject. The user may be a subject receiving medicament or therapy, or may be another user, such as a clinician or healthcare provider, or a parent or guardian. For ambulatory medicament devices that include a user interface, there is a risk that a setting is accidentally modified or is modified (intentionally or unintentionally) by a user that does not fully comprehend his or her action (e.g., a child or a user with a reduced mental capacity). Further, ambulatory medicament devices may accidentally have settings modified by inadvertent interactions with a user interface, such as may occur when an ambulatory medicament device is worn against the body of a subject.

This section relates to an ambulatory medicament device (AMD) to prevent an inadvertent modification in medicament deliver, for example, in the event of a setting of the AMD being accidentally modified by a user or inadvertent interactions with a user interface.

As mention above, in some embodiments the user may modify the control or configuration the AMD using a user interface. There is a possibility that the control or configuration of the AMD is accidentally modified through the user interface. For example, as the user may transport the ambulatory medical device, there is a danger that the user will inadvertently activate input in the ambulatory medical device that initiates a therapy change input (e.g., by applying pressure on the ambulatory medical device that may be placed in the jacket pocket of the user).

Figure 18:
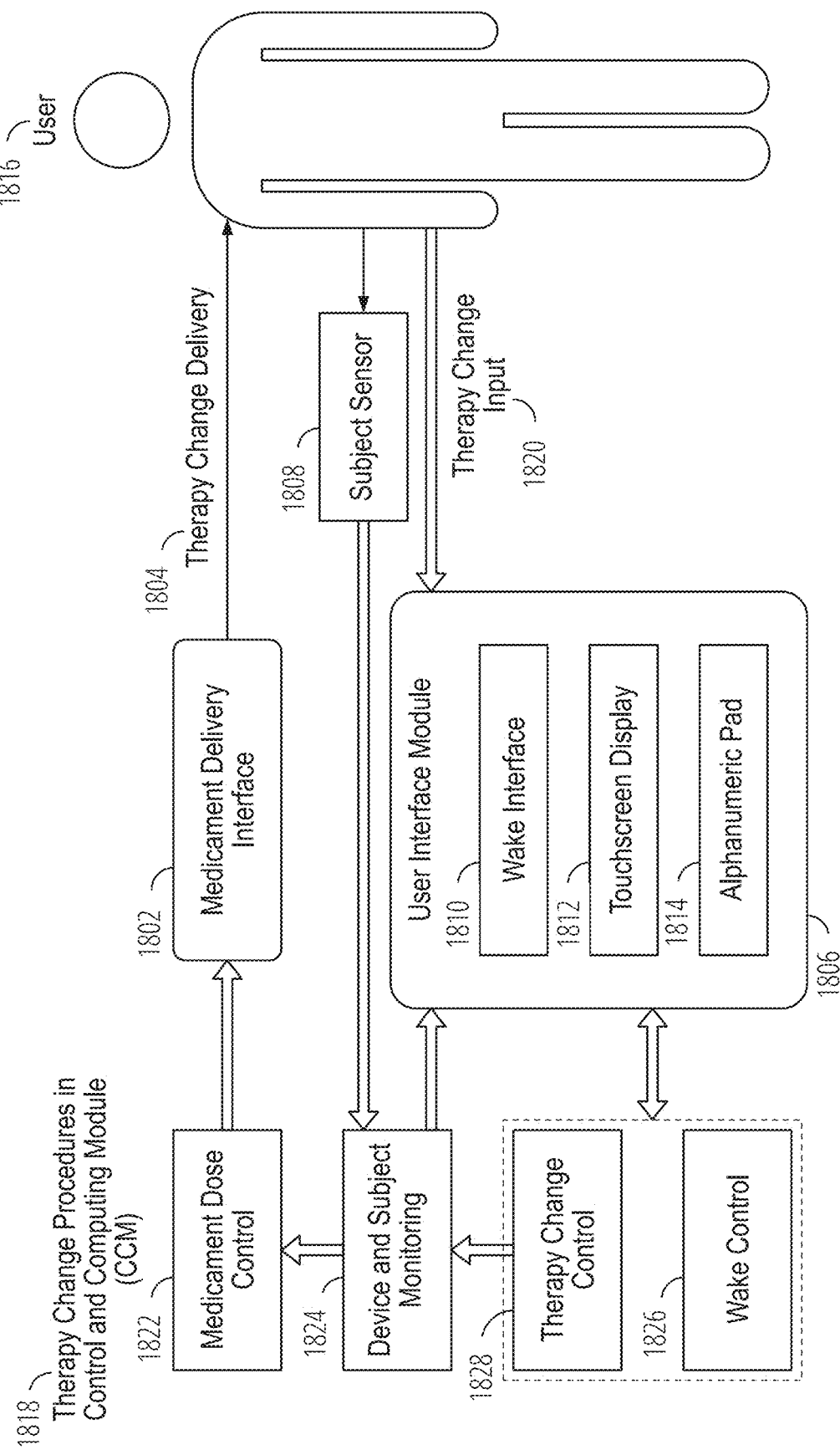
FIG. 18 illustrates the interconnection among modules and procedures in AMD involved in receiving, accepting and/or canceling therapy change request.

With reference to FIG. 18, in some such embodiments, the control and computing module (CCM) of the AMD may include a set of therapy change procedures 1818 implemented to prevent therapy change inputs 1820 that are inadvertent. The therapy change procedures 1818 may be implemented as instructions stored in a memory of CCM (e.g., the main memory 616) and executed by the processor 614. The therapy change input 1820, received from a user 1816, may be verified by the therapy change procedures 1818 before the ambulatory medical device 600 provides the therapy change delivery 1804. All the user interactions with the user interface module 1806 may be controlled and analyzed by the control and computing module 610 (CCM) via one or more therapy change procedures 1818.

In these embodiments, the user 1816 may wake or unlock the AMD by interacting with a wake interface 1810. The wake interface 1810 can be any of the additional user interfaces mentioned above, configured to generate a wake input to the CCM when detecting a pre-set user interaction.

The therapy change input 1820 can be an input provided by the user 1816 to change a therapy that is currently being delivered to the user 1816. In some embodiments, the therapy change input 1820 may cause the insulin or glucagon infusion pump to start infusing an amount of insulin or glucagon into the user 1816. Alternatively, the therapy change input 1820 may modify the rate of insulin or glucagon infusion into the user 1816. The therapy change input 1820 may also cancel insulin or glucagon infusion into the user 1816 from the insulin or glucagon infusion pump.

When a wake action is detected by the wake interface 1810, a wake input is sent to the control and computing module 610 wherein it imitates a wake control procedure 1826 that generates a wake signal to wake/unlock the user interface (e.g., a touch screen display).

When in the wake and/or unlocked state, a user may interact with the touchscreen display 1812, alphanumeric pad 1814 or other types of user interfaces that may be included in the user interface module 1806, to obtain access to therapy change user interface.

The therapy change user interface may be activated by a first user interaction with the user interface (e.g., touchscreen display 1812). When the first user interaction is detected, the user interface module user interface module 1806 sends an input signal to the control and computing module 610 wherein it is analyzed by a therapy change control procedure 1828. If it is determined that the first user interaction satisfies a set of predefined conditions, the therapy change control procedure 1828 generates a signal to the user interface module user interface module 1806 to activate the therapy change user interface.

In some embodiments, the therapy change user interface may be limited based on the first user interaction. For example, the therapy change control procedure 1828 may send one of two signals to the user interface module user interface module 1806. The therapy change user interface may then unlock one of two different therapy change user interfaces that result in different options of therapy change selections for the user 1816. In an implementation of this example, a therapy change selection to make a significant therapy change, such as dramatically increase the rate of insulin or glucagon infusion rate, requires a first user interaction that is different from the first user interaction that would be required for an insulin or glucagon infusion at a normal or prescribed rate. In some examples, the first user interaction may be a simple interaction (e.g., a simple gesture) that unlocks a therapy change user interface with therapy change selections that are limited. Another first user interaction may be a complicated interaction (e.g., a series of complex gestures) that unlocks a therapy change user interface with therapy change selections that have no limits. An example of this implementation may be useful for child users. The child user may perform the first gesture that is made up of a series of simple inputs to unlock therapy change selections that are limited. An adult user may perform the first gesture that is made up of a series of complex inputs to unlock the therapy change user interface with therapy change selections that have no limits.

Once activated, the therapy change user interface that may provide one or more control or configuration elements that enable the user to modify the control or configuration of the ambulatory medicament device. The control or configuration element may include any type of user interface screen on the touchscreen, or other type of user interface in the non-touchscreen context, that enables or permits a user to change a configuration of the ambulatory medicament device. This change in configuration of the ambulatory medicament device may relate to a change in the therapy provided or in the detection of a triggering event that causes therapy (e.g., medicament) to be provided to a subject. For example, the change in configuration may include a selection between one or more hormones that regulate blood sugar level (e.g., insulin or glucagon) of a user, an amount of the one or more hormones that regulate blood sugar level of the user.

In some cases, a change to the configuration of the ambulatory medicament device is automatically and/or instantly recognized or implemented by the ambulatory medicament device, and/or transmitted to the ambulatory medicament device. In other cases, a confirmation of the change may be required before the change is implemented by or transmitted to the ambulatory medicament device.

This confirmation may be entered based on a second user interaction with a user interface (e.g., touchscreen display 1812). When the second user interaction is detected, the user interface module user interface module 1806 sends an input signal to the control and computing module 610 wherein it is analyzed by a therapy change control procedure 1828. If it is determined that the second user interaction satisfies a set of predefined conditions, the therapy change control procedure 1828 implements the change to the configuration of the AMD.

The first and/or second user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMD. In some embodiments, the visual indicia can include animations that suggest or guide user interactions with a touchscreen. For example, the first user interaction can include an arcuate swipe around at least a portion of a generally circular icon or logo. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a configuration screen, and/or confirms a change to the configuration of the ambulatory medicament device may be the same or may differ.

In an exemplary embodiment, the system may have a time-out such that if no interaction occurs for a set period of time, the user interface will turn off and the therapy change request process has to start again. In one implementation of the time-out, if no interaction occurs for more than 30 seconds after the system is waked/unlocked before the second user interaction is received by the user interface, the user interface will be deactivated.

Once the configuration change is confirmed, implemented, or transmitted, the ambulatory medicament device may begin operating with the changed configuration.

This operation may include triggering therapy based on the new configuration or providing therapy based on the new configuration. For example, the ambulatory medicament device may generate a dose control signal based at least in part on the modified configuration or control parameter or may detect a trigger based at least in part on the modified configuration or control parameter that leads to the provisioning of therapy.

With continued reference to FIG. 18, in some embodiments, the changes made through the therapy change user interface are sent to CCM wherein the therapy change control procedure 1828 in CCM transfers the changes to the device and subject monitoring procedure 1824. The device and subject monitoring procedure 1824 may be implemented in the CCM 610 to monitor the status of the AMD (e.g., therapy delivery configuration) and the health condition of the user 1816 (or a subject). For example, the subject monitoring procedure 1824 may receive information about a therapy change requested by a user 1816 through a user interface (a touchscreen display 1812 or alphanumeric pad 1814) or information about glucose level in subject's blood from the subject sensor 1808. Subsequently, the device and subject monitoring procedure 1824 may transmit the information pertaining a health condition of the subject and/or the AMD configuration, to the medicament dose control procedure 1822. In some examples, the parameters in the medicament dose control procedure 1822 may be adjusted based on the changes and/or information captured by the device and subject monitoring procedure 1824. The medicament dose control procedure 1822, controls the medicament delivery interface 1802 by providing a medicament dose signal. The medicament does control may be generated based on detected conditions or physiological characteristics of the subject (e.g., provided by the readings of the subject sensor 1808) and according to parameter values received from the therapy change control procedure 1828. The medicament delivery interface 1802 may provide a therapy change delivery to the user according to the information received by device and subject monitoring procedure 1824.

In some examples, the dose control signals may be produced based on time (e.g., medicament may be delivered on a periodic basis), one or more a command, indication that the subject is planning to engage or is engaging in a particular activity (e.g., eating a meal, exercising, sleeping, fasting, etc.), or any other factor that may relate to or cause the triggering of therapy (e.g., medicament delivery).

Figure 19:
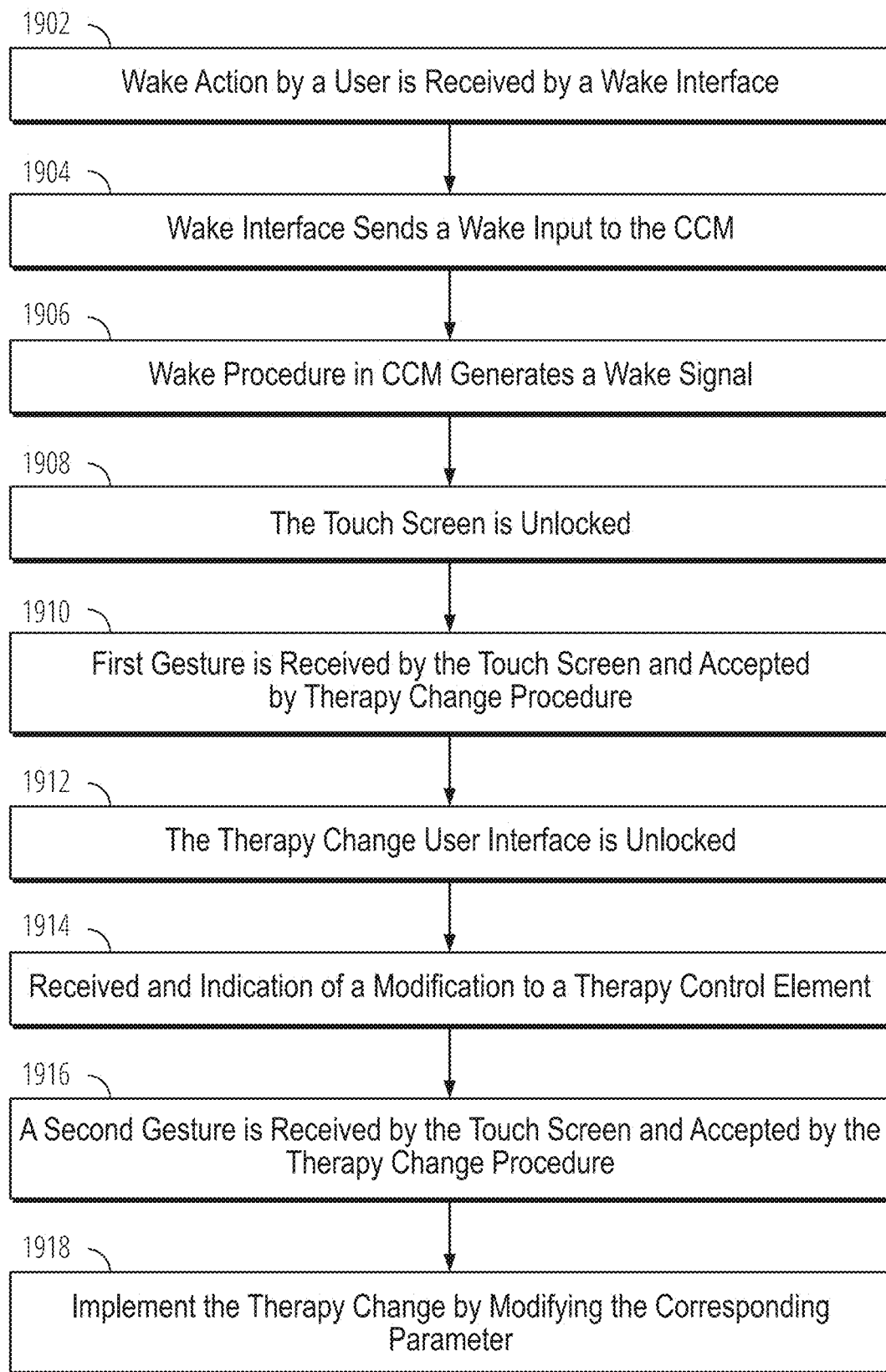
FIG. 19 is a flow diagram illustrating an example method that may be used by an AMD to allow a user to change the configuration of the ambulatory medicament device using a touch screen user interface.

FIG. 19 is a flow diagram illustrating an example method that may be used by an AMD to allow a user to change the configuration of the ambulatory medicament device using a touch screen user interface. The user may initiate the configuration change process by waking/unlocking the touch screen using a wake action. Once the wake action is received by the wake interface (block 1902), the wake interface sends a wake input to CCM (block 1904). At block 1906, the wake procedure generates a wake signal and at block 1908 that unlocks the touch screen (block 1908). Next, in response to receiving a first gesture by the user (block 1910), the therapy change user interface is unlocked (block 1912). Using one or more therapy control or configuration elements provided in the therapy change user interface, the user may change the therapy configuration (block 1914). The user may confirm the changes made, by providing a second gesture on the touch screen 1916. Once the confirmation is received (block 1916) the requested changes will be implemented (block 1918), and the ambulatory medicament device may begin operating with the changed configuration. In some examples, once the user confirms the changes made, a dose control signal may be sent to the medicament delivery interface 1802 that triggers a therapy change delivery to the subject.

In some cases, the ambulatory medicament device, or a control device that enables a user to modify a configuration of the ambulatory medicament device, may have a timeout feature. The timeout feature may cause the ambulatory medicament device or the control device to enter a sleep or locked state after a period of time of inactivity by the user. In some cases, the timeout feature may cause the ambulatory medicament device or the control device to enter a sleep or locked state after a particular period of time regardless of whether the user is interacting with the ambulatory medicament device or control device. Thus, a user may have a limited period of time to modify he configuration of the ambulatory medicament device.

In some examples, the therapy change made by a user may trigger the delivery of a medicament according to the therapy change received and confirmed by a user. This therapy change delivery may occur after a set time from period from receiving the confirmation.

In some embodiments of the AMD, an alarm status indicator may be presented to the user via the user interface. The alarm status indicator can be an alert message or an alert symbol. The alarm status indicator may be related to a configuration change made by a user, a change in the status of the AMD not related to a user input, or the condition of the subject (e.g., detected by the subject sensor).

Figure 20A:
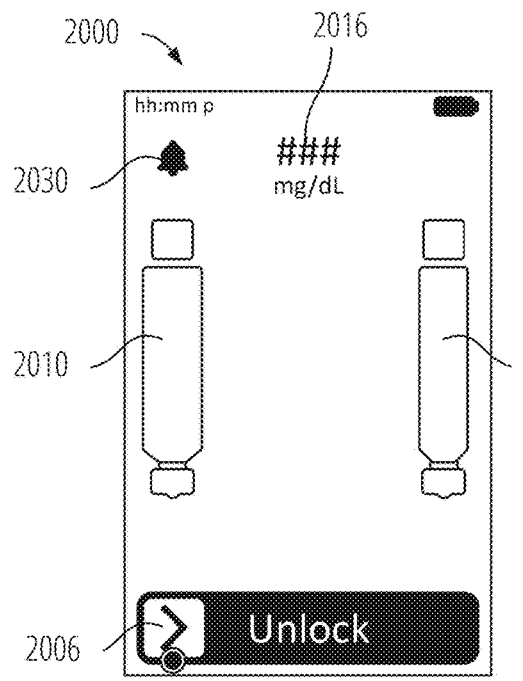
FIG. 20A is an illustration of the touchscreen display of an example AMD after the touch screen is waked/unlocked by a wake action of a user and before the first user gesture is received.

FIG. 20A is an illustration of the touchscreen display 2000 of an example AMD after the touch screen is waked/unlocked by a wake action of a user and before the first user gesture is received. Even while the touchscreen display is locked, the touchscreen display 2000 may display any images, animations, text, or other graphics. The first gesture prompt 2006 displays to the user 1816 the input required to unlock the therapy change user interface. Here, the first gesture prompt 2006 shows the user 1816 that a touch movement that begins at the greater-than symbol and moves right across the "Unlock" text is the acceptable first gesture. In addition to the first gesture prompt, the refill status of the ambulatory medical device 600 is shown in a graphic representation 2010. Here, the graphic representation 2010 shows that the insulin cartridge in the ambulatory medical device 600 is almost full. A current blood sugar level 2016 is shown at the top of the touchscreen display 2000, which can inform the user 1816 of the need for a hormone that regulates blood sugar levels. The touchscreen display 2000 also shows a graphic representation of a cartridge of glucagon 2024. The graphic representation of an alarm 2030 in the touchscreen display 2000 shows that an alert is set on the ambulatory medical device 600.

Figure 20B:
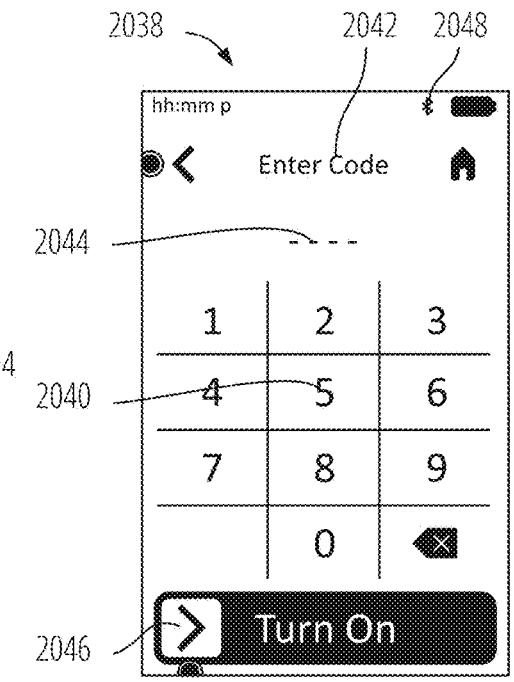
FIG. 20B is an illustration of an example touchscreen display that may prompt the user to enter a predetermined series of inputs for the first gesture or second gesture.

FIG. 20B is an illustration of an example touchscreen display 2038 that may prompt the user to enter a predetermined series of inputs for the first gesture or second gesture. In various embodiments, such as the embodiment shown in FIG. 20B, the touchscreen display 2038 may display touchable number keys 2040. In various embodiments, the touchscreen display 2038 prompts the user 1816 to enter the series of inputs that complete the first gesture or second gesture. The text Enter Code 2042 prompts the user 1816 to enter a predetermined or preselected numerical sequence as part of the first gesture or second gesture. The numerical sequence being typed by the user 1816 is displayed in field 2044 as it is entered as an aid to the user 1816. The input 2046 of the touchscreen display 2038 shows that a touch movement of a swipe right across the bottom of the screen is required to complete the predetermined series of inputs for the first gesture or second gesture. A Bluetooth connection symbol 2048 shows that the ambulatory medical device 600 is paired or can be paired to another electronic device.

Figure 20C:
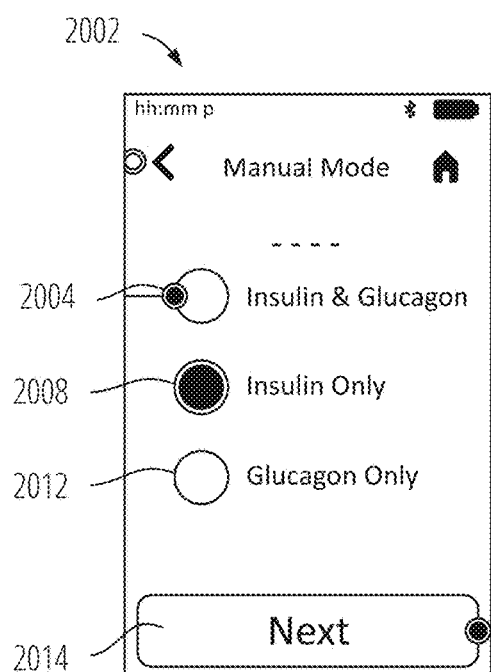
FIG. 20C is an illustration of an example therapy change user interface.

FIG. 20C is an illustration of an example therapy change user interface (in this case a touchscreen display 2002). The touch screen display may the user 1816 prompt to select a hormone that regulates blood sugar level. The touchscreen display 2002 presents the user 1816 with an option to select between two hormones. The touchscreen display 2002 aids the user 1816 by showing the selected hormone 2008 for the user 1816. The selected hormone 2008 is "insulin Only". The user 1816 is also given the options of selecting the hormone Glucagon Only button 2012 or both Insulin & Glucagon button 2004 to regulate blood sugar level. Once the user 1816 selects between the one or more hormones that regulate blood sugar level. The Next button 2014 may be selected to complete the therapy change selection or select more options. In one embodiment, to select more options, the therapy change user interface prompts the user 1816 to select an amount of the one or more hormones that regulate blood sugar level of the user 1816. In other embodiments, the user 1816 may be prompted to select a blood sugar level and the ambulatory medical device may choose the hormone and the amount of the hormone.

Figure 20D:
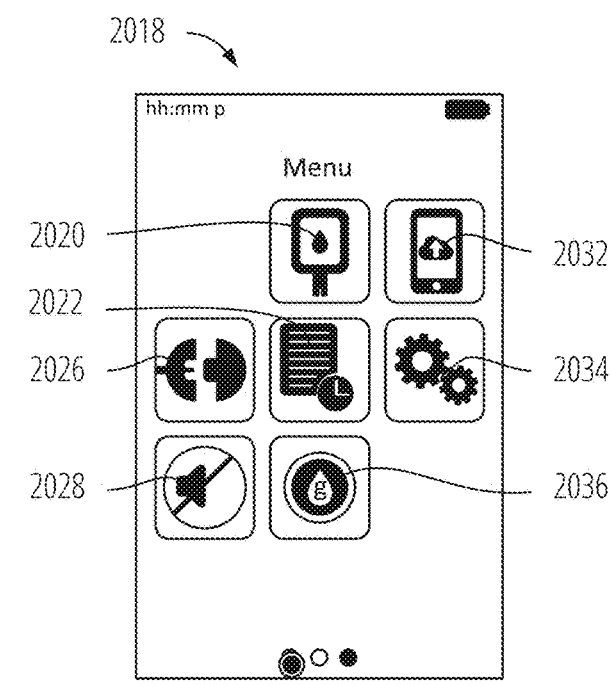
FIG. 20D is an illustration of another therapy change user interface on a touchscreen display.

FIG. 20D is an illustration of another therapy change user interface on a touchscreen display 2018. Here, the user 1816 is given a multitude of options. One or more options in the therapy change user interface allow the user 1816 to make a therapy change selection. Other options are related to the therapy change selection. A Deliver Hormone button 2036 allows the user 1816 to select a therapy change that delivers a hormone that regulates blood sugar to the user 1816. A Test Blood Sugar button 2020 allows the user 1816 to test the blood sugar level of the user 1816. A Generate Report button 2022 generates a document that reports the therapy changes that have been delivered to the user 1816. A Refill Cartridge button 2026 allows the user 1816 to fill a cartridge in the ambulatory medical device 600 with medicament. An Upload to Cloud button 2032 allows the user 1816 to transmit therapy change information to a cloud-based server. A Sound Control button 2028 allows the user 1816 to control the sounds emitted by the ambulatory medical device 600. A Settings button 2034 allows the user 1816 to manipulate other settings of the ambulatory medical device 600.

As mentioned above, in some embodiments of the AMD, an alarm status indicator may be presented to the user via the user interface to alert the user about a change made or occurred in the AMD configuration.

For example, with reference to FIG. 18, the user 1816 may provide a therapy change input 1820 using the user interface and based on the procedure illustrated in FIG. 19. Once therapy change control procedure 1828 implements the therapy change, the AMD may alert the user that a therapy change is implemented. The alert message or symbol may be presented on a user interface (e.g., touch screen display) before and/or during the therapy change delivery 1804. For example, alarm indicator may inform the user 1816 that a therapy change is about to occur. Any number of details of the therapy change may be displayed as part of the alert message or symbol. In some cases, the alarm status indicator may appear after the user unlocks or wakes the user interface using a wake action.

Figure 21:
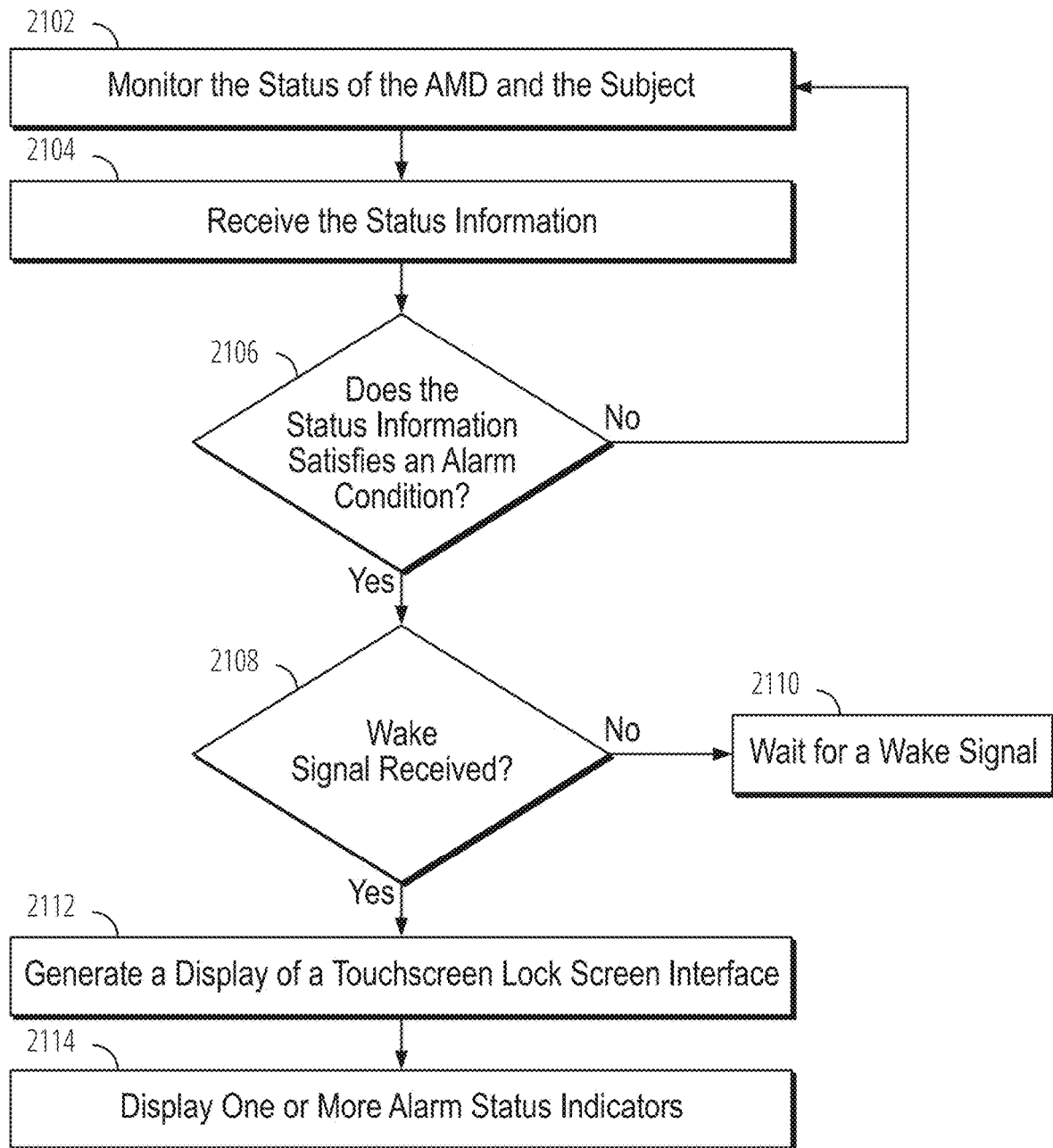
FIG. 21 is a flow diagram illustrating an example method that may be used by an AMD to generate an alarm status indicator.

FIG. 21 is a flow diagram illustrating an example method that may be used by an AMD to generate an alarm status indicator. In some embodiments the device and subject monitoring procedure (excused within CCM), may continuously monitor the status of the AMD (e.g., the user interface, different modules of the AMD and the like) as well as the health condition of a subject (e.g., using various subject sensors such as analyte sensors) 2102. Once a status information is received 2104, the device and subject monitoring procedure may determine whether the received status information satisfies an alarm condition 2106. If the received status information does not satisfy an alarm condition, no cation will be taken and device and subject monitoring procedure continuous monitoring the AMD and the subject. If it is determined that the received status information satisfies an alarm condition, the system search for a wake signal 2108. If no wake signal is detected, the systems wait for or determine a wake signal to be received 2110. Once a wake signal is received via one or more user interfaces or sensors, the CCM may generate a display of a touchscreen lock screen interface 2112 and display one or more alarm status indicators 2114, corresponding to the detected alarm condition, on the lock screen.

Figure 22:
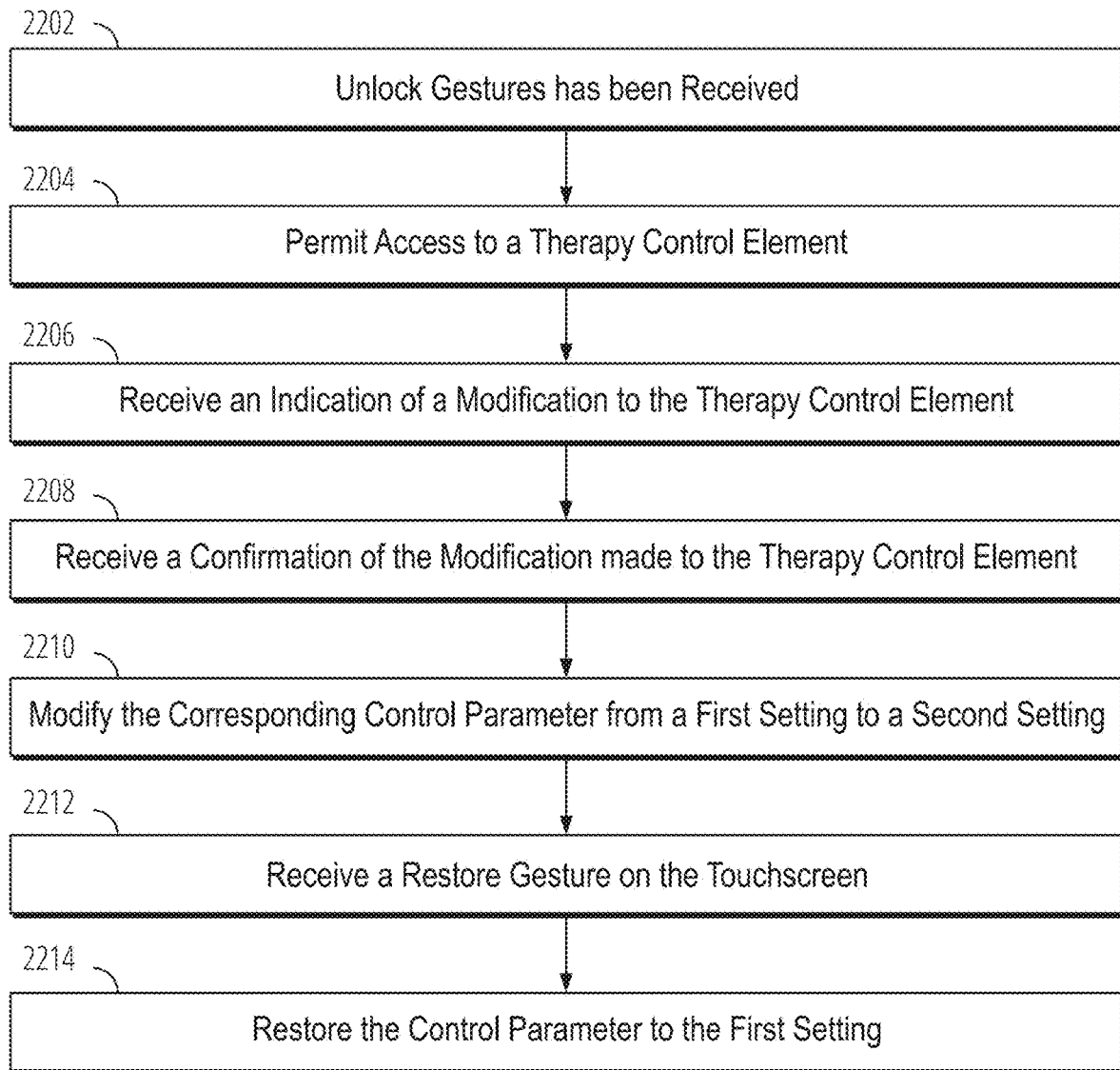
FIG. 22 is a flow diagram illustrating an example method that may be used to cancel a therapy change using a touchscreen interface.

In some embodiments, the AMD may allow the user to provide a therapy change and then cancel the therapy change. FIG. 22 is a flow diagram illustrating an example method that may be used to cancel a therapy change using a touchscreen interface. The user may unlock the touchscreen display 2202 using a wake action and get access to a therapy change user interface 2204 (e.g., using a first gesture), where one or more therapy control elements may be displayed. Next, an indication of a modification to a therapy control element may be received 2206 by the user interface followed by a confirmation of the modification made 2208 (e.g., a second gesture). In response to receiving an indication and confirmation of a modification to a therapy control element, the corresponding control parameter may be changes from a first setting to a second setting 2210. In some examples, once the change is implemented 2210, the user may decide to cancel it, for example, after realizing that requested change is erroneous. In these examples the user may provide a third gesture 2212 on the touch screen. In response to receiving the third gesture from the user interface the therapy change procedure may restore the modified control parameter to the first setting 2214. In some examples the third gesture may a restore gesture. In some cases, the restore gesture may be a swipe gesture. In some examples the swipe gesture may be performed near or in a region of the therapy change user interface that is occupied by the therapy control element. An example of a restore swipe gesture may be performed from a starting swipe position to an ending swipe position located closer to a left edge of the touchscreen than the starting swipe position. In some embodiments, the restore gesture is received on a different user interface screen than a therapy change user interface wherein one or more therapy control element are provided. In various examples, the restore gesture is performed in the opposite direction from a therapy change confirmation gesture that confirms the modification to the therapy control element.

In some examples, in order to cancel a therapy change request, the restore gesture has to be provided within a set time period after the confirmation gesture is received by the user interface. In some such examples, during the set time period one or more dose control signals may be provided to the medicament delivery interface resulting in one or more therapy change deliveries.

In some cases, the system may allow the user, to modify a therapy change before confirmation. In these cases, the user may modify a therapy control element for a second time to change the corresponding control parameter from a second setting to a third setting.

In some examples, the third setting may be the same as the first setting. In some cases, the first setting or the third setting may be a default setting. In some other cases, the first setting or the third setting may be a restore setting.

Figure 23A:
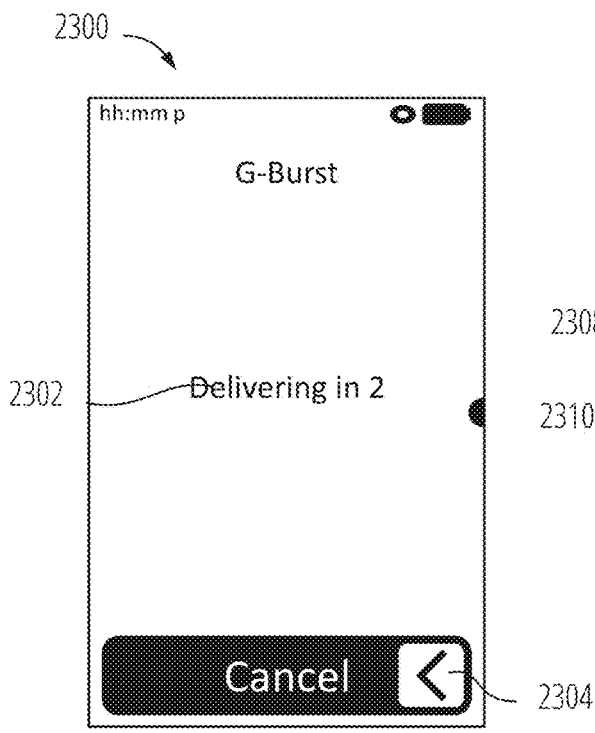
FIG. 23A is an illustration of a touchscreen display alerting the user that the delivery of one or more medicaments will occur.

FIG. 23A is an illustration of a touchscreen display 2300 alerting the user that the delivery of one or more medicaments will occur. The alert may be accompanied by sound or vibration effects. Here, the alert informs the user 1816 a delivery of medicament will occur in 2 seconds 2302. The touchscreen display 2300 is further allowing the user 1816 to perform a gesture to cancel the therapy change. The gesture to cancel the delivery is a touch movement that starts at the less-than symbol 2304 and swipes left across the "Cancel" text. In the embodiment shown in FIG. 23A, a single gesture by the user 1816 may cancel the therapy change. In an exemplary embodiment, input of the wake signal, the first gesture, the therapy change selection, and the second gesture are all required to cancel a therapy that is being delivered.

In some examples, the user may be able to cancel a therapy change delivery triggered based on therapy change made by the user. In these examples, the user may get access to the user interface using a wake action and provide a gesture to cancel the ongoing therapy corresponding to a therapy change delivery.

Figure 23B:
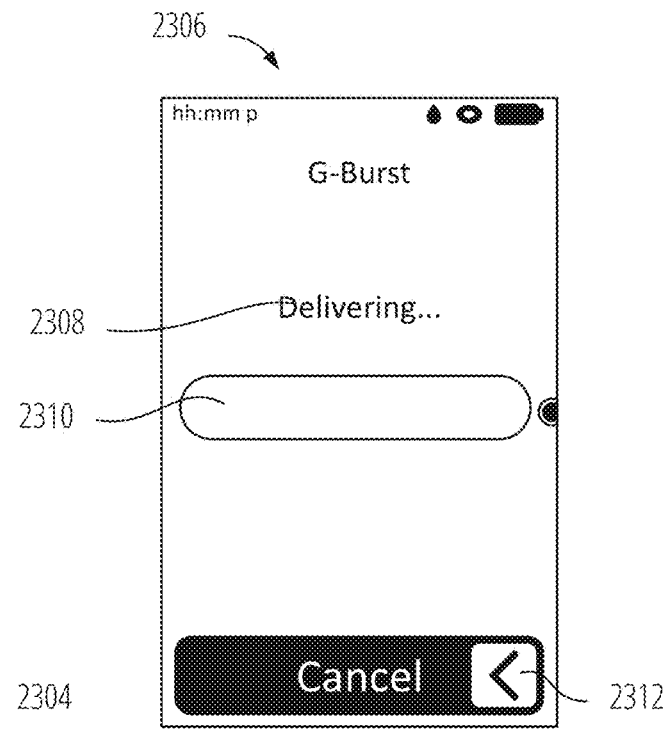
FIG. 23B is an illustration of a touchscreen display showing that a medicament is being delivered to the user.

FIG. 23B is an illustration of a touchscreen display 2306 showing that a medicament is being delivered to the user 1816. The text Delivering 2308 informs the user 1816 that a medicament is currently being delivered to the user 1816. The progress bar 2310 is a graphic representation of the progress of the delivery. In the example shown in FIG. 23B, the delivery has just started and the progress indicates that no medicament has been delivered yet. The touchscreen display 2306 is allowing the user 1816 to perform a gesture to cancel the delivery, which includes interrupting and discontinuing the delivery if it had already begun but has not yet been completed. The gesture to cancel the delivery is a touch movement that starts at the less-than symbol 2312 and swipes left across the "Cancel" text. In an exemplary embodiment that is shown in FIG. 23B, the therapy change delivery 1804 may be canceled by an input by the user 1816. The input to cancel a therapy change delivery 1804 may be any input such as a wake signal input or a series of touch inputs such as a gesture.

Additional embodiments relating to interacting with an ambulatory medicament device that can be combined with one or more embodiments of the present disclosure are described in U.S. Provisional Application No. 62/874,950, which was filed on Jul. 16, 2019 and is titled "PREVENTING INADVERTENT THERAPY CHANGES ON AN AMBULATORY MEDICAL DEVICE," the disclosure of which is hereby incorporated by reference in its entirety herein for all purposes, and in U.S. Provisional Application No. 62/874,954, which was filed on Jul. 16, 2019 and is titled "CAPACITIVE TOUCH WAKE BUTTON FOR AN AMBULATORY MEDICAL DEVICE," the disclosure of which is hereby incorporated by reference in its entirety herein for all purposes.

Automatic Resumption of Medicament Delivery Following Manual Suspension

In some cases, it may be desirable to suspend operation of the ambulatory medicament device or to suspend at least the delivery of medicament by the ambulatory medicament device for a period of time. For example, it may be desirable to suspend an operation associated with the delivery of medicament when the medicament reservoir or cartridge in the ambulatory medicament device is empty or needs replacing. As another example, it may be desirable to suspend delivery of medicament when the ambulatory medicament device is removed or is being moved to another site on the subject. In yet another example, it may be desirable to suspend delivery of the medicament when the subject is taking or ingesting another medicament that may produce a contraindication with the medicament provided by the ambulatory medicament device. In some cases, when a subject suspends the treatment delivered by a medical device, the subject may forget to resume the treatment delivered by the medical device. In other cases, the health condition of the subject may deteriorate during the suspension period requiring therapy delivery prior to end of the suspension period. As such, there is a need for AMDs that allows subjects to safely suspend treatment for temporary amounts of time.

In some embodiments, the AMD may support a therapy suspension and resumption procedure allowing a user to suspend all therapies or a subset of therapies for a period of time defined by the user as well as automatic resumption of one or more therapies at the end of the requested suspension period or when a threshold condition is met (e.g., a threshold condition associated with the health condition of the subject).

In AMDs that support therapy suspension, inadvertent activation and/or resumption of therapy delivery can be dangerous (e.g., when the AMD is an insulin and/or glucagon infusion device). In some examples to mitigate this risk, the AMD may be configured to avoid inadvertent suspension or resumption of therapies. For example, inadvertent activations of suspensions of medicament delivery may be prevented by requiring a user to perform gestures to activate suspension on the ambulatory medical device. In some cases, the gestures may activate a therapy suspension when entered at a particular prompt to.

One particular application of the therapy suspension with automatic resumption feature in an AMD can be in the field of diabetes drug delivery. For example, the may need the ability to suspend delivery of insulin during situations such as exercise, which has a blood glucose lowering effect. Suspension of insulin delivery can prevent a subject from entering a hypoglycemic state (extreme low blood glucose), which carries severe complications. Once the therapy is suspended the user many at the risk of entering a hyperglycemic state (high blood glucose that may result in complications such as diabetic ketoacidosis or neurovascular complications) if the user forgets to reactivate the drug delivery after exercise. Further, the subject's blood glucose level may raise above or below a dangerous level during the period of exercise. In these situations, the automatic medicament delivery resumption may improve the health of the subject.

In certain cases, the AMD may suspend one or more therapy deliveries when the AMD receives an indication that therapy (e.g., delivery of medicament) is to be suspended. The indication that therapy is to be suspended may be a command from a user. Often the user is the subject, but the user may also include other users that may have a say or interest in the care of the subject. For example, the user may be a clinician or other healthcare provider, or a parent or guardian.

In some examples, the indication that the therapy or medicament delivery is to be suspended may be a command received via an interface of the ambulatory medicament device or from another device that provides the user with an interface to request that medicament delivery be suspended. For example, the device may be a smartwatch, smartphone, laptop or desktop, or other control device that can communicate via a wired or wireless connection with the ambulatory medical device.

In some cases, the indication that the therapy or medicament delivery is to be suspended may be received from the ambulatory medicament device itself. For example, if the quantity of medicament available to the ambulatory medicament device drops below a threshold (e.g., the cartridge or reservoir is empty or below a minimum dosage amount), a signal may be generated to suspend medicament delivery. In some embodiments, suspension of therapy occurs based on a loss of a sensor signal, such as the loss of a glucose level signal.

Figure 24:
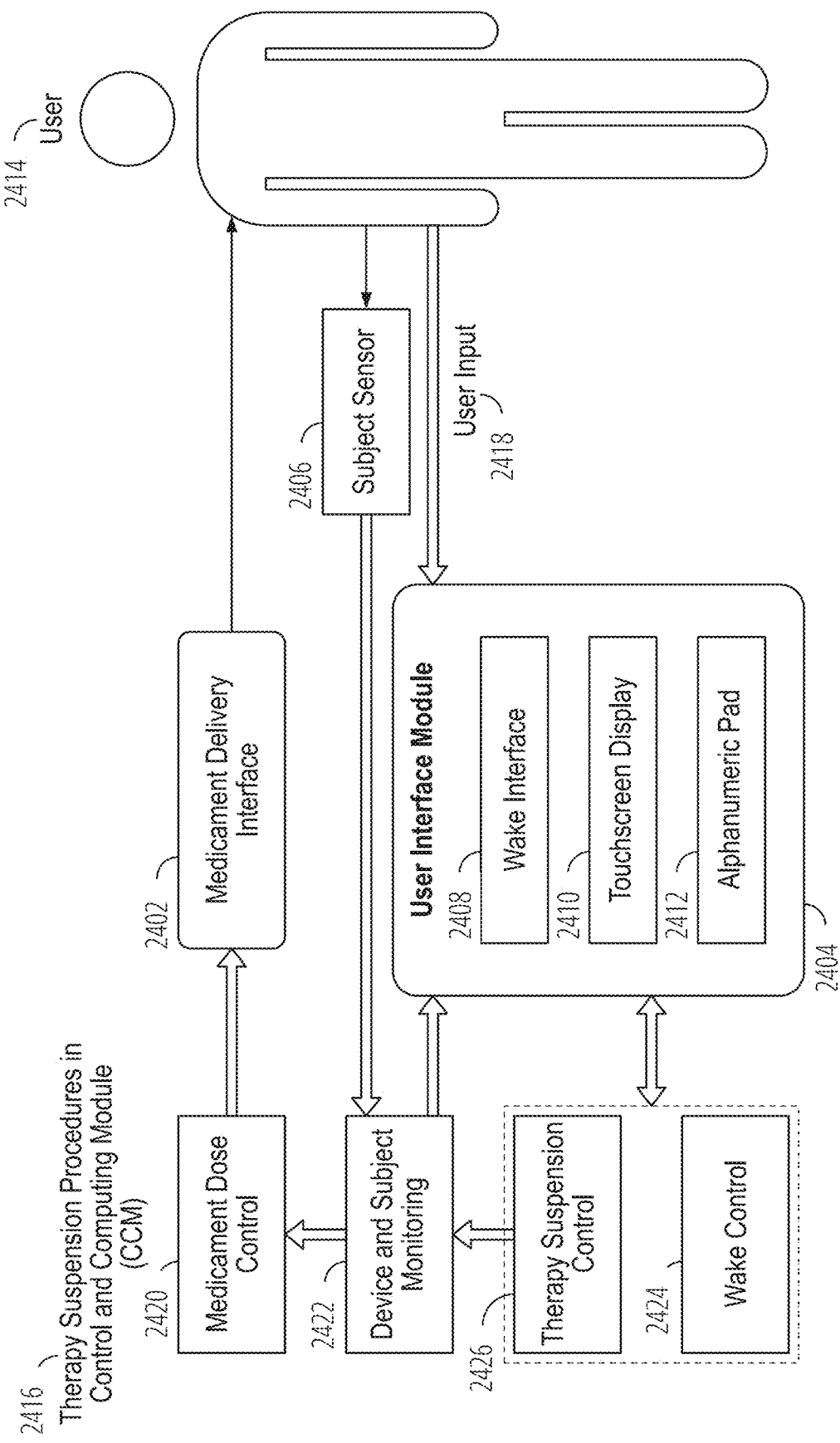
FIG. 24 is a block diagram illustrating the interconnection among modules and procedures in AMD involved in receiving, accepting and/or canceling a therapy suspension request.

FIG. 24 illustrates the interconnection among modules and procedures involved in receiving, accepting and/or canceling a therapy suspension request, in an example AMD. In some embodiments, a request for suspending one or more therapies (e.g., delivery of one or more medicament to the subject) can be made by a user 2414 by providing a user input 2418 (e.g., the start and stop time for therapy suspension, selecting the type of therapy that should be suspended, and the like), through a therapy suspension user interface provided by the user interface module 2404. The therapy suspension user interface sends the suspension request along with the corresponding information to CCM wherein the therapy suspension control procedure 2426 implemented in CCM, processes and sends a therapy suspension signal to the device and subject monitoring procedure 2422. To prevent therapy suspension request user inputs 2418 that are inadvertent, the therapy suspension control procedure may include a therapy suspension request verification procedure to verify the therapy suspension request.

The device and subject monitoring procedure 2422 may be implemented in the control and computing module 2416 to monitor the status of the AMD (e.g., therapy delivery configuration) and the health condition of the user 2414 (or a subject). For example, when the device and subject monitoring procedure 2422 receives the request for therapy suspension, it may send a signal to the medicament dose control procedure 2420 indicating that no does control signal should be send to the medicament delivery interface 2402 during the period request by the user 2414. In some cases, if during the suspension period, certain pre-set conditions are satisfied, the device and subject monitoring procedure 2422 automatically resumes the therapy delivery by sending a signal to the medicament dose control procedure 2420. For example, if during the suspension period the subject sensor 2406 detects an elevation of the level of one or more analytes in subject's blood and/or interstitial fluid beyond a set threshold, it may resume the medicament delivery to the user 2414 by a sending a dose control signal to the medicament delivery interface 2402.

In order to prevent inadvertent activation of a suspension, the user may initiate a therapy suspension request starting with a wake action (e.g., received by the wake interface 2408 and processed by the wake control procedure 2424), that activates the user interface module 2404. Using a first interaction with a user interface (e.g., a touchscreen display 2410 or alphanumeric pad 2412) the user may unlock a therapy suspension user interface where the information pertaining therapy suspension is provided. Next, the user may confirm the requested therapy suspension using a second interaction with the user interface. In some examples, the system may allow access to the therapy suspension user interface and accept the suspension request, when the first and second interaction with the user interface are verified by the therapy suspension control procedure 2426.

In some examples, the therapy suspension control procedure 2426 may receive the request for suspension and suspension information from another device connected to the ambulatory medical device 600 (e.g., through the communication module).

The suspension information provided by the user may include a set of parameters needed for a suspension. For example, the suspension information may include the dates and/or times for starting and ending the therapy suspension, threshold values needed to define a threshold condition that may trigger an early resumption of the therapy delivery, and the like. In some other examples, suspension information may indicate that the suspension of therapy should happen at a particular time or after a particular event (e.g., after the next dose of medicament is delivered or after the condition of the subject reaches a particular state, such as the middle of a desired blood glucose range). In some examples, the threshold values may be associated with input provided by the subject sensor 2406 or other types of sensors that may be used to monitor one or more parameters associated with the health condition of the user 2414.

The parameters for a suspension may include the start and stop conditions for a suspension. The start condition for a suspension may be a condition that, when met, activates a suspension. In some such examples, the start condition is met when a timer runs out. Similarly, the stop condition is a condition that, when met, ends the suspension. In one example, the stop condition is met when a timer runs out. In another example, the stop condition is met when a threshold is met. A threshold may be related to a measurement taken by ambulatory medical device (e.g., by a subject sensor 2406), such as a glucose concentration of the blood of a user. The threshold may be met if the glucose concentration goes above, goes below, or matches a set concentration. Multiple conditions may be set by the suspension request interface component. For example, a time condition and a threshold condition may be set simultaneously. A user may specify that a suspension will end after a set time. However, the suspension may end sooner than the set time if the glucose concentration of the user meets a threshold.

In some cases, the request to suspend therapy may include an indefinite suspension period. In other words, the request may not include a time period specified by a user or an identity of a resumption condition. In some other cases, the indication may include a request to temporarily suspend delivery of therapy for a defined period of time or until a further interaction or event occurs. Thus, the resumption condition can include an expiration of time or an active event (e.g., a command or a determined condition of a subject). Further, the therapy to be suspended may include any type of therapy. For example, the therapy to be suspended may be the suspension of the delivery of medicament, which may include insulin, counter-regulatory agent (e.g., Glucagon), or both insulin and a counter-regulatory agent. In some cases, the ambulatory medicament device may be capable of and/or configured to administer multiple medicaments (e.g., both insulin and a counter-regulatory agent). In some such cases, the request to suspend therapy may include a request to suspend one (e.g., insulin or the counter-regulatory agent) or both of the medicaments.

The interactions with the user interface may include the selection of an icon, a series of taps or inputs, one or more gestures (e.g., a swipe or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds. In some cases, a visual guide may assist the user in generating the user interaction. For example, one or more arrows or images may be presented to the user to guide the user in providing the command to suspend the delivery of therapy.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a therapy suspension user interface, or confirms a suspension request may be the same or may differ.

In an exemplary embodiment, the system may have a time-out such that if no interaction occurs for a set period of time at each step during the therapy suspension request process, the user interface will turn off and the therapy suspension request process has to start again. In one implementation of the time-out, if no interaction occurs for more than 30 seconds after the system is waked/unlocked before the second user interaction is received by the user interface, the user interface will be deactivated.

Figure 25:
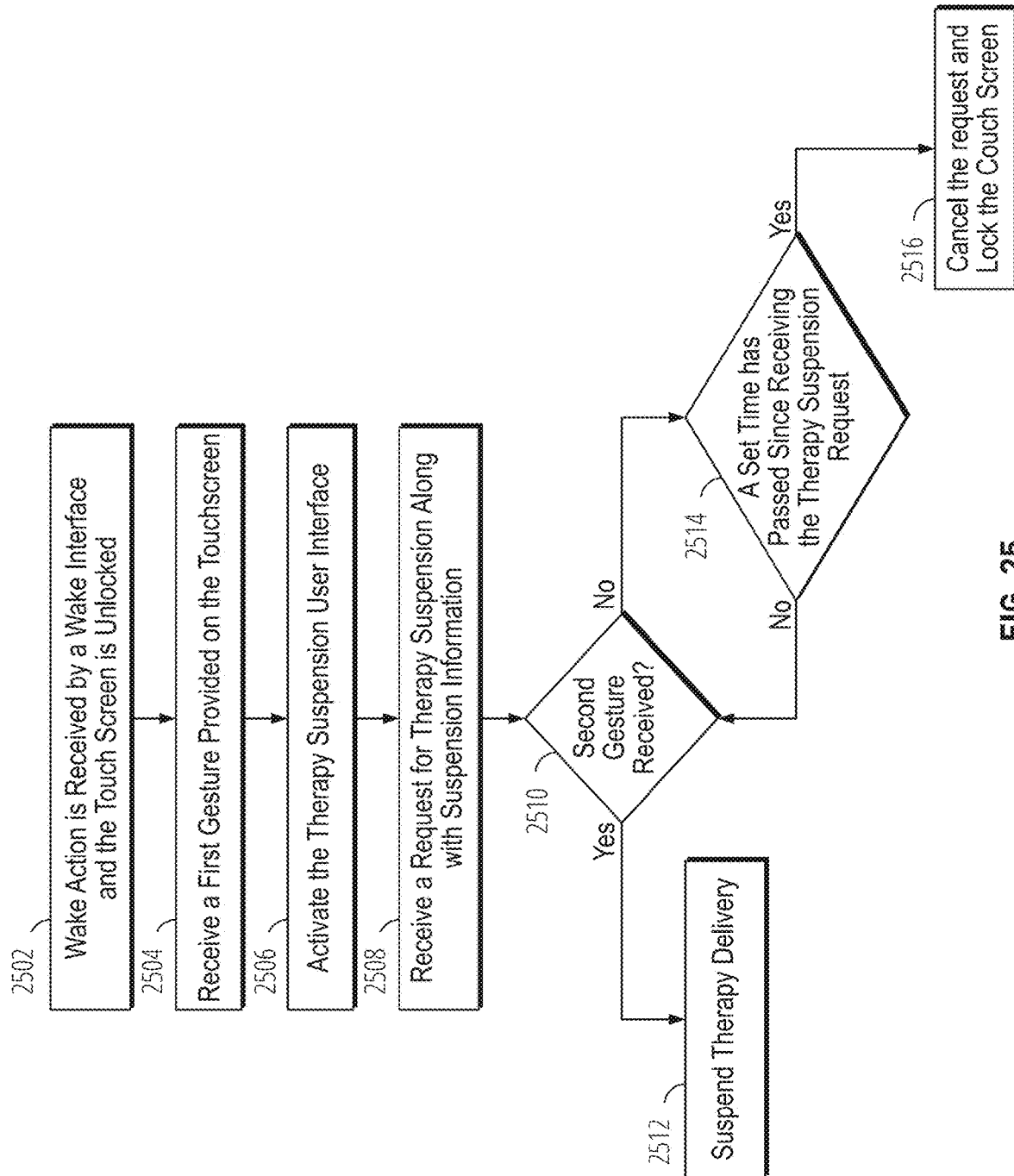
FIG. 25 is a flow diagram illustrating an example method for receiving and implementing a suspension request, which may be implemented by an AMD

FIG. 25 is a flow diagram illustrating an example method for receiving and implementing a suspension request, which may be implemented by an AMD. In this example the user may use a touchscreen interface to request and confirm a therapy suspension. Once the user activates the touchscreen using a wake action 2502, the AMD may wait for a first gesture on the touchscreen. After the user provides the first gesture and the gesture is verified by the therapy suspension control procedure 2426, a therapy user interface may be activated 2506 where the user can request a therapy suspension and provide 2508 the suspension information (e.g., a start day/time and stop day/time and/or a resumption condition). Next, the AMD may wait for second gesture on the user interface 2510. If the second gesture is received and verified by the therapy suspension control procedure 2426, the therapy delivery will be suspended 2512. If the second gesture is not received or not verified by the therapy suspension control procedure 2426, the therapy suspension control procedure 2426, may determine if a set time has passed since receiving the therapy suspension request 2514. If it is determined that a set time has passed since receiving the therapy suspension request, the request will be canceled, and the touch screen will be locked 2516. If it is determined that time from receiving the therapy suspension is less than a set time the AMD may wait for the second gesture to be received.

In some examples, once a wake action is received 2502, the AMD may automatically activate a therapy suspension user interface 2506, without the need for a first gesture 2504. In these examples, once the request for therapy suspension is received 2508, a gesture (e.g., a first gesture) may be required to verify the request. In some such examples, once the therapy delivery is suspended, a second gesture may stop a suspension before any of the conditions of the stop parameter are met. This allows the user the versatility of being able to modify a suspension that has been activated.

Figure 26:
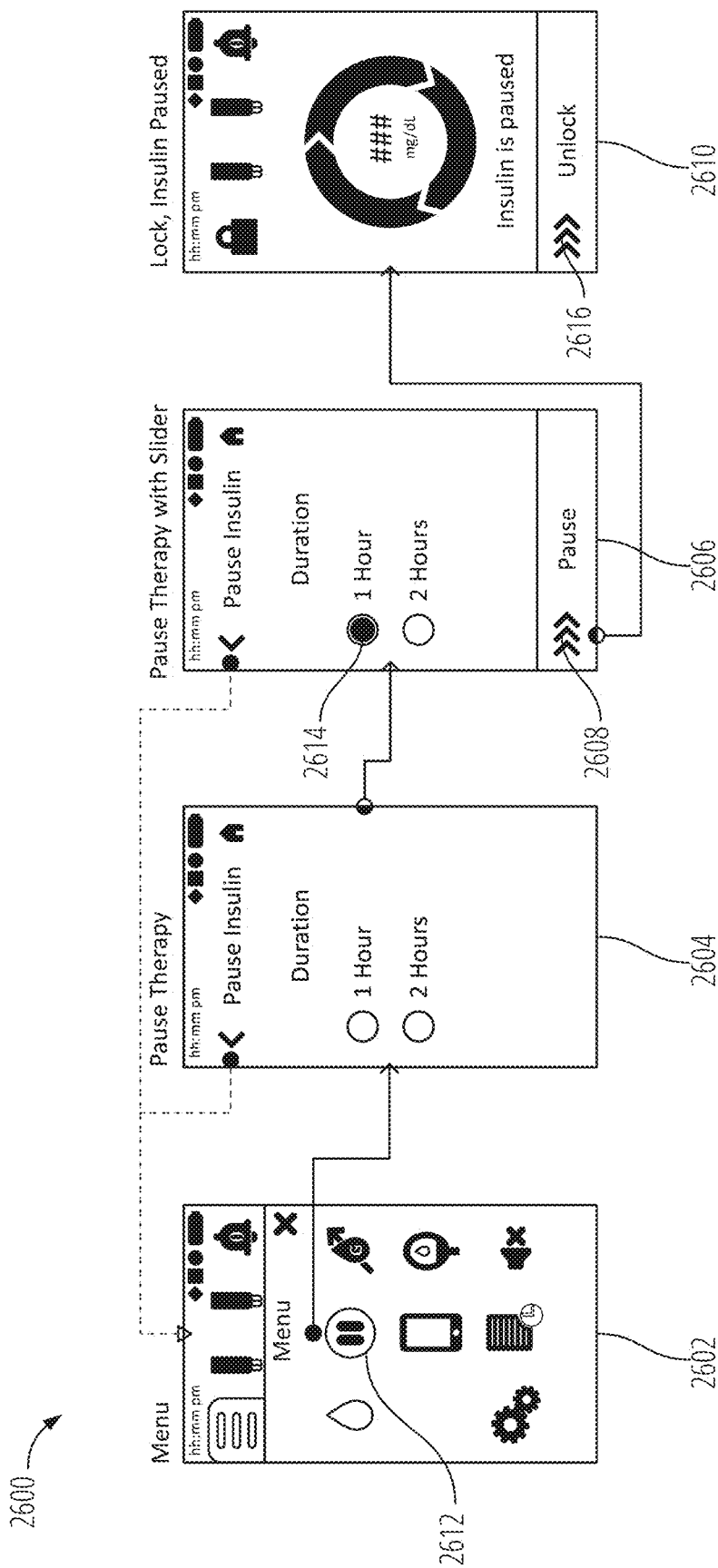
FIG. 26 illustrates a plurality of screens that the ambulatory medical device may display when a user pauses therapy.

FIG. 26 is an illustration of a plurality of screens 2600 that the ambulatory medical device may display when a user activates a therapy suspension user interface. Screen 2602 shows a user interface that an ambulatory medical device may display to a user 2414. The display may be a touchscreen display 2410 that can accept input that includes the first and second gestures. The therapy suspension system (ambulatory medical device 600) is not limited to the displays shown in FIG. 26. Various displays may communicate, to the user 2414, the same information shown in FIG. 26. The screen 2602 allows the user 2414 to select various functions. The pause button 2612, shown on screen 2602 is a function that suspends the delivery of a medicament to the user 2414. When the pause button 2612 is selected, the user 2414 is treated to the pause screen 2604. The pause screen 2604 allows the user 2414 to select a duration of the medicament suspension. The ambulatory medical device 600 may display various interfaces to allow the user 2414 to select a duration of the medicament suspension. The pause screen 2604 shows a simple interface, giving the user 2414 one of two duration options.

When the user 2414 has made a selection of the duration of the medicament suspension on the pause screen 2604, the pause screen 2606 shows the user 2414 the duration 2614 that the user 2414 selected (e.g., in the figure the user 2414 selected 1 hour. Thus, the medicament delivery is suspended for 1 hour after the suspension begins). The pause screen 2606 has a prompt 2608 for the user to make a gesture to confirm the requested suspension before the medicament suspension begins. As shown by the prompt 2608, the user 2414 is being prompted to swipe right across the bottom of the screen. Once the user 2414 performs the gesture to begin the medicament suspension, the suspension screen 2610 is displayed on the touchscreen. The suspension screen 2610 informs the user 2414 that the medicament is paused. The user 2414 has the option of performing another gesture to unlock the ambulatory medical device. The prompt 2616 for the user 2414 to unlock the device forces the user to perform another swipe to execute more functions on the ambulatory medical device 600.

Suspending the medicament delivery may occur by not generating a dose control signal to deliver a dose of medicament. Alternatively, or in addition, suspending the medicament delivery may occur by sending a signal to the medicament pump to cease providing therapy or medicament to the subject.

In some cases, the ambulatory medicament device may not immediately suspend therapy upon receiving a command to suspend therapy. For example, if the ambulatory medicament device is in the process of delivering medicament or determines that a condition of the subject indicates that medicament may soon be required to maintain the subject's condition (e.g., blood glucose) within a particular state (e.g., within a desired blood glucose range), the suspension of therapy may be delayed until at least such time that medicament is not being delivered, is predicted to not be required during the suspension period, or the next therapy has been delivered. In some such cases, the ambulatory medicament device may inform that user that the suspension of therapy is being delayed. Further, the ambulatory medicament device may indicate the reason for the delay. In some cases, the user may be able to override the delay and request immediate suspension of therapy. For example, if the user is replacing the medicament cartridge, the user may override an indication that the suspension of therapy should be delayed. In some cases, the requested start time may be overridden by a determined condition of the subject.

The suspension of therapy or the suspension of the delivery of medicament may continue until a resumption condition occurs. In certain cases, when a resumption condition is met, the suspension period may automatically end without action by the user or subject.

The resumption condition may include the expiration of a time period, a command from a user (e.g., the subject), detection that the ambulatory medicament devise satisfies a condition (e.g., that medicament has been refilled), that the condition of the subject meets certain criteria (e.g., the subject's blood glucose level drops below a threshold range or rises above a threshold range), or any other condition that may satisfy the reason for suspension of therapy or that overrides the request for suspension of therapy. For example, the drug delivery device may be configured to automatically resume drug delivery when a glucose threshold is reached or exceeded. This threshold could be set to 300 mg/dl for example. The resumption condition may include detection of an impending risk of hypoglycemia or hyperglycemia, or a hypoglycemia or hyperglycemia event. Further, the resumption condition may include a meal announcement, or an "exercise concluded announcement," a motion sensing event, a pause of other administered medicament, a conclusion of an undefined suspension length (e.g., during cartridge change), a speed-based resumption event, a location-based resumption, a remote resumption in case of an emergency (e.g., commanded from caregiver admin software or clinician), or any other type of resumption event. In some cases, the resumption condition can include a combination of criteria.

In some cases, automatically resuming therapy may include discontinuing the suspension of therapy before the expiration of the suspension period. For example, if a condition that caused therapy to be suspended is resolved prior to the expiration of the suspension period, therapy may be resumed.

In some cases, when a resumption condition (provided by the user) is met, the ambulatory medicament device may confirm that one or more additional conditions of the ambulatory medicament device are satisfied before therapy is resumed. For example, if the ambulatory medicament device determines that medicament has not been refilled or if there is a problem with the refill (e.g., cartridge is incorrectly installed), the ambulatory medicament device may continue to maintain the suspension of therapy despite the trigger to resume therapy.

In some examples, a therapy suspension may be ended if a third interaction with a user interface (e.g., a gesture) is detected. The third user interface interaction may be detected by the user interface module 2404 and sent to the therapy suspension control procedure 2426. If the therapy suspension control procedure 2426 verifies that third interaction with the user interface is a predetermined third user interface interaction, it may send a signal to the device and subject monitoring procedure 2422 to activate the medicament dose control procedure 2420. This allows the user the versatility of being able to end a suspension that has been activated, during the suspension period set by the user before the confirmation (second interface with the user interface). In some cases, a user may decide to end a therapy suspension to modify one or more suspension conditions set prior to activation of the current therapy suspension. In some other examples, user may decide to end a therapy suspension due to change in user's health condition not included in one or more therapy resumption conditions provided before activating the current therapy suspension.

Figure 27:
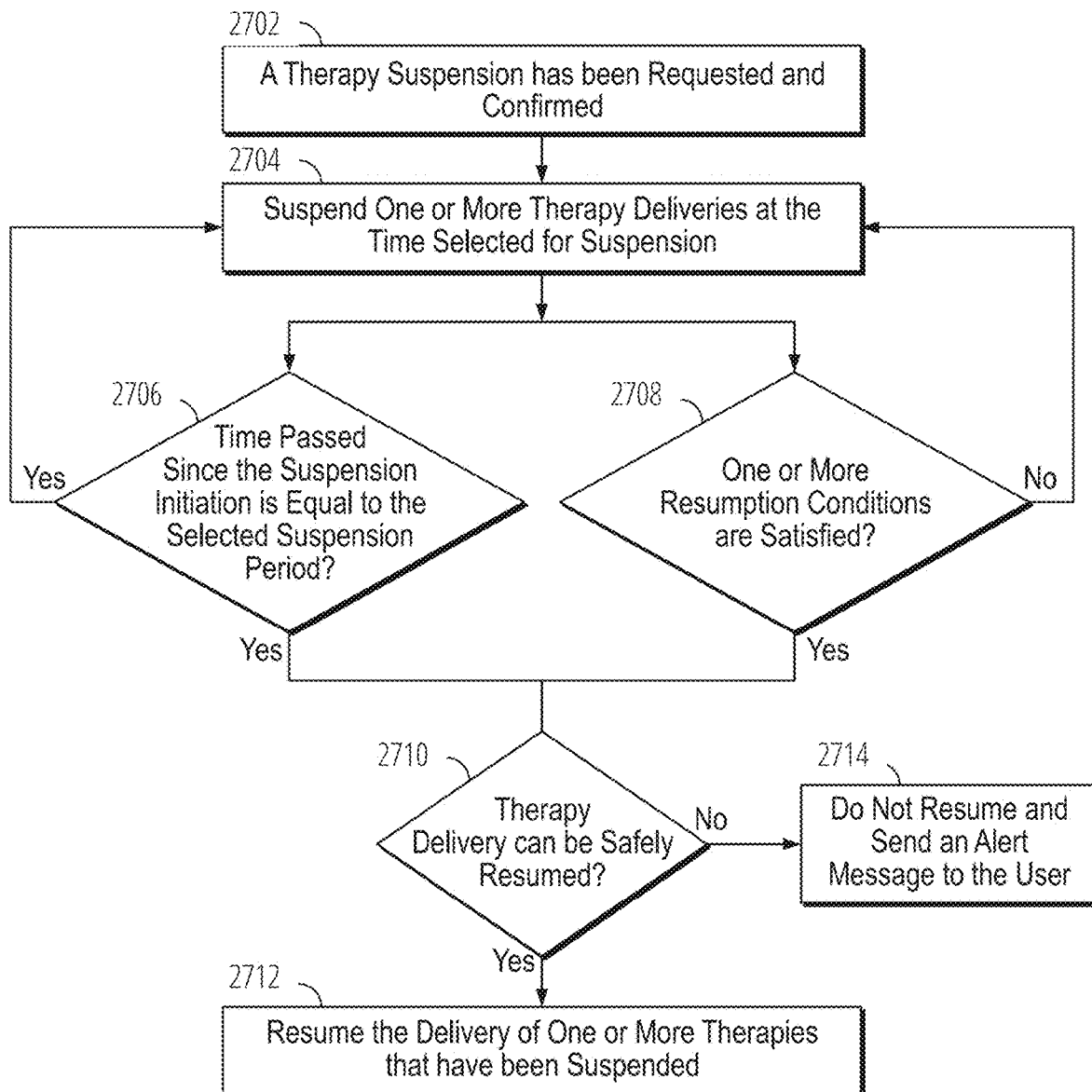
FIG. 27 is a flow diagram illustrating an example method of resuming a suspended therapy that may be implemented by an AMD.

FIG. 27 is a flow diagram illustrating an example method of resuming a suspended therapy that may be implemented by an AMD. Once a therapy suspension has been requested and confirmed by a user (e.g., using the procedure illustrated in FIG. 10) 2702, the AMD suspends one or more therapies selected for suspension 2704 at suspension initiation time received as part of the suspension information. For example, therapy suspension control procedure 2426 deactivates the medicament dose control procedure 2420 using the device and subject monitoring procedure 2422. During the suspension period, the therapy suspension control procedure 2426 continuously monitors the system clock and the subject and device condition (e.g., using medicament dose control procedure 2420).

If the therapy suspension control procedure 2426 determines that the time passed since the suspension initiation is less than the requested suspension time period 2706 and none of condition for resumption has been met 2708, the therapy suspension continues.

If the therapy suspension control procedure 2426 determines that the time passed since the suspension initiation is equal to the requested suspension time period 2706, or one or more resumption conditions have been met 2708, it may check other AMD or subject conditions (not included in the therapy suspension information), in order to determine whether the therapy delivery can be safely resumed 2710. If it is determined that the therapy delivery cannot be safely resumed, an alert message will be sent to the user interface to inform the about the reason for such determination 2714. If it is determined that the therapy delivery can be safely resumed, the one or more suspended therapies will be resumed 2712.

Figure 28:
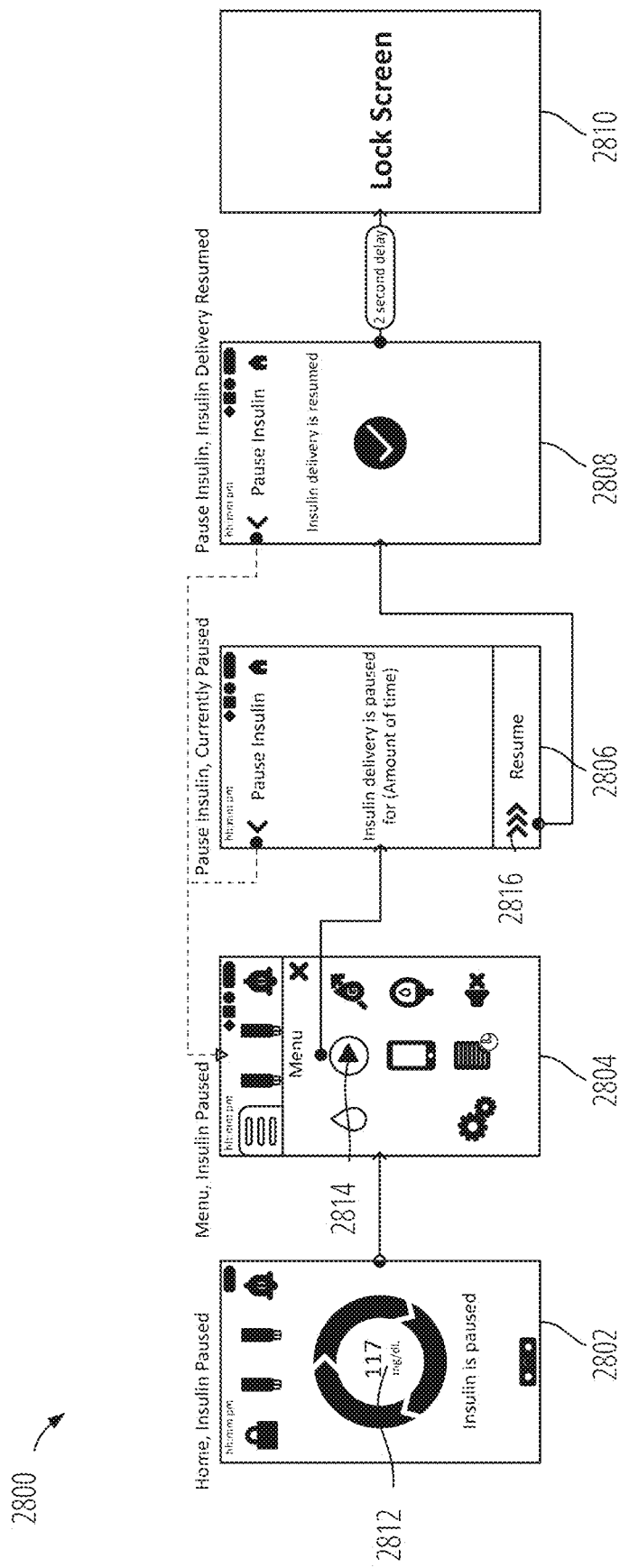
FIG. 28 illustrates a plurality of screens that the ambulatory medical device may display when a user resumes therapy.

FIG. 28 is an illustration 2800 of a plurality of screens that may be displayed, for example, on a touchscreen display when a user 2414 resumes a suspended therapy. Screen 2802 informs the user that the delivery of medicament is currently in a suspended mode. The screen 2812 also shows the user 2414 the current glucose concentration of the blood of the user 2414. The ambulatory medical device 600 may display various vital measurements that are useful to the user 2414. In one implementation, the medicament suspension ends if the glucose concentration of the blood of the user meets or passes a threshold.

The interface screen 2804 allows the user 2414 to select and execute various functions on the ambulatory medical device 600. The resume button 2814 is a function that ends a medicament suspension. When the resume button 2814 is selected, the ambulatory medical device 600 displays a resume screen 2806. The resume screen 2806 has a prompt 2816 that prompts the user 2414 to perform a gesture. In the examples shown, the user 2414 receives a prompt 2816 in the resume screen to swipe right across the bottom of the resume screen 2806. The requirement to perform the gesture to resume medicament delivery prevents the user 2414 from inadvertently resuming medicament delivery in the ambulatory medical device 600.

Once the user 2414 performs the gesture to resume medicament delivery, the medicament suspension ends. The resumption screen 2808 shows the user 2414 that the regular medicament delivery has resumed. Once the resumption screen 2808 has been displayed to the user 2414 for a sufficient amount of time to inform the user 2414 that the suspension is ending, the ambulatory medical device 600 may display a lock screen 2810. The lock screen 2810 prevents the user 2414 from inadvertently executing more functions on the ambulatory medical device 600.

In one embodiment, the ambulatory medical device 600 may end the suspension before the one or more conditions to end the suspension are met, when it receives a second gesture. The purpose of the second gesture is to ensure that the user 2414 does not inadvertently end the suspension. Like the first gesture, the second gesture may be simple or complex.

With reference to FIG. 24, once the AMD device is instructed to resume therapy and/or determines that therapy is to be resumed, the ambulatory medicament device may determine whether a dose of medicament should be supplied to the user based on a control algorithm used by the ambulatory medicament device to control the provisioning of medicament to the subject. For example, the therapy suspension control procedure 2426 may determine a resumption condition has been satisfied or receive a user input from the user interface module 2404 (a third interaction with a user interface) indicating that therapy suspension should be ended. Subsequently the therapy suspension control procedure 2426 may send a signal to the device and subject monitoring procedure 2422 to activate the medicament dose control procedure 2420. If medicament is to be supplied, the medicament does medicament dose control procedure 2420 may generate and send a dose control signal to the medicament delivery interface 2402.

In some cases, the ambulatory medicament device may alert the user and/or the subject that therapy is being resumed. This alert may occur before generating a dose control signal and/or after a resumption condition is satisfied (e.g., a suspension time expires). In some cases, the user may request that the suspension of therapy end early. The user may request the early resumption of therapy be interacting with the aforementioned user interface using one or more of the previously described interaction methods (e.g., gestures or taps).

Additional embodiments relating to suspending medicament delivery to a subject that can be combined with one or more embodiments of the present disclosure are described in U.S. Provisional Application No. 62/910,970, which was filed on Oct. 4, 2019 and is titled "METHOD FOR SU SPENDING DELIVERY OF A DRUG INFUSION DEVICE WITH AUTOMATIC RESUMPTION OF DELIVERY," the disclosure of which is hereby incorporated by reference in its entirety herein for all purposes.

AMD With Security Functionality

An ambulatory medicament device (AMD), such as, but not limited to, an insulin pump, that provides life-saving treatment to subjects or subjects based on the condition of the subject, may include a user interface (e.g., a touchscreen display) that lets a user to modify the settings of the ambulatory medicament device. The setting may include, but not limited to, a condition that triggers the delivery of medicament to a subject, the quantity of medicament delivered when a condition is met, type of the medicament and the like. The setting may also include features of the AMD that may not be directly related to the medicament delivery (e.g., the screen brightness, an alarm sound, and the like). In some examples, it is desirable to manage access to various settings of AMD in order to avoid inadvertent changes while enabling changes that may be necessary for uninterrupted and proper operation of the AMD. For example, it may be desirable to limit the access to some settings to certain authorized users (e.g., a healthcare provider) while enable access to some other settings other authorized users (e.g., the subject, a guardian or parent of the subject).

In many cases, a healthcare provider can modify the settings of the ambulatory medicament device. However, it is often desirable that a non-healthcare provider modify at least some settings of the ambulatory medicament device. For example, when the ambulatory medicament device runs out of or has below a threshold amount of medicament, it is often desirable that a user be able to refill or change a medicament cartridge without visiting a healthcare provider. In some cases, changing the medicament cartridge may include interacting with a user interface and/or one or more settings of the ambulatory medicament device. Another example of when it is desirable for a non-healthcare user (e.g., a subject, parent, or guardian) to modify settings of the ambulatory medicament device is when the initial settings of the ambulatory medicament device are not providing the desired effect (e.g., sufficient medicament, too much medicament, providing the medicament too slowly or too fast, etc.). In some cases, normal maintenance of the ambulatory medicament device and/or subject may require interaction with the ambulatory medicament device settings and/or controls. For example, negative consequences may begin to occur when an ambulatory medicament device remains connected to a subject at the same site for more than a threshold period of time (e.g., for more than 2-3 days, more than 5 days, more than a week, etc.). Thus, the ambulatory medicament device may need to be periodically moved from one site on the subject to another site on the subject (e.g., from left-side to right-side, from arm to leg, from stomach to back, etc.). The change in site location may require interaction with settings of the ambulatory medicament device (e.g., pausing operation until the site change is completed).

Although, as explained above, there are a number of reasons it is desirable to enable a user other than a healthcare provider (e.g., the subject receiving therapy, a parent, or a guardian) to have access to at least some user settings of an ambulatory medicament device, it is also desirable to regulate access to at least some of the ambulatory medicament device settings. For example, it is generally undesirable that a child (subject or otherwise), or a user below a particular age, have access to ambulatory medicament device settings that could cause harm to the subject if modified. Further, it may be undesirable for certain subjects who have diminished mental capacity regardless of age to have access to at least some ambulatory medicament settings.

The user may be a subject receiving medicament or therapy, or may be another user, such as a clinician or healthcare provider, or a parent or guardian of the subject. In some examples, the passcode required for changing one or more setting via an intermediary device may be different that the passcode required for changing the same settings directly using the AMD's user interface.

One solution to regulating access to settings of the ambulatory medicament device is to implement a lock feature to require that a user provide a passcode, a passcode, or other information before the user is permitted to modify a setting of the AMD, such as a control parameter. To simplify discussion, the disclosure will describe using a passcode. However, it should be understood that the passcode can be substituted for a passcode or any other type of secret or semi-secret information. In some examples, when the AMD is in the locked state, it may continue delivering therapy to the subject at the same rate as unlocked state.

The lock feature may be activated by default or may be activated by a user. In some examples, the lock feature can be enabled through a setting in a control menu of the AMD device provided on a user interface (i.e., touchscreen display). The setting may include an on/off toggle (e.g., a software interface element or a hardware interface element) so when the toggle is on, a passcode (e.g., 4 to 8 numeric digits) may be required. In some cases, if the lock feature is on, the passcode (e.g., a 4 to 8 numeric digit code) may be required to turn the lock feature off. When the lock feature is activated, the user may program the ambulatory medicament device with a user passcode selected by the user. Alternatively, or in addition, the user passcode may be set in response to a passcode change request. In some cases, a user passcode may expire. In such cases, a user may be required to generate a new passcode after the previous passcode expires or before the previous passcode is permitted to expire. In other cases, the ambulatory medicament device may periodically generate a new passcode (e.g., an override passcode), or may generate the passcode at a time when a user supplies the passcode.

In some cases, the user interface element used for accessing a user interface that enable changing one or more settings of the AMD may differ from the user interface for modifying the control parameters associated with that setting. For example, a keypad may be used to enter a passcode for unlocking a user interface for changing a control parameter and a touchscreen may be used to modify the control parameter.

When the lock feature is enabled, the user interface screen may look and function the same as if the lock feature were not enabled. If the lock feature is enabled, when a visual guide for unlocking the device (such as, for example, a linear unlock slider, an arcuate unlock slider, or another unlock user interface element) is activated, a passcode entry interface (e.g., a keypad user interface element) may be displayed. If either the user passcode or the global override passcode is entered, the user interface may proceed as normal. Otherwise, the user interface may revert back to the original lock screen.

In some examples, the user action that permits a user to change one or more settings of the AMD may be different from the wake action that activates a user interface. For example, a wake action may be used to activate a touchscreen display that may display a plurality of user selectable elements some of which may be accessible without a passcode. In such examples, a subset of the user selectable elements, for example those allowing the user to change therapy control parameters, may require a passcode. In some cases, access to each user parameter control element may require a different passcode. In some other examples, providing a passcode may to an AMD in locked state, may directly enable access to a subset of control parameter elements.

To help recall the passcode, the passcode may be set by the user enabling the user to select a passcode the user is more likely to remember. However, regardless of who sets the passcode, there is a risk that the user will not remember the passcode. Due to the nature of the device (e.g., a device that may provide life-saving treatment), it is desirable that certain users not be restricted from accessing particular settings of the ambulatory medicament device, and be able to quickly (e.g., within seconds, minutes, prior to a next therapy event, or before harm may occur to the subject) obtain access to the particular settings when required. Thus, while some non-medical devices may implement lockout periods or other restrictions to prevent a malicious user from trying to brute-force determine a passcode for a device, such features are generally undesirable for an ambulatory medicament device. Accordingly, embodiments disclosed herein include an ambulatory medicament device that includes an override passcode that enables access to the ambulatory medicament device (or control settings thereof) regardless of whether the user passcode is provided.

In some examples the passcode or the override passcode can be a series of taps, series of inputs, a complex or a simple gesture (e.g., a swipe or other movement across the touchscreen), The series of inputs may be any combination of touch movements, touch points, numerical characters, alphabetical characters, and other symbols. In some examples, the time that the series of inputs are entered may also be a part of the range of parameters. For example, a series of inputs may need to be entered in no less than 3 seconds or more than 3 seconds, and no more than 15 seconds or less than 15 seconds. One example of the complex gesture is a swipe.

In some other examples the passcode or the override passcode can be a complex or a simple gesture (e.g., a swipe or other movement across the touchscreen), performing a pattern or sequence on the touchscreen (e.g., drawing an image), a multi-touch interaction, a combination of the foregoing, or any other type of interaction with a touchscreen, or portion thereof. Another example of a complex gesture is entering a predetermined sequence of touches. In some cases, the passcode may include a quiz or set of questions, In some examples, the ambulatory medicament device may be configured to receive therapy settings or modifications to therapy settings from an intermediary device via a communication connection. In some cases, this feature may be supported in addition to providing the user with option of modifying one or more settings with a user interface of the AMD. The communication connection between the intermediary device and the AMD may be a direct connection via, for example, Bluetooth®, or a connection via a network, such as over a local area network or a wide area network. In some such cases, the ambulatory medicament device may include a wireless transceiver, such as an NB-LTE transceiver, a Wi-Fi transceiver, or a Bluetooth transceiver. The intermediary device, that provides the user with a user interface to modify settings of the AMD, include any type of device (e.g., a computing device) that can communicate with an ambulatory medicament device. For example, the intermediary device may be a laptop or desktop computer, a smartwatch, a smartphone, or a hardware control device that may be configured to interact with the ambulatory medicament device. Embodiments disclosed herein are applicable regardless of whether the user interface for modifying therapy settings or the configuration of the ambulatory medicament device is generated or presented by the ambulatory medicament device to the user or via another device. In some such cases, a user may provide a user-generated passcode or an override passcode via an interface of the computing device. The computing device may then provide the user-generated passcode or the override passcode to the ambulatory medicament device via the network connection between the devices.

In some examples, even if the AMD is in locked state, certain intermediary devices may have access to user interfaces that may be used to change one or more settings (e.g., therapy settings) of the AMD. For example, the smart phone of a guardian or a parent of the subject may be used to change one or more settings of the AMD while the AMD is in the locked state.

In some examples, the AMD may be configured to receive a passcode from or via a computing systems (e.g., a cloud computing system). In these examples, the AMD may receive passcode through a direct end-to-end connection (e.g., a wireless connection over a wide area network) stablished with the computing system. In some such examples, another computing device (e.g., a smartphone, a laptop, a personal computer, and the like) connected to the computing system, may send a passcode to the AMD and be able to change one or more settings of the AMD if the passcode is validated by the AMD.

In cases where the user cannot recall the user passcode, the user can obtain access to the user interface that permits modification of the control parameter by supplying an override passcode. In some examples, the override passcode may be a universal fixed passcode (e.g., an 8-digit override passcode) that can be used instead of the user set passcode. The override passcode can be stored in the ambulatory medicament device at the time of manufacture and may be shared among multiple ambulatory medicament devices (e.g., a global override passcode), or may be unique to a particular ambulatory medicament device. The override passcode may be managed by the manufacturer or by a third-party service. To obtain the override passcode, the user may contact the manufacturer or passcode managing service. Generally, enabling the passcode may exist to prevent a user with a diminished mental capacity (e.g., a child) from modifying settings of the ambulatory medicament device. Thus, security may be less of a concern and any user can contact the manufacturer or passcode managing service to obtain the override passcode. In some such cases, a single global override may be used for all devices produced by the manufacturer. However, in some cases, a level of security may be desired. In some such cases, it may be necessary for the user to authenticate him or herself. Further, the user may be required to provide a serial number of the ambulatory medicament device. In some cases, each model or each unit of the ambulatory medicament device may have a different override passcode. The user may provide authorization information and a serial number of the ambulatory medicament device to the manufacturer or passcode managing service to obtain the override passcode.

In some examples, may periodically generate a new override passcode or may generate an override passcode at a time when a user supplies the passcode. In these examples, the ambulatory medicament device may use the same parametric values to generate the override passcode as another device may use thereby ensuring a match between the override passcodes. Advantageously, in some cases, by using an algorithm to generate the override passcode, the override passcode can be obtained regardless of whether a user is able to contact a manufacturer or other passcode managing service. In some cases, the user may generate the override passcode without access to a network or phone using, for example, a computing device that can access a common parameter value as the ambulatory medicament device.

In some cases, the override passcode may change over time or be a rotating passcode. For example, in some cases, the override passcode may change every thirty seconds, every minute, every hour, etc. In some such cases, the override passcode may be determined from an algorithm executed by an application. The ambulatory medicament device may store a copy of the algorithm in a memory of the ambulatory medicament device and may execute the algorithm to determine the override passcode that is currently valid. A copy of the algorithm may be executed by another computing device accessible by the user. The output of the algorithm may be based on a value that is commonly accessible by the ambulatory medicament device and the copy of the algorithm accessible by the computing device. For example, the output of the algorithm may be generated based on a time, a user identifier, a provided value, or any other factor that may be used to repeatedly generate the same output. In some cases, the override passcode may be calculated based on a combination of factors. For example, the override passcode may be calculated based on a portion of a serial number or model number for the ambulatory medicament device and the time. The determination of the override passcode may be calculated by the ambulatory medicament device, a computer server, and/or an application on a user device.

In some cases, the override code can be automatically received by the ambulatory medicament device. Thus, a user may not need to see or enter the override code. In some cases, the override code may be transmitted to another device of the user (e.g., a smartphone or laptop). For example, the override code can be texted to a user's smartphone. In some cases, the override code may be received in a coded manner that may not be understandable by a child or user with diminished mental capacity.

In some cases, the override passcode may be linked to a location. For example, the override passcode may be enterable at a healthcare provider's office or at the subject's place of residence. The determination of the location of the ambulatory medicament device may be based on a geolocation system (e.g., a Global positioning System (GPS)) available to the ambulatory medicament device.

In some examples, at least for a subset of therapy settings, the passcode may provide a second level of security in addition to other interactions with the user interface (e.g., a first and a second gesture on a touchscreen display) that may be used to change the therapy settings and/or accept the change made to a therapy setting. In some other examples, at least for a subset of settings, the passcode may be used instead of other interactions with the user interface (described above).

As mentioned above, interacting with the user interface may cause the ambulatory medicament device, or other device that can modify a control of the ambulatory medicament device, to present a passcode input screen to the user. The user may enter the passcode to unlock additional user interface features including, for example, a user interface that enables the user to modify at least one control parameter of the ambulatory medicament device. The control parameter can be modified based on an interaction with a parameter control element of the user interface. Further, modification of the control parameter may cause modification of the generation of a dose control signal that is generated by a control algorithm based at least in part on the control parameter.

In some embodiments, the ambulatory medicament device may have an advanced therapy screen, or other user interface, that permits a healthcare provider, or other user, to obtain additional details relating to therapy provided by the ambulatory medicament device. Although the advanced therapy screen may generally be intended for a knowledgeable user, such as a clinician, in some cases, any user may obtain access to the advanced therapy screen. The advanced therapy screen may permit the healthcare provider to modify control parameters that may not be modifiable by other users. For example, the healthcare provider may be able to control parameters that relate to the calculation of a rate of insulin accumulation, the rate the insulin diminishes within the blood of the subject, the setting of a glucose setpoint, an aggression level or factor of therapy relating to an amount of insulin provided when the subject's glucose level is outside the setpoint range, or when the insulin reaches a point of maximum concentration within the blood of the subject (e.g., $T_{max}$).

Access to the advanced therapy screen may be limited by requirement of a passcode, which may be referred to as a clinician passcode to distinguish it from the user-generated passcode and/or the override passcode. This clinician passcode may or may not be user-generated. However, the clinician passcode may be a separate passcode from the user-generated passcode that permits access to the non-advanced therapy screen interface. Further, the clinician passcode may be separate from the override passcode that permits a user to override the user-generated passcode to obtain access to the non-advanced therapy screen interface. In some cases, the clinician passcode may be used as an override passcode. In some example the clinician passcode can be valid for period of time (e.g., set by a subject or another authorized user such as the guardian or apparent of the subject). For example, the clinician passcode may be valid for a day, a week, or a month. In some examples, the AMD may allow certain authorized users to terminate the clinician access at any time.

In some cases, access to the advanced therapy screen may be limited to a particular period of time. After the time period expires, the ambulatory medicament device may automatically restrict access to the advanced therapy screen. In some cases, the window of access may be extended. For example, if the healthcare provider is continuing to interact with the advanced therapy screen, the screen may remain accessible.

In some cases, the advanced therapy screen may provide additional features. For example, while a user may be able to indicate that an amount of insulin provided for a meal or as a correction factor should be higher or lower, the healthcare provider may be able to specifically adjust the amount of insulin. Moreover, while a user's direction may or may not be followed depending, for example, if the request exceeds a threshold or may cause blood glucose to not satisfy a setpoint range, an indication provided via the advanced therapy screen may be followed regardless or may have a wider range or different threshold that may control whether the instruction is followed. Further, the advanced therapy screen may be used to temporarily pause therapy and/or may prevent subject access.

In some cases, the manufacturer of the ambulatory medicament device may provide a remote unlock signal that can be used to unlock access to the ambulatory medicament device and/or to an advanced therapy screen of the ambulatory medicament device.

As described above, the passcode may be desired to prevent particular users from inadvertently changing certain control parameters of the ambulatory medicament device. However, features of the ambulatory medicament device that do not affect therapy may remain accessible to a user when the ambulatory medicament device is in a locked state. For example, a user may be able to access therapy history, screen brightness settings or colors, or any other feature that is unlikely to harm a subject if modified in a particular manner. Further, as the passcode feature is generally to prevent control parameter changes, the ambulatory medicament device may provide therapy and continue to provide therapy at the same rate and under the same condition, whether or not the ambulatory medicament device is locked or unlocked.

When the ambulatory medicament device receives the user passcode or the override passcode, the ambulatory medicament device validates the passcode. The passcode may be validated by comparing the received passcode to a passcode stored in a memory of the ambulatory medicament device or generated by the ambulatory medicament device. If the passcode received from the user is successfully validated, the user may be granted access to a user interface to modify one or more control parameters. In some cases, the user may be requested to re-enter a passcode to confirm a change to a control parameter. In some other examples, the user may be requested to provide a gesture on a touchscreen to confirm a change to a control parameter.

If the passcode is not validated, the ambulatory medicament device, or other control device that can provide access to control parameters of the ambulatory medicament device, may prevent access to the user interface to modify the one or more control parameters. In some cases, the user interface that presents the user with the ability to enter the passcode may permit the user a particular number of tries or a particular number of tries within a particular time period to enter the user passcode. If the correct user passcode is not entered within the provided number of tries or within the particular time period, the user interface may enter a lock state (e.g., the screen will be turned off) and prevent further attempts to enter a passcode for at least a period of time. In some cases, the user passcode option may be indefinitely locked or blocked. In some such cases, the control parameters of the ambulatory medical device may be accessible when the override passcode is provided. Alternatively, or in addition, a user passcode of a different user may be used to provide access to the control parameters of the ambulatory medical device. In some examples, if the correct override passcode is not entered within the provided number of tries or within the particular time period, the user interface may block any attempt to change the override passcode for at least a period of time.

In some cases, once the passcode is successfully entered or validated, a user may deactivate the passcode feature of the ambulatory medicament device. Deactivating the passcode feature may require use of a separate passcode or the override passcode in addition to the user passcode.

In some cases, the passcode may be optional or omitted based on the computing device connected to the ambulatory medicament device. For example, if the end-to-end connection is established between a smartphone registered to a particular user (e.g., a parent of the subject), the ambulatory medicament device may unlock automatically without requiring a passcode. In other cases, the smartphone, or other computing device, may automatically provide the user-generated passcode or the override passcode to the ambulatory medicament device upon establishing a connection. In some cases, the ambulatory medicament device may automatically be unlocked when connected to a charger or when in a particular geographic area. For example, a geo-fence may be configured in one or more locations, such as the subject's house or the clinician's office. When the ambulatory medicament device determines it is within the geo-fence, the ambulatory medicament device may automatically be unlocked. Similarly, when the ambulatory medicament device determines that it is not within the geo-fenced region, it may automatically be locked. The determination of the location of the ambulatory medicament device may be made based on a geo-location system, such as the Global Positioning System (GPS).

In some cases, after a certain number of unsuccessful passcodes are entered (e.g., after 5 tries), the user interface screen may be turned off or may accept only the global override passcode.

Example AMD With Security Codes

Figure 29:
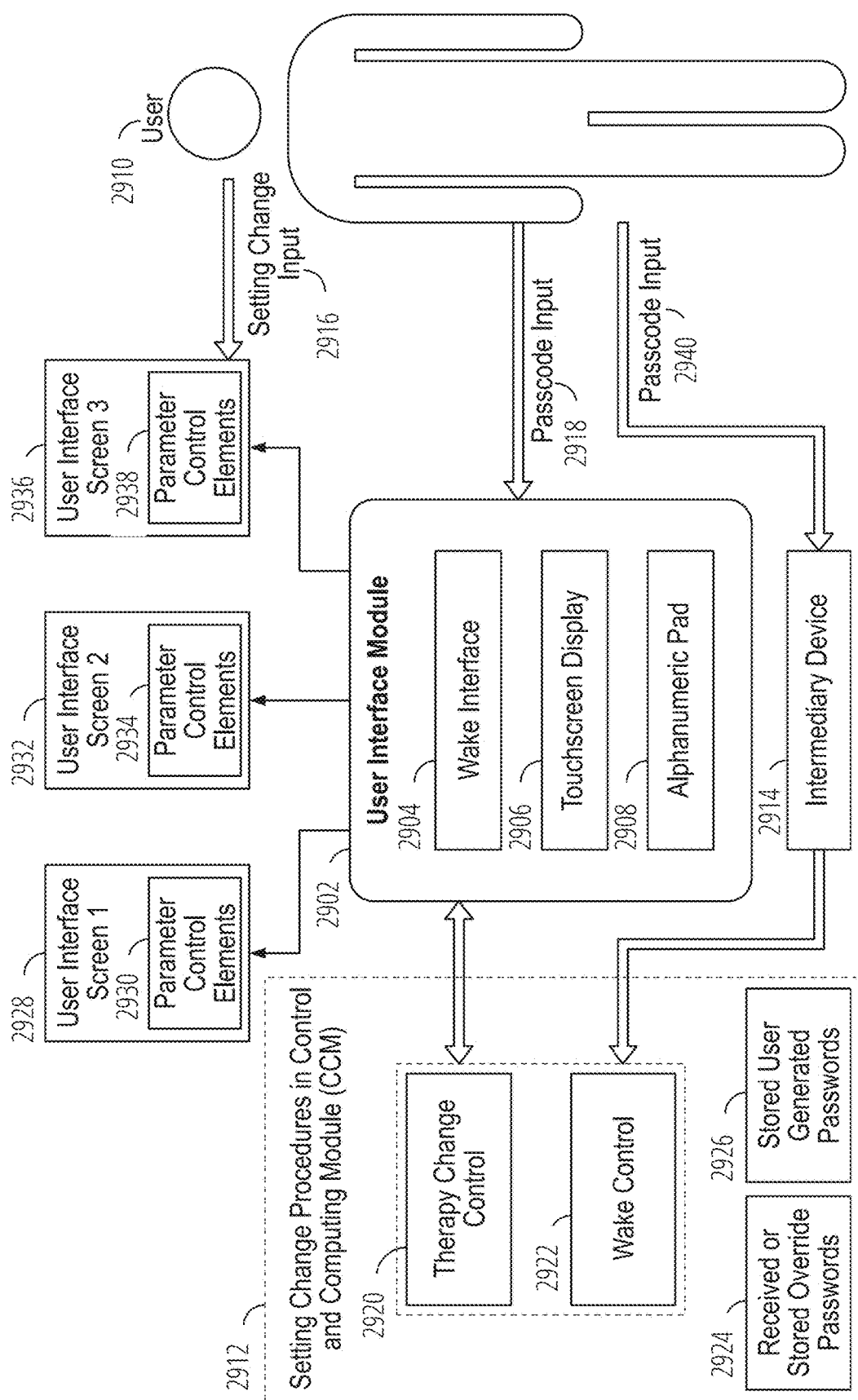
FIG. 29 is a block diagram illustrating the interconnection among modules and procedures in AMD involved in changing the settings of the AMD.

FIG. 29 is a block diagram illustrating the interconnection among modules and procedures in AMD involved in changing the settings of the AMD. In some cases, one or more settings of the AMD may be changed using a setting change input 2916 to one or more parameter control element parameter control elements 2930/2934/2938 presented on one or more setting user interface screens 2928/2932/2936 provided by the user interface module 2902. In some examples, when the lock feature is activated, access to one or more setting control screens 2928/2932/2936 and/or one or more parameter control element 2930/2934/2938, may be protected by a passcode. In order to change a parameter control element 2930/2934/2938, the user may provide a passcode input 2918 (e.g., a user generated passcode or an override passcode), via the user interface module 2902 (e.g., using a touchscreen display 2906 or alphanumeric pad 2908). Alternatively, or in addition, the user 2910 may provide a passcode 2940 using an intermediary device (e.g., a laptop, a smart phone, and the like) that is connected to the AMD (e.g., via a wireless link). In some examples, the access to one or more setting user interface screens 2928/2932/2936 and/or parameter control element parameter control elements 2930/2934/2938, may be managed by setting change procedures 2912 stored in a memory in the control and computing module of the AMD. A hard processor may execute the machine-readable instructions associated with the setting change procedures 2912.

In some examples, the option to provide a passcode may become available, when the user 2910 performs a wake action on a wake interface 2904. In these examples if the wake control procedure 2922 of the CCM determines that a valid wake action is performed, it may present selectable elements associated with the setting user interface screens 2928/2932/2936, for example, on a touchscreen display. In some other examples, the first screen presented on the touchscreen display, may provide other selectable elements including an element to change the settings of the AMD. In such examples, selecting element associated with settings change may activate a second screen that presents selectable elements associated with the setting user interface screens 2928/2932/2936. When the lock feature is activated, access to any of the setting user interface screens 2928/2932/2936 and/or parameter control element 2930/2934/2938 may require a passcode. In some examples, each one of the user interface screens 2928/2932/2936 and/or parameter control element 2930/2934/2938 may require a different passcode. In some other examples, one or more user interface screens 2928/2932/2936 and/or parameter control element 2930/2934/2938 may not require a passcode. For example, access to the first user interface screen 2928 may require a first passcode, the access to the second user interface screen 2932 may require a second passcode and the access to the third user interface screen 2936 may not need a passcode. In yet another examples, all the user interface screens 2928/2932/2936 may be presented without the need for providing a passcode, but access to the one or more control elements in a control screen may require a passcode. For example, the user may select the second user interface screen 2932 without entering a passcode but in order to select one or more parameter control element 2934 on that screen, the user may need to enter one or more passcodes.

In some examples, once a passcode or override passcode received from the intermediary device 2914 or the user interface module 2902, the passcode may be transmitted to the control and computing unit of the AMD where the setting change procedures 2912 (therapy change control procedure 2920 and wake control procedure 2922) determine the validity of the passcode by comparing it to the one or more stored user generated passwords 2926 or received or stored override passwords 2924 stored in a memory of the CCM.

Figure 30:
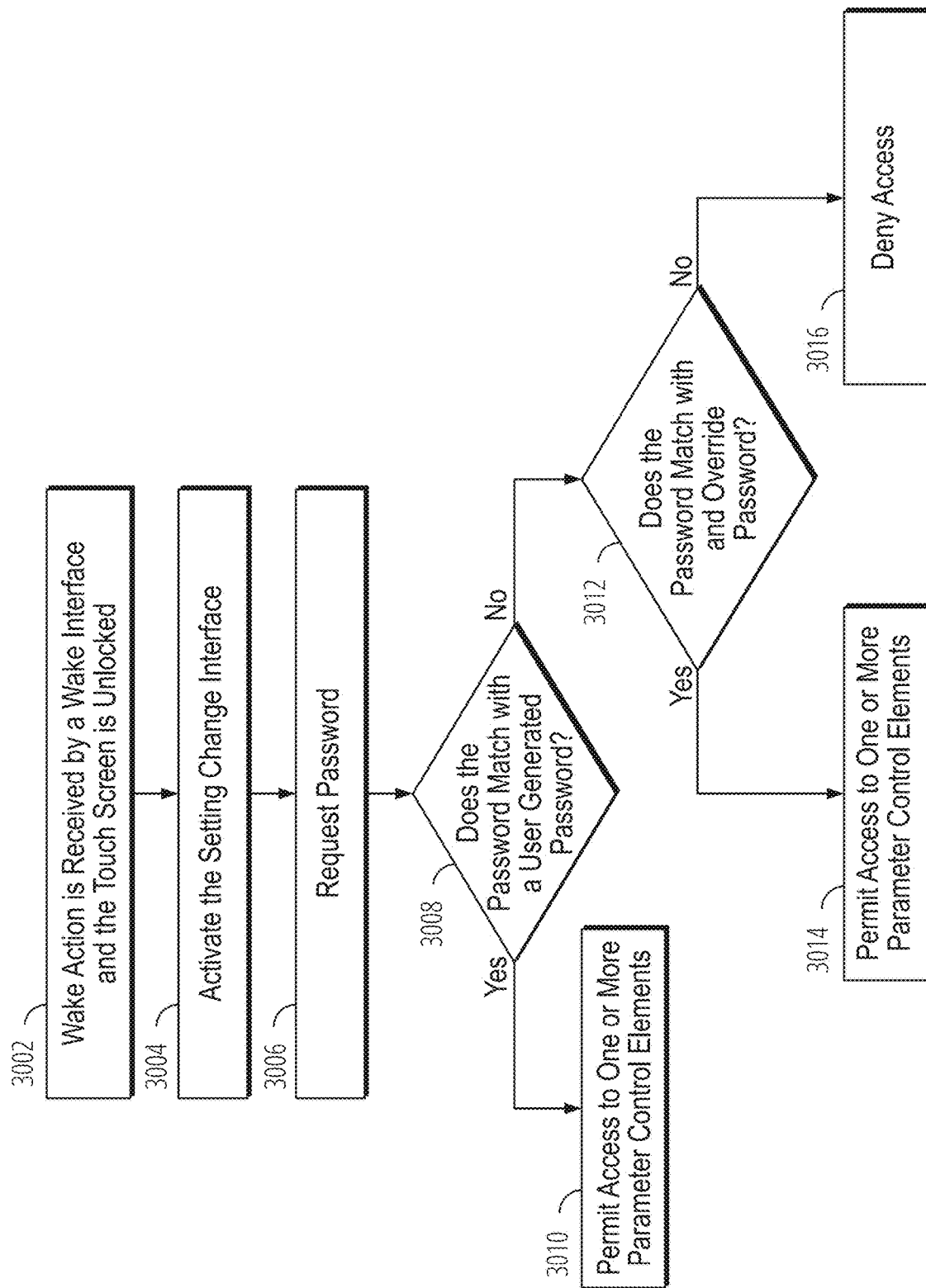
FIG. 30 is a flow diagram illustrating an example method that may be used by an AMD to allow a user to change a setting of the AMD using a user generated passcode or an override passcode.

FIG. 30 is a flow diagram illustrating an example method that may be used by an AMD to allow a user to change a setting of the AMD using a user generated passcode or an override passcode. Once the AMD (e.g., the wake action procedure in the CCM) receives a valid wake action 3002, a user interface may be activated. In some example, the wake action may directly activate a setting change interface 3004 (e.g., a setting change screen presented on a touchscreen display). In some examples, a specific wake action may activate the setting change interface. On the setting change interface 3006, the AMD (e.g., the setting change procedure in the CCM) may request a passcode (e.g., by presenting a window to enter a passcode). Once a passcode is received, the AMD (e.g., the setting change procedure in the CCM) may determine whether the passcode matches a user generated passcode 3008. If it is determined the passcode matches with a user generated passcode, the AMD may provide access 3010 to one or more control parameter elements associated with the received passcode. If the received passcode dose not match with any of the stored user generated passcode, the AMD may determine whether the passcode matches with an override passcode 3012. If it is determined the passcode matches an override passcode stored in a memory of AMD or a memory of an authorized computing device, the AMD may provide access 3014 to one or more control parameter elements associated with the received override passcode. If it is determined the passcode does not matches an override passcode, the AMD denies access 3016 to one or more passcode protected control elements.

Figure 31:
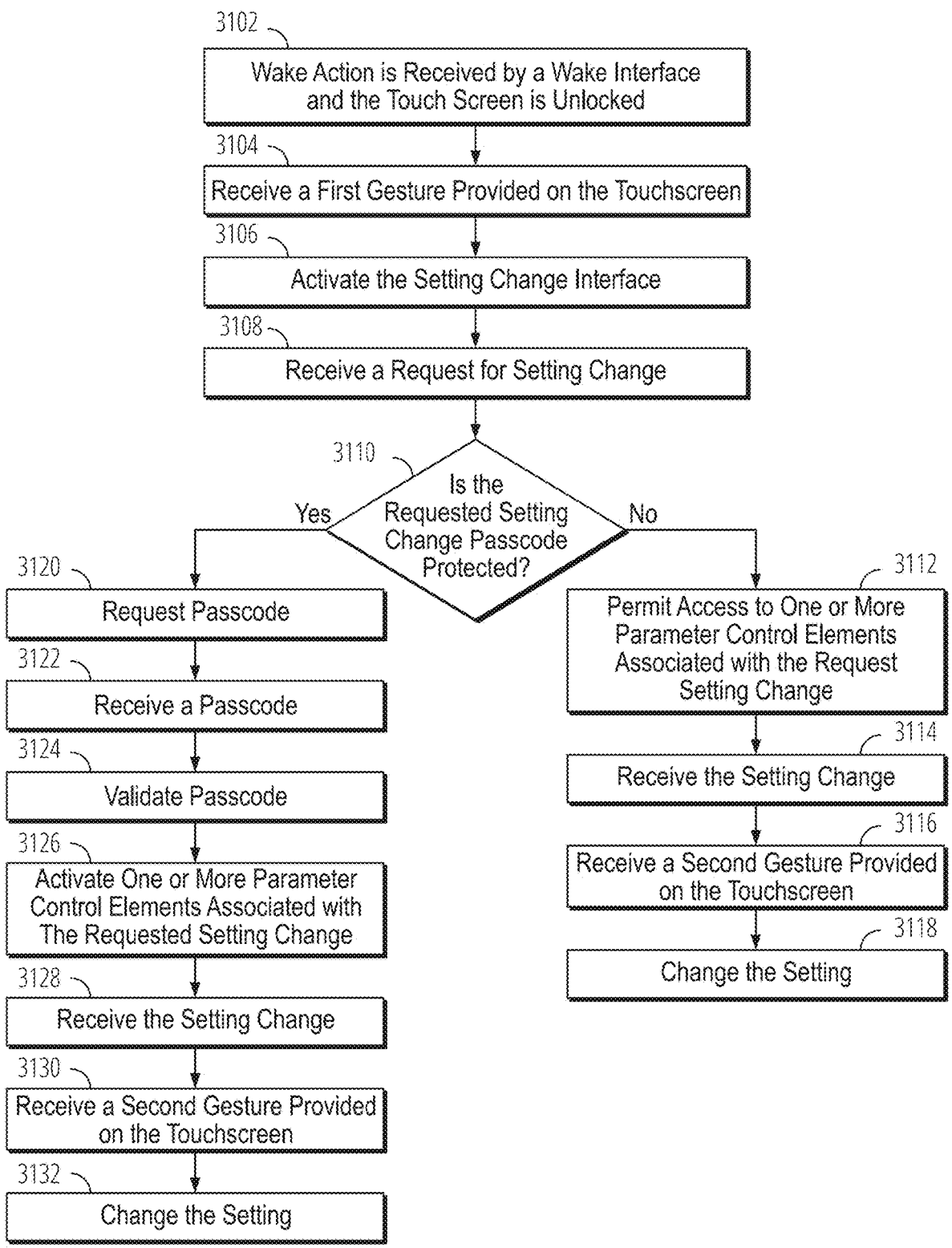
FIG. 31 is a flow diagram illustrating an example method that may be used by an AMD to allow a user to change a setting of the AMD using a user generated passcode or an override passcode.

FIG. 31 is a flow diagram illustrating another example method that may be used by an AMD to allow a user to change a setting of the AMD using a user generated passcode or an override passcode. Once the AMD (e.g., the wake action procedure in the CCM) receives a valid wake action 3102, the AMD may provide a user interface (e.g., a touchscreen display) on which the user can provide a first gesture to activate a setting change interface or screen. When a first gesture is received from a user or subject 3104, the AMD may activate a setting change interface 3106 or a screen. In some examples, the setting change interface or a screen may include one or more parameter control elements associated with one or more settings of the AMD. In some other examples, the setting change interface or a screen may include one or more selectable elements each associated with a setting change screen (e.g., a screen provided on a touchscreen display) that may include one or more control parameters. When a request for setting change is received 3108, the AMD may determine whether the requested setting change is passcode protected or not 3110. In some examples, the request for setting change may include selecting a parameter control element. In some other examples, the request for setting change may include selecting a list of parameter control elements (e.g., included in a separate screen provided on a touchscreen display).

If the AMD determines that the requested setting change is not protected by a passcode, it may permit access to one or more parameter control elements associated with the requested setting change 3112. In some examples, once the changes are received via parameter control elements 3114, the user may need to provide a second gesture on the user interface (e.g., touchscreen display) to confirm the changes made. In response to receiving the second gesture 3116, the AMD may change one or more settings 3118 according to the requested and confirmed changes.

If the AMD determines that the requested setting change is protected by a passcode, it may request a passcode 3120 via a passcode display (e.g., provided on a touchscreen display). In some examples, the request for the passcode may be presented on a display but the passcode may be received via a physical keypad. Once a passcode is received 3122 from the user or subject, the AMD may validate the passcode 3124 by comparing it with one or more user generated passcodes or an override passcode. If it is determined that the passcode matches with a user generated passcode or an override passcode, the AMD may activate 3126 one or more parameter control elements associated with the requested setting change. Subsequently, the AMD may receive a setting change via the selected control parameter element 3128. In some examples, the user may need to provide a second gesture on the user interface (e.g., touchscreen display) to confirm the changes made. In response to receiving the second gesture 3130, the AMD may change one or more settings according to the requested and confirmed changes 3132.

AMD With Alarm System

In some cases, a condition may occur that impacts the operation of the ambulatory medicament device (AMD). This condition may be associated with the ability of the ambulatory medicament device to operate as intended by the manufacturer, a subject receiving therapy from the AMD, and/or user (e.g., healthcare provider, parent, or guardian of the subject). In some cases, the AMD device may be operating as intended, but the condition of the subject may not satisfy a desired level of health. In either case, it is generally desirable to generate an alarm to inform the subject and/or one or more users of the condition of the AMD and/or the subject. Moreover, it is desirable to track the alarm until the condition that caused the alarm is resolved. Further, it is desirable to issue different types of alarms for different conditions to enable a subject or user to easily distinguish the severity of the condition that triggered the alarm. The user may be a subject receiving medicament or therapy, or may be another user, such as a clinician or healthcare provider, or a parent or guardian.

This section of the disclosure relates to an AMD, such as an insulin pump or a combined insulin and counter-regulatory agent (e.g., Glucagon) pump, configured to generate a dose control signal configured to cause a medicament pump to infuse medicament into a subject. Moreover, the present disclosure relates to an ambulatory medicament device configured to detect a condition of the ambulatory medicament device and/or the subject, and to generate an alarm when it is determined that the detected condition satisfies an alarm condition.

As mentioned above, an ambulatory medicament device may include an alarm system configured to monitor the ambulatory medicament device and/or the subject, and to generate an alarm when it is determined that a condition has been detected that satisfies an alarm condition. In some examples, the alarm system may organize an alarm manager list, notify a user of these alarms, and/or allow the user to acknowledge alarms, mute, and/or snooze the alarms. In some examples, the alarm manager list may be a list of pending alarm conditions with which the user can interact using a touchscreen display of the AMD.

In some embodiments, the alarm system may include a plurality of sensors that monitor the AMD or the subject, a monitoring system interface that receives the data from sensors, and alarm generation module that process the received data and generate alarms when an alarm condition is met. In some examples, the monitoring system interface and the alarm generation module are implemented using one or more hardware processors and machine readable. In some other examples, the monitoring system interface and the alarm generation module are separate hardware modules. In implementations, the monitoring system may provide status information received from the plurality of sensors to the alarm annunciation and control system. In some examples, the status information may include one or more status values. In some examples, the status information may include device information pertaining to a condition of the AMD or subject information pertaining to a condition of the subject. In some such examples, the alarm annunciation and control system may be configured to determine based at least in part on the status information received from the monitoring system, whether an alarm condition is satisfied.

As noted above, the AMD may generate an alarm for various situations to notify the user, and further may request a user's acknowledgement to confirm that the user is aware of the current situation to be resolved. The alarm can be generated in various forms to the user in a way that the user can recognize the situation and condition of the alarm or alarms, thus allowing convenient communication between the user and the AMD.

Figure 32:
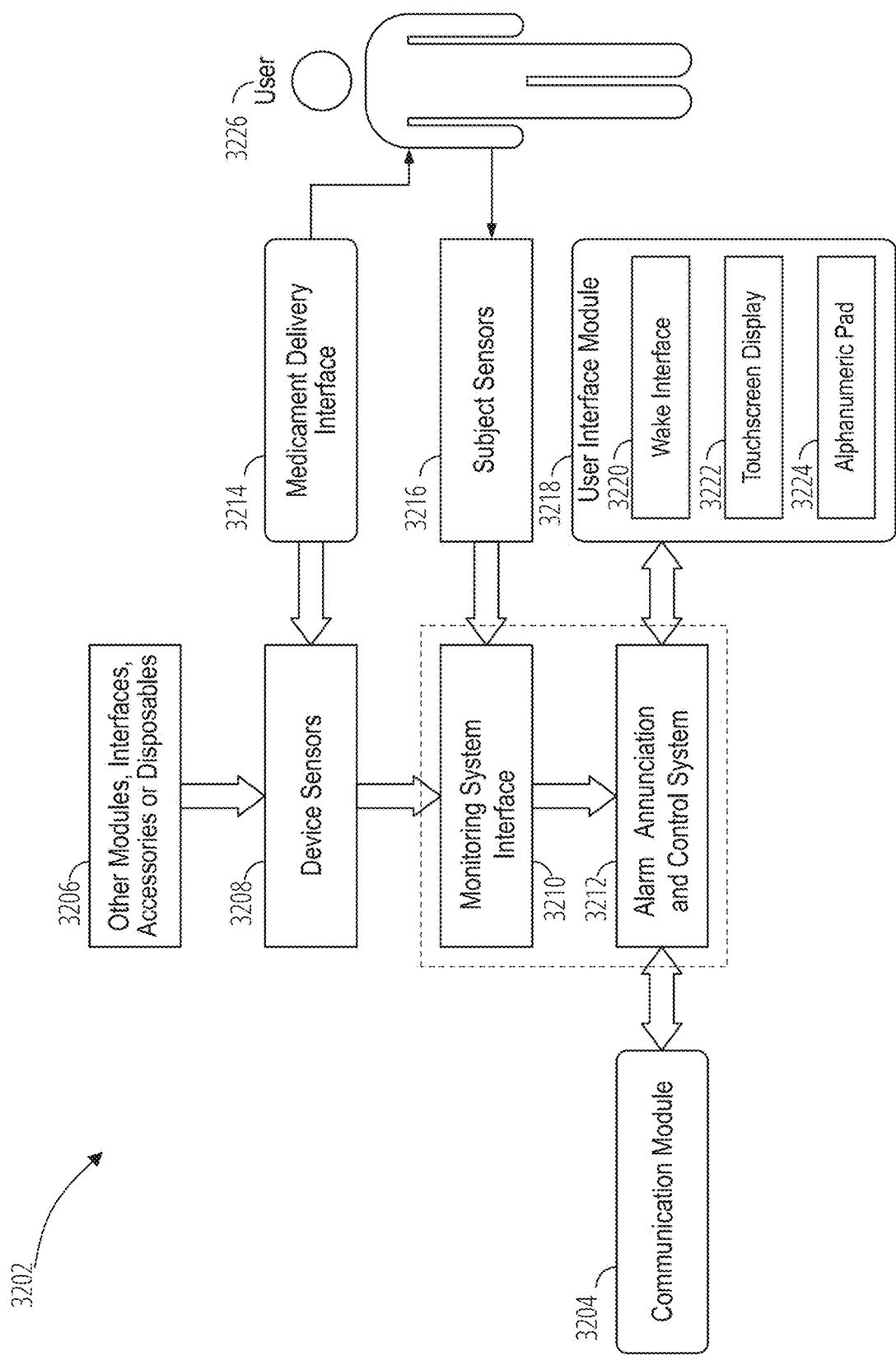
FIG. 32 is a schematic diagram illustrating the interconnection among modules and procedures in an AMD involved in monitoring the status of the AMD and/or the subject and generating alarms when an alarm condition is met.

With reference to FIG. 32, in some embodiments, an alarm system 3202 may implement alarm control procedures in a control and computing module (CCM) of the AMD. The alarm system 3202 can be implemented as instructions stored in a memory of the CCM and executed by a hardware processor to generate an alarm upon detection of a condition of the ambulatory medicament device and/or the subject. In some cases, the hardware processor of the monitoring system may be a hardware processor of the ambulatory medicament device that controls medicament delivery. In some cases, the hardware processor of the monitoring system may be a separate hardware processor.

In some examples, the alarm system 3202 may include a monitoring system interface 3210 and an alarm annunciation and control system 3212. The alarm annunciation and control system 3212 may include sub-systems for determining the severity of an alarm condition, user notification processing, and receiving alarm control commands from the user interface module 3218. The user interface module 3218 may include any type of user interface controller for providing a user interface. The user interface may be provided on a display of the AMD or may be transmitted to a display of an electronic device in communication with the AMD. In some cases, the user interface controller may be a touchscreen controller that is configured to output display signals configured to generate one or more user interface screens on a touchscreen. Further, the touchscreen controller may be configured to receive user input signals corresponding to user interaction with the touchscreen. The monitoring system interface 3210 may monitor the condition or status of the AMD and/or the subject at least partially based on signals or status values received from a set of device sensors 3208 and a set of subject sensors 3216. In some examples, the device sensors 3208 may be configured to track the status of the components or the elements of the AMD, and the subject sensors 3216 can be configured to obtain measurements of one or more physiological characteristics of the subject. In some examples, the device sensor 3208 can include a motion sensor that detects motion or acceleration of the AMD or on the AMD (e.g., tapping or shaking gestures). The motion sensor can include an accelerometer, gyroscope, and/or other electrical or mechanical motion sensors that convert motion or acceleration into electrical signals.

In certain embodiments, the user 3226 may wake the AMD from a sleep state or unlock the AMD by interacting with a wake interface 3220. In certain embodiments, the user 3226 may wake the AMD from another state or mode, such as for example a power saving mode or low power mode, the AMD by interacting with a wake interface 3220. When the AMD is in a sleep state or other state/mode, the touchscreen controller may not receive user input or user input signals corresponding to user input (e.g., via a touchscreen display 3222). When the AMD is in a sleep state or other state/mode, the touchscreen controller may not receive user interaction or user interaction signals corresponding to user interaction (e.g., via device sensors 3208 including an accelerometer or other motion sensors).

Waking the AMD may include activating a touchscreen interface or presenting a lock screen to a user. Further, waking the AMD may include waking the touchscreen controller such that it can receive user input or user input signals corresponding to user input. The wake interface 3220 can include one or more of the additional user interfaces mentioned above that are configured to generate and provide a wake input (or wake signal) to the CCM when detecting a pre-set user interaction. Alternatively, or in addition, the wake interface 3220 can be any type of wake interface element of the AMD that a user can interact with to wake at least a feature (e.g., a touchscreen interface) of the AMD. In some cases, the wake interface 3220 element can be a physical button (e.g., a push button, a slide button, etc.), a capacitive element, a resistive element, or an inductive element. In some cases, the wake interface element can be or can include a biometric element, such as a fingerprint reader, an iris scanner, a face detection scanner, etc. In some cases, the AMD may wake in response to detection of a particular movement or motion. For example, a determination that the ambulatory medicament device is being moved with a particular motion or within a line of sight or a visual range of a user may cause the AMD to awaken or cause the AMD to awake the touchscreen interface of the AMD. The AMD may determine that the AMD is being moved within a line of sight of the user based on the type of motion and/or the detection of a user's eyes via, for example, an iris scanner or a camera. In some cases, the AMD may wake in response to detection of a tapping on the AMD, such as a single tap or a double tap. In some embodiments, a single tap or a double tap may activate one or more elements of the user interface module 3218, such as for example the touchscreen display 3222. The touchscreen display can be a touch digitizer that converts analog interactions of the user (e.g., via electrical or mechanical properties of the user) into digital signals communicated to one or more controllers as discussed herein.

When in the wake and/or unlocked state, a user may interact with the touchscreen display 3222, alphanumeric pad 3224, or other types of user interfaces that may be included in the user interface module 3218. The user interface module 3218 may include any combination of one or more of the touchscreen display 3222, alphanumeric pad 3224, or other types of user interfaces.

In some examples, a device sensor 3208 may be a sensor that generates a signal or status value associated with the condition of modules, interfaces, accessories, disposables of the AMD. In some examples, a device sensor 3208 may generate a signal that corresponds to a parameter associated with a component in a module or interface. For example, one device sensor may record the voltage of a battery and another device sensor may record the follow rate of a pump the medicament delivery interface 3214.

In some examples, a subject sensor 3216 may be any sensor that generates a signal or status value associated with one or more physiological indicators (or parameters) of a subject (e.g., heart rate, blood pressure, body temperature, level of blood sugar, serum levels of various hormones or other analytes). In some such examples, the subject sensor can be a continuous glucose monitoring sensor (CGS). The device and subject monitoring system interface 3210 may continuously receive and analyze signals from device sensors 3208 and subject sensors 3216 to determine the condition of the AMD, the subject, a sensor, and/or other accessories.

In some cases, a single sensor may be used to monitor both the condition of the subject and the ambulatory medicament device or accessories and sensors connected to AMD. For example, a continuous glucose monitoring (CGM) sensor may be used to monitor the condition of the subject and may also be monitored to determine whether the condition of the CGM satisfies an alarm condition (e.g., to alarm a user that the CGM should be replaced).

Although described as sensors of the AMD, one or more of the sensors may be accessories that may or may not be part of the AMD, but that may communicate with the AMD.

In some examples, the alarm system 3202 may implement procedures for allowing the user or subject to change the alarm settings and/or acknowledge an alarm annunciation via the user interface module 3218. In some examples, the user may be able to see one or more alarms annunciated on a user interface (e.g., as a list of alarms), even if the AMD is in a locked state. In these examples, the user may not be able to acknowledge or respond to alarms when the AMD is in the locked state.

In some such examples, the user or subject may access an alarm setting screen or acknowledge an alarm annunciation by providing a wake action or a wake action followed by a first gesture via, for example, the touchscreen display 3222. In some cases, the first gesture may be created by entering predetermined or particular characters on the alphanumeric pad 3224. In some such examples, the user or subject may access an alarm setting screen or acknowledge an alarm annunciation by providing a single, double, or more tap gestures on the AMD. In some such examples, the alarm system 3202 may distinguish inadvertent alarm control inputs from intentional alarm control inputs. An inadvertent alarm control input may be an alarm acknowledgment input that was made without the intent of the user 3226 to acknowledge the alarm that the ambulatory medical device is delivering to the user. For example, an inadvertent alarm acknowledgment may include one that was accidentally executed by the user 3226 by putting pressure on the AMD in a jacket pocket of the user 3226.

In some examples, the alarm system 3202 may implement processes for determination and categorization of an alarm condition based on its severity level (e.g., a severity level between 0 and 5, with for example 0 being least or nonurgent alarm conditions and 5 being urgent or most urgent alar conditions), according to information received through the monitoring system interface 3210. In some examples, once an alarm condition is detected, the alarm annunciation and control system 3212 may place it in the appropriate queue, for example, based on severity or category. In one or more embodiments, a list of alarms may be generated wherein alarms may be sorted numerically in descending order with the highest priority fault or most urgent alarm condition displayed at the top.

In some examples, the alarm system 3202 may implement procedures for controlling the annunciation of alarm conditions via the user interface module 3218, at least partially, based on their severity level. In some such examples, a user interface (e.g., a touchscreen display) may be configured to allow the user 3226 to navigate directly to the issue or fault for which an alarm is being delivered and to address the fault causing the alarm so that it may be corrected, thereby stopping the alarm. Additional embodiments relating to alarm condition for an ambulatory medicament device that can be combined with one or more embodiments of the present disclosure are described in U.S. Provisional Application No. 63/167,563, which was filed on Mar. 29, 2021 and is titled "AMBULATORY MEDICAMENT PUMPS WITH SELECTIVE ALARM MUTING," the disclosure of which is hereby incorporated by reference in its entirety herein for all purposes.

Alarm Conditions

In some examples, the device and subject monitoring system interface 3210 may provide a status information received from the device sensor 3208 and/or subject sensor 3216 to the alarm annunciation and control system 3212. In some examples, the status information may include one or more status values. In some examples, the status information may include device information pertaining to a condition of the ambulatory medicament device or subject information pertaining to a condition of the subject. In some such examples, the alarm annunciation and control system 3212 may be configured to determine based at least in part on the status information received from the monitoring system interface 3210, whether an alarm condition is satisfied.

Determining whether an alarm condition is satisfied may include comparing one or more status values associated with the AMD and/or the subject to one or more alarm thresholds, threshold amounts, or alarm conditions. In some cases, each alarm threshold, threshold amount, or alarm condition may be associated with an alarm profile. In some such cases, determining whether the alarm condition is satisfied may include comparing the status information to one or more alarm thresholds, threshold amounts, or alarm conditions included in one or more alarm profiles. In some examples, the alarm profile may be stored in a memory of the AMD. In some such examples, at least some of the alarm profiles may be provided by an authorized user or the subject via a user interface or directly transferred from another device to the storage (e.g., from USB drive, a laptop, smart phone, PC, and the like). In some examples, at least some of the alarm profiles may be provided at the time of manufacture.

Each of the alarm profiles may indicate the characteristics or status of the AMD and/or subject that triggers an alarm corresponding to the alarm profile. For example, at least some alarm profiles may indicate the threshold status values below or above which an alarm should be triggered. For example, one alarm profile may indicate that when a blood glucose level of the subject exceeds a particular threshold, a particular alarm is to be generated and/or annunciated. As another example, an alarm profile may indicate that when an available amount of medicament is below a particular threshold, a particular alarm is to be generated and/or annunciated. The type of alarm and/or the alarm frequency or intensity associated with the medicament level may differ from the alarm triggered based on the blood glucose level. Although the previous examples described a single condition associated with a single alarm profile, it should be understood that multiple conditions may be associated with an alarm profile. For example, a blood glucose level that exceeds an upper threshold or is below a lower threshold may be associated with different alarm profiles or the same alarm profile. As another example, a blood glucose level that is above an upper threshold or a medicament pump that is unable to supply insulin may be associated with the same alarm profile. On the other hand, a medicament pump that is unable to supply insulin due to an empty insulin cartridge may be associated with a different alarm profile than when the medicament pump is unable to supply insulin due to damage to the medicament pump. Advantageously, by having unique annunciation patterns for at least certain alarm conditions, a user can instantly know the stated of the AMD and/or subject based on the annunciation pattern for the alarm.

When an alarm condition is satisfied, the alarm annunciation and control system can implement an annunciation pattern or alarm condition annunciation pattern selected based at least in part on the status information generated by and/or received from the monitoring system. The annunciation pattern may be selected from a plurality of annunciation patterns based at least in part on the alarm condition and/or the status information. The annunciation pattern may include one or more different text patterns or text information, auditory alarms, visual alarms, or haptic alarms.

Some non-limiting examples of conditions of the AMD or of the subject that may be associated with an alarm profile include conditions relating to a battery capacity (e.g., below a threshold charge capacity or below a capacity associated with a particular amount of operating time (e.g., one day)), a battery condition (e.g., high temperature or low voltage), a medicament or drug delivery condition (e.g., medicament is empty or below a threshold, motor is stalled, catheter is occluded, etc.), subject sensor condition (e.g., blood glucose sensor is expiring, or signal was not received from sensor), calibration failure (e.g., CGM calibration needed or incomplete load sequence), high or low glucose levels, network (e.g., Bluetooth® or BN-LTE) communication errors, haptic interface errors (e.g., motor failure), speaker errors (e.g., noise or low volume), medicament cartridge errors (e.g., empty cartridge, cartridge detection error, etc.), and the like. As explained below, each of these errors or conditions may be associated with different severity levels that cause the annunciation of different alarms.

In some cases, each alarm profile may be associated with a severity level or threshold severity level of the alarm. The severity level or urgency level may be associated with how urgently the condition that triggered the alarm should be addressed or resolved. Further, the severity level may be associated with an amount of harm that may be caused to a subject when the condition that triggered the alarm is not resolved or is not resolved within a particular time period. The number of severity levels may vary based on the type of ambulatory medicament device. Generally, there is no limit to the number of severity levels. However, there may be a point of diminishing returns as the number of severity levels exceeds a particular number because, for example, it may be difficult for a user to distinguish between the different numbers of severity levels or to identify with which severity level a particular alarm is associated. Thus, the number of severity levels may be limited to a particular number, such as 0, 3, 5, 6, 9, or some number in between. However, it is possible for there to be more than 10 severity levels.

There may be multiple alarm profiles associated with a severity level. Or each condition of the AMD and/or subject that is associated with the same severity level may be associated with the same alarm profile.

The AMD may determine a severity of an alarm condition based on the condition of the ambulatory medicament device and/or the subject that triggered the alarm condition. In some cases, the ambulatory medicament device may determine the severity of the alarm condition based at least in part on an alarm profile associated with the alarm condition.

Generally, when the alarm condition does not prevent the AMD from providing therapy, the AMD may continue to provide therapy. In some examples, when the alarm condition interferes with the delivery of therapy, operation of the AMD may be suspended or partially suspended. Generally, alarm conditions that interfere with the provisioning of therapy may be associated with a higher severity level. However, some alarm conditions that interfere with the provisioning of therapy may be associated with lower severity levels. For example, a determination that the AMD cannot supply insulin may normally be associated with a highest severity alarm. But when a user indicates that the site location is currently in process of being changed, the alarm condition may be associated with a lower severity level (e.g., an informational alarm reminding the user that insulin cannot be delivered during site change). In some examples, in response to determining that the severity level of the alarm condition matches an unsafe operation (e.g., a condition that may cause the AMD to provide doses of the medicament that are above or below certain values, or to unreliably determine the subject's condition), the AMD may suspend delivery of the medicament to the subject. Once the condition is resolved, the AMD may resume delivery of medicament to the subject. When it is determined that the alarm condition matches a safe operation severity level, the AMD may be configured to maintain delivery of medicament to the subject.

Alarm Annunciation

When an alarm condition is satisfied, the alarm annunciation and control system can implement an annunciation pattern or alarm condition annunciation pattern selected based at least in part on the status information generated by and/or received from the monitoring system. The annunciation pattern may be selected from a plurality of annunciation patterns based at least in part on the alarm condition and/or the status information. The annunciation pattern may include one or more different text patterns or text information, auditory alarms, visual alarms, or haptic alarms. Determining whether the alarm condition is satisfied may include comparing one or more status values associated with the ambulatory medicament device and/or the subject to one or more alarm thresholds, threshold amounts, or alarm conditions associated with an alarm profile.

Upon verifying that an alarm condition associated with an alarm profile or alarm condition is satisfied, the alarm annunciation and control system annunciates the alarm condition. In some cases, at least some of the alarm conditions may be associated with a unique annunciation pattern. Advantageously, by having unique annunciation patterns for at least certain alarm conditions, a user can instantly know the stated of the AMD and/or subject based on the annunciation pattern for the alarm.

In some cases, the AMD may have a wireless electronic communications interface that can be used to transmit an alarm signal, status information, alarm condition data, and/or an annunciation pattern to a remote electronic device. In some such cases, the remote electronic device may annunciate an alarm when an alarm condition is met. The remote electronic device may include any device that can receive alarm information or status information from the AMD. For example, the remote electronic device may be a smartphone, smartwatch, smart glasses, a laptop, a tablet, or any other computing device.

In some examples, the alarm system may generate a list of pending alarm conditions that can, for example, be displayed on a touchscreen using alarm status indicators. In these examples, any time an alarm condition associated with an alarm profile is satisfied, the alarm system may update the list of pending alarm conditions by adding the new alarm condition to the list of pending alarm conditions. In some examples, the list of pending alarm conditions may include a list of elements (e.g., icons, text, and the like such as alarm status icons) each indicating an alarm condition (e.g., an alarm condition that has been annunciated). In some examples, the AMD may display an alarm status icon including a visual indication of a count of alarm conditions on the list of pending alarm conditions.

In certain embodiments, the alarm system may organize an alarm manager list, notify a user of these alarms, and allow the user to acknowledge or mute the alarms. In some examples, the alarm manager list may be a list of pending alarm conditions with which the user can interact using a touchscreen display of the AMD.

In some examples, the list of pending alarm conditions may be sorted according to the severity level associated with the alarm conditions. In some examples, the alarms are categorized numerically in descending order with the highest priority fault displayed at the top of the list. In some examples, when the list of pending alarm conditions contains multiple alarm conditions of the same severity level, the alarm conditions of the same severity level may be displayed in chronological order. In some examples, a level 0 severity may be for a trivial fault that does not require any action by the user or may be for informational purposes only, thus not warranting an alert notification. Acknowledging the alarm condition may clear the alarm. In some examples, a level 1 severity may be a reminder notification that repeats at a certain frequency (e.g., every 5 minutes) until acknowledged by the user, which results in it being cleared. The annunciation may include a brief vibration and a beep, for example. In some examples, a level 2 severity may be one relating to an imminent, though non-urgent, loss of system function. Such an annunciation may include 1 brief vibration and 1 beep, for example, and repeating at a certain frequency (e.g., every 5 minutes). In various embodiments, alarm annunciation may include an alarm annunciation pattern that is aurally or haptically annunciated. The alarm may be snoozed for a period (e.g., 24 hours) when the user acknowledges the fault; however, the user would still need to address the situation creating the fault to completely stop the annunciation.

In some examples, a level 3 severity may be for when the system is no longer fully functional thus requiring user intervention to correct the issue. The annunciation may begin with a base level intensity with three brief vibrations and three audio beeps, for example, and repeating at a certain frequency (e.g., every 5 minutes). The annunciation escalates at a second frequency, e.g., every 30 minutes, up to a maximum intensity level. The escalation may be a change in vibration intensity and/or audio level, for example. The alarm may be snoozed for a period (e.g., 30 minutes) when the user acknowledges the fault; however, the annunciation when activated may be cleared when the underlying issue is resolved, e.g., glucose level is raised. In some cases, an alarm condition may change severity levels. For example, a level 3 severity may be maintained as a level 3 severity or may be lowered to a level 2 severity. In some cases, when acknowledging the level 3 fault, the user may choose to snooze for a short period (e.g., 30 minutes) or a long period (e.g., 24 hours). When the user selects to snooze for a short period, the severity level may be maintained at level 3. When the user chooses to snooze for a long period, the severity level may be lowered to level 2. Such an alarm condition may be referred to as having a level 2.5 severity.

In some examples, a level 4 severity may be for when the system is no longer functional and not correctable by the user. The annunciation may begin with a base level intensity with three brief vibrations and three audio beeps, for example, and repeating at a certain frequency (e.g., every 5 minutes). The annunciation escalates at a second frequency, e.g., every 30 minutes, up to a maximum intensity level. The escalation may be a change in vibration intensity and/or audio level, for example. The audio and haptic alerts may be cleared when the user acknowledges the fault; however, the base alarm remains because the underlying condition persists. In some examples, a level 5 severity may be for high priority alarms per IEC 60901-1-8. The annunciation may begin with a base level intensity with 5 brief vibrations and 5 audio beeps, for example, and repeating at a certain frequency (e.g., every 5 minutes). The annunciation escalates at a second frequency, e.g., every 30 minutes, up to a maximum intensity level. The escalation may be a change in vibration intensity and/or audio level, for example. The alarm may be snoozed for a period (e.g., 30 minutes) when the user acknowledges the fault; however, the annunciation when activated may be cleared only when the underlying issue is resolved, e.g., glucose level is raised.

In some examples, the alarm system may annunciate the alarm conditions via one or more user interfaces (e.g., a display, a touchscreen display, a speaker, and the like). In some such examples, an alarm may include an audio alarm, a text message, a graphical message, a text or graphical message with audio, vibrations, flashing light and any combination of these. In some examples, the alarm conditions may be transmitted to other devices where, for example, an authorized user (e.g., guardians or parents of the subject), the subject, or an emergency provider can view the alarm condition. In some examples, the alarm system may annunciate the alarm conditions via the user interface module 3218 of the ambulatory medical device 600. For example, the alarm condition may be annunciated via one or more user interfaces (e.g., a display, a speaker, and the like). In some examples, the alarm conditions may be transmitted to other devices, via the communication user interface module 3218 of the AMD where, for example, an authorized user 3226 (e.g., guardians or parents of the subject), the subject or an emergency provider can view the alarm condition. In yet other examples, the alarm annunciation and control system 3212, may establish a direct end-to-end connection with a computing system (e.g., a cloud computing system) using the communication module 3204 and send the alarm condition to the computing system through the end-to-end connection.

In some examples, auditory and haptic annunciation of lower urgency alarms may be muted so as to reduce risk of alert fatigue. Lower urgency alarms may be alarms that do not require urgent user attention and may include at least alarms with severity levels 0, 1, 2, and 3. In some examples, higher urgency alarms may be alarms that require urgent user attention and may not be muted, to protect subject safety. In some examples, each severity level may be pre-defined as low or high urgency. In some other examples, users may define how low and high urgency alarms are defined. In some examples, muting an alarm may include suppressing or not providing auditory and haptic annunciation of the alarm condition. In some examples, the alarm condition may be displayed, such as on a touchscreen display of the AMD, while auditory and haptic annunciation is not provided.

Based on the severity of the alarm condition and/or the alarm profile corresponding to the alarm condition, an alarm may be generated and/or annunciated that is associated with the severity of the alarm condition and/or the type of alarm condition. Different alarm conditions and/or alarm profiles may result in different types of alarms or different annunciations of the alarm. For example, an alarm associated with the highest severity level may include an auditory alarm with a loudness that exceeds a particular decibel level (e.g., above 70 or 80 decibels), a visual alarm (e.g., a flashing or steady light) with a luminance above a particular luminance value (e.g., a luminance between $10^5$ or $10^6$ candelas per square meter), and/or a vibrational alarm. Further, the alarm associated with the highest severity level may not be snoozed or dismissed, as such alarm conditions may require urgent user attention. In some cases, the alarm associated with the highest severity level may be snoozed for a shorter time period than alarms of lower severity levels (e.g., for 5 minutes, for 10 minutes, etc.). An alarm associated with a different severity level than the highest severity level may include a different combination of auditory, visual, and vibrational alarms. Not only may the existence of auditory, visual, and vibrational alarms differ for different severity levels, but so may the characteristics of each of the alarm types. For example, auditory alarms may have different sound patterns, loudness, frequencies, etc. Visual alarms may be of different intensity, color, pattern, etc. Vibrational or haptic alarms may be of different pattern, intensity, etc. Further, an alarm with a different severity level than the highest severity level may be permitted to be snoozed or dismisses or snoozed for a longer period of time, as such alarm conditions may not require urgent user attention. In some examples, the severity of the alarm condition may determine the type of type of the alarm generated (e.g., audio, text, graphical, or any combination of these).

Further, the display of alarm conditions on the user interface may include an icon for each type of alarm condition corresponding to an alarm status indicator for that alarm condition. The user interface may display the number of alarm conditions and/or the number of alarm conditions of a particular type or severity level. In some cases, a duplicate alarm may be omitted from the alarm manager list. In some cases, a count of the occurrence of alarms may be increased to reflect the duplicate alarm. In some cases, a duplicate alarm may result in the annunciation of the duplicate alarm. In some cases, the duplicate alarm is ignored. In some cases, the occurrence of a duplicate alarm may cause an escalation of the existing alarm. For example, when an alarm condition that causes an annunciation of an alarm with a first severity level is detected as occurring a second time, the alarm may be annunciated with a second severity level that indicates a greater degree of severity than the first severity level. It should be understood that an alarm occurring after an alarm condition is resolved may not be considered a duplicate alarm, but instead may be a reoccurrence of the alarm condition and/or an indicator that the resolution for the alarm condition failed (e.g., an insulin cartridge replacement is faulty or is empty). In some cases, an existing alarm may be escalated when left unresolved for a period of time. For example, a low battery alarm may initially be annunciated with a first severity level but may be annunciated at a higher severity level if the battery is not being charged after a certain period of time.

In some cases, the alarm manager list may be observed via a user interface (e.g., a touchscreen display) when the user interface is locked. In some such cases, further details about the alarms may be accessible when the user interface is locked. In some cases, in order to access more details about the alarms and/or resolve the alarms, it may be necessary to unlock the user interface unlocked (e.g., by a wake action and/or a gesture).

Each of the alarm conditions, or information associated therewith, may be added to an indicator or user interface (e.g., a list, or other data structure or user interface element) that may be accessed by a user. This user interface may maintain the alarm condition on the user interface until the alarm condition is resolved. Further, the alarm conditions may be sorted or ranked based on the severity level of the alarm condition, the time that the alarm condition occurred, whether the alarm condition relates to the subject or the ambulatory medicament device, any combination of the foregoing, or any other factor for sorting or ranking the alarm conditions.

In some cases where the alarm is presented on a display using for example one or more alarm status indicators, the displayed information may include details about what caused the alarm, the severity of the alarm, how to respond to or address the alarm, or any other information that may be informative regarding why the alarm was generated and/or how to respond to the alarm. In some cases, the information may provide a workflow or instructions on how to respond to the alarm. The instructions may include a link to a workflow provided by a manufacturer of the ambulatory medicament device or of another entity, such as an entity that provides medicament or site changing kits.

In some cases, different views of an alarm or different information associated with the alarm may be provided based on an identity of the user, or a role of the user, viewing the alarm. For example, a child may be instructed to contact a parent to address an alarm. But a parent may be provided with information to resolve the alarm. The parent may receive simplified information (e.g., blood glucose level is high) about what caused the alarm, but a healthcare provider may receive more detailed information regarding the alarm (e.g., internal control parameter values, insulin flow rates, curvature of insulin diminishment predictions, etc.) that facilitates the healthcare provider caring for the subject.

The alarm conditions may be displayed on a display of the AMD. Alternatively, or in addition, the alarm conditions may be displayed on a remote display that is separate from the ambulatory medicament device. The remote display may be a display that is authenticated or associated with a computing device that is authenticated to access data, such as alarm conditions, from the AMD. In some cases, the alarm manager list may be presented on a mobile device (e.g., a smartwatch or smartphone) or on a computing device (e.g., a laptop or desktop) that can obtain data directly or indirectly from the AMD.

In some cases, annunciating the alarm may include contacting a manufacturer and/or user (e.g., a healthcare worker, a parent or guardian, or other registered user). Further, the alarm may include instructions on repairing the ambulatory medicament device and/or on addressing the alarm condition. For example, the alarm may provide a user with instructions to replace the insulin cartridge and how to replace the insulin cartridge. As another example, the alarm may provide instructions on how to change the battery of the device or on how to change a site where the insulin pump connects to the subject. In some cases, the alarm may include one or more operations associated with the alarm. For example, the alarm may trigger reordering of insulin or may request that the user confirm a reorder request to reorder insulin.

Resolving an alarm

Certain alarms, such as informational alarms, may be dismissible. However, generally the alarm may remain on the alarm list until the condition that caused the alarm is resolved.

In some cases, a user may be able to acknowledge and/or snooze alarms via a user interface. In some examples, in order to acknowledge and/or snooze alarms, the user may first need to activate the user interface (e.g., by providing a wake action) and then provide a gesture to unlock the user interface. For example, the user may use the wake button to activate a touchscreen display and then provide a gesture on the screen to unlock display. In some example, the touchscreen display may be configured to allow the user or subject to navigate directly to the issue or fault for which an alarm is being delivered. This capability provides the user with access to address the fault causing the alarm so that it could be corrected thereby stopping the alarm.

In some cases, a user may be able to acknowledge and/or snooze alarms via motion sensor. As described herein, the AMD may include a motion sensor that detects motion or acceleration of the AMD or on the AMD (e.g., tapping or shaking gestures). The motion sensor can include an accelerometer, gyroscope, and/or other electrical or mechanical motion sensors that convert motion or acceleration into electrical signals. In some examples, the user may tap on the AMD to acknowledge and/or snooze alarms. In some examples, the user may acknowledge and/or snooze alarms via the motion sensor without the AMD activating one or more user interface modules such as the touchscreen display. In some examples, the user may acknowledge and/or snooze alarms via the motion sensor without activating the user interface (e.g., without providing a wake action). The motion sensor may be configured to detect different tap patterns (e.g., a single tap, a double tap, etc.). Each tap pattern may be associated with a different function. In some cases, the AMD can include a user interaction sensor which may include any motion sensor(s) and/or any one of the user interface modules such as the touchscreen or the wake interface. The user interaction sensor can convert electrical or mechanical properties of the user into electrical signals. The electrical signals from the user interaction sensor can be user interaction signals. In some cases, user interaction signals can encompass both user input via a touchscreen and user interaction via a motions sensor as discussed herein.

Resolving the alarm may include any action that addresses the condition that caused the alarm to be generated. For example, resolving the alarm may include replacing an insulin cartridge, changing a site where the ambulatory medicament device is connected to the subject, charging a battery of the ambulatory medicament device, providing insulin or a counter-regulatory agent to the subject and/or the ambulatory medicament device, or any other action that may be performed to address an alarm condition. In some cases, the resolution action may be acknowledging the alarm. For example, when the alarm is informational (e.g., to inform the user that more insulin has been ordered), acknowledging the alarm may be a sufficient resolution action.

In some cases, whether the alarm condition is resolved may depend on an identity of the user. For example, when a child interacts with an alarm related to reordering of insulin, the alarm may remain until a parent or guardian acknowledges the alarm. However, the child may be able to snooze the alarm. In some cases, a user interface that displays alarms may differ based on who is viewing the alarm. For example, a child may view the alarms, but may not be able to interact with the alarms. However, a parent or guardian may be able to snooze or dismiss an alarm. Further, a child may be instructed to bring the device to a parent or adult to address an alarm. In some cases, the child may be informed of how urgently to contact the parent (e.g., contact a parent immediately, within a day, within a week, etc.). Moreover, a designated adult may separately be alarmed (e.g., via a text or email alarm). The parent or guardian may receive additional information not provided to the child or subject (e.g., a link to repair instructions or a workflow to address the alarm condition).

In some cases, certain conditions may self-resolve over time. For example, a low battery alarm may resolve as the battery is charged. In such cases, the alarm may be cancelled automatically as the battery charge level exceeds a particular threshold. In another example, a low blood glucose alarm may be resolved once the subject has a meal. The alarm may be cancelled automatically as the subject's blood glucose level rises. Further, in some cases, one or more alarms and/or the alarm list can be viewed and/or accessed on a home screen, a main screen, or other non-alarm based user interface screen in addition to a user-interface screen designated for display alarms. The alarm list may be accessed from the ambulatory medicament device and/or a computing system in communication with the ambulatory medicament device.

In some cases, the alarm condition may or may not be resolvable when the ambulatory medicament device is locked or in a locked state or mode. The alarm acknowledgement signal may be configured to be detected by the motion sensor and may be one of a gesture input or a touch input, as will be described hereinafter.

A user may interact with the alarms generated based on the alarm condition. In some cases, the user can interact with the alarms when the AMD and/or the user interface is unlocked. In some cases, the user can interact with the alarms to snooze them or to obtain further information, when the AMD is locked. However, the user may not be able to dismiss the alarm without unlocking the ambulatory medicament device. The user may not be able to dismiss the alarm without unlocking the ambulatory medicament device when the alarm is urgent and requires user attention. Interacting with the alarms may include providing information associated with the alarm to a user in response to the user interacting with the alarm, or an indicator representative of the alarm.

Example AMD With Alarm Management System

Figure 33:
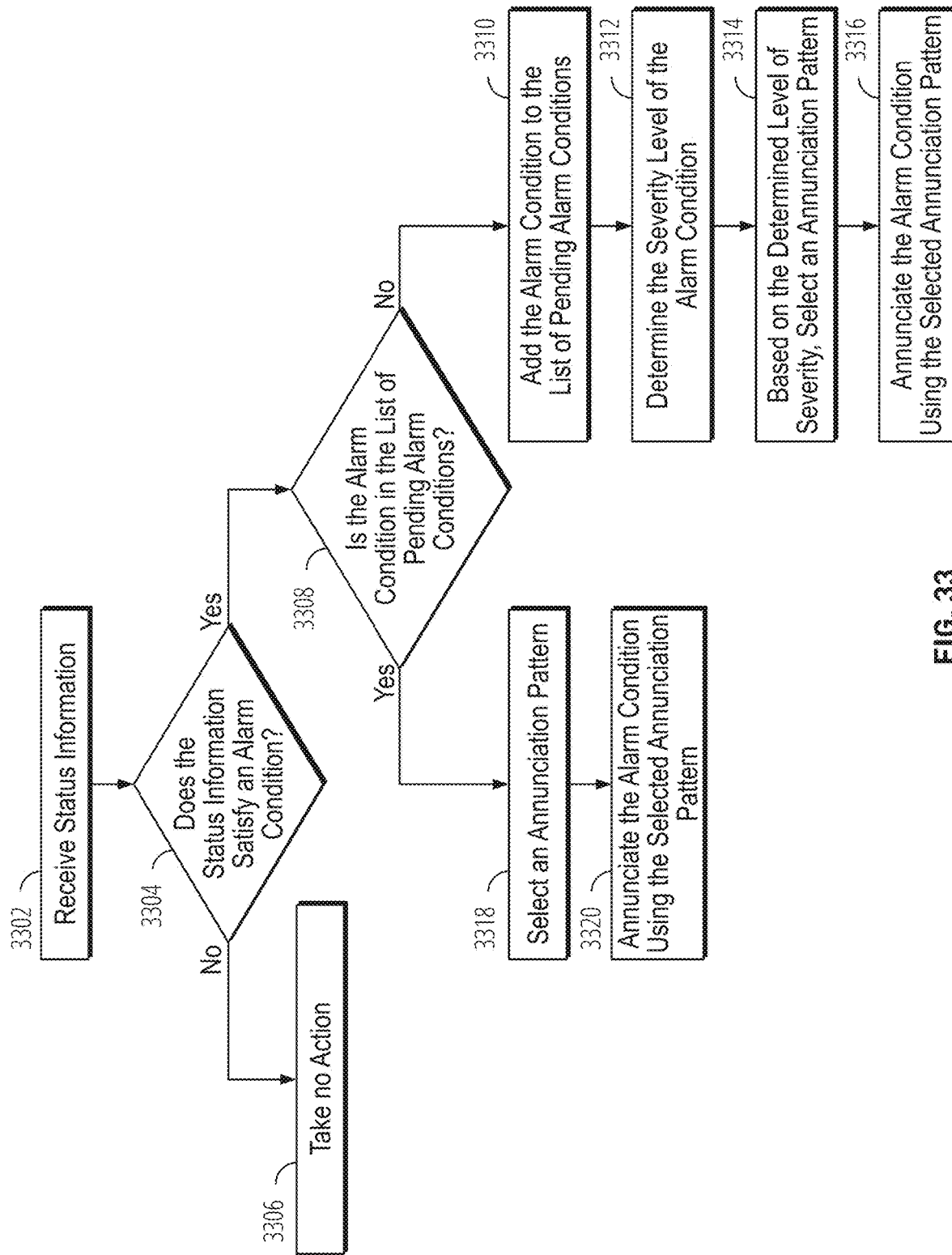
FIG. 33 is a flow diagram illustrating an example procedure that may be used by the alarm system of an AMD to annunciate an alarm condition upon receiving a status information that satisfies an alarm condition.

FIG. 33 shows a flow diagram illustrating an example procedure that may be used by the alarm system of an AMD to annunciate an alarm condition upon receiving a status information that satisfies an alarm condition. In some examples, the alarm system 3202 implements an annunciation process by execution of instructions by a processor in CCM of the AMD, where the instructions can be stored in the main memory, storage of the AMD, or in a memory of a connected electronic device or computing system.

The alarm system 3202 may receive status information 3302 using the monitoring system interface 3210, one or more device sensors 3208 and/or one or more subject sensors 3216. In some examples, the alarm system 3202 determines whether the received status information satisfies an alarm condition 3304. In some examples, the alarm condition may be an alarm condition in an alarm profile. If the received status information does not satisfy an alarm condition, no action may be taken 3306. If the received status information satisfies an alarm condition, the alarm system may determine whether the alarm condition is already present in the list of pending alarm conditions or not 3308. If the alarm condition is not present in the list of pending alarm conditions, the alarm system may add the alarm condition to the list of pending alarm conditions 3310. Next the alarm system, may determine the severity of the alarm condition 3312. Based on the determined level of severity, the alarm system 3202 can select an annunciation pattern 3314 and annunciate the alarm condition using the selected annunciation pattern 3316. If the alarm condition is present in the list of pending alarm conditions, at block 3318, the alarm system may select an annunciation pattern and annunciate the alarm condition using the selected annunciation pattern 3320. In some examples, the annunciation pattern selected at block 3318, may be an annunciation pattern that is different than the previously used annunciation patterns for the alarm condition. In some such examples, the annunciation pattern selected at block 3318, may be selected based on number of times that the same alarm condition is satisfied by a received status information. The process of the alarm detection and control function may repeat each processing cycle so long as the ambulatory medical device is in use. In some examples, after an alarm is annunciated, the alarm system may wait for user acknowledgment of the alarm. If the user acknowledges the alarm, the system proceeds to perform alarm processing. However, if the user fails to acknowledge the alarm, the annunciation continues and may escalate depending on the level of the alarm.

As mentioned above, the alarm conditions may be categorized based and annunciated based on their severity level. In some examples, the alarms are categorized numerically in descending order with the highest priority fault displayed at the top of the list.

In some examples, a level 0 severity, may be for a trivial fault that does not require any action by the user thus not warranting an alarm notification. In some other examples, a level 1 severity may be an informational type notification that repeats at a certain frequency (e.g., every 30 minutes)

until acknowledged by user which results in it being reset. The annunciation may include a brief vibration and a beep, for example. In some examples, a level 2 severity, may be one relating to an imminent loss of system function. Thus, such an annunciation may include two brief vibrations and two beeps, for example, and repeating at a certain frequency (e.g., every 30 minutes). Thus, the user would still need to address the situation creating the fault to completely stop the annunciation. In some other examples, a level 3 fault may be for when the system is no longer fully functional thus requiring user intervention to correct the issue. The annunciation may begin with a base level intensity with three brief vibrations and three audio beeps, for example, and repeating at a certain frequency (e.g., every 5 minutes). The annunciation escalates at a second frequency, e.g., every 30 minutes, up to a maximum intensity level. The escalation may be a change in vibration intensity and/or audio level, for example. The escalation may be cleared to base level when the user acknowledges the fault; however, the base alarm remains if underlying condition persists. Thus, the user would still need to address the situation creating the fault to completely stop the annunciation. In some examples, a level 4 severity, may be for when the system is no longer functional and not correctable by the user. The annunciation may begin with a base level intensity with three audio beeps, for example, and repeating at a certain frequency (e.g., every 5 minutes). The annunciation escalates at a second frequency, e.g., every 30 minutes, up to a maximum intensity level. The escalation may be a change in audio level, for example. The escalation may be cleared when the user acknowledges the fault; however, the base alarm remains because the underlying condition persists. In some other examples, a level 5 severity, may be for high priority alarms per IEC 60601-1-8. The annunciation when activated may be cleared when the underlying issue is resolved, e.g., glucose level is raised.

Additional embodiments relating to determining a severity of an alarm condition and annunciating the alarm based at least in part on the severity of the alarm condition that can be combined with one or more embodiments of the present disclosure are described in U.S. Provisional Application No. 62/911,017, which was filed on Oct. 4, 2019 and is titled "ALARM SYSTEM AND METHOD IN A DRUG INFUSION DEVICE," the disclosure of which is hereby incorporated by reference in its entirety herein for all purposes.
Non-Critical AMD Condition Management In some cases, a condition may occur that impacts the operation of the ambulatory medicament device. This condition may be associated with the ability of the ambulatory medicament device to operate as intended by the manufacturer, a subject receiving therapy from the ambulatory medicament device, and/or user (e.g., healthcare provider, parent, or guardian of the subject). In some cases, the condition or malfunction of the ambulatory medical device may prevent the ambulatory medical device from providing therapy to the subject. In other cases, the condition or malfunction may permit, at least for a period of time, the ambulatory medical device to continue providing at least partial therapy to the subject. In either case, it is generally desirable to generate an alert to inform the subject and/or one or more users of the condition of the ambulatory medical device and/or the subject. Moreover, it is desirable to track the alert until the condition that caused the alert is resolved. Further, it is desirable to issue different types of alerts for different conditions to enable a subject or user to easily distinguish the severity of the condition that triggered the alert.

In many cases, if the nature of the alert is non-critical, it may be safer to continue the underlying therapy and notify the user of the condition than to cease therapy. In some such cases, the best response to a problem with the device for a subject is to notify the device manufacturer, or other user that can address the problem, while the subject continues to receive therapy until a replacement device can be obtained or a repair can be made.

Additionally, alert fatigue can be an issue with medical devices due to excessive alerts which do not necessarily require user interaction. Alert fatigue can be dangerous because it can lead users to ignore serious alerts or alerts that require action in the short term.

The method described herein may be performed by an AMD (e.g., by one or more processor of the AMD) to detect device malfunctions for the AMD and that can generate alerts corresponding to the ambulatory medical device and prioritize the alerts to enable the subject or user to quickly and easily determine whether the device malfunction will impact therapy, should be addressed in the short-term (e.g., immediately, in 1-2 hours, within the day, etc.), and/or can be addressed at the subject's convenience (e.g., within a month, or more). In some cases, the method may be used by other systems.

In certain embodiments, the system disclosed herein can detect a condition in which the ambulatory medical device does not meet a manufacturer's specification (e.g., a failure of a haptic annunciator, a Bluetooth® radio malfunction, glucagon or insulin runs out, there is a medicament delivery malfunction, a touchscreen failure, etc.). In some cases, there can be several tiers of critical and/or non-critical faults. If it is determined that the underlying condition is not sufficient to stop therapy (e.g., delivery of insulin is not stopped), the fault may be deemed non-critical. In some cases, the fault may not be a fault of the device, but may be indicative of required maintenance (e.g., recharge battery indicator, order more medicament indicator, etc.). The condition may be annunciated to the user with appropriate instructions (e.g., call manufacturer for replacement medicament or parts) for addressing the fault or issue.

After the annunciation is acknowledged, the alert may be re-annunciated as a reminder at some later period in time (e.g., the alert may be re-annunciated daily at 4:00 PM or on Saturdays at noon). The length of time between annunciations may depend on the severity of the fault. In some cases, the re-annunciation cannot be stopped by the user, but may only cease if the underlying condition is resolved.

The method may include detecting a condition of the ambulatory medical device. The condition of the ambulatory medical device may be determined by one or more sensors of the ambulatory medical device. Further, the condition of the ambulatory medical device may be determined by the presence or absence of one or more errors when performing one or more functions of the ambulatory medical device. For example, if the ambulatory medical device fails to establish a communication connection with a control system or a data storage system, it may be determined that there is a possible malfunction with the ambulatory medical device. As another example, if the ambulatory medical device fails to deliver medicament or detects an error when attempting to deliver medicament, there may be a malfunction with the medicament pump. In some cases, the condition of the ambulatory medical device may be determined based on one or more configuration values being outside a normal operating range. For example, if the speed of delivery of medicament is faster or slower than a configured operating range, then it may be determined that there is a malfunction with the medicament pump or a connection with a medicament delivery tube (e.g., a catheter).

The method may include comparing the detected condition of the ambulatory medical device to a set of normal operating parameters. The set of normal operating parameters may be the specifications set by the manufacturer for when the ambulatory medical device is operating as intended by the manufacturer. In some cases, the normal operating parameters may be associated with a range of values. For example, the operating parameter for a speed of medicament delivery may be associated with a range of speeds, which may vary based on user settings, medicament type, site location of medicament delivery, or manufacturing tolerances, among other parameters. Comparing the detected condition of the ambulatory medical device to the set of normal operating parameters may include comparing each operating parameter in the specification to a corresponding detected operating parameter of the ambulatory medical device. The ambulatory medical device may generate a user alert based on the determined condition of the ambulatory medical device. For example, the AMD may generate an alert when the detected condition of the ambulatory medical device does not satisfy a set of normal operating parameters.

The method may further include determining whether the detected condition satisfies a minimum set of operating parameters. In some cases, the minimum set of operating parameters may match the normal operating parameters. However, typically the minimum set of operating parameters differ from the normal operating parameters. The minimum operating parameters may include the minimum specifications, minimum parameters, or minimum condition required by the ambulatory medical device to maintain or continue providing therapy to the subject. In other words, the minimum operating parameters are the operating parameters sufficient to provide therapy. However, the minimum operating parameters may not be sufficient to enable all features of the ambulatory medical device. For example, the minimum operating parameters may permit the ambulatory medical device to deliver insulin to the subject, but may not be sufficient to deliver the insulin at a normal delivery speed for the particular ambulatory medical device. As another example, the minimum operating parameters may permit the delivery of therapy, but may not be sufficient to track a log of therapy or to transmit a therapy log to another computing system. In some cases, the normal operating parameters and/or minimum operating parameters may be specified by a subject or healthcare provider (e.g., the minimum amount of medicament that is to be provided in each bolus may be specified by a healthcare provider). In some cases, the normal or minimum operating parameters may be modified.

When it is determined that the condition of the ambulatory medical device satisfies at least the minimum operating parameters, the ambulatory medical device may be configured to maintain delivery of therapy to the subject. Maintaining delivery of therapy may include maintaining therapy at the same rate, at a reduced rate (e.g., providing only basal therapy and therapy responsive to a meal announcement), or at a minimum maintenance rate (e.g., providing only basal insulin). Advantageously, the ability of the ambulatory medical device to distinguish between a minimum set of operating parameters and a normal set of operating parameters enables an ambulatory medical device with a malfunction to continue providing therapy, which sometimes includes life-saving treatment, to a subject until the ambulatory medical device can be repaired or until the condition of the device worsens to a point where the minimum operating parameters cannot be maintained. In some cases, the ambulatory medical device may temporarily maintain delivery of therapy. Temporarily maintaining therapy may provide a subject time to address the issue that caused the ambulatory medical device to not satisfy the normal operating parameters before the subject loses access to therapy. In some cases, the ambulatory medical device temporarily maintains therapy until the device condition makes it no longer possible to maintain therapy.

Figure 34:
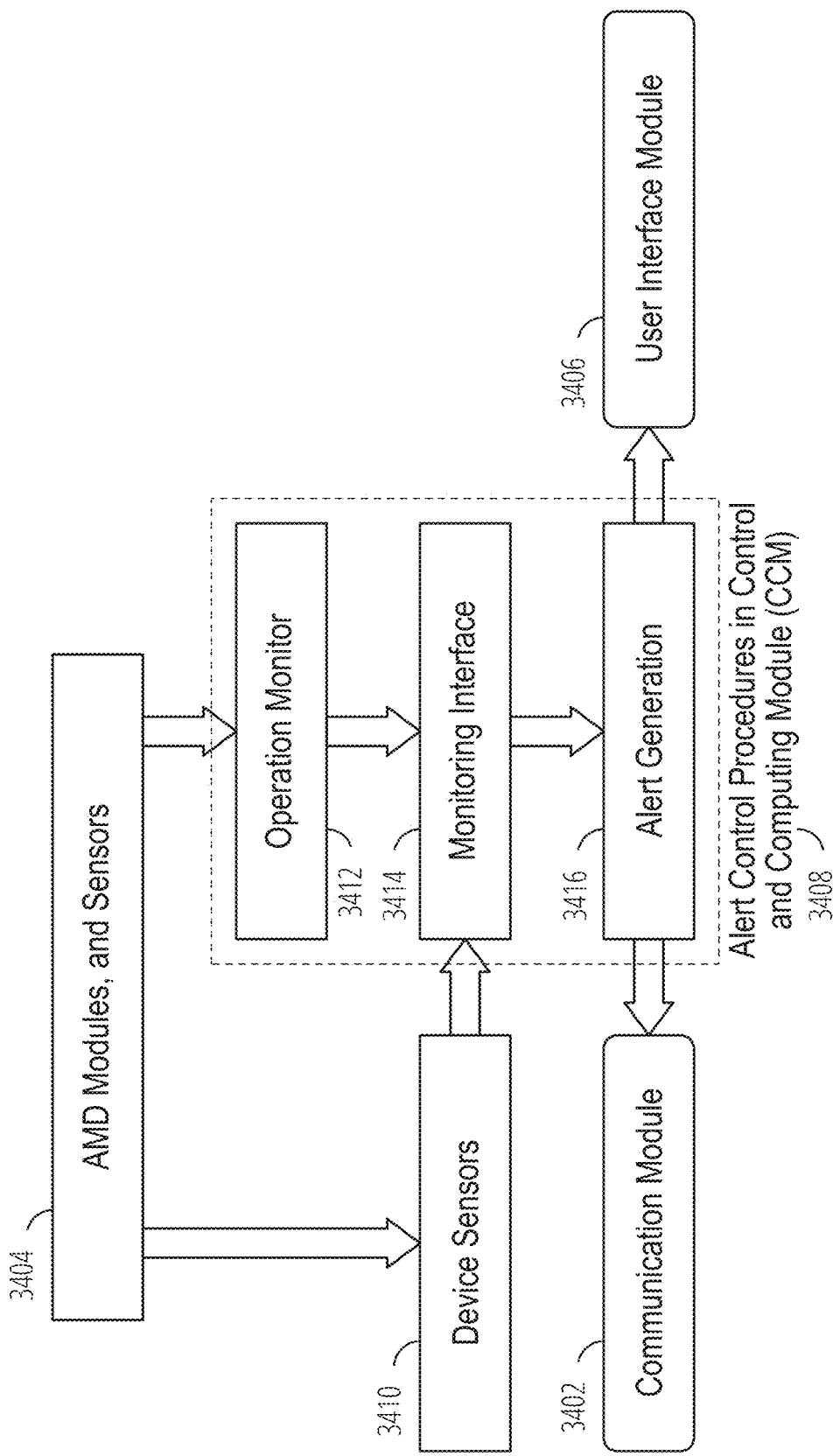
FIG. 34 is a block diagram illustrating the interconnection among modules and procedures in AMD involved in monitoring the condition of the AMD and generating alerts when a device malfunction is detected.

FIG. 34 is a block diagram illustrating the interconnection among modules and procedures in AMD involved in monitoring the condition of the AMD and generating an alert when a device malfunction is detected. In some examples, the condition of AMD may include the status of the modules and components of the AMD, such as AMD modules and sensors 3404 and/or operation of modules and procedures of the AMD. In some embodiments, the alert system may be implemented as a set of alert control procedures 3408 in the control and computing module 610 (CCM) of the AMD. The alert control procedures 3408, may be implemented as instructions stored in a memory of CCM (e.g., the main memory 616) and executed by a hardware processor 614 to generate an alert upon detection of a malfunction of the ambulatory medicament device. In some cases, the hardware processor may be a hardware processor of the ambulatory medicament device that controls medicament delivery. In other cases, the hardware processor of the monitoring system may be a separate hardware processor.

In some examples, the alert control procedures 3408 may include a monitoring interface 3414, an operation monitoring procedure 3412 and alert generation procedure 3416. The monitoring interface 3414 may monitor and evaluate the condition of the AMD and/or the subject at least partially based on the information received from the operation monitoring procedure 3412 and device sensors 3410. In some examples, the device sensors may be configured to track the status of the components or the modules of the ambulatory medicament device and the operation monitoring procedure 3412 may be configured to monitor the operation of the modules and other procedures. In some examples, the detected of the AMD may be provided to the alert generation procedure monitoring interface. The alert generation procedure 3416 may compare the detected condition of the AMD with a set of normal operating parameter. In some examples, the alert generation procedure may also determine whether the detected condition of the AMD satisfies a minimum set of operating parameters. In some examples, if it is determined that the detection condition of the AMD does not satisfy the normal operating parameters, the alert generation procedure may generate an alert. In some examples, the alert may be transmitted to the user interface module 3406 and displayed on a display of the AMD (e.g., a touchscreen display). In some other examples, once an alert is generated the AMD may establish a connection (e.g., a wireless connection) with another device. This other device may include a local device (e.g., a laptop, smartphone, or smartwatch of the user) or a computing system of a cloud-based service. In some such examples, the alert may be transmitted by the communication module 3402 to the computing systems where it may be displayed on user interface associated with the computing system. In some cases, the additional device may receive data from the ambulatory medical device enabling it to monitor the condition of the ambulatory medical device.

The type of the alert, and the frequency at which the alert is repeated, or whether an alert is dismissible or not, may be determined by the alert generation procedure based on the detected condition of the AMD and the alert information stored in a memory of the AMD. In some examples, the alert information may be provided by the subject, an authorized user, or a healthcare provider. In some other examples, the alert information may be stored in the AMD at time of manufacturing.

In some examples, upon determination that the detected AMD condition does not satisfy a set of normal operating parameters, the alert generation procedure may cause the medicament delivery interface, such as the therapy delivery module 606, to stop therapy delivery or modify one or more delivery parameters (e.g., therapy delivery rate). In some examples, upon determination that the detected AMD condition does not satisfy a set of normal operating parameters, but satisfies a set of minimum operating parameters, the therapy delivery may be maintained at a normal rate.

The alert may include any type of alert. For example, the alert may be a visual alert (e.g., a light or changing light), an audible alert (e.g., a beep or series of beeps), a haptic or vibration alert, an email alert, a text alert, or any other type of alert. Different device conditions may be associated with or may trigger different alerts. Thus, the user alert may enable the user to determine the device condition of the ambulatory medical device based on the alert. For example, an indication that the ambulatory medical device failed to deliver a medicament may trigger one type of alert while an indication that the ambulatory medical device has below a particular level of medicament available may trigger a different alert. In some cases, the user alert is dismissible and/or may be snoozed by the user. In other cases, such as when the ambulatory medical device fails to satisfy a set of minimum operating parameters, the user alert may not be dismissible or cannot be snoozed.

A dismissible alert may be scheduled to repeat on a particular schedule until an alert modification condition occurs. The frequency with which the dismissible alert repeats may depend on the severity of the condition or the particular operating parameters that do not satisfy normal or minimum operating parameters. More urgent device conditions may result in alerts that repeat more frequently. Further, alerts may vary based on when the condition was detected, the time of day, or the detected activity of a subject (e.g., sleep, abnormal activity, or elevated activity, such as exercise). Similarly, the snooze options may vary for different alerts or any of the aforementioned conditions. In some cases, the ambulatory medical device may escalate an alert if it detects that the condition of the ambulatory medical device has become more critical.

The alert frequency may be for a static time period (e.g., every 5 hours) or may ramp towards more frequency (e.g., every 5 hours for 1 to 3 reminders, every 4 hours for 3 to 6 reminders, etc.), or may change based on time of day (e.g., snooze alerts during sleeping hours for non-urgent alerts), etc.

The alert modification condition may include any action that causes the operating parameters of the ambulatory medical device to return to normal operating parameters. For example, the alert modification condition may be a repair or replacement of a faulty component. In some cases, the alert modification condition may include an acknowledgement of the alert. In other cases, the alert modification condition may include a worsening of the ambulatory medical device condition. In such cases, the modification to the alert may include the substitution of the alert to a different alert that indicates a different or more serious condition of the ambulatory medical device. For example, an urgent condition may become critical if the detected malfunction is addressed after generating certain number of alerts. When an urgent condition becomes critical, it may trigger a different alert type (e.g., a louder sound, or brighter image) and/or escalation in the alert frequency. For example, the audible alert may become louder and may be combined with a vibration alert from a haptic annunciator. Moreover, if the condition reaches a critical state, the ambulatory medical device may cease providing therapy to the subject.

In some cases, generating the alert may further include contacting a manufacturer and/or healthcare provider (e.g., clinician). Further, generating the alert may include ordering replacement parts. In some cases, the alert may instruct a subject or user on how to repair the ambulatory medical device.

Once the malfunction is addressed, the ambulatory medical device is repaired, or the condition that caused the alert is resolved, a user may permanently (or until the next time a device condition triggers the alert) dismiss the alert. Alternatively, or in addition, the ambulatory medical device may automatically dismiss the alert if it senses that the device condition that caused the alert has been resolved. In some cases, the ambulatory medical device may periodically recheck the device condition to determine whether the alert condition has been resolved.

In some cases, the manufacturer or healthcare provider may remotely clear or stop an alert using, for example, an NB-LTE connection. In some cases, only the manufacturer and/or healthcare provider can clear or stop the alert. Further, in some cases, a manufacturer and/or a healthcare provider may notify a user (e.g., a subject, or parent or guardian) of an issue or impending issue with the ambulatory medical device. The notification may be received by the ambulatory medical device via the NB-LTE connection. Alternatively, or in addition, the notification may be received via a computing device, such as a smartphone or laptop.

Figure 35:
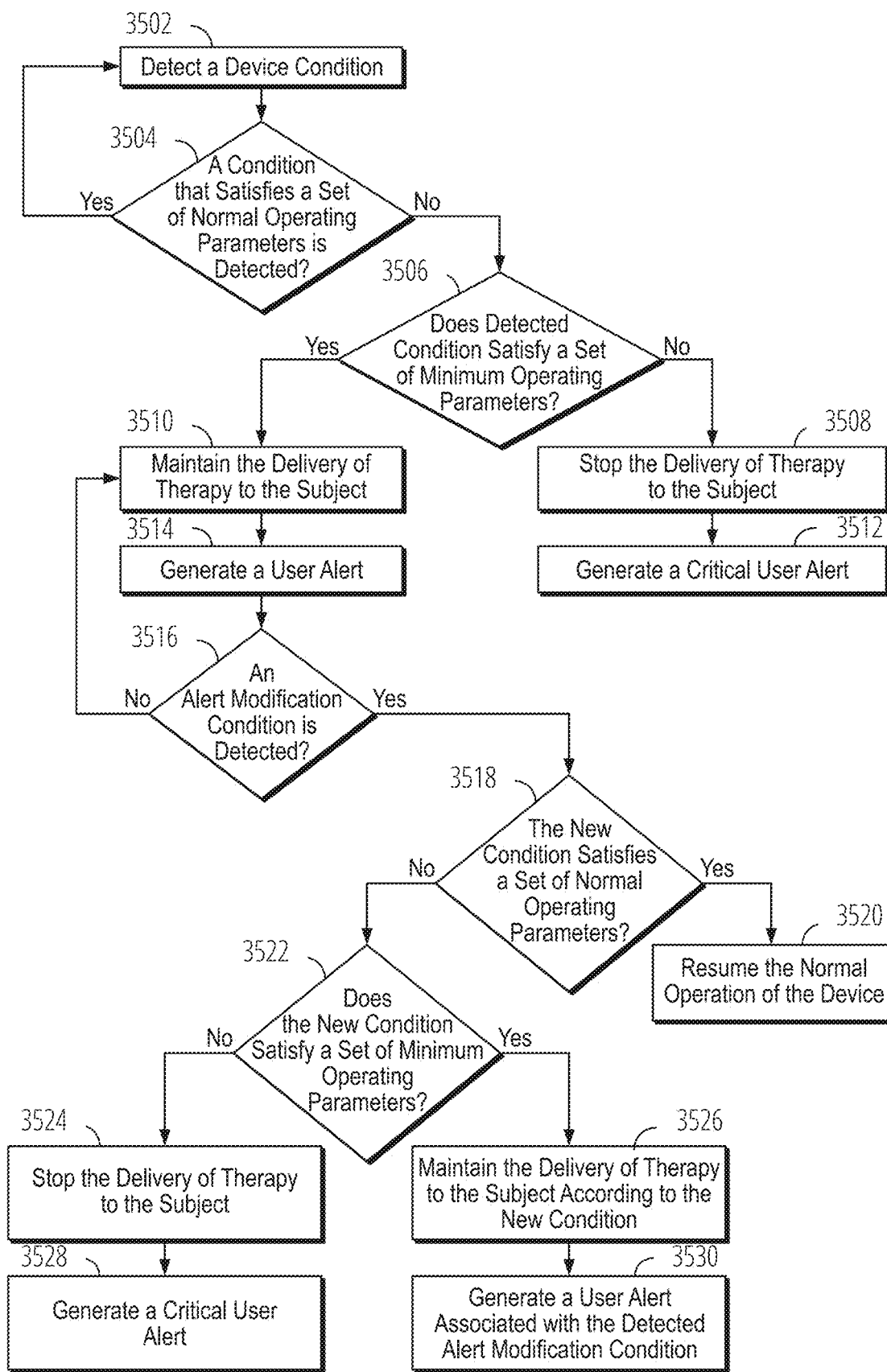
FIG. 35 is a flow diagram illustrating an example procedure that may be used by the alert system of an AMD to monitor the operation of an AMD and generate alerts when a device malfunction is detected.

FIG. 35 is a flow diagram illustrating an example procedure that may be used by the alert system of an AMD to monitor the operation of an AMD and generate alerts when a device malfunction is detected. In some examples, the alert system continuously monitors the status of all modules and components associated with AMD as well as the operation of all modules and procedures of the AMD. When a device condition is detected 3502, the alert system may determine whether the detected device condition satisfies a set of normal operating parameters 3504. If it is determined that the detected device condition satisfies a set of normal operating parameters, the alert system takes no action and continuous monitoring the AMD. If it is determined that the device condition does not satisfy a set of normal operating parameters, the alert system determines whether the detected device condition satisfies a set of minimum operating parameters. If, at block 3506, it is determined that the device condition does not satisfy a set of minimum operating parameters, the alert system may send a signal to the therapy delivery module to stop delivery of therapy to the subject 3508, and immediately generate a critical user alert 3512 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user. If, at block 3506, it is determined that the device condition satisfies a set of minimum operating parameters, the alert system may maintain the delivery of therapy to the subject 3510 and generate a user alert 3514. In some such examples, the alert system may maintain the delivery of the therapy at rate associated with the detected condition of the AMD (e.g., normal rate or minimum maintenance rate) until an alert modification condition is detected 3516. Upon detection of an alert modification condition 3516, the alert system may determine whether the new device condition satisfies a normal set parameters 3518. If, at block 3518, it is determined that the new device condition satisfies a set of normal operating parameters, the alert system may resume the normal operation of the AMD 3520 (e.g., deliver the therapy at a normal rate). If at block 3518, it is determined that the new device condition does not satisfy a set of normal operating parameters, the alert system may determine whether the new device condition satisfies a minimum set parameters 3522. If, at block 3522, it is determined that the new device condition satisfy a set of minimum operating parameters. The alert system may maintain or modify the rate of therapy delivery according to the new device condition 3526 and generate a user alert 3530 according to the according to the new device condition. If, at block 3522, it is determined that the new device condition does not satisfy a set of minimum operating parameters, the alert system may send a signal to the therapy delivery module to stop delivery of therapy to the subject block 3524, and immediately generate a critical user alert 3528 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user.

Managing Doses of Glucose Control Agents

Ambulatory medical devices allow subjects the freedom to treat themselves while being mobile. Self-managed medical treatment comes with inherent risks to the subject.

An automated blood glucose control system may automatically provide insulin and/or a counter-regulatory agent (e.g., Glucagon) to a subject to help control the blood glucose level of the subject. Generally, a control algorithm is implemented by an automated blood glucose control system (BGCS) to determine when to deliver one or more glucose control agents and how much agent to provide to the subject. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a sensor, such as a continuous glucose monitoring (CGM) sensor, that obtained automated blood glucose measurements from the subject. Moreover, in some cases, the control algorithm may deliver a bolus of insulin in response to an indication of a meal to be consumed or being consumed by the subject.

Insulin may be administered subcutaneously into blood of a subject. There is often a delay between when the insulin is provided and when the amount of insulin in the subject's blood plasma reaches maximum concentration. This amount of time may vary based on the type of insulin and on the physiology of the particular subject. For example, with a fast-acting insulin, it may take approximately 65 minutes for a bolus of insulin to reach maximum concentration in the blood plasma of the subject. For some other types of insulin, it may take anywhere from 3-5 hours to reach maximum concentration in the blood plasma of the subject. Accordingly, the blood glucose control system may implement a predictive algorithm that implements a bi-exponential pharmacokinetic (PK) model that models the accumulation of insulin doses in the blood plasma of the subject. The blood glucose control system may modify its predictions based on the type of insulin, one or more blood glucose readings, and/or characteristics of the subject.

In some cases, a subject may receive a manual bolus of insulin or medicament. For example, a user (e.g., healthcare provider, parent, or guardian) or subject may inject a dose of insulin into the subject. As another example, the user or subject may manually direct the automated blood glucose control system to provide a bolus of insulin to the subject.

It is generally undesirable to have too much insulin. An excess of insulin can lead to Hypoglycemia. As described above, it may take time for insulin to reach maximum concentration in the blood plasma of the subject. Thus, a blood glucose level reading from a sensor may not immediately, or even after a particular period of time, reflect the amount of insulin within a subject. Thus, a manual bolus of insulin may not be detected by the automated blood glucose control system. As a result, if the automated blood glucose control system is operating during delivery of a manual bolus or is configured to operate on the subject prior to blood glucose level readings reflecting the effect of the manual bolus on the subject, the automated blood glucose control system may unnecessarily administer additional insulin to the subject potentially leading to hypoglycemia.

The present disclosure relates to an automated blood glucose control system configured to provide automatic delivery of glucose control therapy to a subject and receive information about manual glucose control therapy provided to the subject. Using the received information about the manual glucose therapy, the automated blood glucose control system can adjust the blood glucose control algorithm to account for the manual dosing of insulin (or counter-therapy agents). The manual glucose control therapy may be provided by injection therapy, or it may be provided by an insulin pump.

In some cases, the automated blood glucose control system may receive an indication of insulin or medicament to administer to a subject in place of an automatically calculated dose of insulin. For example, the automated blood glucose control system may receive an indication that a subject is consuming or will consume a meal. The indication may include a type of meal to be consumed (e.g., breakfast, lunch, or dinner) and an estimate of the quantity of food or carbohydrates to be consumed (e.g., less than usual, a usual amount, more than usual, 30-40 grams of carbohydrates, 45-60 grams of carbohydrates, etc.). Based on the indication, or meal announcement, the automated blood glucose control system may calculate an amount of insulin to administer to the subject. The calculation may be based on an insulin to carbohydrate ratio provided by a clinician and/or determined by the automated blood glucose control system. Moreover, the calculation may be based at least in part on a history of blood glucose level measurements for the subject when consuming particular meals.

The calculated amount of insulin for the meal announced by the user may be presented to the user. The user (e.g., the subject) may modify the amount of insulin to administer. For example, the user may determine that for the size meal the subject is consuming or planning to consume, more or less insulin should be administered. In such cases, the user may modify the calculated insulin dosage to match the user's determination of the amount of insulin to administer. In some cases, the automated blood glucose control system may modify its control algorithm based on the user's input.

Thus, future meal announcements may result in a calculation of insulin that satisfies the subject's insulin needs and/or preferences.

In some cases, the indication of an amount of a manual bolus may be received by a user entering a numerical value (e.g., an amount of insulin, a number of carbohydrates, or another calculation) associated with administering insulin. As described above, the automated blood glucose control system may automatically-calculate a meal dose of insulin and present it to a user via a user interface where a user may enter the manual bolus information. At the time of making the meal announcement, the user may have an option to enter the manual bolus. The meal controller of the blood glucose pump can provide a recommendation against the manual entry if there is a prior history of online operation or a basis for making the recommendation.

The information may be received from a user via a user interface. This user interface may be provided by the automated blood glucose control system. Alternatively, or in addition, the user interface may be generated by another device, such as a laptop or desktop, a smartphone, a smartwatch, or any other computing device that can communicate via wired or wireless communication with the automated blood glucose control system. The information may include one or more of: an indication of delivery of a manual bolus (e.g., via injection therapy), an amount of the manual bolus, a type of the insulin (or other medicament), a time when the manual bolus was delivered, a general location that the manual bolus was administered to the subject (e.g., back, stomach, arm, leg, etc.), a reason for the manual bolus (e.g., a meal, a maintenance dose, a blood glucose level reading, in advance of exercise, etc.), and any other information that may be useable by the blood glucose control system in controlling the blood glucose level of the subject.

Advantageously, in certain embodiments, providing manual dosing information to the automated blood glucose control system can help the blood glucose control system maintain the blood glucose level of the subject within a desired range when the automated features of the blood glucose control system are active or operational. For example, if the automated blood glucose control system determines from a CGM sensor reading that a subject's blood glucose level is high, the automated blood glucose control system might normally administer a bolus of insulin. However, if the automated blood glucose control system receives an indication that a manual bolus of insulin was administered recently (e.g., within the past thirty minutes), the automated blood glucose control system may reduce or not administer a bolus of insulin, thereby preventing a Hypoglycemic event. In some such cases, the automated blood glucose control system may continue monitoring the blood glucose level of the subject and may administer additional insulin at a later time if the blood glucose level readings do not reflect an expected blood glucose level based on the reported manual bolus of insulin.

In some cases, it may be unnecessary to receive an indication of the manual bolus because, for example, a user may cause the automated blood glucose control system to provide the manual bolus. In such cases, the automated blood glucose control system may track the amount of insulin delivered and the timing of the administering of the bolus. To track the manual bolus, the automated blood glucose control system may store the information associated with the manual bolus in a therapy log. Accordingly, when the automated blood glucose control system is operating in an automatic mode, the automated blood glucose control system can access the therapy log to determine whether any manual bolus were administered and, if so, the timing and amount of the manual bolus.

In some cases, the automated blood glucose control system may model the diminishing of insulin, or other medicament, in the blood plasma over time based on the information associated with the manual bolus. Modeling the diminishing of medicament over time may be used to estimate a future effect of the medicament previously administered. In some cases, the model may account for previously administered medicament by the automated blood glucose control system. Further, in some cases, the model may account for physiological characteristics of the subject, such as the subject's weight or an input parameter related to the subject's weight (e.g., body mass index). Moreover, the model may account for perfusion over time of the medicament bolus from a subcutaneous infusion site into the blood plasma of the subject. Further, the automated blood glucose control system may model an accumulation of insulin, model time course of activity of insulin, or model a finite rate of utilization of insulin.

Based on the model, the automated blood glucose control system may adjust the automated administering of insulin, or other medicament when operating in an automatic mode. Further, the automated blood glucose control system may operate the administering of medicament (e.g., by controlling a medicament pump) based on a glucose level of the subject and the modeled concentration of medicament in the subject.

In some cases, the automated blood glucose control system may confirm that the manual bolus was delivered to the subject. The confirmation may be determined based at least in part on whether blood glucose level readings by the CGM sensor match or are within a threshold level anticipated by the automated blood glucose control system based on the manual dosing information. Alternatively, or in addition, the automated blood glucose control system may request, via a user interface, that a user confirm that the manual bolus was delivered. In cases where the manual bolus in delivered by the automated blood glucose control system, a user may be requested to confirm the administering of the manual bolus by using a particular gesture or sequence of interactions with a user interface (e.g., a touchscreen) of the automated blood glucose control system or of a device (e.g., laptop or smartphone, etc.) that communicates with the automated blood glucose control system.

As previously described, in some cases, the information relating to the manual bolus may include an amount of insulin and a reason the manual bolus was administered (e.g., for a meal of a particular size). In some such cases, the automated blood glucose control system may determine an amount of insulin the automated blood glucose control system would administer in an automatic operating mode based on the manual dosing information if the manual bolus had not been supplied. If the automated blood glucose control system determines it would have supplied a different quantity of the medicament, and if the difference exceeds a threshold, the automated blood glucose control system may adjust a blood glucose control algorithm to account for the difference. For example, the automated blood glucose control system may change the operating setpoint or range of insulin the automated blood glucose control system attempts to maintain in the subject. As another example, the automated blood glucose control system may supplement the manual bolus with additional insulin to account for an under-administering of insulin or may reduce a subsequent dosage of insulin to account for an over-administering of insulin.

As previously indicated, the automated blood glucose control system may maintain a therapy log of manual insulin therapy. This therapy log may be maintained based on the use of the automated blood glucose control system to provide a manual bolus or based on information provided by the user based on manual administering of insulin (e.g., via injection). The manual boluses may be supplied when the automated blood glucose control system is not operating, is not operating in an automatic mode, or is not connected to the subject. Once the automated blood glucose control system is connected to the subject and is configured in automatic mode, the automated blood glucose control system may determine therapy, if any, to provide to the subject based on a combination of the therapy log and the glucose control algorithm implemented by the automated blood glucose control system.

The automated blood glucose control system may generate a dose control signal based on the determined therapy. This dose control signal may be supplied to a medicament pump, which may control delivery of the medicament (e.g., insulin) to the subject.

In some cases, a user may control whether the automated blood glucose control system is operating in a manual mode or an automatic mode by interacting with a user interface of the automated blood glucose control system or of a device that communicate with the automated blood glucose control system. The user interaction may include any type of user interaction with a user interface. For example, the user interaction may include interaction why physical buttons or interactions with a touchscreen including gestures or taps on the touchscreen.

Additional embodiments relating to managing meal medicament doses and manual dosing that can be combined with one or more embodiments of the present disclosure are described in U.S. Provisional Application No. 62/911,143, which was filed on Oct. 4, 2019 and is titled "SYSTEM AND METHOD OF MANAGING MEAL DOSES IN AN AMBULATORY MEDICAL DEVICE," the disclosure of which is hereby incorporated by reference in its entirety herein for all purposes.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: providing an option to a user to select between receiving medicament using a manual delivery component or an automated delivery system. The method also includes receiving, by the automated delivery system, subjective information regarding the activity or action that may alter the blood-glucose level. The method also includes receiving, by the manual delivery component, an amount of the medicament to be infused. The method also includes storing a time and the amount of medicament that is infused into the automated delivery system that controls blood glucose level. Other embodiments of this aspect include corresponding computer systems, apparatus, and computer programs recorded on one or more computer storage devices, each configured to perform the actions of the methods.

Implementations may include one or more of the following features. The method where the automated delivery system modifies medicament delivery based on the time and the amount of medicament that was received from either the manual delivery component or the automated delivery system. The method where the manual delivery component includes a keypad which allows the user to type in the dosage amount of the desired medicament. The method where providing the option to select is provided prior to a user performing the activity that may alter the blood-glucose level. The method where the activity that may alter the blood-glucose level includes of consuming food or exercising. The method where the subjective information regarding the activity of consuming food includes the approximate relative size of the food that is to be digested. The method where the approximate relative size of the food is compared to the recommended meal doses for the user and depending on whether the approximate relative size is the same, larger, or smaller than the recommended doses, the model predictive control component is able to determine the actions that is required to regulate the glucose level of the blood. The method where the subjective information regarding the activity of exercising includes the intensity and the duration of the exercise. The method where the intensity and the duration of the exercise is compared to the recommended intensity and duration, and depending on whether it is the same, larger, or smaller than the recommended intensity and duration, the automated delivery system is able to determine the actions that is required to regulate the glucose level of the blood. Implementations of the described techniques may include hardware, a method or process, or computer software on a computer-accessible medium.

One general aspect includes a system having a medical device configured to provide an option to a user to select between receiving medicament using a manual delivery component or an automated delivery system. The system also includes automated delivery system configured to receive subjective information regarding the activity that may alter the blood-glucose level. The system also includes a manual delivery component configured to receive an amount of the medicament to be infused. The system also includes where the medical device storing a time and the amount of medicament that is infused into an automated delivery system that controls blood glucose levels. Other embodiments of this aspect include corresponding computer systems, apparatus, and computer programs recorded on one or more computer storage devices, each configured to perform the actions of the methods.

Upon utilizing an ambulatory medical device to request for a therapy change, users may have different preferences. Therefore, it is desirable for modern technology, specially the ambulatory medical devices to be equipped with optionality features. These optionality features may fulfill the different preferences of the users and subjects. The optionality features may allow users to control the therapy changes more closely and may allow them to be more engaged with the medical assistance of the ambulatory medical device.

In order to fulfill the variety of preferences, an ambulatory medical device needs to provide options which allows the user to either manually request the amount of the desired medicament or chose an automated delivery system that automatically delivers the right amount of the medicament at the right time without further assistance. For the manual component, the user may personally input the desired amount on a keypad that is provided by the medical device. The medical device further confirms and delivers the requested medicament. After the medicament is infused through a manual delivery component, the data is stored into a model predicative control component which is further used to control and regulate the blood glucose level. However, if the user decides to use the automated delivery system, the user must provide subjective information regarding the activity or the action that may alter the blood-glucose level. For example, if the blood-glucose level changing activity is consuming food, the user must provide the time and the dosage amount of the food that is going to be digested. This information is tied to the automated delivery system, and the subjective information is further stored into a model predicative control component.

Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk-free transition from the manual delivery component and the automated delivery system.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size meal. Embodiments may include correlating the manual inputs to asking the user what the size of the meal was and learning how the insulin affects the user. Embodiments may include correlating the manual inputs to asking the user what activity the user performed and learning how the glucagon affects the user for a particular activity.

BGCS With Manual Dose Management

Figure 36:
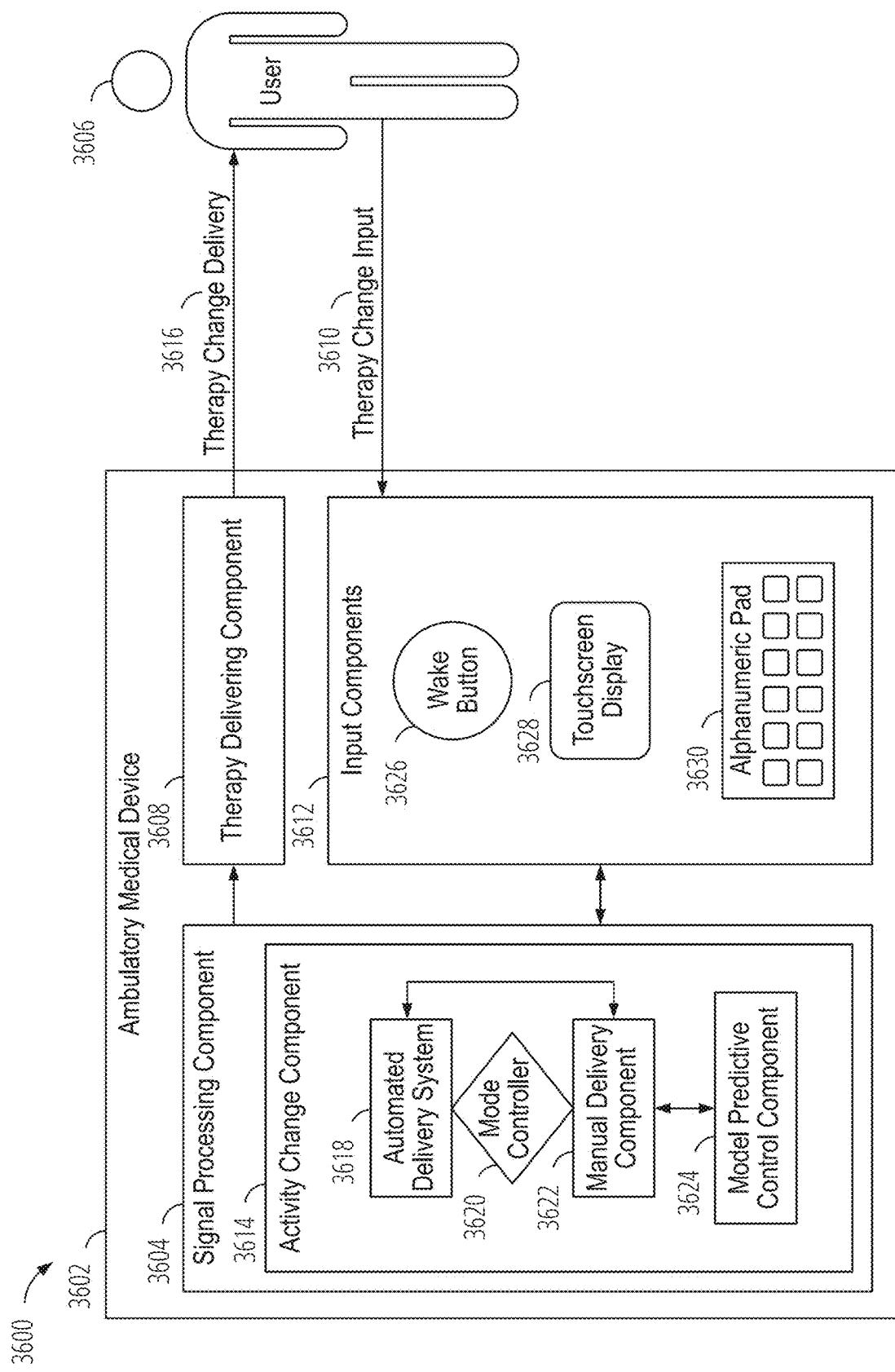
FIG. 36 is a schematic diagram illustrating an ambulatory medical device that provides the user with various options for providing medicament.

FIG. 36 illustrates a schematic of the therapy change delivery system 3600 in an ambulatory medical device 3602 that allows the user the choice of receiving manual delivery of medicament or automated delivery of medicament. Moreover, the therapy change delivery system 3600 allow the user to transition between the manual mode and the automated mode with ease. The therapy change delivery system 3600 includes the ambulatory medical device 3602, a signal processing component 3604, a user 3606, a therapy delivering component 3608, a therapy change input 3610, input components 3612, activity change component 3614, and a therapy change delivery 3616. When the user intends to receive a therapy from an ambulatory medical device 3602, the user 3606 may initiate a therapy change input 3610 to request the manual or automated medicament.

The ambulatory medical device 3602 is any medical device that a user 3606 may carry around and use with the approval of a medical professional. There are many different types of ambulatory medical devices 3602. In one embodiment, the ambulatory medical device 3602 is an insulin and/or glucagon infusion device for user 3606 that have type I diabetes. Ambulatory medical devices 3602 allow users 3606 the freedom to receive medical care in any setting at their convenience. However, the drawback of using an ambulatory medical device 3602 could be the user 3606 making mistakes when the user is away from the medical professionals. One possible issue may be caused the user 3606 switches from a manual delivery mode to an automated delivery mode when the automated delivery mode is unable to determine the amount of medicament in the user's blood stream. Embodiments are directed to the manual medicament delivery information being provided to the automated medicament delivery system so that it can adjust its operations based on the current and future medicament in the user's blood stream. In some cases, such as the embodiment where the ambulatory medical device 3602 is an insulin and/or glucagon infusion device, doing automated delivery of medicament can be problematic.

The ambulatory medical device 3602 includes a signal processing component 3604, a therapy delivering component 3608, and input components 3612. The signal processing component 3604, therapy delivering component 3608, and input components 3612 may be physically connected, wirelessly connected, connected via a cloud-based computer system, or connected in any other way.

The signal processing component 3604 is a computing system that performs the computing functions for the ambulatory medical device 3602. The signal processing component 3604 includes a processor, memory, and storage. The signal processing component 3604 may be a single computing system or may be made up of several computing systems. The signal processing component 3604 may perform the computing functions for a single ambulatory medical device 3602 or many ambulatory medical devices. The signal processing component 3604 receives signals from the therapy delivering component 3608 and from the input components 3612. The signal processing component 3604 also transmits signals to the therapy delivering component 3608 and the input components 3612. Signals of the therapy change input 3610, the therapy change delivery 3616, and all steps of the activity change component 3614 may be received or transmitted by the signal processing component 3604.

The user 3606 is any individual that uses the ambulatory medical device 3602. In one embodiment the user 3606 is an individual with diabetes that requires a periodic infusion of insulin or glucagon to maintain healthy blood sugar levels. In various embodiments, the ambulatory medical device 3602 infuses insulin or glucagon into the user 3606. The user 3606 may transport the ambulatory medical device 3602. Thus, as the user 3606 moves around, there is a danger that the user 3606 will inadvertently activate input in the ambulatory medical device 3602 that initiates a therapy change input 3610.

The therapy delivering component 3608 provides medicaments to the user 3606. Signals received from the signal processing component 3604 are executed by the therapy delivering component 3608 to change therapy such as starting, modifying, or stopping a therapy. The therapy delivering component 3608 may have a computing component for interpreting and executing instructions from the signal processing component 3604. Thus, the therapy delivering component 3608 can follow a program that is controlled by the signal processing component 3604. In one embodiment, the therapy delivering component 3608 is one or more infusion pumps. An infusion pump is capable of delivering fluids at varying rates to a user 3606. The infusion pump may deliver any fluid, including medicaments. The infusion pump may be connected to a user 3606 through any means. In one example, the infusion pump is connected to the body through a cannula. In an exemplary embodiment, the therapy delivering component 3608 is an insulin infusion pump. Also, in an exemplary embodiment, the therapy delivering component 3608 is an insulin and glucagon infusion pump. Signals received from the signal processing component 3604 may be interpreted by an insulin and glucagon pump to start, stop, or change the rate of insulin and glucagon being delivered into a user 3606.

In an exemplary embodiment, the therapy delivering component 3608 is an electrical stimulation device. An example of an electrical stimulation device is a cardiac pacemaker. A cardiac pacemaker stimulates the cardiac muscle to control heart rhythms. Instructions received from the signal processing component 3604 may be interpreted by a cardiac pacemaker to start stimulating a cardiac muscle, stop stimulating a cardiac muscle, or change the rate of stimulation of a cardiac muscle. Another example of an electrical stimulation device is a deep brain stimulator to treat Parkinson's disease or movement disorders. Instructions received from the signal processing component 3604 may be interpreted by the deep brain stimulator to start, stop, or modify the stimulation of the brain.

The therapy change input 3610 is an input provided by the user 3606 to change a therapy that is currently being delivered to the user 3606. The change of therapy may be to start a therapy, modify a therapy, or cancel a therapy. There are many types of possible therapy changes, and the types of therapy changes are dependent on the type of ambulatory medical device 3602. In one embodiment, the ambulatory medical device 3602 is an insulin or glucagon infusion device. However, there are many possible embodiments of ambulatory medical devices 3602 for the disclosed subject matter. The therapy change input 3610 in an insulin or glucagon infusion device may be an instruction, that when executed, causes the insulin or glucagon infusion device to start infusing an amount of insulin or glucagon into the user 3606. Alternatively, the therapy change input 3610 may be an instruction to modify the rate of insulin or glucagon infusion into the user 3606. The therapy change input 3610 may also be an instruction to cancel insulin or glucagon infusion into the user 3606 from the insulin or glucagon infusion device. In an exemplary embodiment, the ambulatory medical device 3602 is an electrical implant, that when operated, stimulates a part of the body. An example is an electrical brain implant for users 3606 with Parkinson's disease or for pain management. The implementation of the therapy change can be to modify the rate of electrical stimulation to the body.

Figure 43:
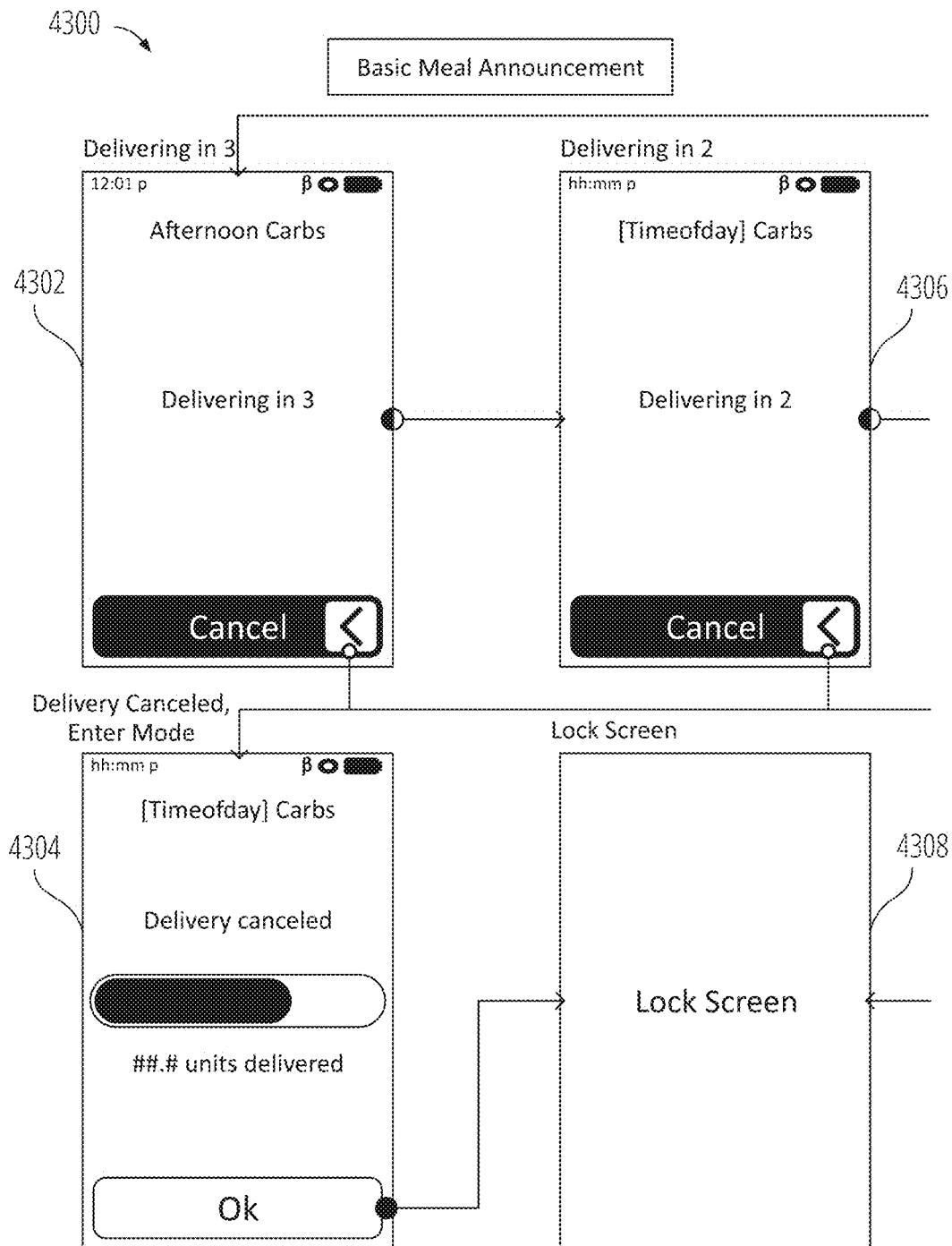
FIG. 43 is a series of screen displays showing an ambulatory medical device delivering the units and cancelling the delivery of the units.

The therapy change delivery 3616 is the performance, by the ambulatory medical device 3602, of the therapy change input 3610 that was verified by the 3614. The therapy change that is delivered by the therapy change delivery 3616 corresponds to the therapy change selection made by the user 3606. In one embodiment, the ambulatory medical device 3602 alerts the user 3606 that it is performing a therapy change delivery 3616. In an example of various embodiments, the ambulatory medical device 3602 displays the therapy change during the therapy change delivery 3616. Any number of details of the therapy change may be displayed during the therapy change delivery 3616. As shown in FIG. 43, a simple message of "Delivering" may be displayed during the therapy change delivery 3616. Alternatively, more exact details, such as "Delivering 2 units of insulin" or "Delivering insulin at 2 units per minute" may be displayed. In another example, the ambulatory medical device 3602 plays a sound effect during the therapy change delivery 3616. In an exemplary embodiment that is shown in FIG. 43, the therapy change delivery 3616 may be canceled by an input by the user 3606. The input to cancel a therapy change delivery 3616 may be any input such as a wake signal input or a series of touch inputs such as a gesture.

The input components 3612 allow the user 3606 to interact with and control the ambulatory medical device 3602. The amount of control that a user 3606 has may vary based on the type of ambulatory medical device 3602 and the user 3606. For example, an ambulatory medical device 3602 that delivers pain medication may allow the user more control than an ambulatory medical device 3602 that controls heart rhythms. In another example. a user 3606 that is a young child (less than about 10, 11 or 12 years) may be allowed less control over an ambulatory medical device 3602 than a user 3606 that is a teen or an adult. The input components 3612 include a wake button 3626, a touchscreen display 3628, and an alphanumeric pad 3630.

The wake button 3626 is activated by a user 3606 to create a wake signal input to unlock an ambulatory medical device 3602. The wake button 3626 may be any input button. In one embodiment, the wake button 3626 is a capacitive button that detects a change in capacitance. The wake button 3626 may have a computing component for interpreting and executing instructions from the signal processing component 3604. Thus, the wake button 3626 can follow a program that is dictated by the signal processing component 3604.

The touchscreen display 3628 may display a therapy change user interface for the user 3606 and receive user 3606 inputs on the touchscreen display 3628 input surface. Inputs on the touchscreen display 3628 may be registered by any touch technology including, but not limited to capacitive and resistive sensing. The touchscreen display 3628 may be a part of a mobile computing device, such as a cellular phone, tablet, laptop, computer, or the like. The touchscreen display 3628 may have a computing component for interpreting and executing instructions from the signal processing component 3604. Thus, the touchscreen display 3628 can follow instructions that are directed by the signal processing component 3604. To receive input, the touchscreen display 3628 may display buttons, alphanumeric characters, symbols, graphical images, animations, or videos. The touchscreen display 3628 may display an image to indicate when the ambulatory medical device 3602 is locked or inaccessible via the touchscreen display 3628. The touchscreen display may receive the series of inputs that make up the first gesture and the second gesture.

The alphanumeric pad 3630 registers numerical inputs, alphabetical inputs, and symbol inputs. The alphanumeric pad 3630 includes a multitude of keys corresponding to numerical, alphabetical, and symbol inputs. The alphanumeric pad 3630 may have a computing component for interpreting and executing instructions from the signal processing component 3604. Thus, the alphanumeric pad 3630 can follow instructions that are dictated by the signal processing component 3604. The alphanumeric pad 3630 may be configured to provide haptic feedback from its keys. The alphanumeric pad or pads 3630 may have any number of keys and any number of characters and may span multiple screens that the user 3606 can toggle between in order to find all of their sought-after characters. In one embodiment, the wake button 3626 is incorporated into the alphanumeric pad 3630. In various embodiments, the wake button 3626 may be any one or more keys of the alphanumeric pad 3630. In an exemplary embodiment, the alphanumeric pad 3630 is displayed as part of the touchscreen display 3628. Characters from the alphanumeric pad 3630 may be used as input for the wake signal input, first gesture, therapy change selection, and second gesture. In an exemplary embodiment, the first gesture and/or second gesture are created by entering predetermined characters on the alphanumeric pad 3630.

The activity change component 3614 may be part of a specialized software that is executed on an ambulatory medical device or include a specialized hardware that performs the various functions described here. The activity change component 3614 may receive inputs from the user regarding weather the user is about to conduct activities that will change the blood glucose of the user. For example, the user may provide input using the input components 3612 that the user is about to perform exercise that may lower their blood sugar or eat a meal that will increase their blood sugar. Upon receiving the activity change from the input components 3612, the activity change component 3614 offers the user the option via the mode controller 3620 to select between the automated delivery system 3618 or the manual delivery component 3622. As shown in FIG. 36, the manual delivery system may inform the automated delivery system 3618 and the model predictive control component 3624 regarding any manual medicament deliveries of insulin or glucagon.

In various embodiments, the user may choose the dosage amount, the drug type (insulin or glucagon; fast or slow acting) and the time of the delivery and the manual delivery component 3622 may receive such information and deliver the medicament(s) accordingly. In one embodiment, the manual delivery component 3622 may inform the automated delivery system 3618 and the model predictive control component 3624 regarding the drug type (insulin or glucagon; fast or slow acting) and the time of the delivery.

When the user activates the automated delivery system 3618, the data from previous manual medicament infusions can be readily available so that the automated delivery system 3618 may be able to determine how much medicament is still in the user's blood stream. The automated delivery system 3618 may make that determination by tracking the finite rate of utilization of infused insulin by the subject based on the time and amount of any manual medicament infusions reported to the automated delivery system 3618.

Figure 37:
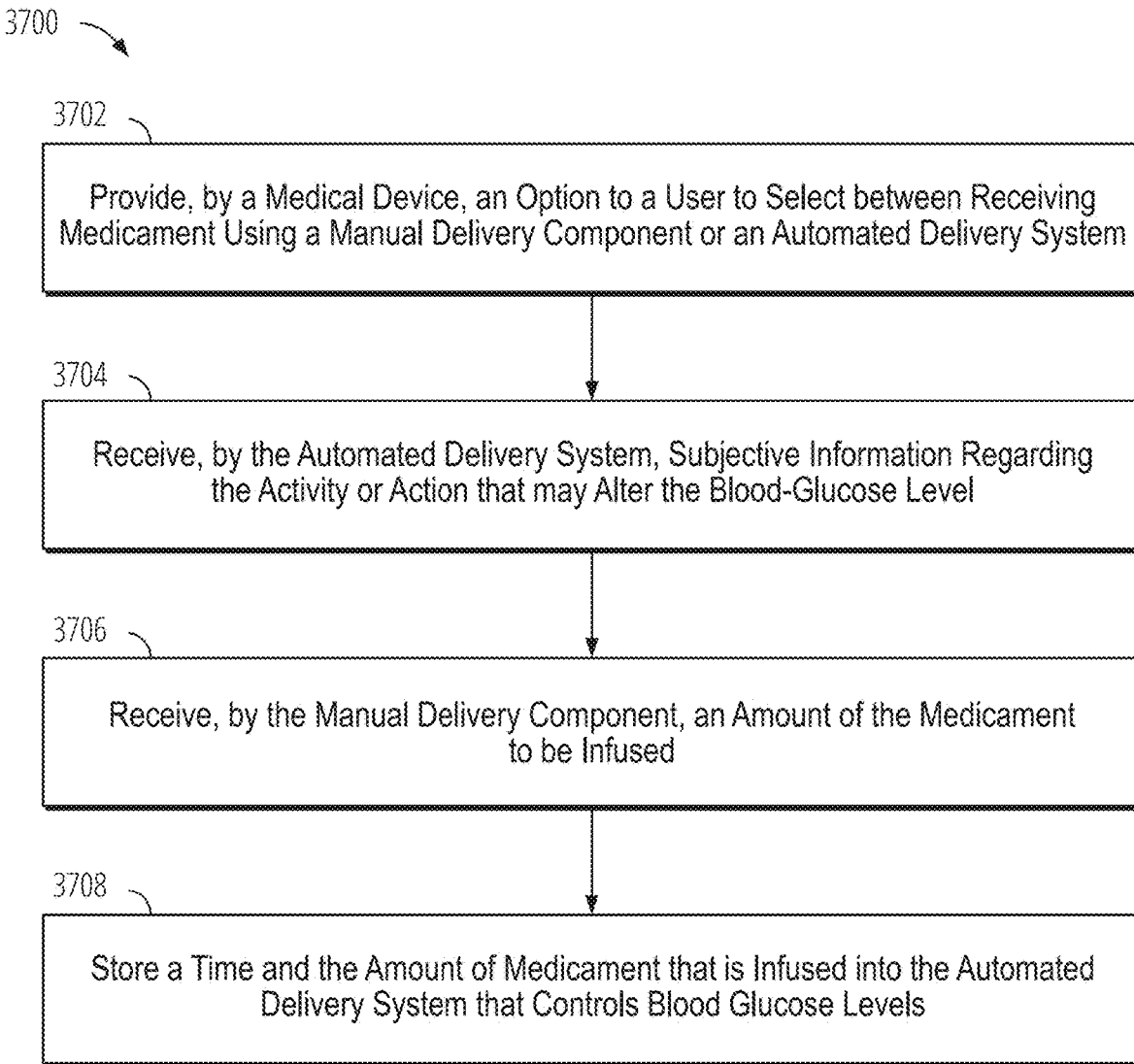
FIG. 37 is a flow diagram of a process for providing options for meal dosage selection on an ambulatory device.

FIG. 37 is a flow chart of a process 3700 detailing a medicament selection process, according to an exemplary embodiment. In step 3702, the medical device provides an option to a user to select between receiving medicament using a manual delivery component or an automated delivery system. By using the mode controller 3620, the user can select the method for the therapy change request between manual delivery component and the automated delivery system.

In step 3704, the medical device may receive subjective information regarding the activity or action that may alter the blood-glucose level. Subjective information may include the size of the meal and/or the type of physical activity. In step 3706, the manual delivery component may receive an amount of the medicament to be infused. The medicament may be a plurality of hormones, including but not limited to, glucagon or insulin. At step 3708, the medical device may store a time and the amount of medicament that was infused into the automated delivery component that controls the blood glucose level. The systems that are disclosed in FIG. 36 will be utilized to accomplish each and every step from steps 3702, 3704, 3706 and 3708.

Figure 38:
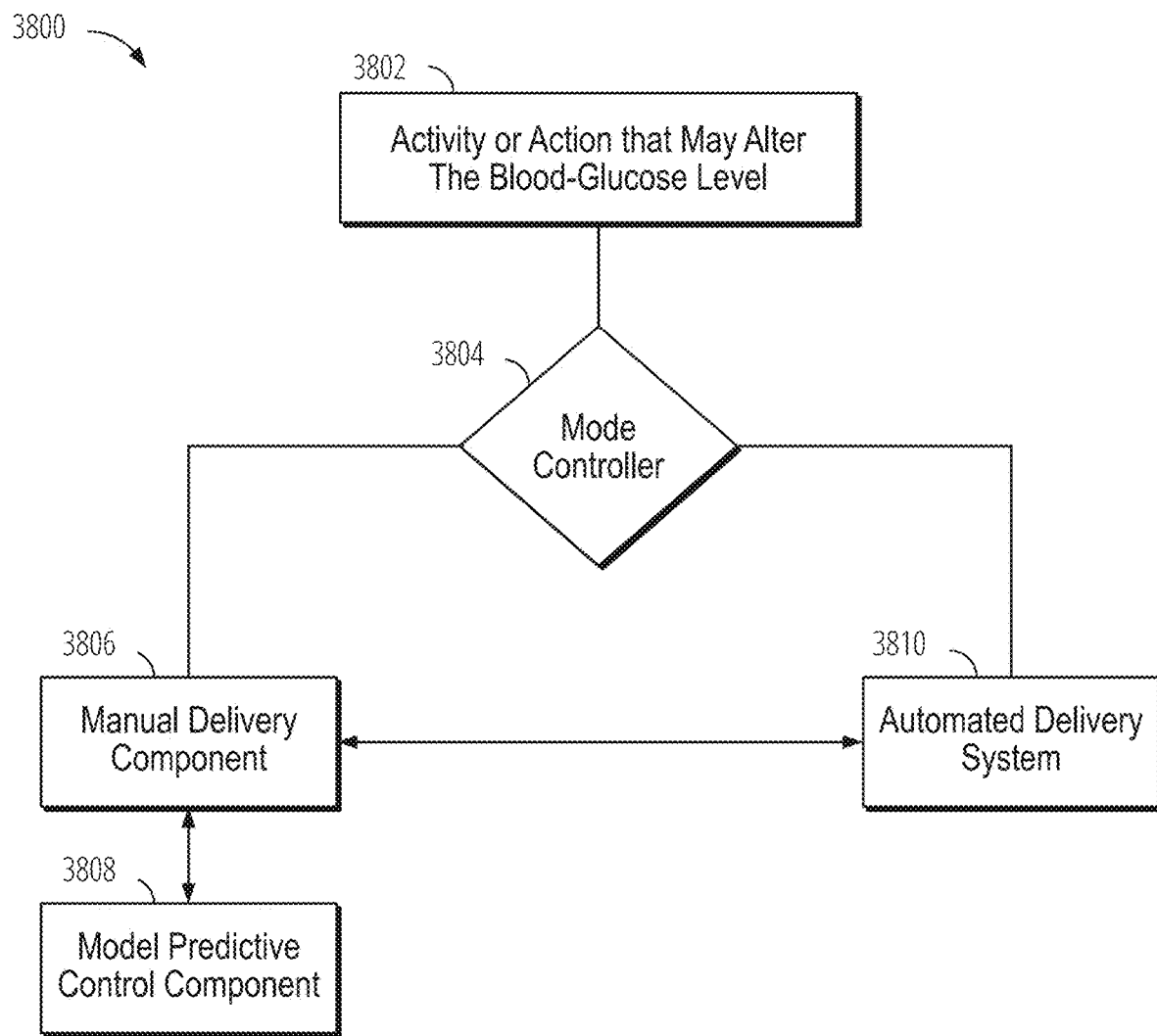
FIG. 38 is another flow diagram of a process for providing options for meal dosage selection on an ambulatory device.

FIG. 38 is another flow diagram of a process 3800 for providing options for meal dosage selection or physical activity of the user on an ambulatory device. Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk-free transition from the manual delivery component and the automated delivery system.

At block 3802, the user may inform the activity change component 3614 that the user is about to engage in activities that may alter the blood-glucose level of the user. The mode controller 3620 may be activated at decision block 3804 and ask whether the user wants to use the manual delivery component 3806 or the automated system 3810. If the user chooses to use the manual delivery component 3806 and the user provides an input to infuse medicament, the ambulatory device 3602 may delivery the medicament to the user. Upon the manual delivery process completion, the manual delivery component 3806 may inform at least one of the model predictive control component 3808 and the automated delivery system 3810 regarding the type of medicament, amount of medicament and the time when the medicament was delivery. The predictive control component 3808 and automated delivery system 3810 may track these manual infusions of medicament and determine that based on the rate of decay or the half-life of the medicament the total amount of medicament that remains in the user's blood stream at a particular time or a period of time. Accordingly, when the automated delivery system 3810 is activated by the user, the automated delivery system 3810 may change its medicament infusion based on the medicament that remains in the user's blood stream after a manual infusion by the user.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size mean. Embodiments may include correlating the manual inputs to asking the user what the size of the meal was and learning how the insulin affects the user. Embodiments may include correlating the manual inputs to asking the user what activity the user performed and learning how the glucagon affects the user for a particular activity.

Figure 39:
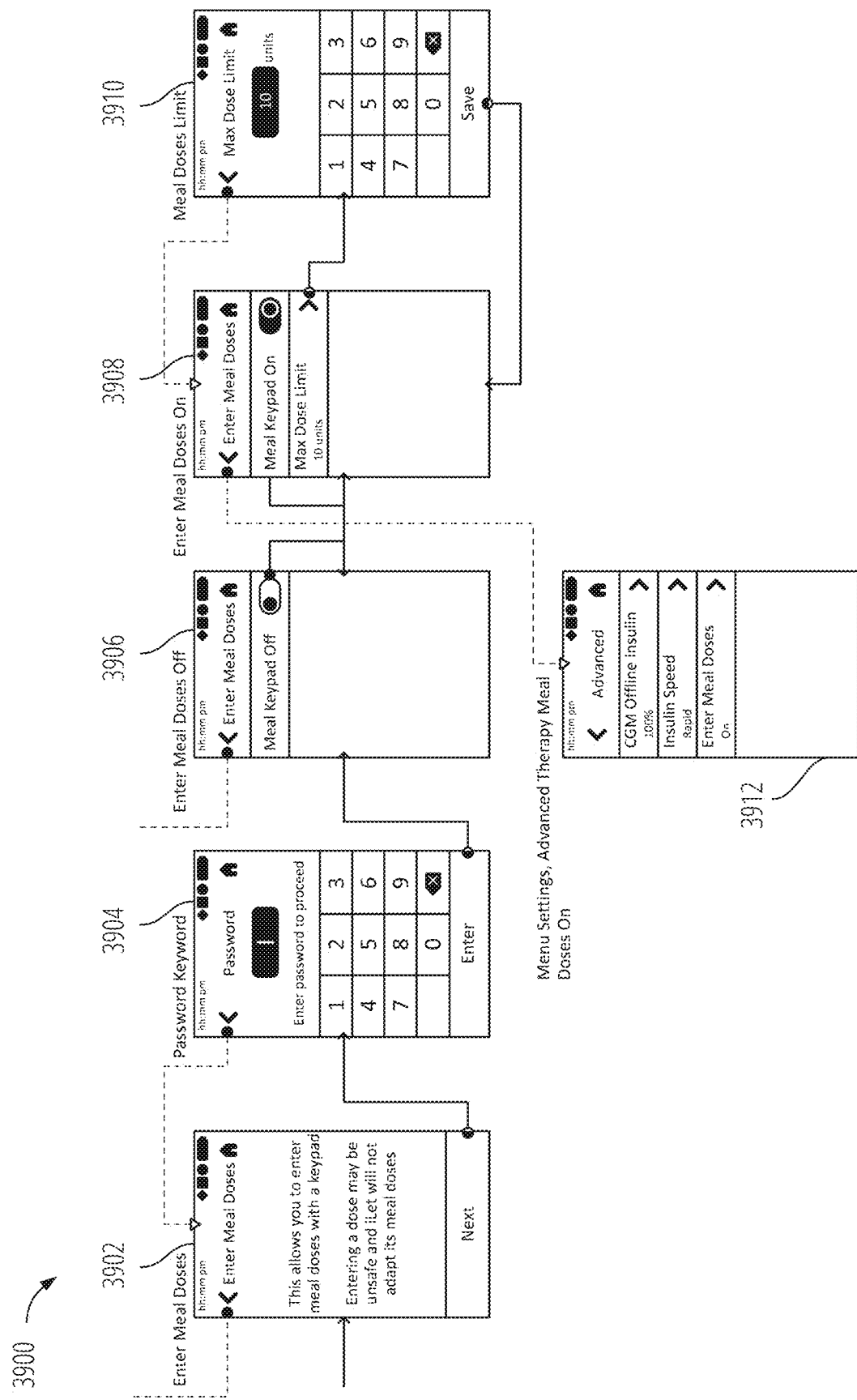
FIG. 39 is a series of screen displays showing a user initiating the activation of meal dosage on an ambulatory device.

FIG. 39 illustrates a plurality of screens 3900 that may be produced by the ambulatory medical device 3602. The plurality of screens 3900 demonstrates a process that a user may take in order to enter meal doses. When the activity change component 3614 is activated, the enter meal doses screen 3902 may be displayed. Once the screen 3902 is displayed, a warning text may be displayed for the user to ensure safety. The warning text states that entering a dose may be unsafe and the device will not adapt its meal doses. This warning text cautions the user of the risks that may be involved in the process of using the ambulatory medical device 3602. After a user acknowledges the warning sign and choses to proceed, a password screen 3904 may be displayed. Once the password screen 3904 is displayed, a keypad is provided for the user to enter a predetermined sequence of numbers to ensure that the user is the actual registered user of the ambulatory medical device 3602. When the ambulatory medical device 3602 receives the correct predetermined password from the user, the enter meal doses official screen 3906 and meal doses official screen 3908 may be displayed. The user may decide to access the advanced screen 3912, and upon doing so, the advanced screen 3912 will allow the user to double check the CGM Insulin levels and change the speed of the of the insulin pump. In screen 3906 and screen 3908, the user is provided the option to have the meal keypad on or off. If the user selects to have the keypad on, then an option may be provided for the user to choose the max dose limit. If the user decides to choose the max dose limit, the official max dose limit screen 3910 is displayed, where the user may enter up to 10 units of the dose. The provided number of units is then stored in the model predictive control component 116 for further regulation of the blood glucose level.

Figure 40:
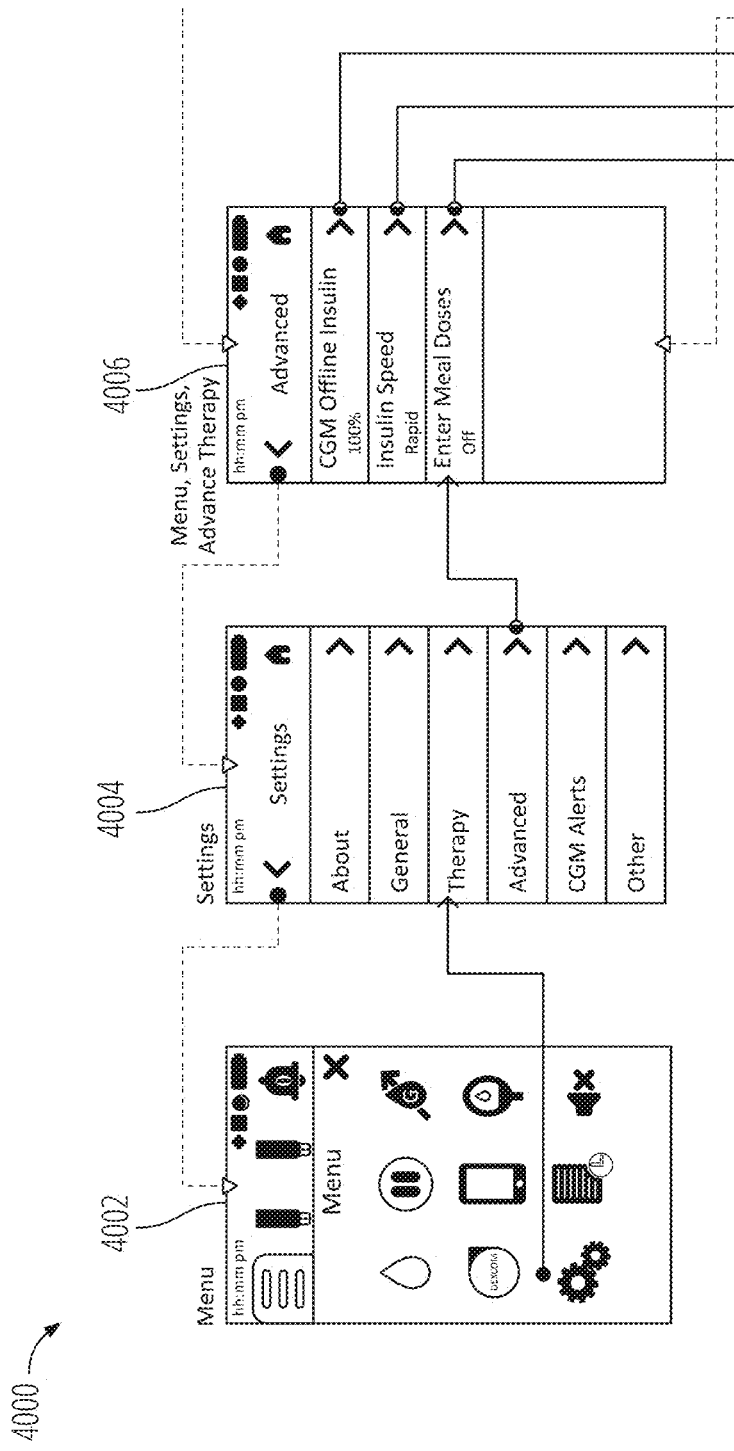
FIG. 40 is a series of screen displays showing a user activating meal dosage on an ambulatory device.

FIG. 40 illustrates a plurality of screens 4000 that may be produced by the ambulatory medical device 3602. Upon activating the ambulatory medical device (e.g., the ambulatory medical device 500, 600, or 3602) the initial menu screen 4002 may be displayed. In the menu screen 4002, options regarding functionalities of the ambulatory medical device 3602 is provided. The list of functionalities may cover all the aspects of the ambulatory medical device 3602. The user may access and control many aspects of the device by choosing the setting option. The setting option will allow the user to further assess and regulate the adjustable functionalities of the ambulatory medical device 3602. Upon selecting the setting option, the setting screen 4004 may be displayed and the user may select the advanced setting option. Upon selecting the advanced option, the advanced setting screen 4006 is displayed, and the user is provided the option to double check the CGM insulin levels and change the speed of the of the insulin pump. The user may speed up the process or slow down the process depending on the regulation stats that are provided by the model predictive control component 3624.

Figure 41:
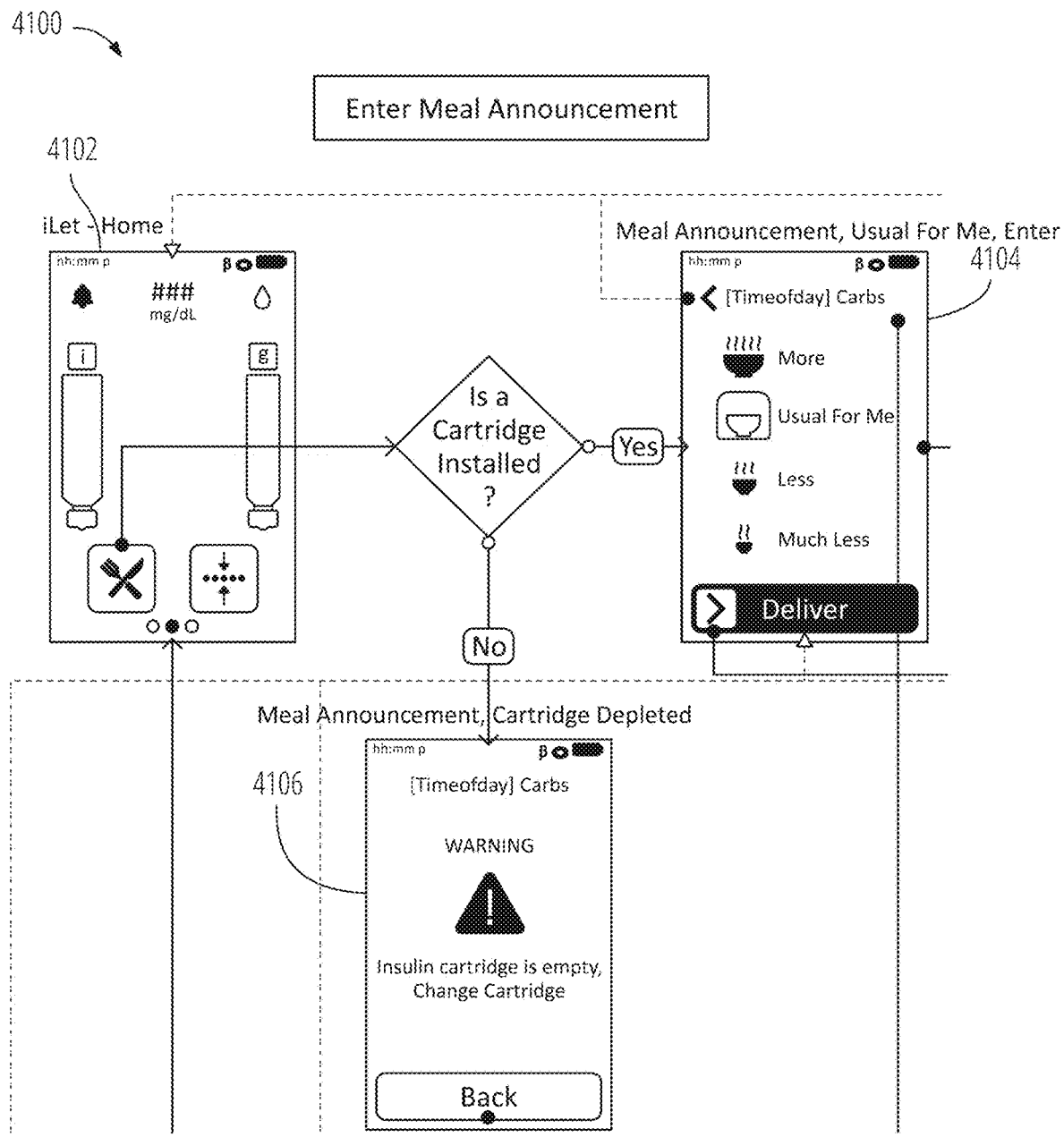
FIG. 41 is a series of screen displays showing a user activating meal announcement on an ambulatory device.

FIG. 41 illustrates a plurality of screens 4100 that may be produced by the ambulatory medical device 3602. The plurality of screens 4100 is the process that a user may take in order to enter meal announcements. The home screen 4102 provides information and stats regarding the cartridge of the ambulatory medical device 3602. The user may select the meal button with or without an installation of a new cartridge. If a user selects the meal button without installing a new cartridge, the ambulatory device 3602 will display the warning screen 4106, where the user is warned that the insulin cartridge is empty, and the device further advises the user to change the cartridge. However, if a new cartridge is already installed and the food button is pressed, the ambulatory medical device 3602 will display the carbs screen 4104, where the user is provided the option to choose a meal dose option. The carbs screen 4104 allows the user to provide subjective information regarding the food that is to be digested. This subjective data provided by the user is further stored in the model predictive control component 3624 for further regulation of the blood glucose level.

Figure 42:
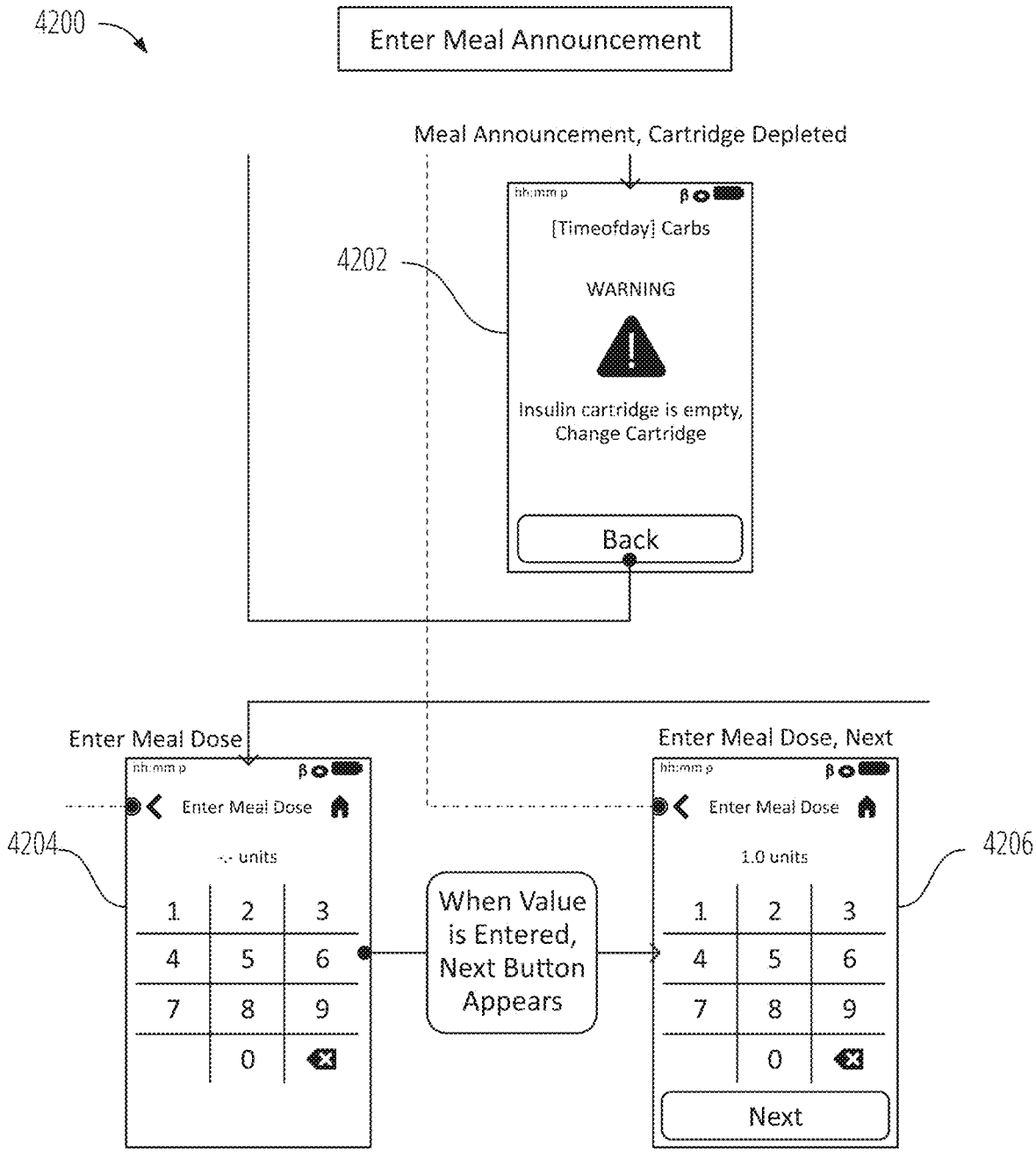
FIG. 42 is a series of screen displays showing a user inputting the total number of units on an ambulatory device.

FIG. 42 illustrates a plurality of screens 4200 that may be produced by the ambulatory medical device 3602. The plurality of screens 4200 demonstrates the process of the user being alerted about the empty cartridge and having the option to replace the cartridge and further enter the meal doses. Warning screen 4202 alerts the user that the insulin cartridge is empty and the fact that it needs to be replaced. Upon replacing the cartridge, screens 4204 and 4206 will be displayed. Screen 4204 is initially displayed, and a user may enter a specified dose for each meal on a numerical pad. Upon inserting a numerical specified dose, screen 4206 is displayed where a next button is provided for the user to further complete the therapy change. The numerical specified dose is further stored in the model predictive control component 3624 for further regulation of the blood glucose level.

FIG. 43 illustrates a plurality of screens 4300 that may be produced by the ambulatory medical device 3602. Upon selecting the delivery request, a user may cancel the delivery of the medicaments prior to the completion of the delivery. The ambulatory medical device 3602 displays a countdown prior to delivery. The initial countdown screen 4302 is proceeded by the secondary countdown screen 4306. During these countdown screens, a cancel button is provided for the user to cancel the therapy change. During the initial countdown screen 4302 or the secondary countdown screen 4306, the user may cancel the delivery at any time. By swiping the cancel button, the user may officially stop the delivery of the therapy change. If the user does not cancel, the therapy change may be delivered successfully. Furthermore, the time and the amount of the therapy change delivery is stored in the model predictive control component 3624 for further regulation of the blood glucose level. However, if the user decides to cancel the delivery, the delivery will be canceled and the screen 4304 will be provided. Once the delivery cancelation is requested and the screen 4304 is displayed, upon pressing the ok button, the ambulatory medical device 3602 will display a lock screen 4308 and take the time to officially cancel the therapy change request.

Figure 44:
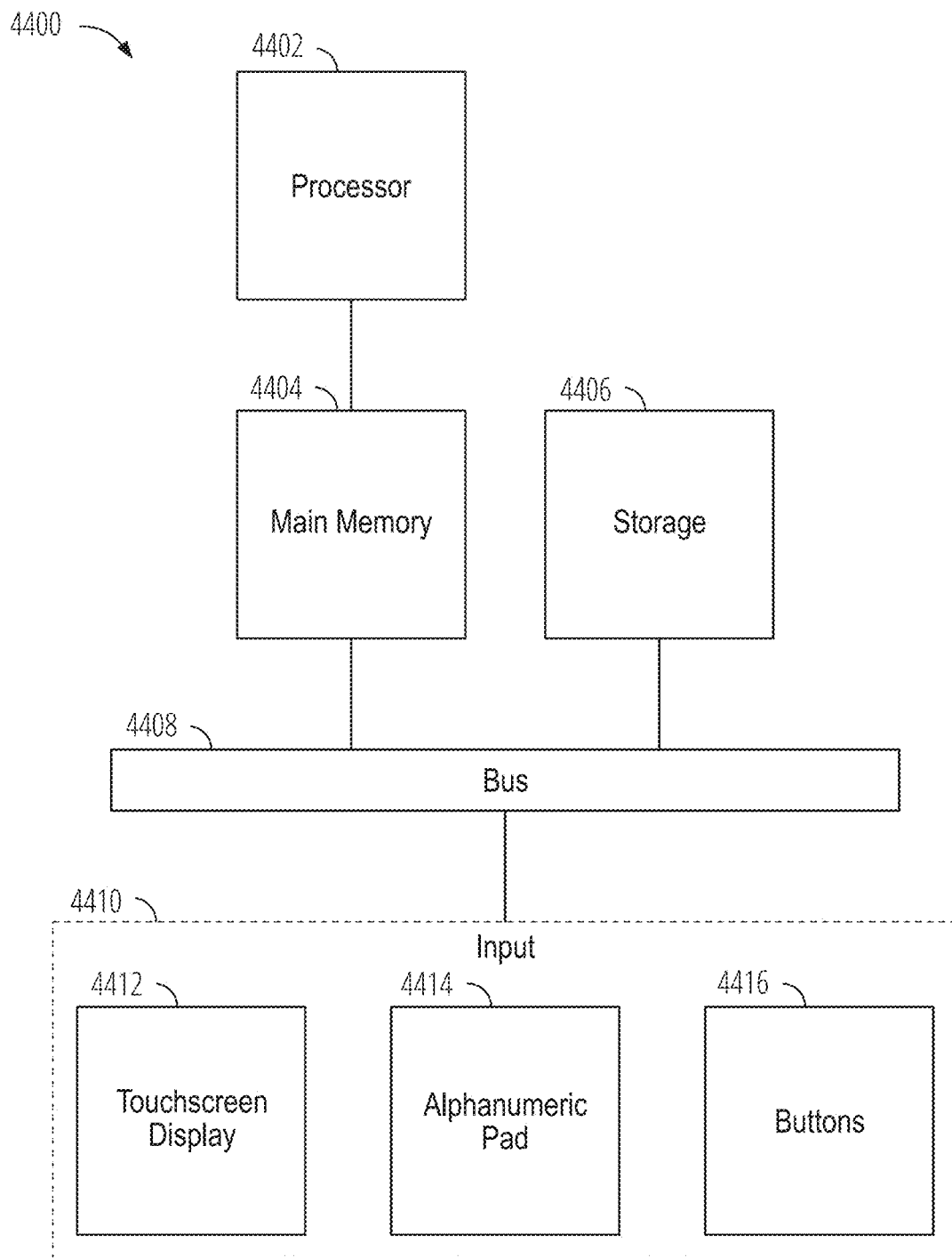
FIG. 44 is a schematic illustrating a computer system that can be implemented in various embodiments of the described subject matter.

FIG. 44 is a block diagram illustrating a computer system 4400 that may be implemented in the various embodiments in the described subject matter. The computer system 4400 includes a processor 4402 (e.g., electronic or hardware processor), main memory 4404, storage 4406, a bus 4408, and input 4410. The processor 4402 may be one or more processors. The processor 4402 executes instructions that are communicated to the processor through the main memory 4404. The main memory 4404 feeds instructions to the processor 4402. The main memory 4404 is also connected to the bus 4408. The main memory 4404 may communicate with the other components of the computer system through the bus 4408. Instructions for the computer system 4400 are transmitted to the main memory 4404 through the bus 4408. Those instructions may be executed by the processor 4402. Executed instructions may be passed back to the main memory 4404 to be disseminated to other components of the computer system 4400. The storage 4406 may hold large amounts of data and retain that data while the computer system 4400 is unpowered. The storage 4406 is connected to the bus 4408 and can communicate data that the storage holds to the main memory 4404 through the bus 4408.

The processor 4402 may be any type of general-purpose processor including, but not limited to a central processing unit ("CPU"), a graphics processing unit ("GPU"), a complex programmable logic device ("CPLD"), a field programmable gate array ("FPGA"), or an application-specific integrated circuit ("ASIC"). Some embodiments of the computer system 4400 in the ambulatory medical device 102 features a CPU as the processor 4402. However, embodiments may be envisioned for the computer system of the ambulatory medical device 102 that incorporate other types of processors 4402.

The main memory 4404 can be any type of main memory that can communicate instructions to the processor 4402 and receive executed instructions from the processor 4402. Types of main memory 4404 include but are not limited to random access memory ("RAM") and read only memory ("ROM"). In some embodiments, the computer system 4400 incorporates RAM as the form of main memory 4404 to communicate instructions to the processor 4402 and receive executed instructions from the processor 4402. Other embodiments may be envisioned that incorporate other types of main memory 4404 in the computer system 4400.

The storage 4406 can be any type of computer storage that can receive data, store data, and transmit data to the main memory 4404 via the bus 4408. Types of storage 4406 that can be used in the computer system 4400 include, but are not limited to, magnetic disk memory, optical disk memory, and flash memory. In some embodiments, flash memory is used as the storage 4406 in the computer system 4400 of the ambulatory medical device 102. Other embodiments that use other types of storage 4406 for the computer system 4400 may be envisioned.

The bus 4408 connects the internal components of the computer system 4400. The bus 4408 may include a multitude of wires that are connected to the components of the computer system 4400. The wires of the bus 4408 may differ based on the components of the computer system 4400 to which the bus 4408 connects. In various embodiments, the bus 4408 connects the processor 4402 to the main memory 4404. In various embodiments, the processor 4402 is directly connected to the main memory 4404.

The input 4410 of the computer system 4400 may include a touchscreen display 4412, an alphanumeric pad 4414, and buttons 4416. The touchscreen display 4412 may both produce output and accept input. The touchscreen display can generate user input signals corresponding user input. A touchscreen controller can receive user the user input signals. The touchscreen display can display user interface screens generated by computer system 4400 as discussed herein (for example, the critical status information interface illustrated in FIG. 55). The bus 4408 may be coupled to the touchscreen display 4412 to produce visual output. The touchscreen display 4412 may also accept input via capacitive touch, resistive touch, or other touch technology. The input surface of the touchscreen display 4412 can register the position of touches on the surface. Some types of touchscreen display 4412 can register multiple touches at once. The alphanumeric pad 4414 may include a multitude of keys with numerical, alphabetical, and symbol characters. Signals from the alphanumeric pad 4414 may be communicated by the bus 4408 to the main memory 4404. Keys of the alphanumeric pad 4414 may be capacitive or mechanical. In some embodiments, the alphanumeric pad 4414 is displayed on the touchscreen display 4412. Buttons 4416, such as the wake button or interface, may be capacitive, mechanical, or other types of input buttons. The wake interface may include one or more of the embodiments described herein with respect to the wake interface 3220 of FIG. 32.

The input 4410 may be a user interface module as disclosed with respect to the user interface module 3218 of FIG. 32. The user interface module may include any type of user interface controller for providing a user interface as discussed herein. The user interface may be provided on a display 4412 of the computer system 4400 (e.g., an AMD 100), or may be transmitted to a display of an electronic device in communication with the computer system 4400 (e.g., an AMD 100). In some cases, the user interface controller may be a touchscreen controller that is configured to output display signals configured to generate one or more user interface screens on a touchscreen. Further, the touchscreen controller may be configured to receive user input signals corresponding to user interaction with the touchscreen.

Occlusion Detection

When a subject is receiving therapy, often there may be an occlusion (e.g., a kink or obstruction in the medicament delivery path). The occlusion may be detected by a system and/or the medicament pump. However, sometimes a false signal may be detected that would otherwise cause a system to slow and/or stop therapy delivery. Systems and methods described herein can be effective at reducing the likelihood of needlessly slowing and/or stopping therapy delivery by better detecting false occlusion signals. The systems and methods can protect the user from dangerous occlusions while minimizing false alarms of occlusions. False alarms may be the result of one or more signals, such as an electrical signal (e.g., increased current), an increased friction within the system, or some other signal.

FIG. 45A illustrates a schematic of an example ambulatory medicament pump 4500 that is configured to maintain delivery of therapy to a subject after determining that a possible occlusion exists in a medicament delivery system. The medicament delivery system can include the ambulatory medicament pump 4500 and/or other components described herein, such as elements described with respect to FIG. 29, FIG. 33 (deleted), FIG. 34, and FIG. 36. The ambulatory medicament pump 4500 includes a medicament reservoir 4502, a pump motor 4508, a non-transitory memory 4510, and an electronic hardware processor 4512. The ambulatory medicament pump 4500 can include a medicament passageway 4506 configured to couple to a medicament delivery interface 4504. The medicament passageway 4506 may include a delivery tube operatively coupled between the medicament reservoir 4502 and an infusion site or a subcutaneous depot of the subject and may be configured to deliver the medicament through the skin of the subject. The medicament delivery interface 4504 may be at the infusion site or a subcutaneous depot of the subject, and of the subject where medicament is delivered to the subject as therapy.

The ambulatory medicament pump 4500 is any medical device that the subject may carry around and use with the approval of a medical professional. The ambulatory medicament pump 4500 may correspond to and/or share certain functionality with one or more devices described herein, such as the ambulatory medical device 3602 or therapy delivering component 3608 described above with respect to FIG. 36. There are many different types of ambulatory medicament pumps 4500. In one embodiment, the ambulatory medicament pump 4500 is an insulin and/or glucagon infusion device for subjects that have type I diabetes. Ambulatory medicament pumps 4500 allow subjects the freedom to receive medical care in any setting at their convenience.

However, the ambulatory medicament pump 4500 could malfunction during use by the subject in the absence of a medical professional. For example, an interference or occlusion may develop within the ambulatory medicament pump 4500 and/or associated elements. An occlusion may develop in a variety of possible scenarios. For example, a tube (e.g., the medicament passageway 4506) may become kinked, the pump motor 4508 may become jammed or obstructed (e.g., from sand or debris), the medicament reservoir 4502 may become jammed or obstructed, etc. When an occlusion alert is identified, this could be an indication of an actual occlusion that requires attention and perhaps repair by a professional. Additionally or alternatively, the occlusion alert may suggest that there is an anomaly or other condition in the therapy delivery and/or functionality of the ambulatory medicament pump 4500 but not that an occlusion is present. For example, the anomaly could correspond to a false alarm. The false alarm could be due to one or more conditions, such as an increase of pressure in the medicament reservoir 4502, an increased pressure on a pump piston operatively coupled to pump motor 4508, slippage of the piston, a spike or drop in electrical current delivered to the pump motor 4508, and/or something else.

The ambulatory medicament pump 4500 can include a wireless data interface may be physically connected with the ambulatory medicament pump 4500, wirelessly connected, connected via a cloud-based computer system, or connected in any other way.

The processor 4512 is part of a computing system that performs the computing functions for the ambulatory medicament pump 4500. The processor 4512 may be a single processor or may be made up of several processors. The processor 4512 may perform the computing functions for a single ambulatory medicament pump 4500 or many ambulatory medicament pumps. The processor 4512 receives signals from the pump motor 4508 and/or from the wireless data interface. The processor 4512 also transmits signals to the pump motor 4508 and/or from the wireless data interface.

The subject is any individual that uses the ambulatory medicament pump 4500. In some embodiments the subject is an individual with diabetes that requires a periodic infusion of insulin or glucagon to maintain healthy blood sugar levels. In various embodiments, the ambulatory medicament pump 4500 infuses insulin or glucagon into the subject. The subject may transport the ambulatory medicament pump 4500. Thus, as the subject moves around, there is a danger that the subject will be away from medical professionals who can provide any necessary therapy if an occlusion develops within the ambulatory medicament pump 4500.

The ambulatory medicament pump 4500 can include therapy delivery components, such as the pump motor 4508. The therapy delivery components may include one or more elements of an infusion pump, such as the pump piston, a cannula, and/or other components as described herein. The therapy delivery components provide medicaments to the subject. Signals received from the processor 4512 are executed by the therapy delivery components, such as the pump motor 4508, to change therapy such as starting, modifying, or stopping a therapy. The therapy delivery components may include a computing component for interpreting and executing instructions from the processor 4512. Thus, the therapy delivery components can follow a program that is controlled by the processor 4512.

The therapy change delivery 3616 is the performance, by the ambulatory medicament pump 4500, of the therapy change input 3610 that was verified at the therapy delivering component 3608. The therapy change that is delivered by the therapy change delivery 3616 corresponds to the therapy change selection made by the subject. In some embodiments, the ambulatory medicament pump 4500 alerts the subject that it is performing a change in therapy delivery. In an example of various embodiments, the ambulatory medicament pump 4500 displays the therapy change during the change in therapy delivery. Any number of details of the therapy change may be displayed during the change in therapy delivery, such as shown in FIG. 43 and described above.

The ambulatory medicament pump 4500 may include a user interface, such as a graphical user interface. The user interface may be operatively coupled to the ambulatory medicament pump 4500 via, for example, the wireless data interface. The user interface can include a touchscreen display. The touchscreen display may display an occlusion detection interface for the subject and/or receive subject inputs on the occlusion detection interface. Inputs on the touchscreen display may be registered by any touch technology including, but not limited to capacitive and resistive sensing. The touchscreen display may be a part of a mobile computing device, such as a cellular phone, tablet, laptop, computer, or the like. The touchscreen display may have a computing component for interpreting and executing instructions from the processor 4512. Thus, the touchscreen display can follow instructions that are directed by the processor 4512. To receive input, the touchscreen display may display buttons, alphanumeric characters, symbols, graphical images, animations, or videos. In some embodiments, the user interface is not a touchscreen display. The user interface may include one or more mechanical buttons. The user interface may include an alert generator, such as a light emitter, a speaker, a haptic feedback system, or other sensory alert system.

The ambulatory medicament pump 4500 may be configured to detect possible occlusions and probable occlusions. A possible occlusion suggests that an occlusion may exist but that more information is needed to adequately determine that an occlusion probably exists. A probable occlusion suggests that the ambulatory medicament pump 4500 or other system element may take action based on the detection that a probable occlusion exists.

To determine whether an occlusion is possible or probable, the ambulatory medicament pump 4500 may undertake one or more of a variety of actions. For example, the system may be configured to detect one or more fluid delivery parameters associated with the medicament delivery system. The fluid delivery parameter can include an electrical parameter, such as a current supplied by the pump motor 4508, an electrical resistance associated with the pump motor 4508, or a voltage associated with the pump motor 4508. The fluid delivery parameter can include any other detectable parameter, whether via a sensor (e.g., a pressure sensor, a flow rate sensor, or the like) or via some other way.

For example, the fluid delivery parameter can include a fluid flow rate and/or a fluid flow acceleration through the cannula, through the medicament reservoir 4502, through the medicament passageway 4506, through the medicament delivery interface 4504, or through some other portion of the ambulatory medicament pump 4500 or of the medicament delivery system. The fluid delivery parameter can include a pressure on the pump motor 4508, on the medicament reservoir 4502, on the medicament passageway 4506, on the medicament delivery interface 4504, or on some other component or components of the medicament delivery system. In some cases, the pressure on or inside any components of the medicament delivery system may be obtained by a pressure sensor (e.g., a pressure sensor integrated with the component). For example, the acceptable pressure within the ambulatory medicament pump 4500 may be around 2-3 pounds per square inch (psi), and the fluid delivery parameter may be a pressure threshold of any pressure above a threshold pressure level (e.g., about 15 psi).

The ambulatory medicament pump 4500 may determine that a fluid delivery parameter satisfies an initial occlusion condition. The first initial occlusion condition may indicate that a possible occlusion exists that interferes with delivery via the medicament delivery system. Because it may be advantageous to continue the delivery of medicament to the subject when only a possible occlusion exists (as opposed to a probable occlusion), in response to the determination that the fluid delivery parameter satisfies the initial occlusion condition, the ambulatory medicament pump 4500 can maintain delivery of therapy to the subject. Maintaining delivery of therapy can include providing therapy at the same rate as prior to the determination that the initial fluid delivery parameter satisfies the initial occlusion condition. In some embodiments, maintaining delivery may mean providing therapy at a different rate from prior to the determination. For example, maintaining delivery may include providing delivery at a different speed (e.g., half speed). In some embodiments, in response to the determination that the fluid delivery parameter satisfies the initial occlusion condition, the ambulatory medicament pump 4500 may modify an attribute of the delivery of therapy while maintaining delivery of the therapy to the subject. For example, the attribute may include a delivery speed, a delivery interval, a delivery pressure, or impulse, etc. In some examples, the ambulatory medicament pump 4500 can begin injecting the fluid slowly and then inject quickly to invoke a jerk. This may be helpful at clearing a possible occlusion. Other examples are possible. For example, the ambulatory medicament pump 4500 may pulse the delivery of delivery of therapy at regular and/or irregular intervals.

In some embodiments, maintaining delivery may include slowing delivery and then suddenly pushing hard (e.g., to invoke a jerk). Invoking a jerk may be helpful in dislodging a cause of the occlusion (e.g., a jammed piece of sand or other debris). In some embodiments, the ambulatory medicament pump 4500 may delivery the therapy slowly or faster in an attempt to clear the occlusion. In some embodiments, the ambulatory medicament pump 4500 may modify (e.g., reduce) the pressure within the ambulatory medicament pump 4500 and/or related system parts. In response to the determination that the fluid delivery parameter satisfies the initial occlusion condition, the ambulatory medicament pump 4500 may pause delivery of therapy for a length of time. The length of time of the pause may be at least about 1 second, at least about 2 seconds, at least about 3 seconds, at least about 5 seconds, at least about 10 seconds, at least about 15 seconds, at least about 30 seconds, at least about 1 minute, or any length of time therebetween or fall within a range of any time having endpoints therein. In some embodiments, in response to the determination that the verification parameter satisfies the final occlusion condition, the ambulatory medicament pump 4500 may increase delivery of therapy to the subject after a passage of an amount of time. The amount of time may be about 10 seconds, about 20 seconds, about 30 seconds, about 45 seconds, about 1 minute, at least about 2 minutes, about 3 minutes, about 5 minutes, or any amount of time therebetween or fall within a range of any time having endpoints therein.

The ambulatory medicament pump 4500 may be configured to receive a verification parameter associated with the possible occlusion. The verification parameter can serve as a way for the ambulatory medicament pump 4500 to determine whether the possible occlusion is actually a probable occlusion. The verification parameter may be a separate indication that tends to confirm the existence of the occlusion. For example, the verification parameter may be received from a glucose detector operatively coupled to the ambulatory medicament pump 4500. The verification parameter can include a glucose level signal received from the glucose sensor configured to detect a glucose level of the subject. The glucose level signal can include one or more glucose parameters, such as a glucose level of the subject and/or an indication of a glucose trend indicating at least a predicted change in the glucose level of the subject. Additionally or alternatively, the verification parameter can include an amount of time before receiving another indication of the status of the possible occlusion. For example, the ambulatory medicament pump 4500 may wait about 10 seconds, about 30 seconds, about 1 minute, about 2 minutes, about 5 minutes, about 10 minutes, about 15 minutes, about 30 minutes, about 45 minutes, about an hour, about 2 hours, about 3 hours, or any amount of time therebetween or fall within a range of any time having endpoints therein. In some embodiments, the verification parameter can include a result from an action taken by the ambulatory medicament pump 4500 in an attempt to further diagnose or otherwise characterize a possible occlusion (e.g., to support a determination that it is a probable conclusion). Such an action may include supplying a sudden increase in pressure by the pump motor 4508 or other action.

The ambulatory medicament pump 4500 may determine that the verification parameter satisfies a final occlusion condition. If the verification parameter supports the inference toward a probable occlusion, then this may suggest that the final occlusion condition is satisfied. The final occlusion condition indicates that a probable occlusion exists in the medicament delivery system. The final occlusion condition includes a glucose level indicating a threshold value of at least 150 mg/dL of blood glucose concentration. Other values are possible. The initial occlusion condition and the final occlusion condition can be based on different parameters. For example, the initial occlusion condition may be based on a current drawn by the pump motor 4508 while the final occlusion condition may be based on a glucose level signal of the subject. Other combinations are possible.

In response to the determination that the verification parameter satisfies the final occlusion condition, the ambulatory medicament pump 4500 can modify (e.g., reduce) delivery of therapy to the subject. The modification of therapy may include providing less than the amount of therapy delivered during the maintaining of therapy. For example, the modification of therapy can include reducing and/or essentially stopping the delivery of therapy. The stopping of delivery may be temporary. In some examples, after stopping or reducing delivery for an amount of time (e.g., about 10 seconds, about 30 seconds, about 1 minute, etc.), the ambulatory medicament pump 4500 may increase delivery of therapy to the subject after a passage of an amount of time. Because of the pause in therapy, in some examples the ambulatory medicament pump 4500 will increase delivery, at least temporarily, at a greater rate than the rate prior to the pause.

The ambulatory medicament pump 4500 can further generate a first user alert based at least in part on the determination that the fluid delivery parameter satisfies the initial occlusion condition. Additionally or alternatively, the ambulatory medicament pump 4500 can generate a second user alert based at least in part on the determination that the verification parameter satisfies the final occlusion condition. The first and/or second user alert can be displayed via the user interface. The first and/or second user alerts can be a sensory alert, such as a visual, tactile, aural, or other sensory alert. The sensory alert may be an annoying and/or loud tone or voice, audible alarm, phone call, and/or other kind of sensory alarm. The second user alert may be provided to the subject receiving the therapy and/or another person or persons. The second user alert may be configured to wake a sleeping subject and/or caregiver.

In some embodiments, the ambulatory medicament pump 4500 may identify an intermediate occlusion condition and that the fluid delivery parameter satisfies the intermediate occlusion condition. In some cases, the intermediate occlusion condition may be satisfied after the determination of the initial occlusion condition. The ambulatory medicament pump 4500 can determine that the fluid delivery parameter satisfies an intermediate occlusion condition, wherein the intermediate occlusion condition indicates that the possible occlusion persists. In response to the determination that the fluid delivery parameter satisfies the intermediate occlusion condition, the ambulatory medicament pump 4500 may modify an attribute of the delivery of therapy. The attribute of the delivery of therapy that is modified may include a rate of delivery and/or a size of a bolus of therapy. The attribute may include a delivery speed, a delivery interval, a delivery pressure, or impulse, etc. The ambulatory medicament pump 4500 may modify the attribute of the delivery of therapy in order to invoke a jerk or to otherwise address a potential occlusion. In some examples, the attribute may relate to an action taken by the ambulatory medicament pump 4500 in an attempt to further diagnose or otherwise characterize a possible occlusion (e.g., to support a determination that it is a probable conclusion).

Figure 45B:
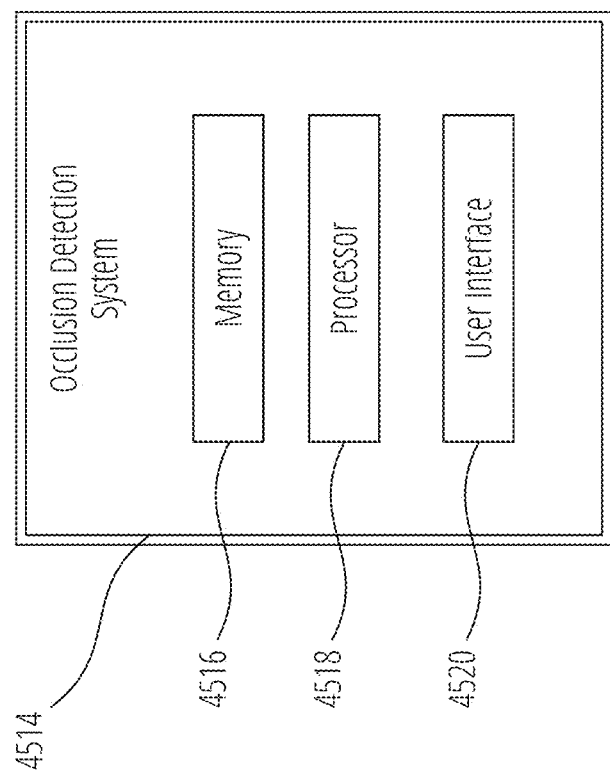
FIG. 45B is a schematic illustrating an example occlusion detection system.

Some embodiments of an occlusion detection system are described with reference to FIG. 45B. FIG. 45B is a schematic illustrating an example occlusion detection system 4514. The occlusion detection system 4514 can include a non-transitory memory 4516, an electronic hardware processor 4518, and a user interface 4520. The user interface 4520 may include an interactive graphical user interface, such as a smartphone or another mobile device.

The processor 4518 may execute instructions stored on the memory 4516 to perform various functions. The occlusion detection system 4514 can receive a fluid delivery parameter associated with a medicament delivery system. The medicament delivery system may include an ambulatory medicament pump (e.g., the ambulatory medicament pump 4500) and/or other medicament delivery system components, such as describe above. The fluid delivery parameter may be the fluid delivery parameter described above. The occlusion detection system 4514 can determine that the fluid delivery parameter satisfies an initial occlusion condition. The initial occlusion condition may indicate that a possible occlusion exists in the medicament delivery system. The occlusion detection system 4514 can send an instruction to the medicament delivery system to maintain delivery of therapy to the subject in response to the determination that the fluid delivery parameter satisfies the initial occlusion condition. Additionally or alternatively, the occlusion detection system 4514 may generate a user alert based at least in part on the determination that the fluid delivery parameter satisfies the initial occlusion condition. The user alert may be generated via the user interface 4520.

The occlusion detection system 4514 can also receive a verification parameter associated with the possible occlusion. The occlusion detection system 4514 can then determine that the verification parameter satisfies a final occlusion condition. The final occlusion condition can indicate that a probable occlusion exists in the medicament delivery system. The occlusion detection system 4514 can send an instruction to the medicament delivery system to modify (e.g., reduce) delivery of therapy to the subject in response to the determination that the verification parameter satisfies the final occlusion condition. The occlusion detection system 4514 can generate a user alert based at least in part on the determination that the verification parameter satisfies the final occlusion condition.

Figure 46A:
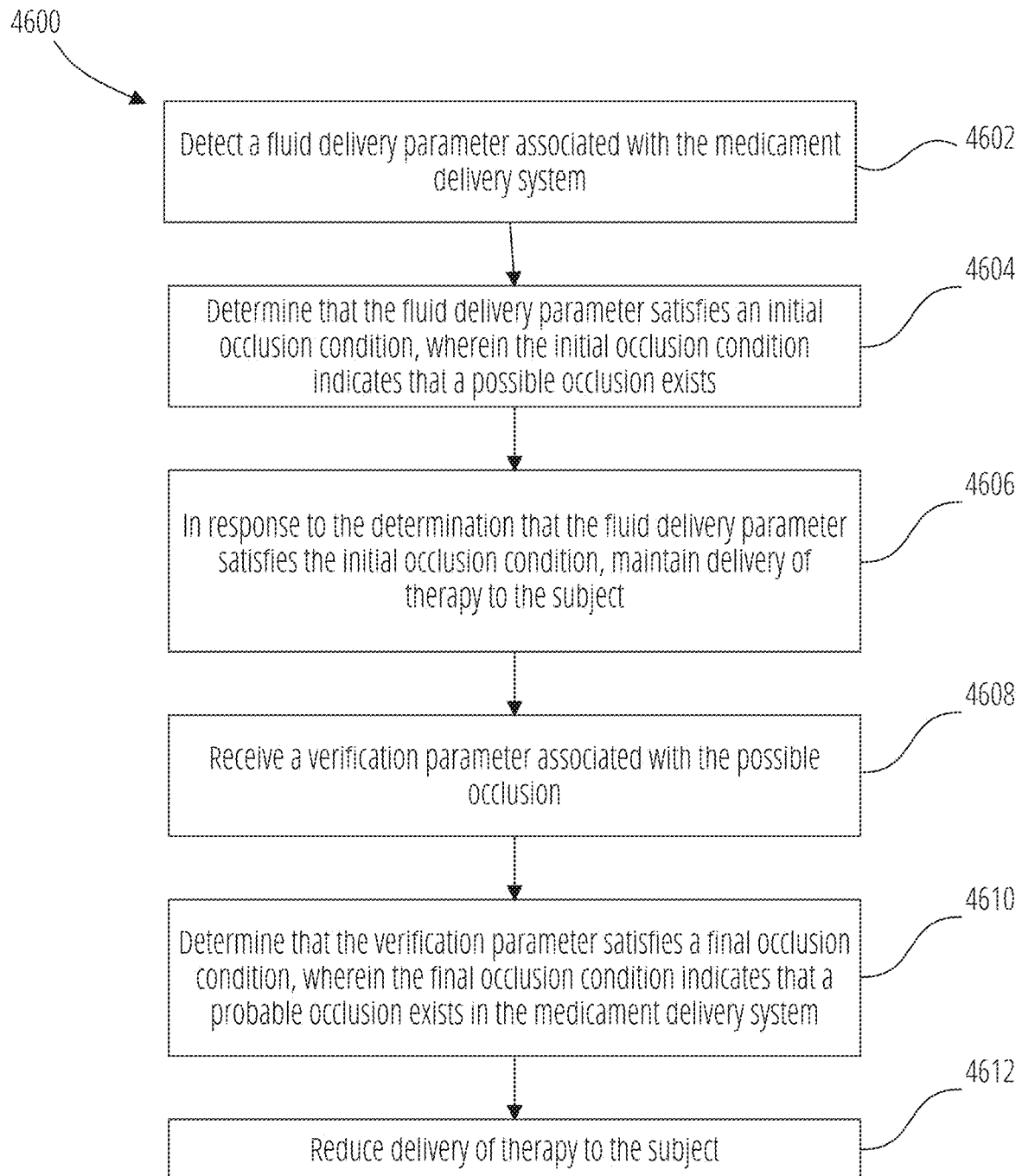
FIG. 46A is a flow chart flow diagram illustrating an example method that may be used by an AMD to maintain delivery of therapy to a subject after determining that a possible occlusion exists in a medicament delivery system.
Figure 46B:
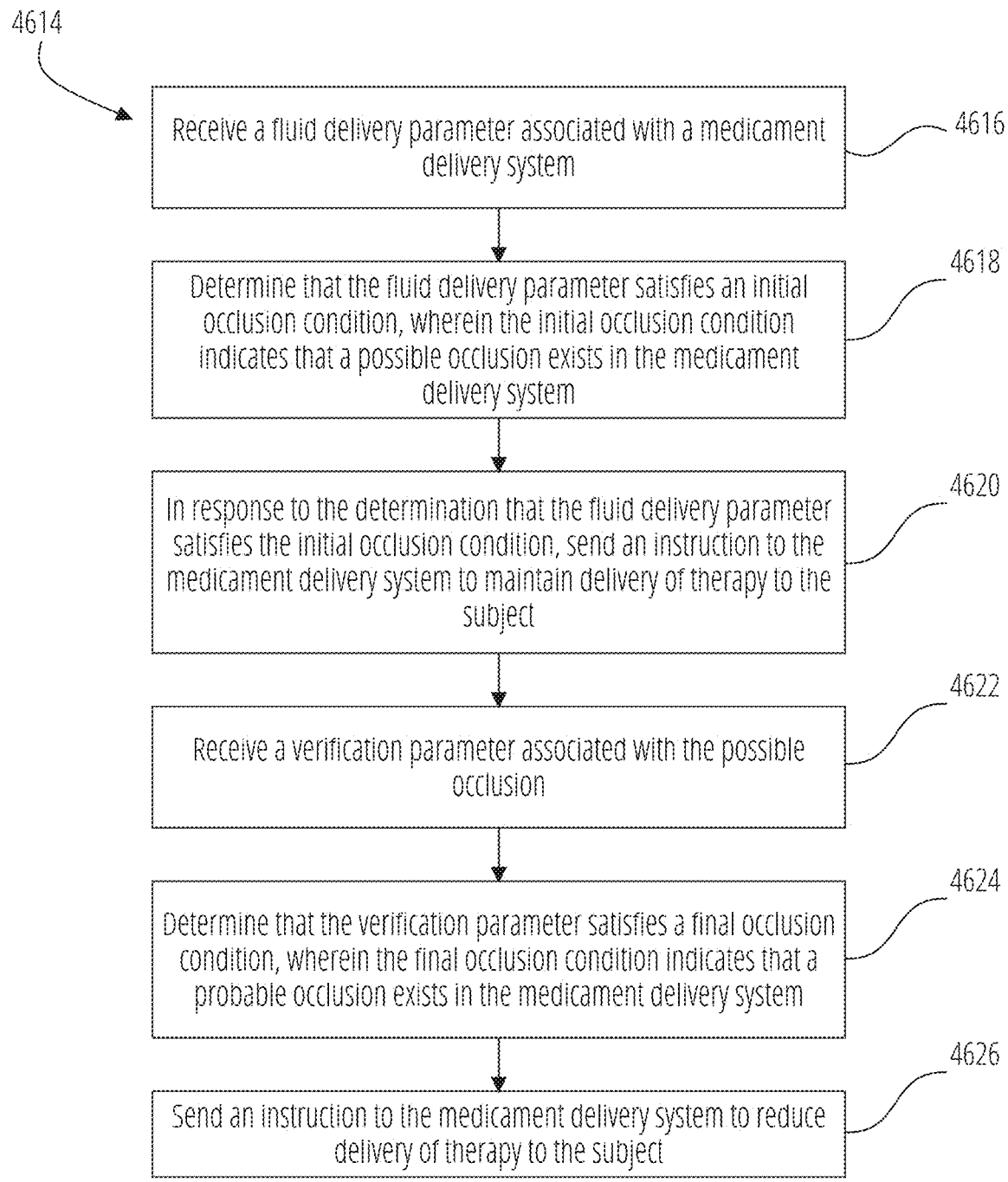
FIG. 46B is a flow chart flow diagram illustrating an example method that that may be used by an occlusion detection system to maintain delivery of therapy to a subject after determining that a possible occlusion exists in a medicament delivery system.

FIG. 46A and FIG. 46B show methods for determining possible and/or probable occlusions. FIG. 46A is a flow chart flow diagram illustrating an example method 4600 that may be used by an ambulatory medical device to maintain delivery of therapy to a subject after determining that a possible occlusion exists in a medicament delivery system. The method 4600 may be performed by a system such as a medicament delivery system including the ambulatory medicament pump 4500. At block 4602, the system detects a fluid delivery parameter associated with the medicament delivery system. At block 4604, the system determines that the fluid delivery parameter satisfies an initial occlusion condition. The initial occlusion condition can indicate that a possible occlusion exists. At block 4606, the system maintains delivery of therapy to the subject in response to the determination that the fluid delivery parameter satisfies the initial occlusion condition. At block 4608, the system receives a verification parameter associated with the possible occlusion. At block 4610, the system determines that the verification parameter satisfies a final occlusion condition. The final occlusion condition indicates that a probable occlusion exists in the medicament delivery system. At block 4612, the system may modify (e.g., reduce) delivery of therapy to the subject. The modification of therapy may be based on the determination that the verification parameter satisfies the final occlusion condition.

FIG. 46B is a flow chart flow diagram illustrating an example method 4614 that may be used by an occlusion detection system to maintain delivery of therapy to a subject after determining that a possible occlusion exists in a medicament delivery system. The method 4614 may be performed by a system such as an occlusion detection system such as the occlusion detection system 4514. At block 4616, the system receives a fluid delivery parameter associated with a medicament delivery system. At block 4618, the system determines that the fluid delivery parameter satisfies an initial occlusion condition. The initial occlusion condition can indicate that a possible occlusion exists. At block 4620, the system sends an instruction to the medicament delivery system to maintain delivery of therapy to the subject in response to the determination that the fluid delivery parameter satisfies the initial occlusion condition.

At block 4622, the system receives a verification parameter associated with the possible occlusion. At block 4624, the system determines that the verification parameter satisfies a final occlusion condition. The final occlusion condition indicates that a probable occlusion exists in the medicament delivery system. At block 4626, the system may send an instruction to the medicament delivery system to modify (e.g., reduce) delivery of therapy to the subject. The modification of therapy may be based on the determination that the verification parameter satisfies the final occlusion condition.

Example AMD With Alarm Muting

Alert fatigue can be an issue with medical devices due to excessive alerts which do not necessarily require user interaction. In many cases, an alarm condition may occur that does not require immediate user attention or may only be resolved by the manufacturer of the AMD. Persistent annunciation of such alarms may cause alert fatigue, which can be dangerous because it can lead users to ignore all alerts, including serious alerts or alerts that require action in the short term. Advantageously, the disclosed alarm system and methods may implement a Do Not Disturb mode which users may activate to mute non-urgent alarms. The system and methods described herein can suppress lower urgency alarms during user selected periods. The user-selected periods can include times when a user is sleeping or in a meeting. These periods of Do Not Disturb activation and deactivation can be controlled by the user. The system and methods can also provide for automatic or user preselected/scheduled activation of the Do Not Disturb mode during recurring time periods or intervals, such as during the night when the user is sleeping, with the Do Not Disturb mode being activated by the system during the recurring time period or interval. In some cases, a recurring time interval may include a time interval occurring every day (e.g., every day between 18:00 and 7:00, or between 20:00 and 6:00, or other time intervals.)

In some cases, lower urgency alarms may include at least alarms with severity levels 0, 1, 2, and 3, as disclosed herein. Higher urgency alarms (e.g., severity levels 3, 4, 5, etc.) may not be muted, both during usual operation of the AMD and when Do Not Disturb mode is activated. In some cases, the user may define which severity levels are to be considered urgent in a Do Not Disturb session. It should be noted that severity level alone may not be enough to determine whether an alarm may be muted. In some cases, one severity level may encompass both mute-eligible and mute-ineligible alarms. For example, in some cases, only some level 3 alarms may be muted. In such cases, when Do Not Disturb mode is activated, only the mute-eligible level 3 alarms may be muted during Do Not Disturb mode, while the mute-ineligible alarms will be annunciated as urgent alarms. In some cases, mute-eligible level 3 alarms may include the level 2.5 alarms as described herein.

It should be noted that the alarm muting processes described herein may mute but not postpone detected alarm conditions. Though auditory and haptic annunciations may be muted, details relating to each detected alarm condition may be displayed on a list of pending alarm conditions in real time and can be viewed by the user at any time. U.S. Pat. No. 11,135,364 disclosing alarm status indication is incorporated by reference herein and made a part of this specification.

Figure 47:
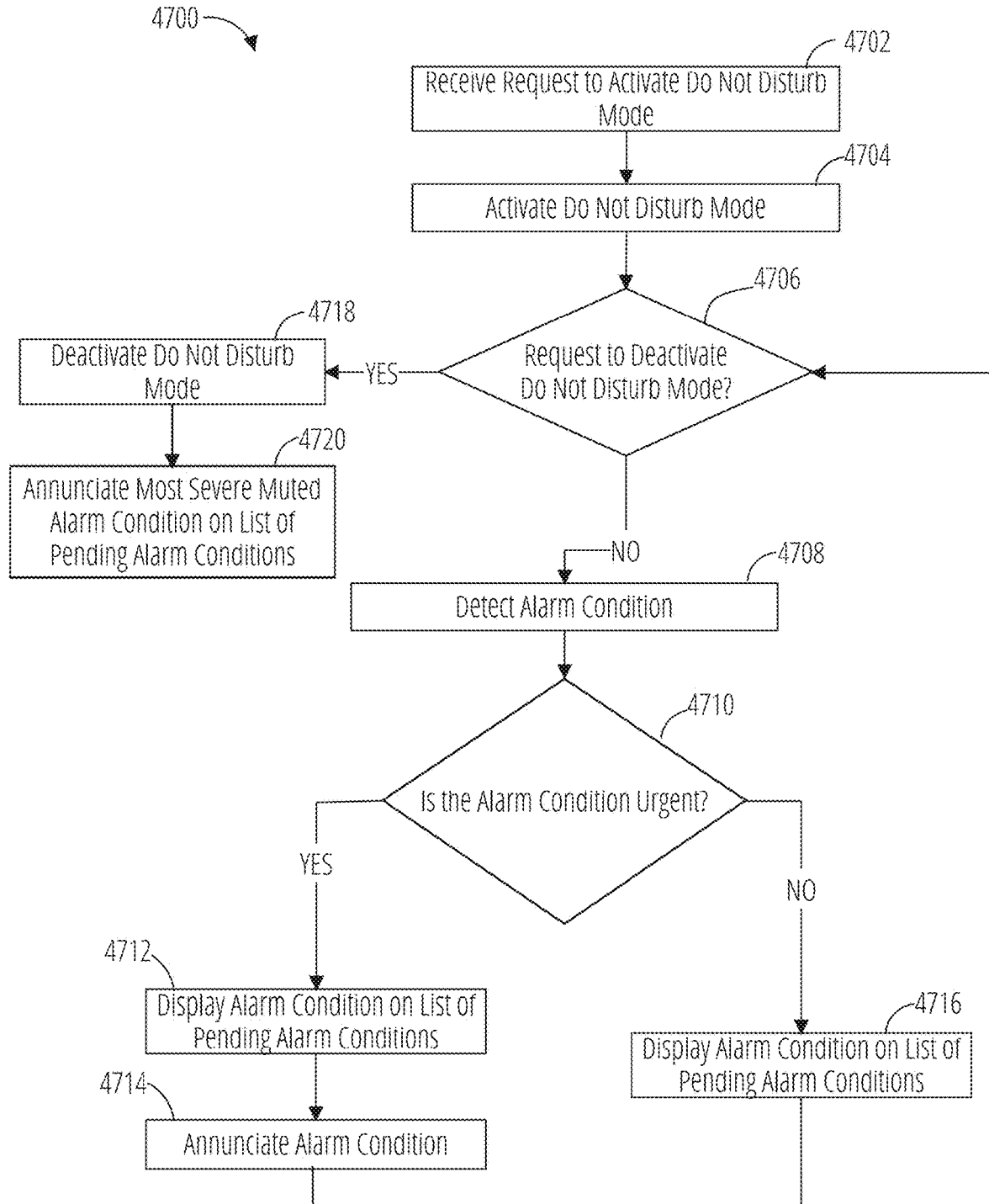
FIG. 47 is a flow diagram illustrating an example procedure to activate a Do Not Disturb mode in an AMD.

FIG. 47 shows a flow diagram illustrating an example procedure that may be used by the alarm system of an AMD to mute non-urgent alarm conditions or in annunciating alarms. The process 4700 begins at block 4702, when the device receives a request to activate alarm muting, or Do Not Disturb mode. As used herein, alarm muting may include activation of the Do Not Disturb mode and vice versa. For example, the request to activate Do Not Disturb mode may include alarm muting instructions. As described herein, alarm muting or alarm muting instructions may include silencing auditory and/or haptic annunciation of alarms while maintaining visual annunciation of the alarm condition (e.g. displaying the alarm condition on a list of pending alarm conditions). In some cases, the do not disturb mode of the ambulatory medicament device may be activated in response to determining that alarm annunciation should be muted in accordance with the alarm muting instructions. In some such cases, at least some alarm annunciation patterns may not be aurally or haptically annunciated.

As described herein, a user may input various parameters as part of the alarm muting instructions when activating Do Not Disturb mode. In some cases, the user may define a start and end time between which alarm muting is to remain activated. In some cases, the user may define a length of time over which alarm muting is to remain activated. In some other cases, the user may set alarm muting to recur at regular intervals or time intervals, such as every night during a time frame the subject is typically asleep. If the defined Do Not Disturb period does not begin immediately, the system may annunciate alarms on an accelerated schedule prior to activation of Do Not Disturb mode. For example, snoozed alarms may have alarm reminders that are annunciated at regular or predetermined intervals until the alarm is resolved. In such cases, if a reminder annunciation is scheduled to annunciate during the Do Not Disturb period (e.g., user scheduled Do Not Disturb period), the system may annunciate the reminder for the unresolved alarm prior to the activation time of Do Not Disturb mode. In some cases, the user may select which alarms to mute when activating Do Not Disturb mode. In some cases, Do Not Disturb mode may be activated with a default selection of alarms to be muted. In some cases, alarm muting instructions may include a recurring time interval indicating a time interval during which the do not disturb mode may be activated. In some examples, the recurring time interval may include a time interval (e.g., time between a start and an end time) occurring periodically (e.g., every day).

In response to the request, at block 4704, the system may activate alarm muting in accordance with the specified alarm muting instructions. At decision block 4706, the system may check whether a request to deactivate Do Not Disturb mode has been received. A request to deactivate Do Not Disturb mode may be created manually by the user or may be created automatically by the system. For example, if the defined period lapses for a Do Not Disturb session, the system may automatically request to deactivate Do Not Disturb mode. In some cases, the user may manually terminate a Do Not Disturb session prior to the scheduled deactivation time, as described herein in relation to FIG. 51. In such cases, the system may receive a deactivation request when the user cancels the current Do Not Disturb session. If a request to deactivate Do Not Disturb mode has been received, the process 4700 may proceed to block 4718. If a request to deactivate Do Not Disturb mode has not been received, Do Not Disturb mode remains active and the process 4700 may proceed to block 4708.

At block 4708, the system may detect an alarm condition. At decision block 4710, the system may determine whether the detected alarm condition is an urgent alarm condition requiring urgent user attention in the short term. In some cases, determining whether the alarm condition is urgent may include comparing the severity level of the alarm condition against a threshold severity level. If the severity level of the alarm condition exceeds the defined threshold severity level, the alarm condition may be considered an urgent alarm requiring urgent user attention. In some cases, the threshold severity level may be predetermined. In other cases, the threshold severity level may be defined by the user as part of the alarm muting instructions. Further details relating to determining alarm urgency is described herein in relation to blocks 4810 and 4812 of FIG. 48.

If the alarm condition is determined to be urgent, the process 4700 continues to blocks 4712 and 4714, and the alarm condition may be displayed on a list of pending alarm conditions 5200 (FIG. 52) and annunciated in real time. After block 4714, the system may loop back or return to decision block 4706.

The system may maintain an indication of the alarm condition on the list of pending alarm conditions 5200 until the alarm condition is resolved. In some cases, the list of pending alarm conditions may be an alarm manager list, and the user may interact with each listed alarm condition to view alarm details, acknowledge the alarm, snooze the alarm, or otherwise resolve the alarm. If the alarm condition is determined not to be urgent, the process 4700 proceeds to block 4716, where the alarm condition is added to the alarm manager list, or list of pending alarm conditions, and the auditory and haptic annunciation associated with the alarm condition is muted. After block 4716, the system may loop back or return to decision block 4706.

While Do Not Disturb mode is activated, all alarms may continue to be raised, but auditory and haptic annunciation of some alarms may be muted. Raised alarms may be added to the alarm manager list at the time of detection and displayed on a user interface until the condition that caused the alarm is resolved. Thus, although an alarm condition may not have an auditory or haptic alert, the user may still view the alarm condition information and resolve the alarm condition. Resolving the alarm condition may include, but is not limited to, the user taking action to correct the condition that caused the alarm, the user acknowledging the alarm, the user snoozing the alarm, or the device no longer detecting the alarm condition (e.g., low blood glucose condition is no longer present).

At block 4718, Do Not Disturb mode may be deactivated. As described herein, Do Not Disturb mode may terminate automatically (e.g. the defined time period in the alarm muting instructions has lapsed) or may be manually deactivated. The user may override Do Not Disturb mode by manually cancelling Do Not Disturb mode at any point while alarm muting is activated. In some cases, the user may override a current Do Not Disturb session by inputting new alarm muting instructions. At block 4720, the system may annunciate the most severe alarm condition from the list of pending alarm conditions that has not yet been annunciated. The most severe alarm condition may be associated with the highest severity level of the non-urgent alarms on the list of pending alarm conditions. The other alarm conditions on the list may remain muted but may continue to be displayed on the list until the alarm conditions are resolved. Previously annunciated alarms (e.g. urgent alarm conditions) may not be annunciated again in response to deactivation of Do Not Disturb mode.

In an example application of the process described in FIG. 47, the system may detect a first alarm condition, a second alarm condition, and a third alarm condition while in Do Not Disturb mode. The system may first detect the first alarm condition at block 4708. At decision block 4710, the system may determine that the first alarm condition is an urgent alarm condition. As such, the first alarm condition may be both added to the list of pending alarm conditions and annunciated in real time, according to blocks 4712 and 4714. The system may then return or loop back to decision block 4706. Do Not Disturb mode may remain active if the system does not receive a request to deactivate alarm muting. Without deactivating Do Not Disturb mode, then, the system may detect the second alarm condition. At decision block 4710, the system may determine that the second alarm condition is not an urgent alarm condition. Thus, the second alarm condition may be added to the list of pending alarm conditions without auditory or haptic annunciation, according to block 4716. Returning again to decision block 4706, Do Not Disturb mode may remain active if the system does not receive a request to deactivate alarm muting. Continuing to block 4708 without deactivating Do Not Disturb mode, the system may detect the third alarm condition. At decision block 4710, the system may determine that the third alarm condition is also a non-urgent alarm condition. The third alarm condition may have a severity level lower than the second alarm condition. At block 4716, the third alarm condition may be added to the list of pending alarm conditions without auditory or haptic annunciation. Returning or looping back to block 4706, the system may then receive a request to deactivate Do Not Disturb mode. The system may then deactivate Do Not Disturb mode, at block 4718. In response to the deactivation of Do Not Disturb mode, the system may annunciate the muted alarm with the highest severity level, at block 4720. In this example, the system would annunciate the second alarm condition, since the first alarm condition was already annunciated as an urgent alarm and the third alarm condition has a lower severity level.

In some cases, the system may deactivate the Do Not Disturb mode upon or in connection with annunciating the above first alarm condition, as discussed further below.

Figure 48:
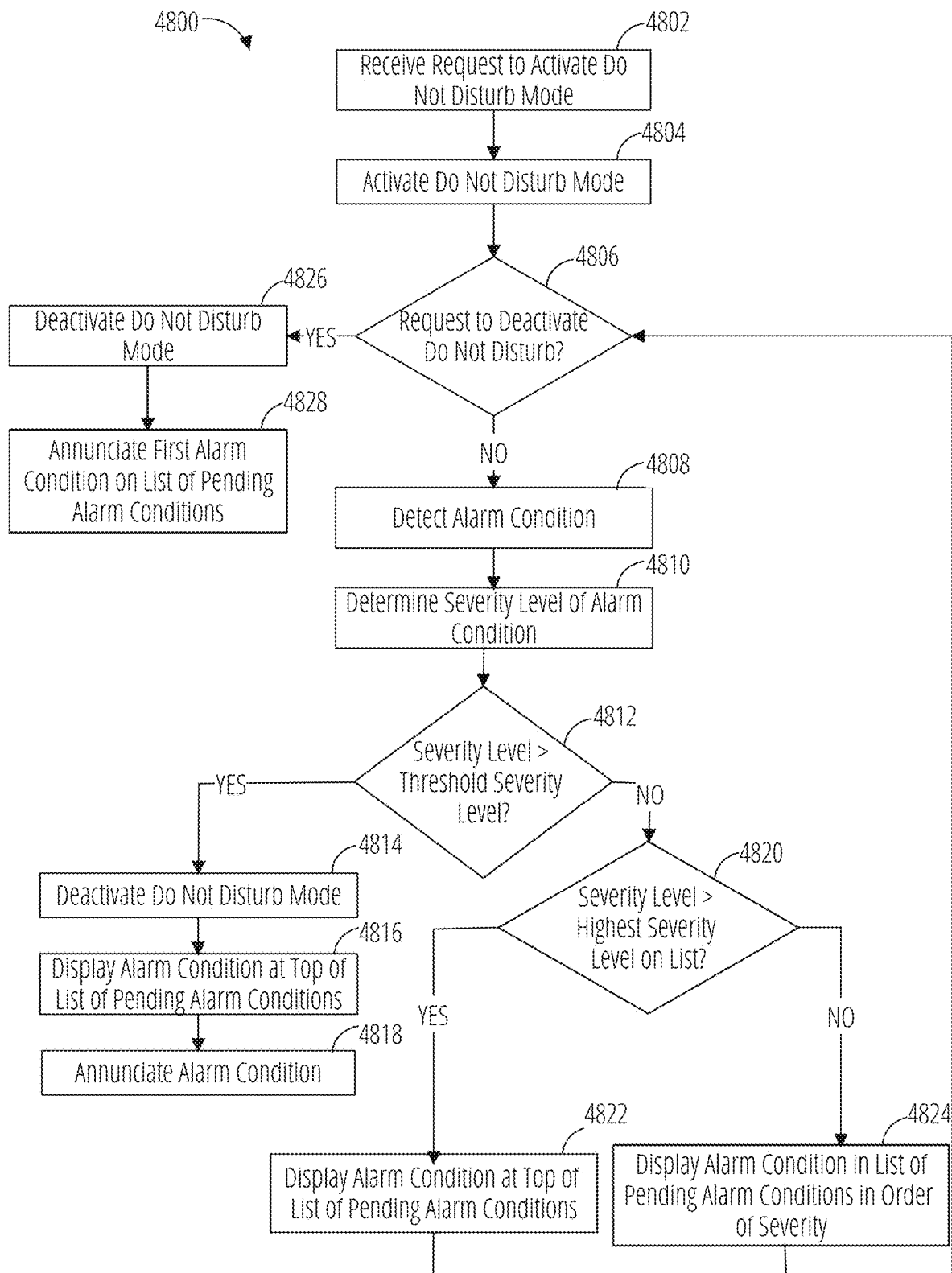
FIG. 48 is a flow diagram illustrating another example procedure to activate a Do Not Disturb mode in an AMD.

FIG. 48 is a flow diagram illustrating another example procedure in annunciating alarms or activating a Do Not Disturb mode in an AMD. The process 4800 begins at block 4802, when the system receives a request to activate Do Not Disturb mode. In response to the request, the system may activate Do Not Disturb mode at block 4804. At decision block 4806, the system may determine whether a request to deactivate Do Not Disturb mode has been received. The process at blocks 4802, 4804, and 4806 may proceed according to the disclosure related to blocks 4702, 4704, and 4706 of FIG. 47. If a request to deactivate Do Not Disturb mode has been received, the process 4800 may proceed to block 4826. If a request to deactivate Do Not Disturb mode has not been received, Do Not Disturb mode remains active and the process 4800 may proceed to block 4808.

At block 4810, the system may determine a severity level of the alarm condition. The severity level may be based on the underlying fault of the alarm condition. For example, a low battery warning may be assigned a low severity level (e.g. level 1), while an extremely low blood glucose measurement may be assigned a high severity level (e.g. level 5). At decision block 4812, the system may determine whether the severity level of the first alarm condition exceeds a threshold severity level. The threshold severity level may be a predefined severity level, which if exceeded, may cause the system to determine that the alarm condition is an urgent alarm condition requiring urgent user attention in the short term. In some cases, the threshold severity level may be defined by the user as part of the alarm muting instructions. For example, the user may want to be immediately alerted of any alarms that are level 2 or higher. If the severity level of the alarm condition exceeds the defined threshold severity level, then the alarm condition is considered urgent and the process 4800 proceeds to block 4814. If the severity level of the alarm condition does not exceed the defined threshold severity level, the alarm condition is not considered urgent and the process 4800 proceeds to decision block 4820.

In block 4814, the system may automatically deactivate Do Not Disturb mode in response to detecting an urgent alarm condition. As described herein, in some cases, the list of pending alarm conditions may be arranged in order of severity. In some cases, the alarm condition with the highest severity level may be listed at the top of the list of pending alarm conditions and the rest of the alarm conditions would be listed in descending order of severity level. In blocks 4816 and 4818, the alarm condition may be displayed at the top of the list of pending alarm conditions 5200 as the alarm condition with the highest severity level and annunciated in real time. In some cases, the system may only annunciate the urgent alarm condition upon deactivation of Do Not Disturb mode. In some other cases, the system may also annunciate the second alarm on the list of pending alarm conditions (e.g. the muted alarm condition with the highest severity level).

At decision block 4820, the system may determine whether the severity level of the detected alarm condition exceeds the severity level of the most severe alarm condition currently on the list of pending alarm conditions. If the severity level of the detected alarm condition exceeds the highest severity level on the list of pending alarm conditions, the process 4800 proceeds to block 4822, where the alarm condition may be listed at the top of the list of pending alarm conditions. After block 4822, the system may loop back or return to decision block 4806.

If the severity level of the alarm condition does not exceed the highest severity level on the list of pending alarm conditions at the time, the process 4800 may proceed to block 4824, where the alarm condition may be added to the list of pending alarm conditions in order of severity level. If the severity level of the detected alarm condition is equal to the severity level of one or more other alarm conditions present on the list, the detected alarm condition may be added to the list of pending alarm conditions in chronological order within its severity level group. After block 4824, the system may loop back or return to decision block 4806.

At block 4826, Do Not Disturb mode may be deactivated. As described herein, Do Not Disturb mode may terminate naturally (e.g. the defined time period in the alarm muting instructions has lapsed) or may be manually deactivated. At block 4828, the system may annunciate the first alarm condition from the list of pending alarm conditions (e.g. the most severe alarm condition). The other alarm conditions on the list may remain muted but may continue to be displayed on the list until the alarm conditions are resolved.

Figure 49:
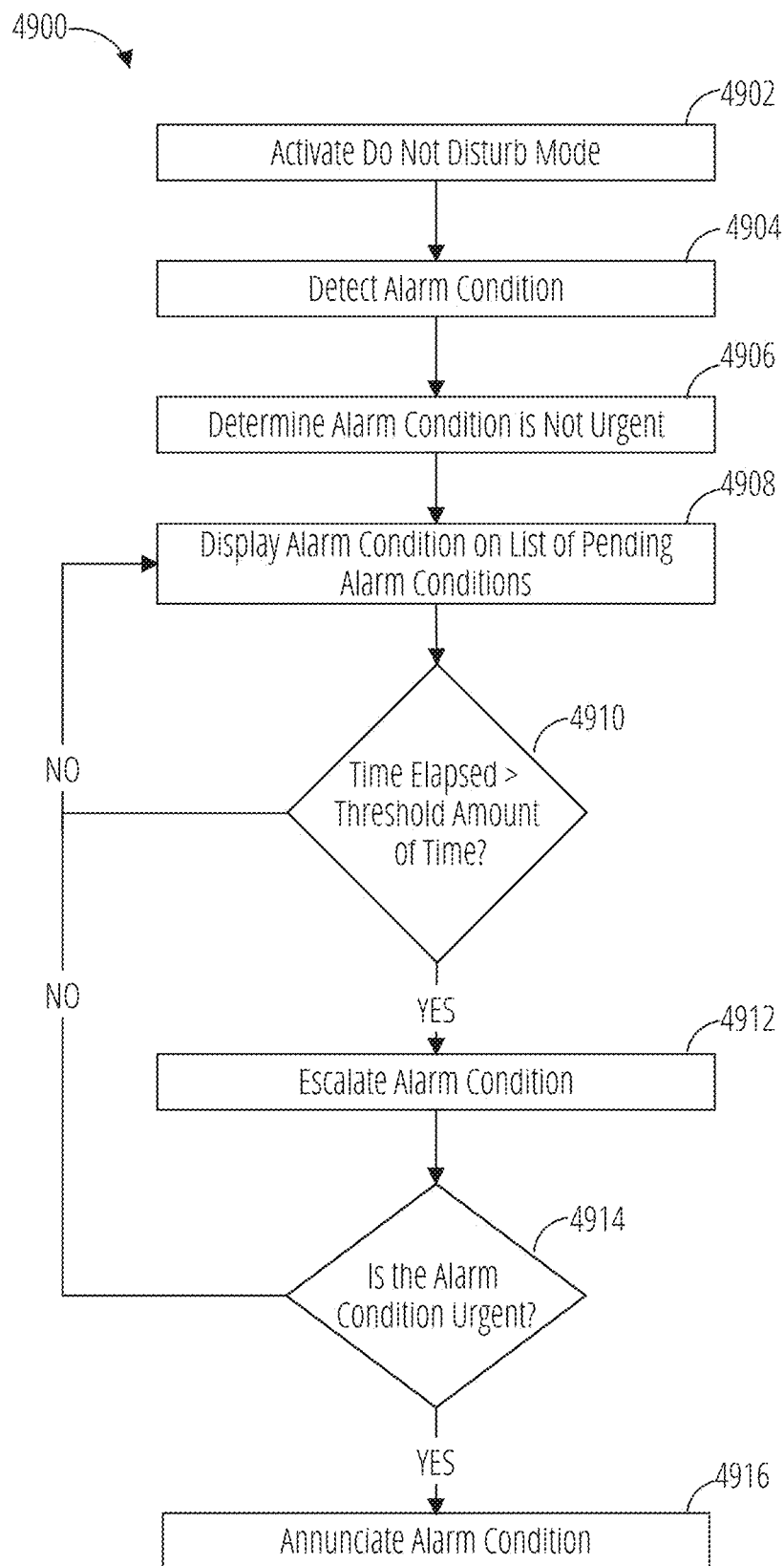
FIG. 49 is a flow diagram illustrating an example procedure that may be used by the alarm system of an AMD to escalate non-urgent alarms.

FIG. 49 is a flow diagram illustrating an example procedure that may be used by the system to escalate a non-urgent alarm when Do Not Disturb mode is activated. The process 4900 begins at block 4902, where the system may activate Do Not Disturb mode. Do Not Disturb mode may be activated in response to alarm muting instructions. In some cases, the user may manually activate Do Not Disturb mode by inputting alarm muting instructions for immediate activation. In some cases, the user may input alarm muting instructions to schedule a Do Not Disturb session to begin at a later time. In such cases, the system may automatically activate Do Not Disturb mode at the scheduled recurring time. In some cases, the user may input alarm muting instructions to schedule recurring sessions and the system may automatically activate Do Not Disturb mode for each recurring session.

At block 4904, the system may detect an alarm condition. At block 4906, the system may determine that the alarm condition is not urgent (e.g. does not require urgent user attention in the short term). In response to a determination that the alarm condition is not urgent, the system may display the alarm condition on a list of pending alarm conditions, at block 4908.

At decision block 4910, the system may determine whether the time elapsed from the detection of the alarm condition has exceeded a threshold amount of time. In some cases, the threshold amount of time may be predetermined by the system. In some other cases, the threshold amount of time may be defined by the user as part of the alarm muting instructions or through AMD settings. If the time elapsed since the detection of the alarm condition has not exceeded the threshold amount of time, the process 4900 may return to block 4908 and the system may maintain the alarm condition on the list of pending alarm conditions. In some cases, maintaining the alarm condition on the list of pending alarm conditions may include maintaining the order in which the alarm condition is displayed on the list. In some cases, maintaining the alarm condition on the list of pending alarm conditions may include maintaining the alarm condition details but adjusting the order of the alarm condition as later alarms are added to the list.

If the time elapsed since the detection of the alarm condition exceeds the threshold amount of time, the process 4900 may proceed to block 4912 and the alarm condition may be escalated. Escalating an alarm condition may include increasing the severity level of the alarm condition (e.g. increasing the severity level of the alarm condition from level 2 to level 3). It should be noted that the alarm condition may be escalated by more than one severity level at a time (e.g. increasing the severity level of the alarm condition from level 1 to level 4 or starting from any level (e.g., level 0) to be escalated to any other level (e.g., level 5)).

At decision block 4914, the system may determine whether the alarm condition at the new severity level is urgent. If the escalated alarm condition is not urgent, the process 4900 may loop or return to block 4908 and maintain the alarm condition display as disclosed herein. If the escalated alarm condition is urgent, the process 4900 may proceed to block 4916 and the alarm condition may be annunciated. For example, if a level 2 alarm is considered non-urgent, it may be muted when the alarm condition is first detected. However, if the alarm condition has not been resolved after a period of time, the system may escalate the alarm condition from level 2 to level 3. If level 3 alarms are considered urgent alarms requiring urgent user attention, then the alarm condition may be annunciated upon escalation. If level 3 alarms are also considered not urgent, then the alarm condition may remain muted.

Figure 50:
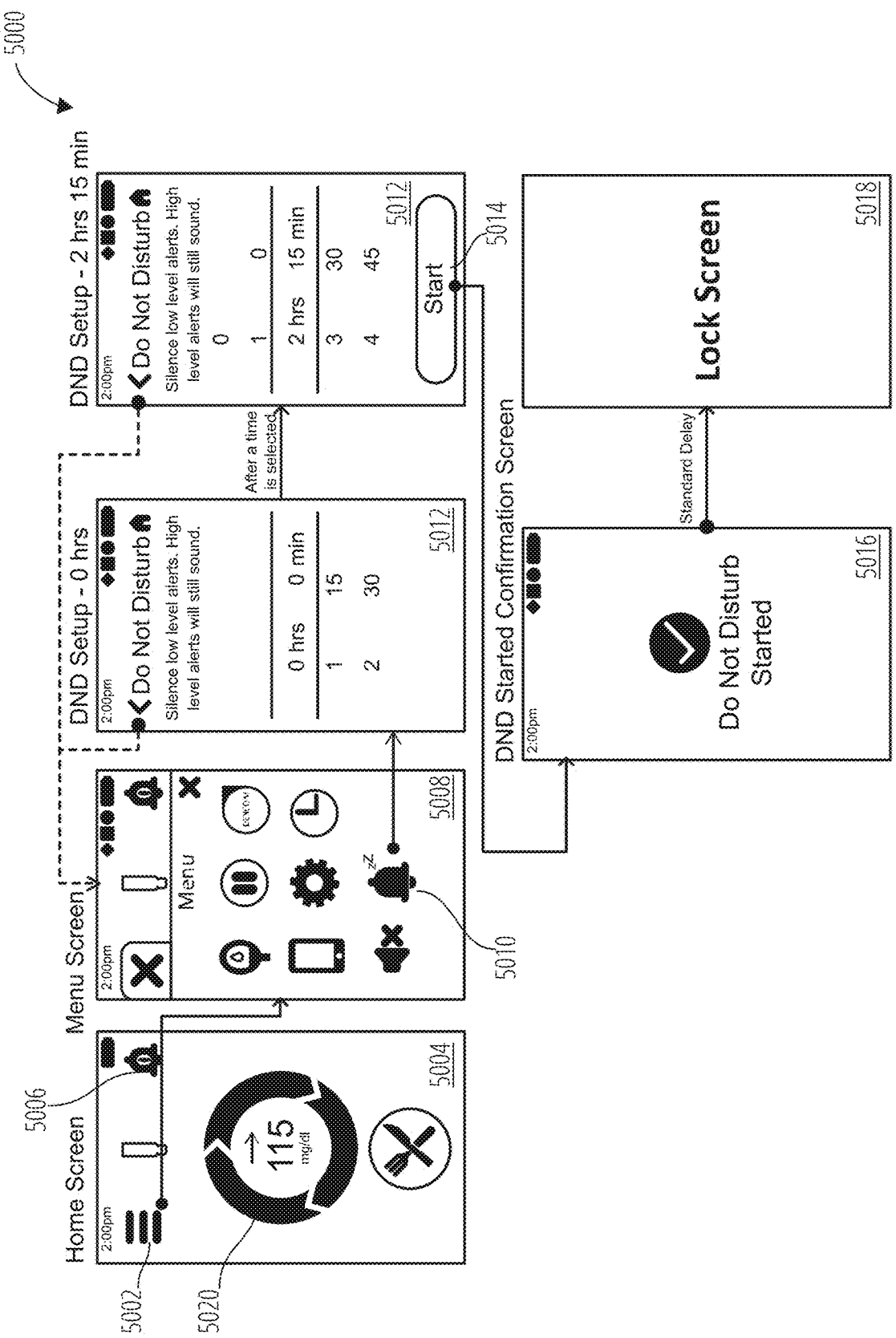
FIG. 50 illustrates a plurality of screens that may be displayed on a touch screen display of an AMD for activating Do Not Disturb mode on the AMD.

FIG. 50 is an illustration of a plurality of screens 5000 that may be displayed on a touch screen display of an AMD for activating alarm muting (Do Not Disturb Mode) on the AMD. As illustrated, a home screen 5004 may include a menu icon 5002, an alarm status icon 5006, and a pump operation field 5020. The pump operation field 5020 may be automatically updated at regular intervals to show high level subject information. The alarm status icon 5006, in this exemplary embodiment, may be shaped as an alarm bell. The alarm status icon 5006 may be updated to provide high level information about alarm conditions of the AMD. In some cases, the alarm status icon 5006 may be an alarm bell with a counter in the middle indicating the number of annunciated alarms. In some cases, if there are no detected alarm conditions, the alarm status icon 5006 may display "0" or may not display any number or text. In some other cases, the alarm status icon 5006 may be updated with "zzz" or other visual cues to indicate that alarm muting, or Do Not Disturb (DND) mode, is activated. In some other cases, the alarm status icon 5006 may be in a shape of a crescent moon to indicate that alarm muting is activated. In yet other cases, the alarm status icon 5006 may not be a displayed icon. In such cases, alarm status may be indicated by other forms of notification, such as, but not limited to, auditory, haptic, or visual cues (e.g. a light on the device that flashes when alarm conditions are detected). Selecting the alarm status icon 5006 may provide the user with access to the list of pending alarm conditions 5200 (see FIG. 52). The menu icon 5002, when selected, may display a menu screen 5008 through which the user may control operation of the AMD. The menu screen 5008 may include an alarm muting button 5010. In some cases, the alarm muting button 5010 may be shaped as an alarm bell with "zzz" to represent that the alarm alerts are silenced or snoozed.

Selecting the alarm muting button 5010 may display a Do Not Disturb (DND) setup screen 5012. The DND setup screen 5012 may display an alarm muting control interface through which the user may input alarm muting instructions (e.g. defining a time frame for the Do Not Disturb session). The alarm muting control interface may be controlled via touchscreen controller. In some cases, the alarm muting control interface may be a dropdown or scroll-through menu from which the user may select a length of time for which to activate alarm muting, as illustrated in FIG. 50. In some cases, the alarm muting control interface may be a time wheel, and the user may rotate the wheel to increase or decrease the length of time for which to activate alarm muting. In some cases, the alarm muting control interface may include one or more text boxes in which the user may enter the amount of time for which to activate alarm muting. In some cases, the alarm muting control interface may list time periods at regular increments, such as 15-minutes increments, 30-minutes increments, 1-hour increments, 2-hour increments, or the like. In some other cases, the alarm muting control interface may allow users to input a start time and an end time for the Do Not Disturb session, rather than inputting a length of time. The start time can be in the future to allow the user to plan or schedule a Do Not Disturb session. In yet other cases, the alarm muting control interface may have additional features to define recurring Do Not Disturb sessions. Once the user has input the alarm muting instructions, the user may select the Start button 5014. If Do Not Disturb mode is set to begin immediately, selection of the Start button 5014 will cause the system to display a confirmation page 5016 to inform the user that Do Not Disturb mode was activated. If Do Not Disturb mode is set to begin after a period of time, the confirmation page 5016 may display Do Not Disturb confirmation information, including, but not limited to, recurrence information, defined start time, defined end time, and total alarm muting time. For subject privacy, after a period of inactivity, the system may automatically lock the AMD and display a lock screen 5018.

For subject safety, the system may include limitations on the permissible length of time over which alarms may be muted. In some cases, the system may include limitations on the number of consecutive hours or the total number of hours alarm muting is activated within a day, within a week, or other timeframe. For example, the user may be able to activate Do Not Disturb mode up to a typical sleeping time but substantially less than a day. In some cases, the system may allow longer periods of Do Not Disturb based on safe access level. Accordingly, the system may monitor the number of hours that Do Not Disturb has been active. Some alarms may include one set of limitations while other alarms may have a different set of limitations, including depending on the number of hours that Do Not Disturb has been active. In some cases, some types of alarms (e.g., audio annunciation) may be silenced, while other alarms (e.g., haptic annunciation) may not be silenced. In some cases, the user may define which types of alarms are to be silenced.

As disclosed herein, Do Not Disturb mode may mute but not postpone detected alarm conditions. Though auditory and haptic annunciations may be muted, the list of pending alarm conditions 5200 may be updated in real time and can be viewed by the user at any time.

Figure 51:
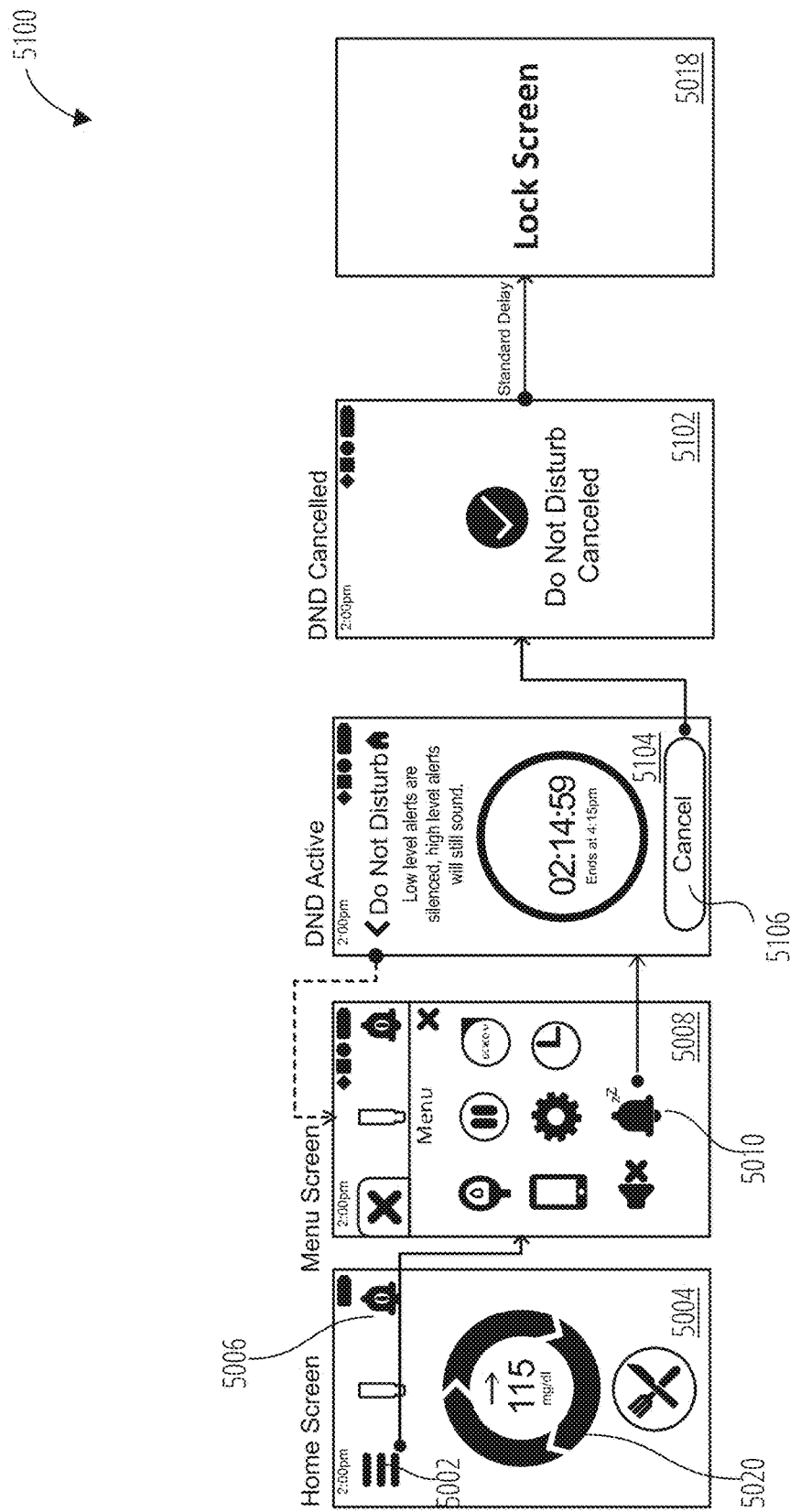
FIG. 51 illustrates a plurality of screens that may be displayed on a touch screen display of an AMD for deactivating Do Not Disturb mode on the AMD.

FIG. 51 is an illustration of a plurality of screens 5100 that may be displayed on a touch screen display of an AMD for deactivating alarm muting, or Do Not Disturb mode, on the AMD. As described herein, the home screen 5004 may include a menu icon 5002, an alarm status icon 5006, and a pump operation field 5020. As illustrated, the alarm status icon 5006 may be the shape of an alarm bell with "zzz" or other text to indicate that alarm muting is activated. As described herein, the menu icon 5002, when selected, may display a menu screen 5008 through which the user may control the AMD. The menu screen 5008 may include an alarm muting button 5010. Selecting the alarm muting button 5010 may display the alarm muting control interface. In some cases, while alarm muting is activated, the alarm muting control interface may be updated to show a Do Not Disturb setting screen 5104. In some cases, the setting screen 5104 may show the time that the active Do Not Disturb session will expire. If the user changes the display time of the device, the remaining duration of the Do Not Disturb period may be maintained such that the end time is updated with the new device display time. Alternatively, or in addition, the setting screen 5104 may show how much longer the Do Not Disturb mode is set to last. As described herein, the user may override Do Not Disturb mode by manually cancelling Do Not Disturb mode at any point while alarm muting is activated. The setting screen 5104 may include a Cancel button 5106. Selecting the Cancel button 5106 may cause the system to deactivate alarm muting and display a cancellation confirmation page 5102. For subject privacy, after a period of inactivity, the system may automatically lock the AMD and display the lock screen 5018.

In some cases, the Do Not Disturb setting screen 5104 may include additional options to change the current alarm muting settings. The user may override the existing alarm muting settings by inputting new alarm muting instructions. Submitting new alarm muting instructions may terminate the existing session. The newly defined alarm muting instructions may override the existing Do Not Disturb parameters and begin a Do Not Disturb mode session in accordance with the newly defined alarm muting instructions, such that the new Do Not Disturb session does not add onto the currently defined period. In some cases, the system may not have a limit on the number of times which the user can initiate Do Not Disturb. For subject privacy, after a period of inactivity, the system may automatically lock the AMD and display the lock screen 5018.

Figure 52:
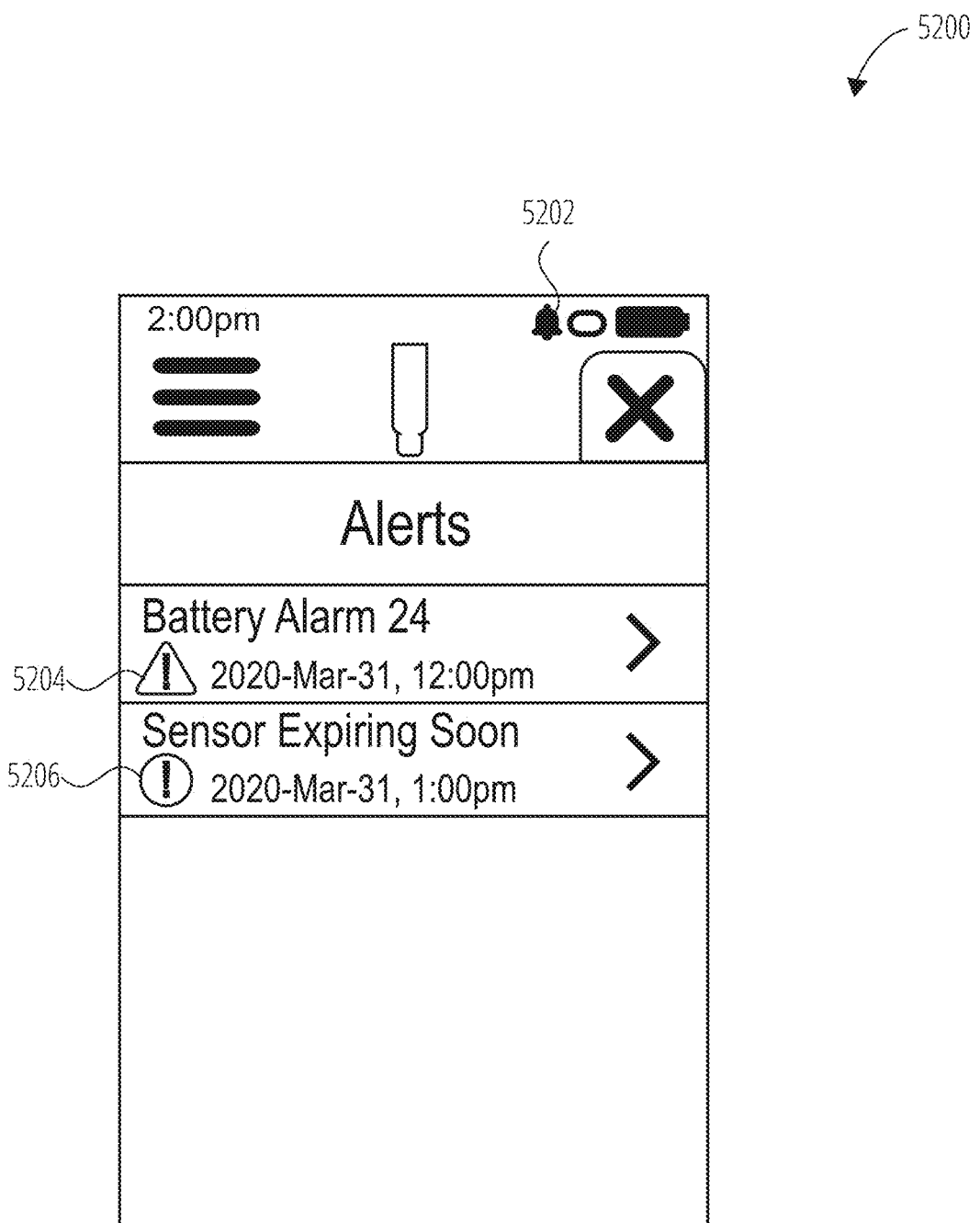
FIG. 52 is an illustration of a user interface provided on a touch screen display for viewing alarm notification details.

FIG. 52 shows an example list of pending alarm conditions 5200 when Do Not Disturb mode is not activated. The list of pending alarm conditions 5200 may include an alarm notification icon 5202. As illustrated, the alarm notification icon 5202 may be in the shape of an alarm bell. In some cases, the alarm notification icon 5202 may be any shape that matches the alarm status icon 5006 displayed on the home screen 5004. In some cases, the alarm notification icon 5202 may be displayed when one or more alarm conditions have been detected without otherwise being displayed when no alarm conditions have been detected. The list of pending alarm conditions 5200 may display information regarding the alarm conditions, including, but not limited to alarm condition description, cause of alarm condition, and date and time of alarm condition. Each alarm condition may have an associated alarm status indicator 5204, 5206. The alarm status indicator 5204, 5206 may be updated to reflect various annunciation patterns. For example, as illustrated, an exclamation mark in a triangle may represent an urgent annunciation pattern. As illustrated, an exclamation mark in a circle may represent a non-urgent annunciation pattern. In some cases, low level alarm conditions may be represented by a letter "i" to indicate a notification-only or informational alarm condition. In some cases, urgent alarm conditions may be represented by multiple exclamation marks in a triangle or circle. Each alarm condition in the list of pending alarm conditions 5200 may be selected to view further details about the alarm and to resolve the alarm. In some cases, an alarm status indicators, may indicate whether an alarm condition was annunciated or muted.

In some examples, urgent alarms may not be muted or snoozed, even when Do Not Disturb mode is activated. In such cases, the alarm status indicator 5204 for urgent alarms may not change as Do Not Disturb mode is activated and deactivated. In some examples, non-urgent alarms may be muted or snoozed, either manually by the user or automatically as defined by alarm muting instructions during a Do Not Disturb session. In such cases, the alarm status indicator 5206 for non-urgent alarms may be updated to represent that the alarm condition has been muted or snoozed (FIG. 53A and FIG. 54A).

In some examples, the user may view an alarm using a user interface provided on a touchscreen display, both when the display is locked and when the display is unlocked. FIG. 53A and FIG. 53B are illustrations of such a user interface for accessing the alarm notifications screen when the display is locked. As illustrated, the home screen 5004 may include a lock status icon 5302, an alarm status icon 5006, and a pump operation field 5020. The lock status icon 5302, as illustrated, may be in the shape of a padlock when the AMD is locked. In some cases, the lock status icon 5302 may be updated when the AMD is unlocked. For example, the lock status icon 5302 may be changed to the shape of an open padlock or replaced with the menu icon 5002 when the device is unlocked. If there are existing alarm conditions, the alarm notification icon 5202 may also be displayed on the interface.

Figure 53A:
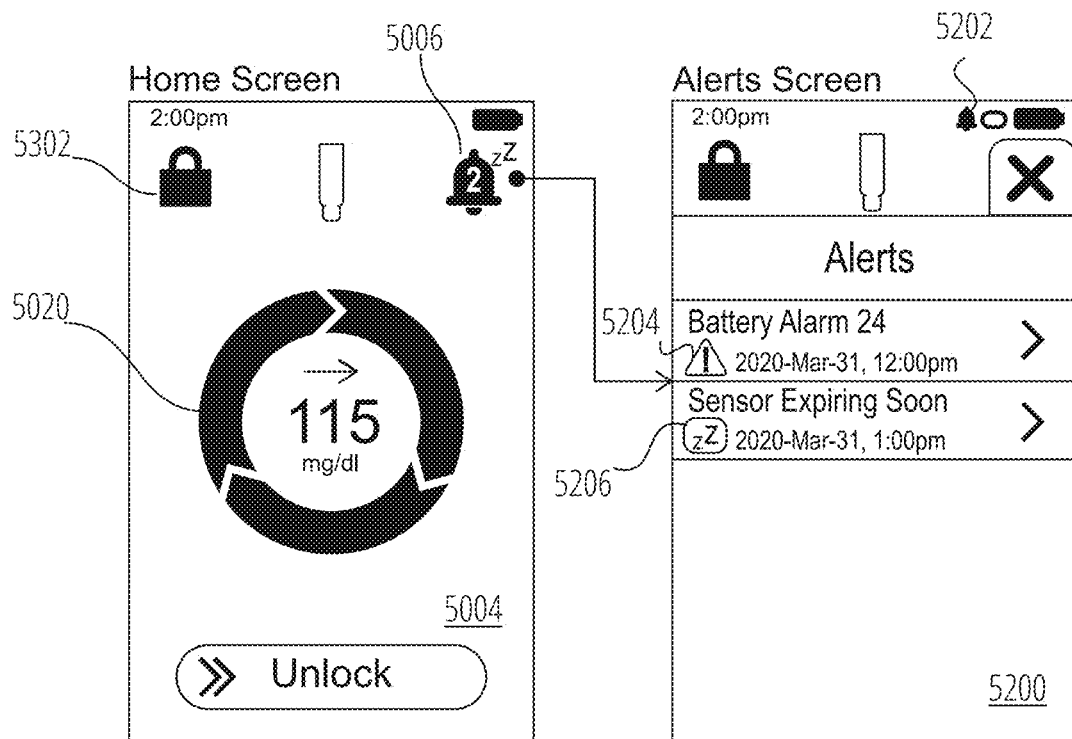
FIG. 53A and FIG. 53B are illustrations of a user interface provided on a touch screen display for accessing an alarm notifications screen when Do Not Disturb mode is activated and when the touch screen display is locked.
Figure 53B:
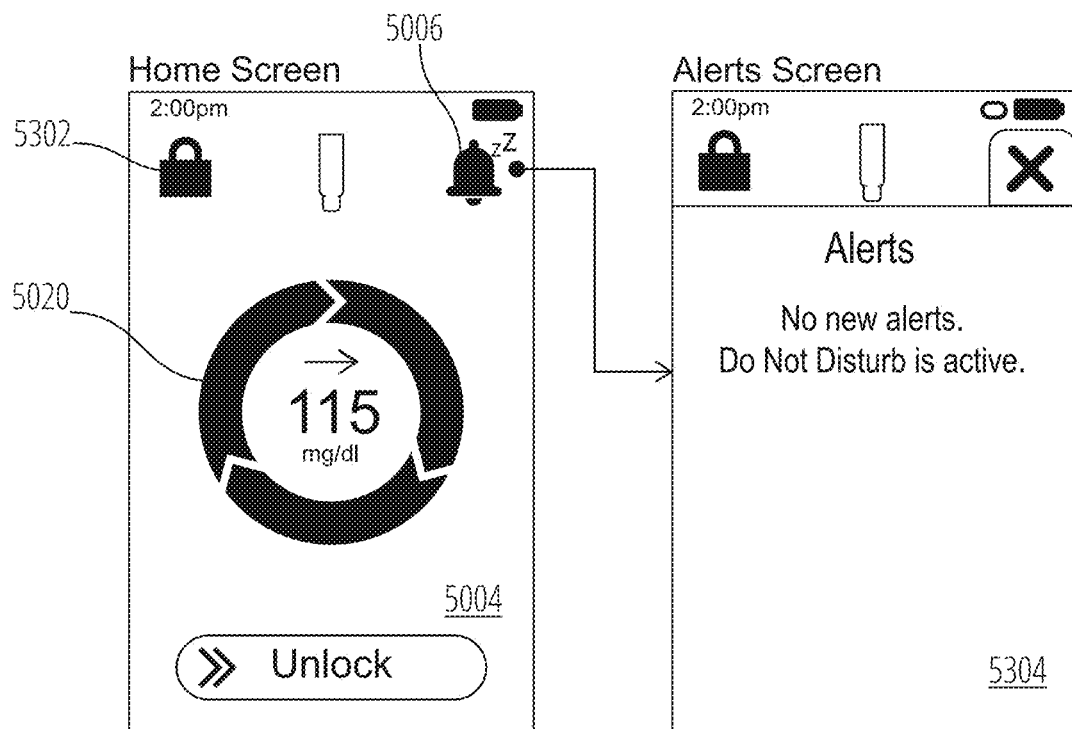
Figure 54A:
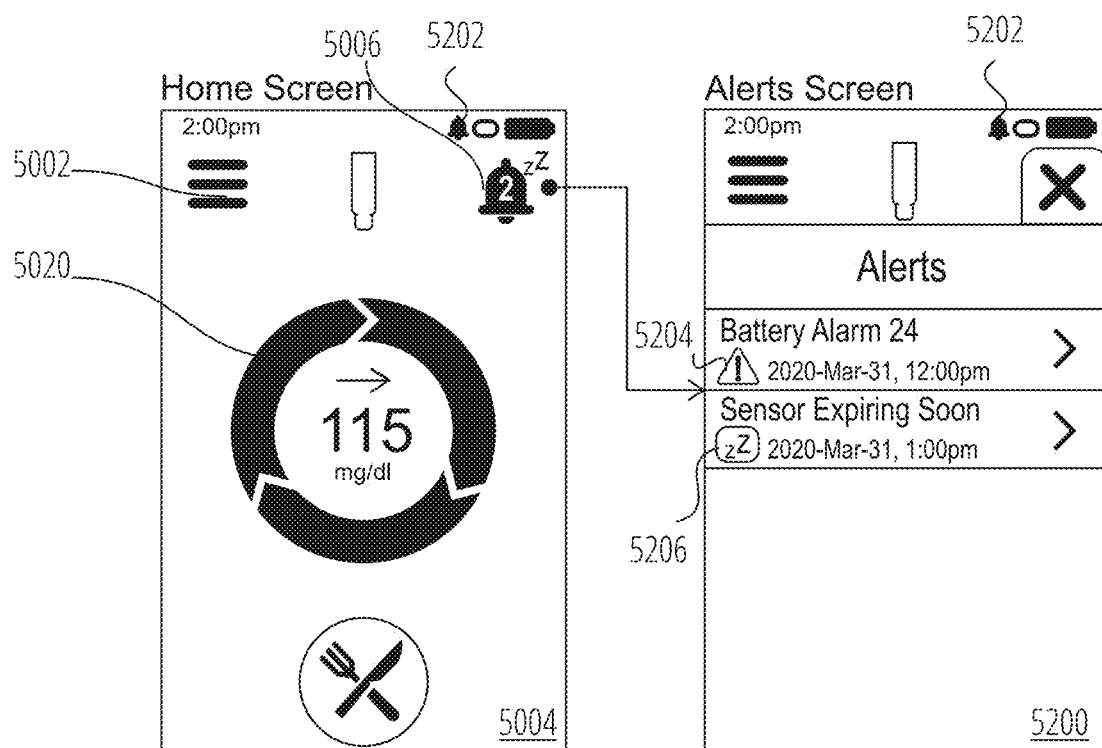
FIG. 54A and FIG. 54B illustrations of a user interface provided on a touch screen display for accessing an alarm notifications screen when Do Not Disturb mode is activated and when the touch screen display is unlocked.

FIG. 53A illustrates the user interface when there are detected alarm conditions. The alarm status icon 5006 may display the number of detected alarm conditions. The user may view the list of pending alarm conditions 5200 without unlocking the interface. Thus, for example, if the user selects the alarm status icon 5006 while there are existing alarms in the system, the list of pending alarm conditions 5200 may appear. However, the user may not be able to select the alarms (e.g., to see more information or interact with the alarms) because the device is locked. In such cases, the list of pending alarm conditions 5200 may include the lock status icon 5302. If alarm muting is activated, muted alarms may be associated with an alarm status indicator 5206, which may be updated to represent that the alarm was muted or snoozed ("zz" as illustrated). As described herein, urgent alarms may not be muted while Do Not Disturb mode is active, and thus the associated alarm status indicator 5204 for urgent alarms may remain unchanged. If the alarm muting is deactivated while pending alarms are still on the list of pending alarm conditions 5200, the alarm status indicator 5206 for non-urgent alarms may be updated to the usual alarm status indicator associated with the alarm condition, even if the alarm alert is not annunciated. For example, as illustrated, the "sensor expiring soon" alarm may not be annunciated even when Do Not Disturb mode is deactivated, if the "battery alarm 24" alarm is a higher-severity non-urgent alarm. Nonetheless, the alarm status indicator 5206 may be updated to an exclamation point or information symbol as discussed herein, for example, with reference to FIG. 51.

FIG. 53B shows the user interface when there are no detected alarm conditions. The alarm status icon 5006 may display "0" or may not display any number when there are no pending alarm conditions. In such cases, selecting the alarm status icon 5006 may cause the system to display the display interface 5304 illustrated. The display interface 5304 illustrated may inform the user that there are no alarm conditions. In such cases, because there are no alarm conditions, the alarm notification icon 5202 may not be displayed. In some cases, the display interface 5304 illustrated may further include information as to whether Do Not Disturb is activated.

Figure 54B:
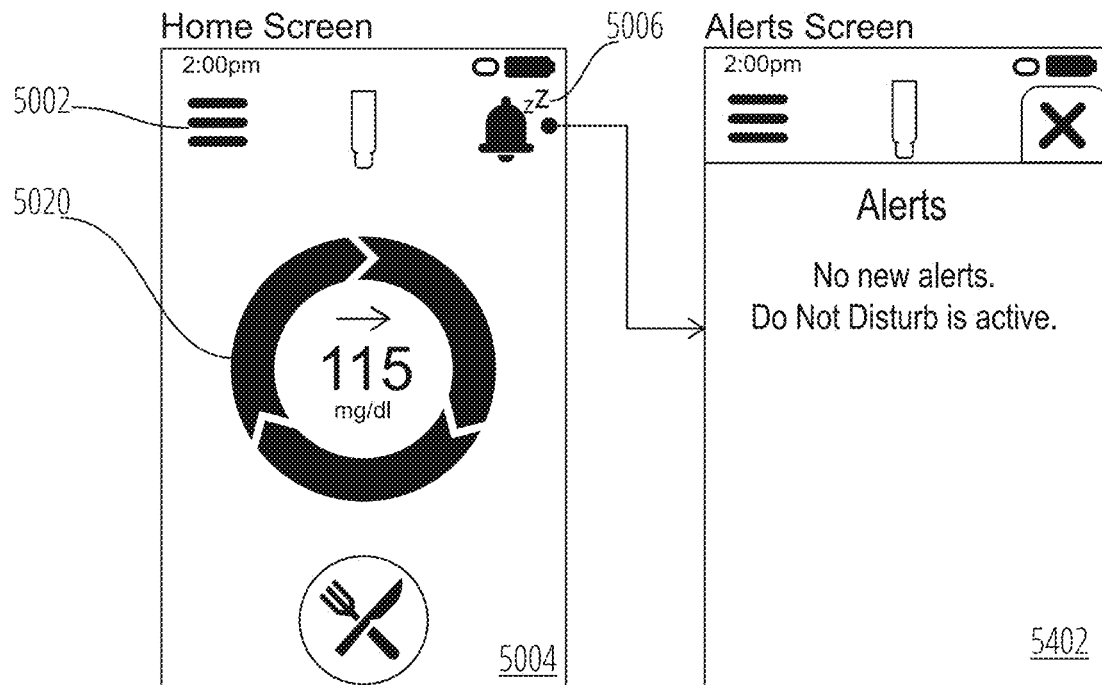

In some examples, if the user unlocks the device, the home screen 5004 illustrated in FIG. 54A and FIG. 54B may be displayed. FIG. 54A and FIG. 54B are illustrations of a user interface for accessing the alarm notifications screen when the display is unlocked. As illustrated, the home screen 5004 may include a menu icon 5002, an alarm status icon 5006, and a pump operation field 5020. Selecting the menu icon 5002 may allow the user to update AMD settings.

FIG. 54A illustrates the user interface when there are detected alarm conditions. The alarm status icon 5006 may display the number of detected alarm conditions. Selecting the alarm status icon 5006 may cause the system to display the list of pending alarm conditions 5200. The user may then access alarm control functions by selecting an alarm condition of interest. If alarm muting is activated, muted alarms may be associated with an alarm status indicator 5206 for non-urgent alarms, which may be updated to represent that the alarm was muted or snoozed ("zz" as illustrated). As described herein, urgent alarms may not be muted while Do Not Disturb mode is active, and thus the associated alarm status indicator 5204 for urgent alarms may remain unchanged. If the alarm muting is deactivated while pending alarms are still on the list of pending alarm conditions 5200, the alarm status indicator 5206 for non-urgent alarms may be updated to the usual alarm status indicator associated with the alarm, even if the alarm alert is not annunciated. For example, as illustrated, the "sensor expiring soon" alarm may not be annunciated even when Do Not Disturb mode is deactivated, if the "battery alarm 24" alarm is a higher-severity non-urgent alarm. Nonetheless, the alarm status indicator 5206 may be updated to an exclamation point or information symbol as discussed herein, for example, with reference to FIG. 51.

FIG. 54B illustrates the user interface when there are no detected alarm conditions. The alarm status icon 5006 may display "0" or may not display any number when there are no pending alarm conditions. In such cases, selecting the alarm status icon 5006 may cause the system to display the display interface 5402 illustrated. The display interface 5402 illustrated may inform the user that there are no alarm conditions. In such cases, because there are no alarm conditions, the alarm notification icon 5202 may not be displayed. In some cases, the display interface 5402 illustrated may further include information as to whether Do Not Disturb is activated.

Example AMD With Power Saving Mode

The AMD may be operated in various modes to extend battery life. The AMD may operate in a sleep mode, a low power mode, and/or a power saving mode. It shall be understood that the described modes are merely illustrative and that the AMD may be configured to operate in other modes not described herein, which may also extend battery life of the device.

The AMD may operate in a power saving mode to save power and minimize user disturbances as discussed herein. In some cases, the power saving mode may be activated by the user via one or more user inputs or interaction as discussed herein. In some cases, the power saving mode can be entered or exited via a wake interface of the AMD as discussed herein. In some cases, the power saving mode can be entered or exited via a tap or other gestures on the AMD as discussed herein. In some cases, the power saving mode may be activated automatically by the AMD after the AMD does not receive one or more user inputs or interactions (e.g., via the motion sensor or touchscreen) for a predetermined amount or period of time associated with a period of inactivity of a user not interacting with the AMD or providing user input to the AMD.

In some cases, the AMD may have an always on screen (which can be a type of user interface screen) that displays in the power saving mode certain desired or predetermined status information, including critical status information, that may be relatively more important for quick review during glucose control therapy without having to unlock or wake the AMD. The AMD can display the always on screen in the power saving mode. The critical status information may be part of the status information received by the AMD via the monitoring system interface as discussed herein. The status information can include device information pertaining to a condition of the ambulatory medicament device or subject information pertaining to a condition of a subject. Advantageously, an always on screen displaying certain status information in the power saving mode can allow a user to view the important or critical therapy and device information without having to turn on or wake the AMD. The power saving mode features discussed herein can reduce the number of times the user fully wakes the AMD.

Figure 55:
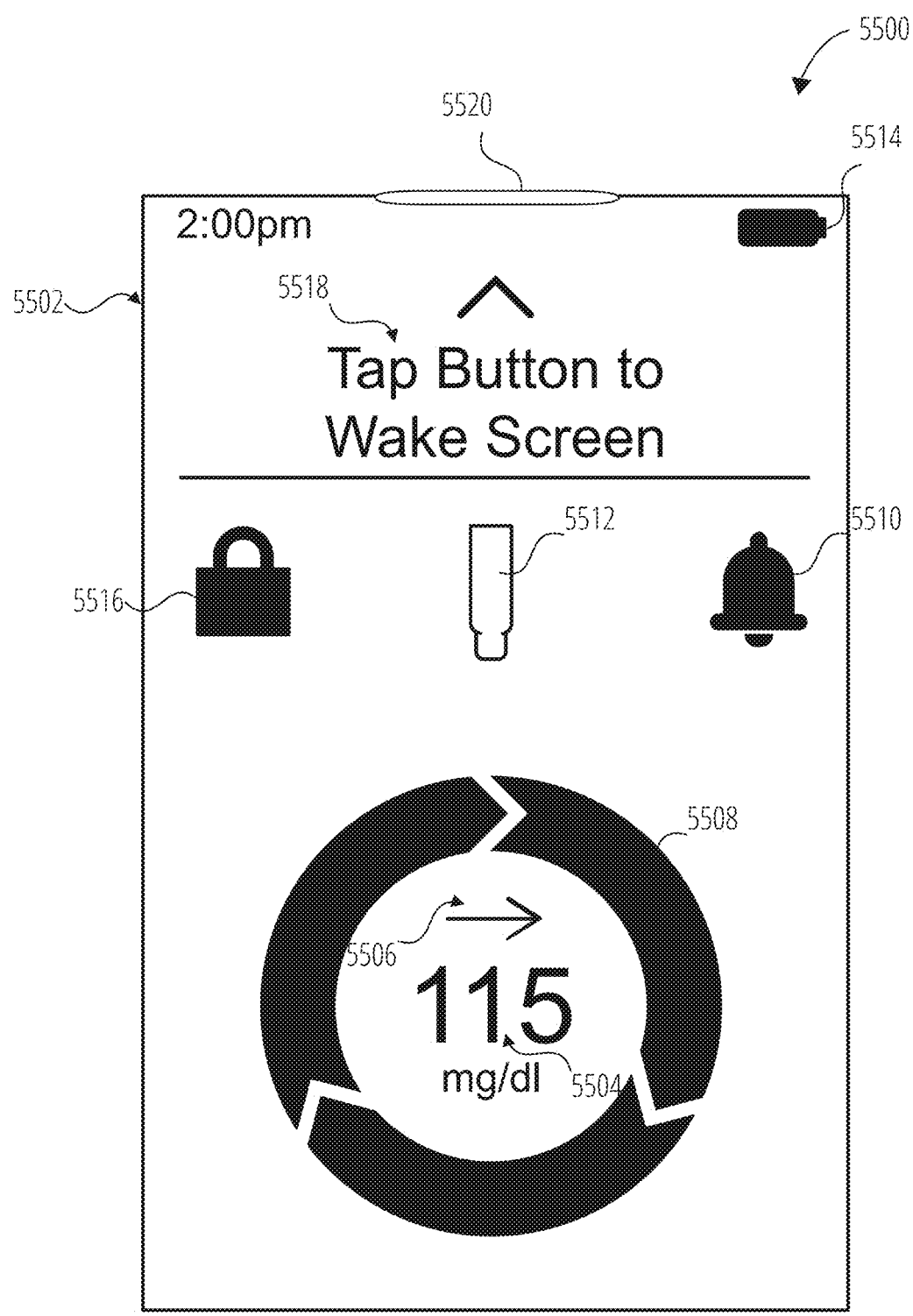
FIG. 55 illustrates a user interface that may be displayed by an ambulatory medical device in a power saving mode.

FIG. 55 illustrates an example AMD 5500 with an always on user interface provided on a display or touchscreen display 5502 while the AMD 5500 is in the power saving mode. The user interface may include certain critical status information as part of the critical status information interface screen displayed on the touchscreen display 5502 while the AMD 5500 is in the power saving mode. In some cases, while in the power saving mode, the AMD 5500 may turn off a backlight used to illuminate the touchscreen display 5502. In some cases, while in the power saving mode, the AMD 5500 may cause the touchscreen controller to not receive or not respond to user input signals. For example, the AMD 5500 may not respond to any user inputs on the touchscreen display 5502 via touching or otherwise motioning on the touchscreen display 5502. The touchscreen display 5502 can have a filter configured to have a predetermined viewing angle range relative to the touchscreen display such that information cannot be seen on the touchscreen when viewed from an angle outside of a predetermined viewing angle range relative to the plane of the display. The filter can be part of the privacy features of the AMD 5500 (e.g., privacy mode as discussed herein.)

In some cases, the critical status information interface screen may display a glucose level indicator 5504 as a critical status indicator. For example, as illustrated in FIG. 55, the glucose level of the subject as discussed herein may be 115 mg/dL. The glucose level indicator 5504 can be considered to be a subject status indicator. The AMD 5500 can determine whether a glucose level of the subject is within a predetermined glucose range and generate a display of a glucose interface screen (which may be a type or be part of user interface screen). The AMD can display on the touchscreen display 5502 the glucose level indicator via a glucose interface screen to prioritize displaying the status information corresponding to the glucose level not being within the predetermined glucose range.

In some cases, the critical status information interface screen may display a glucose trend indicator 5506 as a critical status indicator. For example, as illustrated in FIG. 55, the arrow may be flat to indicate that the glucose level is stable. In some instances, an arrow pointing up may indicate that the glucose level is rising. In some instances, an arrow pointing down may indicate that the glucose level is falling. The glucose trend indicator 5506 can be considered to be a subject status indicator.

In some cases, the critical status information interface screen may display a therapy status indicator 5508 as a critical status indicator. For example, as illustrated in FIG. 55, the therapy status indicator 5508 may be a circle that is animated (e.g., rotating) to indicate that the AMD 5500 is operating and providing glucose control therapy. The therapy status indicator 5508 may indicate when the delivery of medicament is paused or suspended. Another therapy status indicator may indicate when glucose level is low. The therapy status indicator 5508 can be considered to be a medicament device status indicator.

In some cases, the critical status information interface screen may display an alarm status indicator 5510 as a critical status indicator. The alarm status indicator 5510 can be considered to be a medicament device status indicator and can also be a type of alert status indicator. As illustrated in FIG. 55, the alarm status indicator 5510 may be a bell or bell icon. In some cases, the bell may include a number displayed on the user interface within the bell indicating the number of alarms presently on, for example, the list of pending alarms. The alarm status indicator 5510 may be an alarm bell with a counter in the middle indicating a count of alarm conditions. In some cases, when there are no detected alarm conditions, the alarm status indicator 5510 may display "0" or may not display any number or text as illustrated in FIG. 55. In some cases, the alarm status indicator 5510 may not include a counter and, instead, a separate alarm state icon may be displayed to indicate the count of alarm conditions. In some cases, the alarm status indicator 5510 can include the alarm state icon such as the counter being displayed within the alarm status indicator 5510. In some cases, the alarm status indicator 5510 may be updated with "zzz" or other visual indicators or icons to indicate that alarm muting, or Do Not Disturb mode, is activated or that one or more alarms have been snoozed. In some cases, the alarm status indicator 5510 may be in a shape of a crescent moon to indicate that alarm muting is activated.

In some cases, the critical status information interface screen may display a remaining medicament level indicator 5512 as a critical status indicator. For example, as illustrated in FIG. 55, the remaining medicament level of, for example, insulin is indicated to presently be full (e.g., a solid outline of an insulin cartridge). The medicament level indicator 5512 can be considered to be a medicament device status indicator and can also be a type of alert status indicator.

In some cases, the critical status information interface screen may display a battery level indicator 5514 as a critical status indicator. For example, as illustrated in FIG. 55, the battery level of the AMD 5500 is indicated to presently be at full charge (e.g., a solid outline of a battery). The battery level indicator 5514 can be considered to be a medicament device status indicator and can also be a type of alert status indicator. In some cases, the AMD 5500 can determine that a power level of a battery of the AMD 5500 is below a predetermined power level threshold and generate a display of a battery status interface (which may be a type or be part of user interface screen). The AMD can display on the touchscreen display 5502 a battery charging indicator on a battery status interface to prioritize displaying the status information corresponding to the power level being below the predetermined power level threshold. The battery charging indicator may include, but is not limited to, an image of a battery charger for the battery of the AMD 5500.

With continued reference to FIG. 55, the user interface may include certain other status information displayed on the touchscreen display 5502 while the AMD is in the power saving mode. The status information interface screen may include the critical status information interface screen. The indicators 5504, 5506, 5508, 5510, 5512, and/or 5514 may considered critical status information relative to other status information such indicators 5516 and/or 5518. The critical status information can include other information, icons, and/or indicators important or critical for user review while receiving glucose control therapy, including while in the power saving mode.

In some cases, the status information interface screen may display a lock status indicator 5516 as a status indicator. For example, as illustrated in FIG. 55, the lock status icon is displayed to be locked or closed to indicate that the AMD 5500 is presently in a locked state/mode, including while in a power saving mode. While the AMD 5500 may exit out of the locked mode via a wake mode indicator/interface 5520 as discussed herein, other user interaction gestures such as tapping may cause the AMD 5500 to exit out of a locked state, where for example the lock status indicator 5516 is no longer displayed. The lock status indicator 5516 can be considered to be a medicament device status indicator. The lock status icon, as illustrated, may be in the shape of a padlock when the AMD 5500 is locked. In some cases, the lock status icon may be updated when the AMD 5500 is unlocked. For example, the lock status icon may be changed to the shape of an open padlock or replaced with a menu icon when the AMD 5500 is unlocked. When there are existing alarm conditions, the alarm status indicator 5510 may be updated to indicate unresolved alarm conditions.

In some cases, the status information interface screen may display a wake mode indicator or message 5518 as a status indicator. For example, as illustrated in FIG. 55, the wake mode indicator or message 5518 indicates that user can tap the wake interface or button 5520 of the AMD 5500 to wake the screen and/or cause the AMD 5500 to exit the power saving mode. Waking the screen can include activating the touchscreen controller such that the AMD 5500 is responsive to user input on the touchscreen display. The wake mode button/interface 5520 can be considered to be a medicament device status indicator. The wake mode of the AMD 5500 can be considered a full functionality mode of the AMD 5500 as described herein, for example, in reference to paragraphs [0094]-[0108] and [0332]-[0384] with all functions including the touchscreen display fully active and functioning with minimal (e.g., certain select) or no power saving features active. The wake mode of the AMD 5500 can include a fully functioning and interactive touchscreen display that refreshes at desired rate, such as 60 hertz, and updates that status icons and indicators at a desired standard rate. In some cases, the refresh rate of the touchscreen display can be greater than 60 hertz, such as for example, 120 hertz or greater. The wake mode of the AMD 5500 can include a fully functioning motion sensor as discussed herein.

The user interface screen may include other wake mode indicator or message 5518, that indicate to the user what the wake mode button/interface 5520 is and/or provides information for activating the wake mode. When in the wake mode, the user interacting with the wake mode button/interface 5520 (e.g., pressing the wake mode indicator/interface 5520) can cause the AMD to enter or activate the power saving mode, including low power mode or sleep mode as discussed herein. The wake mode indicator or message 5518 may correspond to and indicate the location of the wake interface, may be a message to interact with the wake interface to activate the wake mode, or both. The AMD 5500 can generate and cause to display a power saving interface screen that includes the wake mode indicator. The power saving interface screen can be or be part of the user interface screens discussed herein. Once in the wake mode, the AMD 5500 may not display or stop displaying the wake mode indicator or message 5518.

The user may interact with a wake mode button/interface 5520 to create a wake request signal to unlock the AMD 5500. In response to the wake request signal, the AMD 5500 may deactivate or exit power saving mode. In some cases, when the wake request is received during a predefined period of the day, the AMD can turn on or increase the brightness of the backlight as part of entering the wake mode. For example, the AMD can turn on or increase brightness the backlight between 8 PM and 7 AM (e.g., when it is dark or nighttime) in response to receiving a wake request. During other times (e.g., 7 AM to 8 PM), the backlight can be turned on or brightness increased by for example holding the wake mode button/interface 5520 for a first predetermined period of time (such as 1-2 seconds). By holding the wake mode button/interface 5520 for a first predetermined period of time, the AMD 5500 can turn on or increase brightness of the backlight to a dimmer state, such as 40-60% brightness, relative to maximum brightness. When the user holds the wake interface for a second predetermined period of time (such as 2-3 seconds), the AMD 5500 can turn on or increase brightness of the backlight to maximum brightness. The AMD 5500 can track or count a length of time that the user interacts with or presses the wake mode indicator/interface 5520. In the wake mode, the AMD may enter or reactivate the power saving mode when the user interacts with the wake mode button/interface 5520 as discussed herein.

The wake mode button/interface 5520 may include, but is not limited to, a physical button, a capacitive sensor, or an inductive sensor. In some cases, a wake button may be incorporated into the alphanumeric pad 3224. In some cases, the wake interface may be any one or more keys of the alphanumeric pad 3224. In some cases, the wake interface may be a capacitive button that detects a change in capacitance. The wake interface may have a computing component for interpreting and executing instructions from the signal processing component. Thus, the wake interface can follow a program that is dictated by the signal processing component.

In some cases, the AMD 5500 in the power saving mode can refresh, update, change, or animate the status information screens, including the critical status information screens, less frequently or at a less frequent rate than updating the status interface screens in a wake mode. For example, the AMD 5500 can refresh, update, change, or animate the status information icons or indicators, including the critical status information indicators or icons, less frequently or at a less frequent rate than updating the status information indicators or icons in a wake mode. In some cases, certain critical status indicators may be updated at different rates. For example, some critical status indicators may be updated at a wake mode refresh rate, while other critical status indicator or other status indicators may be updated at a less frequent or power saving refresh rate. Certain status information may not be updated in the power saving mode. For example, the lock status indicator 5516 may not be updated until the AMD 5500 changes modes from the power saving mode to the wake mode.

In some cases, the AMD 5500 in the power saving mode can lower a refresh rate of the touchscreen to a lower refresh level relative to a maximum refresh rate of touchscreen. The lower refresh rate in the power saving mode can be for example 0.1, 0.5, 1, 1.5, 2, 2.5 3, 4, 5 or more hertz. The lower refresh rate in the power saving mode is less than the refresh rate of in the wake mode of, for example, 60 hertz. In some cases, the AMD 5500 in the power saving mode can lower brightness or dim of the touchscreen display 5502 to a lower brightness level relative to a full brightness level of the display. For example, the brightness may be 5, 10, 15, 20, 25, 30, 40, 50, or 60% brightness relative to the full brightness of the touchscreen display 5502.

In some cases, the AMD 5500 in the power saving mode can lower brightness or dim a backlight of the touchscreen display 5502 to a lower illumination level relative to a maximum illumination level of the backlight. For example, the brightness may be 5, 10, 15, 20, 25, 30, 40, 50, or 60% brightness relative to the full brightness of the backlight. The backlight can illuminate the touchscreen display 5502 and have an adjustable brightness separate from the adjustable brightness of the touchscreen display 5502. While in the power saving mode, the AMD 5500 can display the critical status information interface screen while using, for example, 5-10% additional electric current relative to electric current used with the display turned off (e.g., sleep mode as discussed herein) with the AMD 5500 operating (providing glucose control therapy). For example, the AMD 5500 can draw an additional 100-200 milliamps of additional current (5-10% more) without changes/updates to the screen on top of the 2-4 milliamps that the AMD 5500 may draw while delivering glucose control therapy without the display being on.

The combination of the AMD 5500 displaying certain critical status information, less frequent update of status indicators/icons, lower refresh rate of the display, lower brightness of the display, and/or lower brightness of the backlight (or turning of the backlight) can be considered to be a low power mode. For example, in low power mode, the AMD 5500 may update the display less frequently compared to when in the wake mode. For example, the AMD may update the display every 1 minute, every 2 minutes, every 5 minutes, or more. Between updates, the display can be a static screen that draws minimal current to stay on as discussed herein.

The low power mode can be a variant of the power saving mode that for example allows display of certain critical status information as discussed herein. The low power mode can be a type of power saving mode. For example, the power saving mode can include displaying certain critical status information with an always on screen as discussed herein. When the AMD 5500 functions to achieve additional power savings via lower frequency refresh or updates, lower brightness, etc., this can be considered a low power mode that helps achieve the lowered 5-10% additional electric current draw relative to the display being off.

When the display (as well as the backlight) is turned off while the AMD 5500 continues to provide glucose control therapy, this can be considered a sleep mode. The sleep mode can be a variant of the power saving mode that for example allows for certain user interaction such as tapping as discussed herein while the display and backlight are off. The low power mode can be a type of power saving mode. The sleep mode can be used during the day or at night while the subject sleeps. With the display and backlight off, the AMD may achiever further power savings relative to the lower power mode.

In some cases, the AMD 5500 can have a privacy mode. The privacy mode may be activated by the user or the AMD 5500 can activate the privacy mode automatically based on time of day or geolocation. The user may activate the privacy mode via one or more user interface via a menu or icon selection as discussed herein. The AMD 5500 can generate a privacy mode interface screen and display on the privacy mode interface screen one or more status indicators corresponding to the status information without displaying at least one of the critical status indicators that may contain relatively sensitive information. For example, the critical status information interface screen or the privacy mode interface screen may omit or not display the glucose level indicator, the therapy status indicator, or both. In some cases, none of the critical status indicators are displayed while privacy mode is active. For example, the critical status information interface screen may only show a lock symbol or an indication that privacy mode is activated.

In some cases, privacy mode can include activating the sleep mode such that display is off while the AMD 5500 delivery glucose control therapy. In some other cases, the display may be turned off while privacy mode is activated. Privacy mode may be activated independently or in conjunction with power saving mode. For example, the AMD 5500 may allow the user to configure the power saving mode to activate the privacy mode when the power saving mode is activated as discussed herein. In some cases, the AMD 5500 may allow the user to configure to activate the privacy mode after the power saving mode is activated. In some cases, the AMD 5500 may allow the user to configure to activate the privacy mode without the power saving mode being activated. The privacy mode can be configured to be activated via a wake interface discussed herein.

Figure 56:
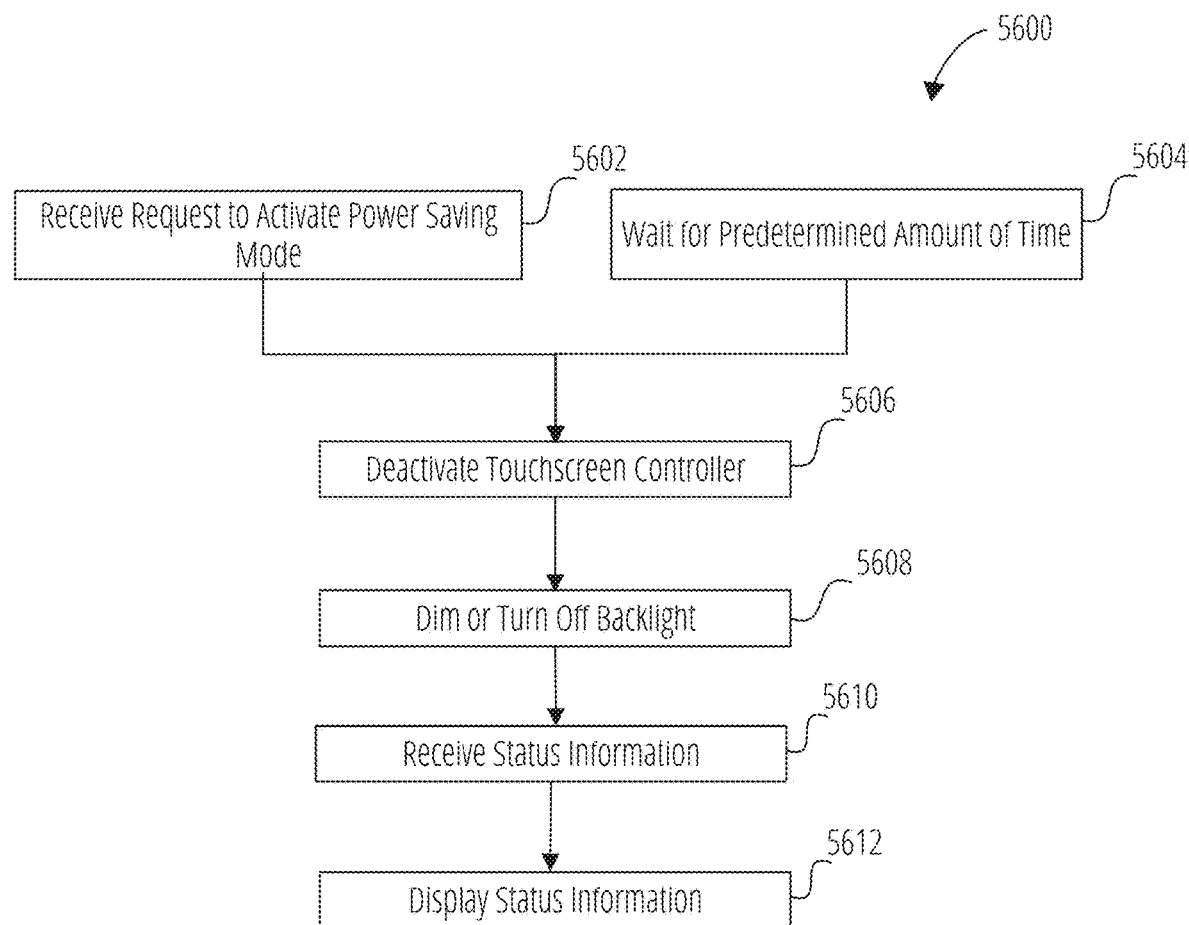
FIG. 56 is a flow diagram illustrating an example procedure to activate a power saving mode of an ambulatory medical device.

FIG. 56 is a flow diagram 5600 illustrating an example procedure to activate a power saving mode in an AMD. As discussed herein, the AMD can activate the power saving mode upon receiving a request from the user 5602 (e.g., via a wake interface or menu selection on the touchscreen display). In some cases, when the AMD does not receive a user request to activate the power saving mode and the user is otherwise not interacting with the AMD (e.g., selecting through menus, reviewing alarms, reviewing information on the AMD, etc.), the AMD can activate the power saving mode after a predetermined amount of time has passed 5604 associated with a period of inactivity of a user not interacting with the AMD or providing user input to the AMD. Once the AMD has entered or begun entering into the power saving mode, the AMD can deactivate the touchscreen controller 5606 such that the touchscreen controller does not receive or does not react to user input signals corresponding to the user input on the touchscreen display. In some cases, when the backlight was on for example, the AMD can lower or dim the brightness or the backlight (e.g., lower or dim illumination level of the display relative to a maximum illumination level) or turn off the backlight 5608 to achieve power savings in the power savings mode. In some cases, the AMD may implement other power saving features as discussed herein, such as reduced refresh and update rates, etc. The AMD may receive status information, including critical status information, 5610 as discussed herein. The AMD may then display the status information, including critical status information, 5612 as discussed herein. The AMD may utilize the always on screen functionality, including variation thereof, as discussed herein.

In some cases, the AMD may exit out of the power saving mode when the user wakes the device via a wake interface as discussed herein. In some cases, the AMD may exit out of the power saving mode via other user interactions or gestures. For example, the AMD may exit out of the power saving mode via a user interaction corresponding to a single or double tap on the AMD that the AMD determines via a motion sensor. In some cases, the user may interact with the AMD and command the AMD via user interaction with the AMD corresponding to taps or other gestures on the AMD while the AMD remains in the power saving mode. For example, the user may snooze alarms or toggle the display to turn on or off without the AMD exiting the power saving mode (e.g., without entering the wake mode).

Example AMD With Motion Sensor

As discussed herein, the AMD can have one or more user interaction sensors. The user interaction sensors can include motion sensors. The motion sensor can include an accelerometer, gyroscope, and/or other electrical or mechanical motion sensors that convert motion or acceleration into electrical signals. The electrical signals can be sent to the one or more controllers of the AMD as user interaction signals. In some cases, the motion sensors can be part of the device sensors 3208 as discussed herein. The motion sensor can detect, for example, a single tap or a double tap anywhere on the AMD, including on the touchscreen display. The motion sensor can detect and send user interaction signals associated with any number of taps, such as for example, a triple tap, a quadruple or more taps on the AMD. In some cases, other user interaction gestures detected by the motion sensor can be used with the AMD as discussed herein in combination with or in lieu of taps. For example, other user interaction gestures may include shaking the AMD, moving the AMD, tilting the AMD, picking up the AMD, and/or the like that may activate or initiate functionality of the AMD as discussed herein in reference to tapping.

Figure 57:
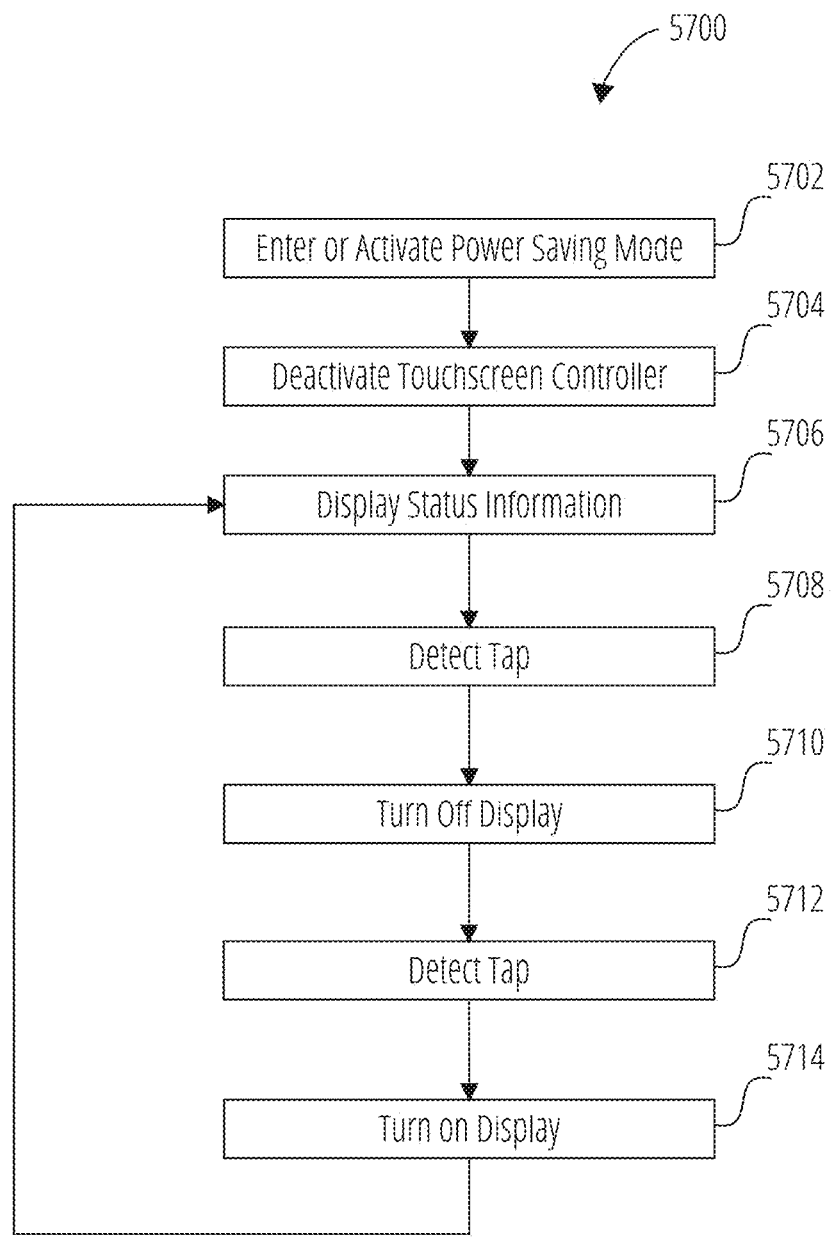
FIG. 57 is a flow diagram illustrating an example procedure for tap interaction in a power saving mode of an ambulatory medical device.

FIG. 57 is a flow diagram 5700 illustrating an example procedure for tap interaction in a power saving mode of an AMD. The tap interaction can be a single tap. In some cases, the tap interaction for flow diagram 5700 as discussed below in reference to FIG. 57 can be a double tap. In some cases, the user interaction with AMD for flow diagram 5700 can be another user interaction with the AMD as discussed herein.

A tap interaction, such as a single tap, can turn on or off the display. Turning on or off the display via taps, for example single taps, can be called toggling the display or toggling on or off the display without deactivating or exiting the power saving mode while toggling certain power saving mode features, such as temporarily turning on the display.

With reference to FIG. 57, the AMD can enter or activate the power saving mode 5702 as discussed herein. Upon entering or activating the power saving mode, the AMD can deactivate the touchscreen controller 5704 as discussed herein so that the AMD does not register or react to user input on the touchscreen display. In the power saving mode, the AMD can display status information 5706, which can include critical status information, on the display, for example with an always on screen. The motion sensor of the AMD can remain active such that the AMD can receive and respond to user interaction with the AMD.

The AMD can detect a tap 5708, such as a single tap, on the AMD as discussed herein via the motion sensor sensing user interaction with the AMD corresponding to the tap. The AMD can turn off the display 5710. For example, in turning off the display, the AMD may enter into the sleep mode as discussed herein while still continuing to provide glucose control therapy.

The AMD can detect another tap 5712, such as another single tap, after turning off the display. The AMD can turn on the display 5714 and continue displaying the status information 5706.

Figure 58:
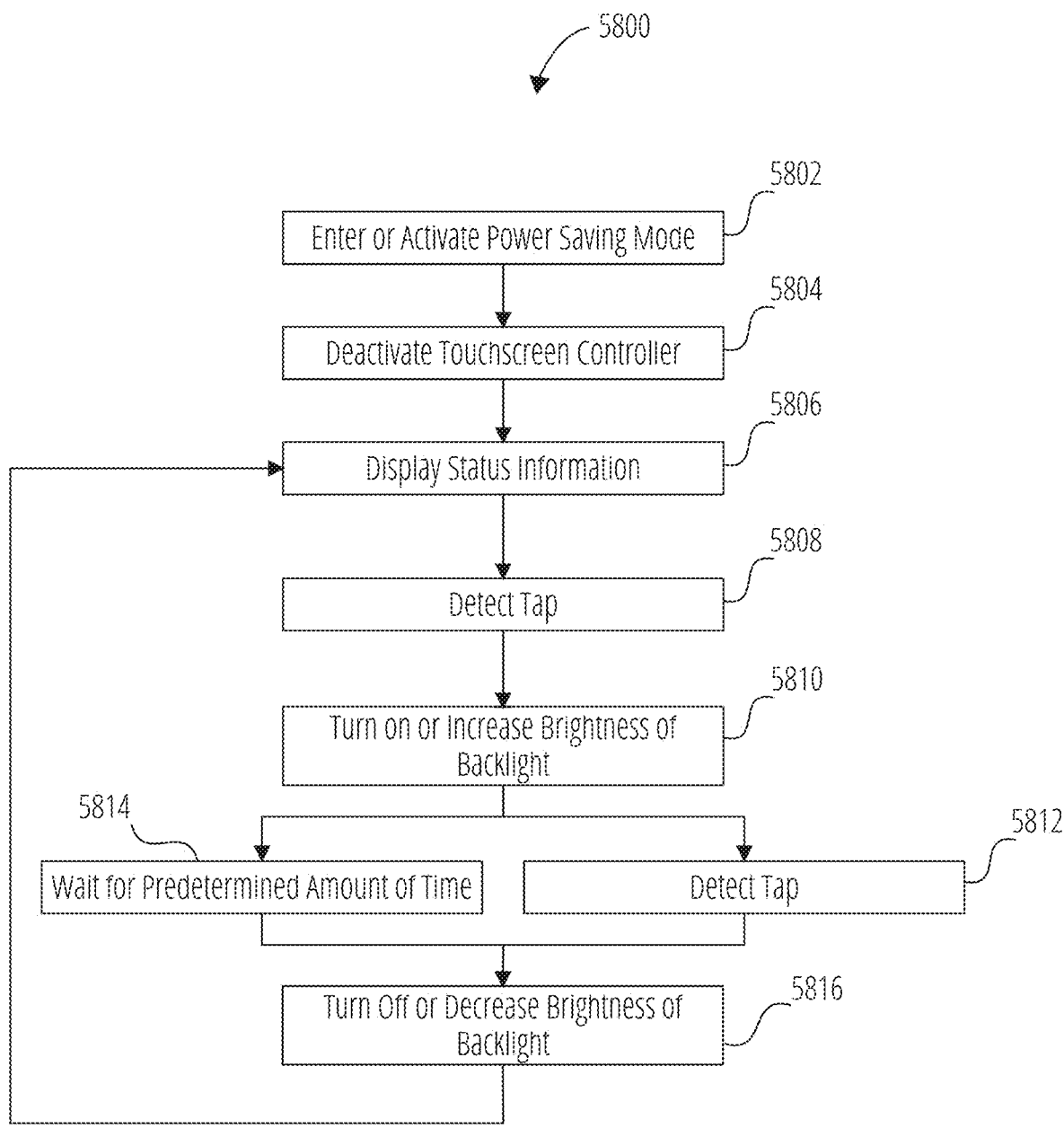
FIG. 58 is a flow diagram illustrating another example procedure for tap interaction in a power saving mode of an ambulatory medical device.

FIG. 58 is a flow diagram 5800 illustrating another example procedure for tap interaction in a power saving mode of an AMD. The tap interaction can be a double tap. In some cases, the tap interaction for flow diagram 5800 as discussed below in reference to FIG. 58 can be a single tap. In some cases, the user interaction with AMD for flow diagram 5800 can be another user interaction with the AMD as discussed herein.

A tap interaction, such as a double tap, can turn on or off the backlight. Turning on or off the backlight via taps, for example double taps, can be called toggling the backlight or toggling on or off the backlight without deactivating or exiting the power saving mode while toggling certain power saving mode features, such as turning on the display.

With reference to FIG. 58, the AMD can enter or activate the power saving mode 5802 as discussed herein. Upon entering or activating the power saving mode, the AMD can deactivate the touchscreen controller 5804 as discussed herein so that the AMD does not register or react to user input on the touchscreen display. In the power saving mode, the AMD can display status information 5806, which can include critical status information, on the display, for example with an always on screen. The motion sensor of the AMD can remain active such that the AMD can receive and respond to user interaction with the AMD.

The AMD can detect a tap 5808, such as a double tap, on the AMD as discussed herein via the motion sensor sensing user interaction with the AMD corresponding to the tap. The AMD can turn on or increase the brightness of the backlight 5810 used to illuminate the display. The AMD can turn on the backlight when the backlight was off, for example, in the power saving mode. The AMD can increase brightness of the backlight when the backlight was on, but not at maximum illumination for example, in the power saving mode.

The AMD can detect another tap 5812, such as another double tap, after turning on or increasing the brightness of the backlight of the display. At step 5816, the AMD can turn off the backlight when the backlight was previously off when the first double tap in step 5808 was received. In some case, at step 5816, the AMD can keep the backlight on and decrease the brightness when the backlight was on when the first double tap in step 5808 was received and the brightness was increased in step 5810.

In some cases, when the AMD does not detect another tap, such as another double tap, the AMD can turn off the backlight or decrease the brightness of backlight 5816 after a predetermined amount of time has passed 5814 associated with the backlight being on or at increased brightness for a certain time period when the AMD is in the power saving mode. The AMD can continue displaying the critical status information 5806.

Figure 59:
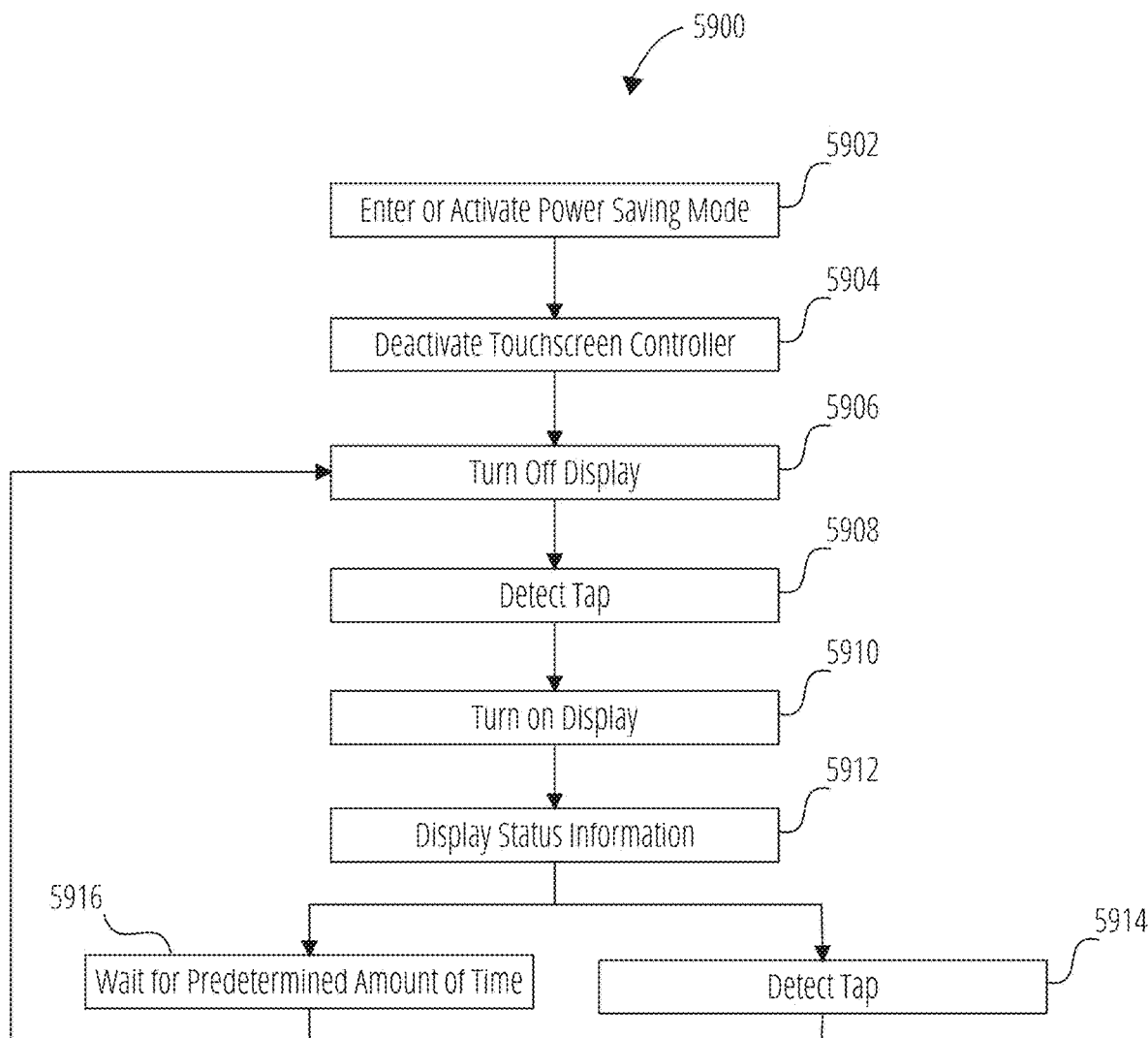
FIG. 59 is a flow diagram illustrating another example procedure for tap interaction in a power saving mode of an ambulatory medical device.

FIG. 59 is a flow diagram 5900 illustrating another example procedure for tap interaction in a power saving mode of an AMD. The tap interaction can be a single tap. In some cases, the tap interaction for flow diagram 5900 as discussed below in reference to FIG. 59 can be a double tap. In some cases, the user interaction with AMD for flow diagram 5900 can be another user interaction with the AMD as discussed herein.

With reference to FIG. 59, the AMD can enter or activate the power saving mode 5902 as discussed herein. Upon entering or activating the power saving mode, the AMD can deactivate the touchscreen controller 5904 as discussed herein so that the AMD does not register or react to user input on the touchscreen display. The power saving mode of flow diagram 5900 can include turning off the display as discussed herein for example in reference to a sleep mode. Accordingly, the AMD can turn off the display 5906 as part of entering or activating the power saving mode. The motion sensor of the AMD can remain active such that the AMD can receive and respond to user interaction with the AMD.

The AMD can detect a tap 5908, such as a single tap, on the AMD as discussed herein via the motion sensor sensing user interaction with the AMD corresponding to the tap. The AMD can turn on the display 5910. At step 5912, the AMD can display status information, which can include critical status information, on the display. In some cases, the AMD can display alarms that were previously snoozed (e.g., indication via alarm status icons) in response to the tap 5908 when turning on the display 5910. In some cases, the AMD may activate the touchscreen controller as part of turning on the display 5910 such that the user can interact with the AMD via user input using the touchscreen display as discussed herein.

The motion sensor of the AMD can remain active such that the AMD can receive and respond to user interaction with the AMD. The AMD can remain in the power saving mode after detecting the tap 5908. In some cases, the AMD may exit or deactivate the power saving mode and enter a different mode in response to the tap. For example, the AMD may enter a wake mode in response to the tap 5908.

The AMD can detect another tap 5914, such as another single tap, after turning on the display and displaying the status information. The AMD can turn off the display 5906 after detecting the other tap 5914. In some cases, the AMD can enter or activate the power saving mode in response to tap 5914. For example, the AMD can enter or activate the power saving mode when the AMD entered the wake mode in response to tap 5908.

In some cases, when the AMD does not detect another tap, such as another single tap, the AMD can turn off the display after a predetermined amount of time has passed 5916 associated with the display being on for a certain time period. In some cases, when the AMD does not detect another tap, such as another single tap, the AMD can turn off the display after a predetermined amount of time has passed 5916 associated with the display being on for a certain time period when the AMD is in the power saving mode. In some cases, the AMD can reenter or reactivate the power saving mode after a predetermined amount of time of not detecting another tap where the AMD had exited the power saving mode, such as for example, in response to the detecting the tap 5908.

Figure 60:
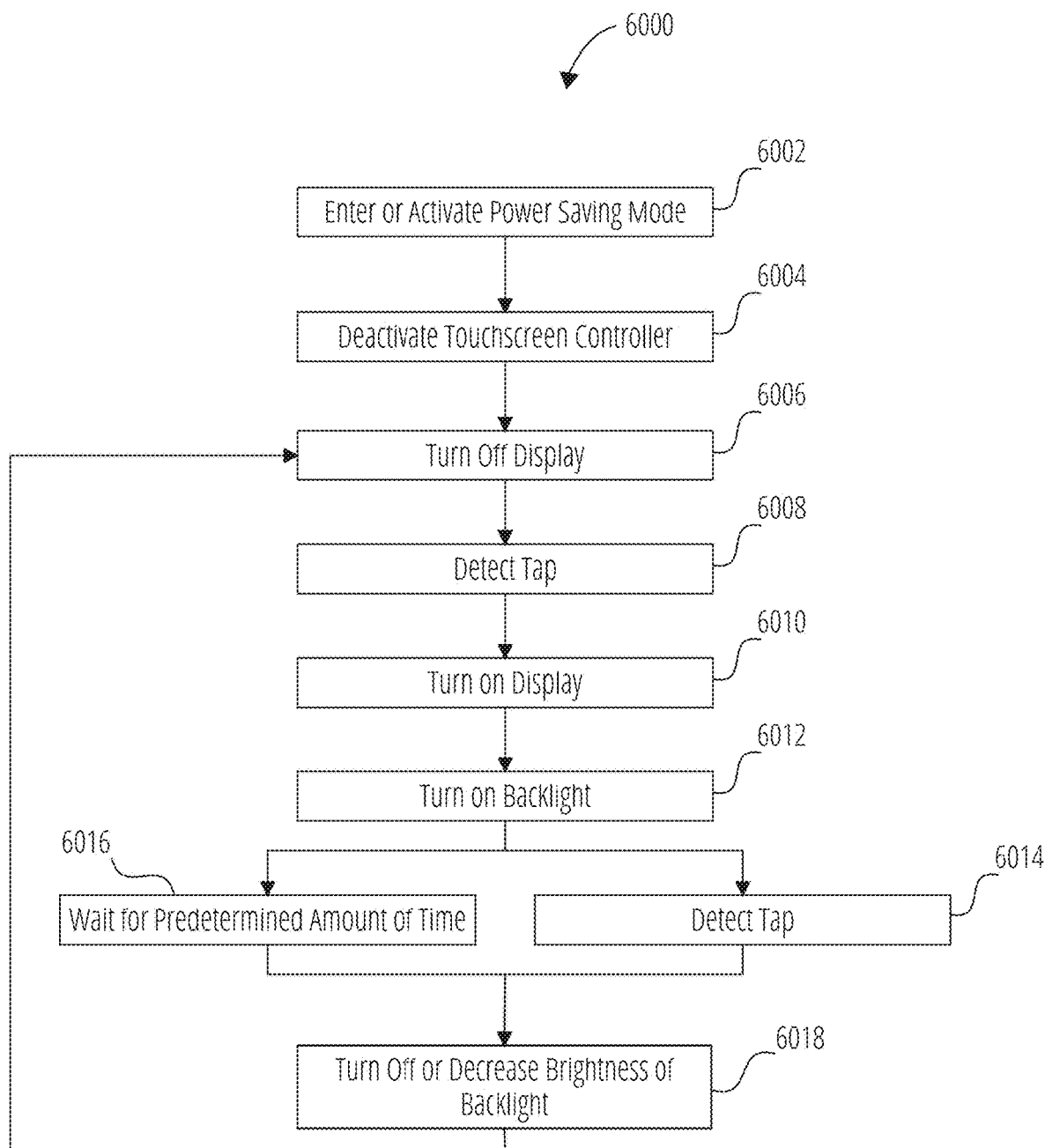
FIG. 60 is a flow diagram illustrating another example procedure for tap interaction in a power saving mode of an ambulatory medical device.

FIG. 60 is a flow diagram 6000 illustrating another example procedure for tap interaction in a power saving mode of an AMD. The tap interaction can be a double tap. In some cases, the tap interaction for flow diagram 5900 as discussed below in reference to FIG. 60 can be a single tap. In some cases, the user interaction with AMD for flow diagram 6000 can be another user interaction with the AMD as discussed herein.

The AMD can enter or activate the power saving mode 6002 as discussed herein. Upon entering or activating the power saving mode, the AMD can deactivate the touchscreen controller 6004 as discussed herein so that the AMD does not register or react to user input on the touchscreen display. The power saving mode of flow diagram 6000 can include turning off the display as discussed herein for example in reference to a sleep mode. Accordingly, the AMD can turn off the display 6006 as part of entering or activating the power saving mode. The motion sensor of the AMD can remain active such that the AMD can receive and respond to user interaction with the AMD.

The AMD can detect a tap 6008, such as a double tap, on the AMD as discussed herein via the motion sensor sensing user interaction with the AMD corresponding to the tap. The AMD can turn on the display 6010. In some cases, the AMD may activate the touchscreen controller as part of turning on the display 6010 such that the user can interact with the AMD via user input using the touchscreen display as discussed herein. The AMD can turn on backlight 6012 used to illuminate the display. In some cases, the AMD may delay turning on the backlight after turning on the display for a predetermined time period and/or until detecting another user interaction with the AMD such as the AMD being moved, including being picked up.

In some cases, the AMD can display status information, which can include critical status information, on the display as discussed herein, for example in reference to step 5912. The motion sensor of the AMD can remain active such that the AMD can receive and respond to user interaction with the AMD. The AMD can remain in the power saving mode after detecting the tap 6008. In some cases, the AMD may exit or deactivate the power saving mode and enter a different mode in response to the tap 6008. For example, the AMD may enter a wake mode in response to the tap 6008.

The AMD can detect another tap 6014, such as another double tap, after turning on the display and the backlight. The AMD can detect another tap 6014, such as another double tap, and turn off the backlight or decrease the brightness of backlight 6018. In some cases, the AMD can enter or activate the power saving mode in response to tap 6014. For example, the AMD can enter or activate the power saving mode when the AMD entered the wake mode in response to tap 6008.

In some cases, when the AMD does not detect another tap, such as another double tap, the AMD can turn off the backlight or decrease the brightness of backlight 6018 after a predetermined amount of time has passed associated with the backlight being on. In some cases, when the AMD does not detect another tap, such as another double tap, the AMD can turn off the backlight or decrease the brightness of backlight 6018 after a predetermined amount of time has passed associated with the backlight being on when the AMD is in the power saving mode. In some cases, the AMD may decrease the brightness of the backlight after the predetermined amount of time before turning off the display 6006 after another or second predetermined amount of time as discussed below.

The AMD can turn off the display 6006 after detecting the other tap 6014. In some cases, when the AMD does not detect another tap, such as another double tap, the AMD can turn off the display 6006 after a predetermined amount of time has passed 6016 associated with the display being on for a certain time period. In some cases, when the AMD does not detect another tap, such as another double tap, the AMD can turn off the display 6006 after a predetermined amount of time has passed 6016 associated with the display being on for a certain time period when the AMD is in the power saving mode. In some cases, the AMD can reenter or reactivate the power saving mode after a predetermined amount of time of not detecting another tap where the AMD had exited the power saving mode, such as for example, in response to the detecting the tap 6008.

In some cases, the AMD can first dim or decrease the brightness of the backlight after a first predetermined amount of time has passed 6016 without receiving another tap. After a second predetermined amount of time has passed (e.g., with a dimmed backlight), the AMD can turn off the display 6006.

Figure 61:
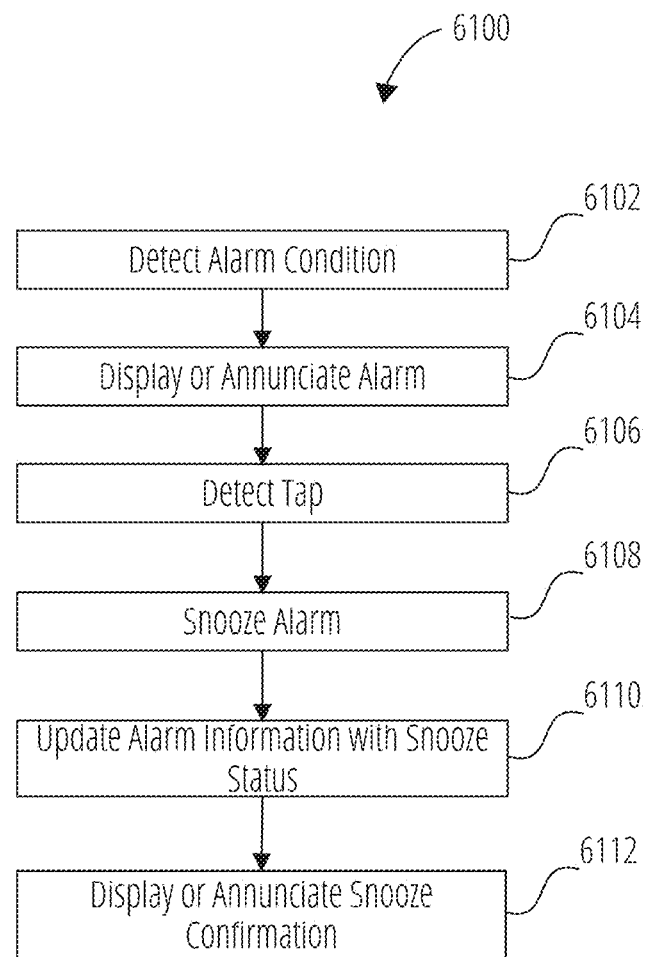
FIG. 61 is a flow diagram illustrating another example procedure for tap interaction with an ambulatory medical device.

FIG. 61 is a flow diagram 6100 illustrating another example procedure for tap interaction with an ambulatory medical device. The tap interaction can be a double tap. In some cases, the tap interaction for flow diagram 6100 as discussed below in reference to FIG. 61 can be a single tap. In some cases, the user interaction with AMD for flow diagram 6100 can be another interaction with the AMD as discussed herein.

In some case, the AMD may operate based on the flow diagram 6100 in the power saving mode with an always on screen as discussed herein. In some cases, the AMD may operate based on the flow diagram 6100 in the power saving mode without an always on screen, such as in the sleep mode with the display off as discussed herein. The AMD may turn on the display to notify of an alarm condition and turn off the display after the alarm is snoozed or otherwise acknowledged without exiting the power saving mode. In some cases, the AMD may exit or deactivate the power saving mode when the alarm condition detected in flow diagram 6100 corresponds to an urgent or high severity alarm as discussed herein. In some cases, the AMD may operate based on the flow diagram 6100 in a wake mode to snooze an alarm via tapping gesture(s) as discussed herein.

With reference to FIG. 61, the AMD can detect an alarm condition 6102 being present as discussed herein. For example, the AMD may receive status information via the monitoring system interface. The AMD may determine that the status information satisfies an alarm condition for the ambulatory medicament device and/or for the subject. The AMD can then display on the display one or more alarm status indicators corresponding to the alarm condition 6104 as discussed herein.

In some cases, the AMD can turn on the display when the display was off as discussed herein for the power saving mode or sleep mode. In some cases, the AMD may be operating with an always one screen as discussed herein. In some cases, the AMD can announce the alarm condition 6104 using an auditory annunciation pattern or a haptic annunciation pattern, or both. The AMD can use the auditory and/or haptic annunciation pattern in combination with displaying the one or more alarm status indicators or can use the auditory and/or haptic annunciation pattern when not displaying the one or more alarm status indicators (e.g., the display is off). The various annunciation and display combinations can be set by the user for the AMD and/or can be part of the modes of operation of the AMD discussed herein. For example, in the sleep mode, the AMD may default to auditory and/or haptic annunciation pattern without turning on the display when the display is off.

As discussed herein, the motion sensor of the AMD can remain active such that the AMD can receive and respond to user interaction with the AMD. The AMD can detect a tap 6106, such as a double tap, on the AMD as discussed herein via the motion sensor sensing user interaction with the AMD corresponding to the tap. The AMD can snooze the alarm or alarm condition 6108. In some cases, snoozing the alarm can include the AMD no longer displaying the one or more alarm status indicators on the display after being displayed in response the alarm condition. For example, the AMD can display the one or more alarm status indicators in response to the alarm condition and stop displaying the one or more alarm status indicators when the user snoozes the alarm. In some cases, when the AMD was in the sleep mode with the display off, the AMD can turn on the display to display the one or more alarm status indicators, and after a predetermined period of time, turn off the display again to reenter the sleep mode with the screen mode (without exiting the power saving mode).

In some cases, the AMD can determine that alarm condition requires urgent user attention based on, for example, a severity level of the alarm as discussed. When the alarm condition requires urgent user attention, the AMD can prevent or not allow the alarm to be snoozed via for example taps or other user interactions as discussed herein. In some cases, in response to determining that the alarm requires urgent user attention, the AMD can deactivate or exit the power saving mode into, for example, the wake mode. In some cases, in response to determining that the alarm requires urgent user attention, the AMD can deactivate or exit the sleep mode (e.g., operating with the display off) and continue operating in the power saving mode with, for example, an always on screen. In some cases, the AMD can allow low priority or not urgent alarms to be snoozed as discussed herein. In some cases, whether AMD allows the alarm to be snoozed or not, the AMD can deactivate or exit the power saving mode into, for example, the wake mode when an alarm condition is detected (e.g., inter wake mode regardless of whether the alarm is urgent or low priority)

In some cases, in response to snoozing the alarm, the AMD may update the alarm condition or alarm information with snoozed status 6110, such as updating the one or more alarm status indicators to indicate that a particular alarm has been snoozed. For example, the alarm status indicators may include or be changed to alarm status icons that indicate an alarm condition has been snoozed.

In some cases, the AMD can move or add the snoozed alarm status indicators to a list of pending alarm conditions. The list of pending alarm conditions can include indications or the alarm status icons associated with the alarm status indicators that indicate the alarm condition has been snoozed. Adding the snoozed alarm status indicators or alarm status icons to the list of pending alarm conditions can be part of the step of no longer displaying the one or more alarm status indicators on the display in response to the alarm being snoozed. For example, the AMD may not display the list of pending alarm conditions (which can include snoozed or as well as non-snoozed alarms) on an always one screen in a power saving mode of the AMD. The list of pending alarm conditions may then be later access via user input/interaction with AMD or for example, when entering the wake mode.

In some cases, the AMD can update, increment, and/or display an alarm status indicator (e.g., alarm status indicator 5510) with a counter that shows the number of alarm on the list of pending alarm conditions and/or whether one or more alarm conditions have been snoozed. After updating the alarm condition as snoozed, the AMD can display on the display and/or annunciate (auditory and/or haptic annunciation pattern) a snooze confirmation 6112 that the alarm condition has been snoozed. In some cases, the snooze confirmation may be or include the step of updating and/or changing the alarm status icons and/or incrementing a counter of the alarm status icon. After snooze confirmation 6112, the AMD can stop displaying the alarm status indicators on the user interface screen in, for example, the always on screen in the power saving mode of the AMD. In some cases, the AMD can stop displaying the alarm status indicators on the user interface screen when a predetermined period of time has passed after snoozing the alarm.

Additional embodiments relating to interacting with an ambulatory medicament device that can be combined with one or more embodiments of the present disclosure are described in PCT Application No. PCT/US2020/054025, filed on Oct. 2, 2020 and titled "BLOOD GLUCOSE CONTROL SYSTEM," the disclosure of which is hereby incorporated by reference in its entirety herein for all purposes.

AMD Motion Detection

In some cases, an unexpected situation may occur that impacts the operation of the ambulatory medicament device (AMD) such as an external impact or damage to the AMD. For an AMD that includes various mechanical components, there is a risk that external or internal damage to the mechanical components (intentionally or unintentionally) may cause a change in therapy previously set by a user or any other user, so that the medicament may not be properly delivered to a subject. Further, the AMD may have settings inadvertently modified by a collision when the AMD is accidentally dropped. In various embodiments, a user may be the subject who is receiving medicament or therapy, a clinician or healthcare provider, a parent or guardian, or any other user who may be permitted to modify settings of the ambulatory medicament device.

When there is a high acceleration impact, such as by a sudden drop of the AMD, a pump motor (e.g., motor 312) can be externally and/or internally damaged to operate in delivery of the accurate therapy to the subject. When there is an external damage to the AMD, medicament delivery error may occur which can lead to a dangerous situation for the subject. For example, in a case in which the motor is suddenly damaged while delivery of the medicament is being performed, a change in the delivery amount may unintentionally happen without any notice. In this situation, the subject may not even be aware of such a change. In addition, the AMD may stop operating, manually or automatically when the AMD is dropped. In some cases, when the AMD is not programmed to store or have any backup data (e.g., the number of turns of the motor used to provide the specific therapy individualized for a specific subject), an inaccurate amount of delivered medicament may be recorded. The user may not even be aware of any such circumstances.

In addition, current regulations require that the delivered amount of medicament match the amount prescribed. Thus, the delivery of medicament to the subject may need to be immediately terminated when damage to the AMD is anticipated. The delivery of an inaccurate amount of medicament can be averted in contravention with the prescribed amount of medicament.

In some embodiments, therefore, an ambulatory medicament device (AMD) may be configured to detect the sudden motion and to prevent an inadvertent modification to a control parameter and/or to medicament delivery. The sudden motion may include an event of sudden dropping of the AMD by a user or any external impact to the AMD.

Accordingly, in some embodiments, the AMD may include a sensor (e.g., device sensors 3208 in FIG. 32) which may be one or more motion sensors, an accelerometer, or a geolocation system to detect an external impact on the AMD or a motion of the AMD. The aforementioned sensor or sensors may be used to determine or detect a velocity of the AMD and/or the subject. In various embodiments, one or more motion sensors, such as an accelerometer and/or gyroscope, can be implemented for detecting a freefall motion or any other external movement of the AMD based on motion data. The motion data may be associated with movement of the AMD and collected from the one or more motion sensors. For instance, a motion sensor can detect any motion made around or on the AMD, e.g., a freefall motion of the AMD based on the motion data. The term "freefall" may refer to a condition where the object under consideration experiences substantially unimpeded downward acceleration due to gravity.

The motion sensor may detect such a gravitational acceleration of an object (e.g., AMD) in freefall. When the gravitational acceleration (falling toward the center of the Earth at an acceleration rate of about 9.81 m/s$^2$) or a certain acceleration or higher set in the AMD is detected by the one or more sensors, the AMD determines that there is a freefall motion of the AMD, falling from the top of, e.g., about 1.2-1.5 m, to the ground. The motion detection is however not limited to the freefall motion, but may include other movements, for example, a shake (e.g., left to right movement and/or up and down movement for certain displacement for a certain period of time or more), swiping, pinching, tapping, etc. In certain embodiments, when motion or motions have been detected by the one or more sensors, the AMD may act to stop certain actions or functions of the AMD to prevent damage to internal components and/or incorrect delivery of medication (e.g., erroneous dosing). In addition, when there is zero output from the accelerometer, the controller may determine the freefall motion and thus control the operation of the AMD (e.g., halt operation as discussed herein).

In some embodiments, the AMD may detect motion or motions via motion sensors in various forms as noted above and may store in motion data. In certain embodiments, the stored motion data can be used not only for merely detecting a motion of the device such as freefall as described above, but also for interaction with users so as to alert the user regarding any potential or actual malfunction of the device and to receive user acknowledgement of the alert. Therefore, motion data detected by the AMD can provide useful information both to alert the user to potential problems and to allow the user to initiate interaction with the AMD, if the user so chooses. However, it is of particular importance that the AMD alert the user in a situation where a medicament is potentially erroneously delivered to a subject/patient which can result in a critical situation, for example, a situation where the AMD is damaged in a fall, by being dropped, accidentally thrown etc. as described above. In various embodiments as will be described herein, the motion detection can be employed for various uses as further described below.

Figure 62:
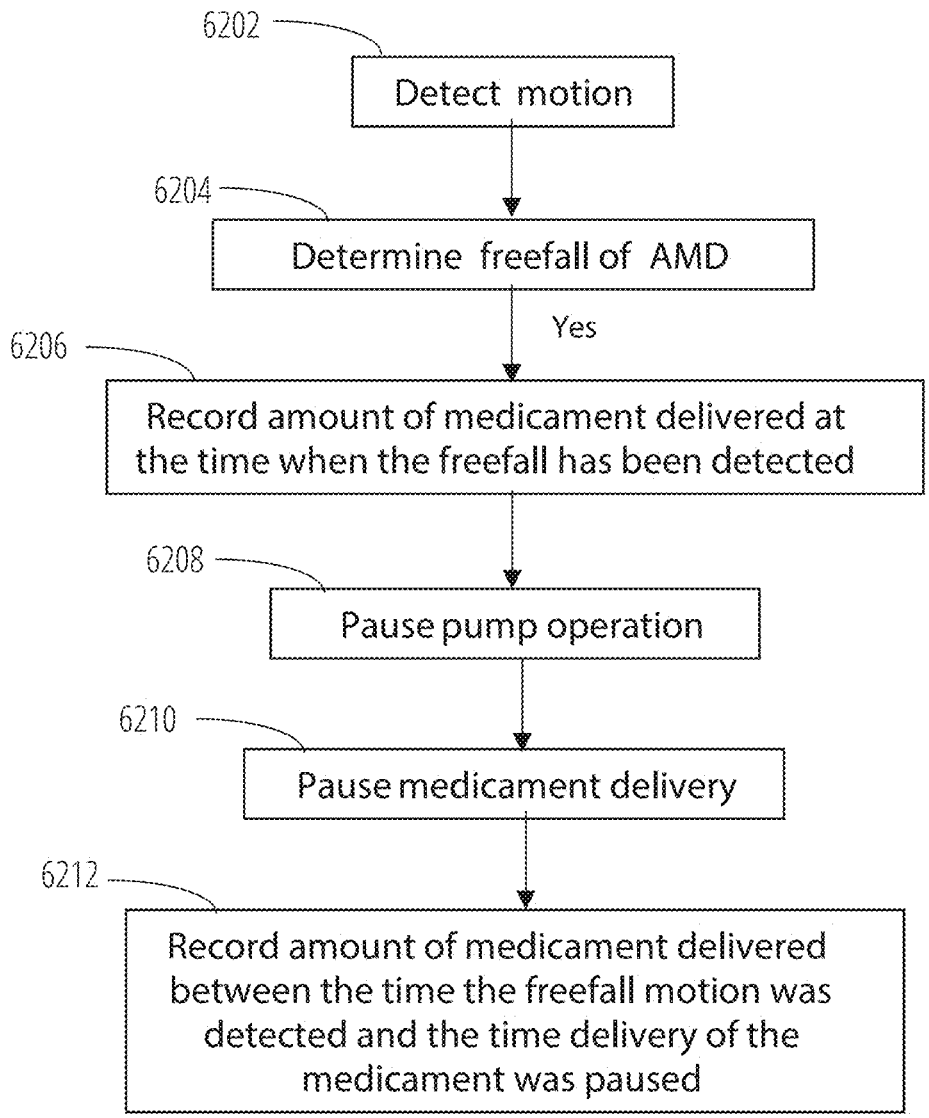
FIG. 62 is a flow diagram illustrating an example procedure to control an operation of an ambulatory medical device pump based on motion detection.

For example, referring the process 6200 of FIG. 62, when a motion has been detected by one or more motion sensors in the form of motion data 6202, the AMD may determine whether the motion is a freefall motion of the AMD 6204 as discussed herein. Upon determining that the detected motion is in a freefall motion 6202, the operation or functions of one or more of components of the AMD (e.g., a pump of the AMD) may be controlled to be paused 6208. As part of step 6208, the AMD may lock the touchscreen (e.g., disable touchscreen controller to prevent touch inputs) and/or lock the AMD into, for example, a sleep or locked state. As described above, pausing the pump may also pause the medicament delivery to the subject. Upon determining that the motion is the freefall motion, the number of cycles of the pump may be recorded at the instance when the freefall motion is detected at step 6206. Then, the motor 312 might be ceased to stop or pause the pump operation at step 6208 and pause or stop the delivery of medicament to the subject at step 6210. In addition, the amount of medicament delivered between the time the freefall motion was detected and the time delivery of the medicament was paused may be also recorded at step 6212. In some cases, the AMD may execute steps 6202, 6204, and 6210 upon determining that the AMD is in freefall without recordation of medicament delivery of steps 6206 and 6212.

In certain embodiments, the pump of the AMD may have a pump mechanism including, e.g., a housing, DC servomotor, a reservoir, cartridges, circuitries, batteries, and the like, which are sensitive to any outside impact due to an inadvertent or accidental collision, drop, etc. The pump mechanism may be adapted to use a general pump mechanism. The ambulatory medicament pump can be any pump that can be used in medicament pumps known to those of skill in the art, for example, a peristaltic pump but not limited thereto.

Ambulatory Medicament Pump Motor Control

In certain embodiments, as noted above, one or more motion sensors such as an accelerometer can detect a freefall motion of the AMD based on motion data, which is associated with movement of the AMD, collected from the one or more motion sensors. For instance, a motion sensor can detect a freefall motion of the AMD based on the motion data and the AMD may paused or stopped, which may cease operation of medicament delivery.

The term "paused" may refer to stoppage for a predetermined period of time and may automatically resume operation after a certain period of time or when a certain condition has met. In some cases, paused can include stopping the AMD until the user directs the AMD operations to resume. When the AMD is paused or operation is halted, such as in a case where the AMD is halted until further instructed by the user after the detection of the freefall motion, the delivery of medicament to the subject can be paused as a result. The halt operation of pausing delivery of medicament to the subject can be carried out by instructing the controller to cease rotation of the motor 312 of the ambulatory medicament pump, by cutting power supply to the ambulatory medicament pump, or switching from a closed loop circuit to an open loop circuit by controlling a switch unit. In some embodiments, the user may be informed via a user interface (e.g., touchscreen display 504) when the AMD has stopped operating the pump/motor 212, 312. In some cases, when a freefall motion of the AMD is detected, the AMD may pause the delivery of the medicament for a period of time. In some such cases, the period of the time can be one minute, five minutes, ten minutes, thirty minutes, an hour, or an amount of time defined by the subject.

Alarm Generation Based on AMD Condition

In alternative, or in addition to the cessation of the AMD's internal operation, an alarm can be outputted in various ways to inform a user. An acknowledgement of the user of the alarm may be required in certain situations. The alarm may alert the user regarding various conditions regarding the AMD and may warn the user regarding. For example, the various conditions may include potential damage to the system and changes in medicament parameters, cessation of AMD operation. The alarm conditions may further include instances where the user may be informed regarding either potential or actual changes to the system's operation. In various embodiments, the user interface may be a touchscreen interface or a non-touchscreen interface, or the wake interface 3220. The user interface may present one or more user-interface screens to a user informing the user of the status of the AMD or to receive a user's direct manipulation. The user interface can be implemented via an electronic device that includes a display and one or more buttons, switches, dials, capacitive touch interfaces, or touchscreen interfaces.

As discussed above, the ambulatory medicament device may include an alarm system configured to monitor the ambulatory medicament device and/or the subject, and to generate an alarm when it is determined that a condition has been detected that satisfies an alarm condition.

In some embodiments, with reference to FIG. 32, the CCM may include control methods of the AMD implemented to prevent unintended therapy changes by detecting particularly a certain motion of the AMD. In addition to the above-described elements, the blood glucose control system that provides blood glucose control via an ambulatory medicament pump may further include a medicament reservoir (e.g., reservoir 408) configured to store a medicament and from which the medicament can be delivered to the subject by the pump 212. In some examples, the pump 212 can include one or more medicament cartridges or can have the integrated reservoir 408 of medicament. In various embodiments, the operation of the pump 212 can be controlled by the controller 400.

In some examples, as also noted above, the motion sensor can sense an end of the freefall motion and resume the delivery of the medicament upon detecting the end of the freefall motion or resume the delivery of the medicament after a specifically set period time has lapsed. In this case, the user may be notified with the resumption of medicament delivery via the user interface, or in certain embodiments, the user interface may display an option button for the user to accept or decline the resumption of medicament delivery.

In some embodiments, the AMD may be programmed to record an amount of medicament administered to the subject upon detecting the freefall motion and determine an amount of medicament administered between a time the freefall motion was detected and a time delivery of the medicament was paused. In this manner, the amount of medicament delivered to the patient between the instance of the freefall motion and the instance of the pause may be determined in accordance with therapeutic protocols. The amount of medicament administered to the subject can be determined for example based on the number of cycles completed by the ambulatory medicament pump. The number of cycles can be calculated based on how many turns the motor 312 has made prior to the stopping of the motor.

As noted above, the AMD may detect an end of the freefall motion. In response to the detection of the end of the freefall motion, the AMD may resume administering the medicament to the subject based on the recorded amount of medicament by controlling the pump. The end of freefall motion may be detected by a baseline output of the motion sensor. For example, when the motion sensor includes an accelerometer, the baseline output may be the signal output detected by the accelerometer and may correspond to the signal output due to gravity when the AMD is at rest. In some cases, the baseline output can be within a range of acceleration values surrounding the acceleration of gravity. For example. The range of acceleration values can encompass accelerations felt by the ambulatory medicament device while attached to the subject.

In some cases, when the motion sensor detects less than the baseline output beyond a predetermined freefall threshold signal output, the AMD can determine the AMD is in free fall motion. For example, when the motion sensor detects zero output, the AMD is in free fall motion. In some cases, the AMD can determine that AMD is in freefall when the output is greater than zero, but less than the predetermined freefall threshold. When the signal output is greater than the predetermined freefall threshold, the AMD can determine that the AMD is not at rest or that subject is moving the AMD, but that the AMD is not in freefall motion because the motion sensor provides an output signal between the baseline output and the predetermined freefall threshold signal output. When the signal output from the motion sensor is between zero and the predetermined freefall threshold signal output, the AMD can determine that the AMD is in freefall. In some cases, the predetermined freefall threshold may correspond to when the AMD has experienced freefall acceleration due to gravity from 2-6 feet, including 3-5 feet, including 4-5 feet, including any values in-between.

In response to the detection of an end of the freefall motion, the AMD may further calculate a jerk of the ambulatory medicament device during the freefall motion based on the acceleration and determine whether the jerk exceeds a threshold value. If the jerk does not exceed a threshold value, the AMD may resume administering the medicament to the subject. If, however, the jerk exceeds the threshold value, the AMD may generate an alarm to notify a user, and request that the user acknowledge the alarm in the form of an alarm response signal from the user (or subject). The alarm may be configured to include an urgency level based on the calculated jerk. The alarm, and the alarm response signal, may be implemented in multiple formats. For example, the alarm response signal may include an alarm snooze signal, which snoozes the alarm, or an alarm acknowledgement signal configured to dismiss the alarm. In certain embodiments, the alarm associated with the highest alarm severity level however may not be snoozed or dismissed. Alternatively, the alarm associated with the highest severity level may be snoozed for a shorter time period than alarms of lower severity levels, which will be described in more detail further below.

The alarm herein may be generated due to various reasons, e.g., due to the drop of the AMD as described above, and in addition the motion sensor may detect further motions of the device, and the motion sensor may be further configured to detect the motion of the user responding to the alarm. That is, the ambulatory medicament device may not only detect the motion of the device itself as freefall, but may also be configured to detect the motion of the device by an external impact (e.g., tap, shake, etc.) on the device body.

In addition, another alarm may be generated after a specific period of time has lapsed, and in this case, an alarm acknowledgement response may be received, and the alarm may be dismissed. The alarm or alarms can be categorized by the level of intensity, for example, a low-level alarm, a medium-level alarm, or a high-level alarm, that is determined based on the alarm condition. That is, the alarm may have an urgency level, for example, between 0 and 5 determined based on the alarm condition, such that the alarm can be generated differently based on the level of urgency associated with the alarm condition. In some examples, the alarm condition may be an alarm condition in an alarm profile as will be described below in more detail.

For some examples, referring back to FIG. 62, upon determining that the motion is the freefall motion, the number of cycles of the pump may be recorded at the instance when the freefall motion is detected at step 6206. Then, the motor might be ceased to stop or pause the pump operation at step 6208 to ultimately pause or stop the delivery of medicament to the subject at step 6210. In addition, the amount of medicament delivered between the time the freefall motion was detected and the time delivery of the medicament was paused may be also recorded at step 6212.

Figure 63:
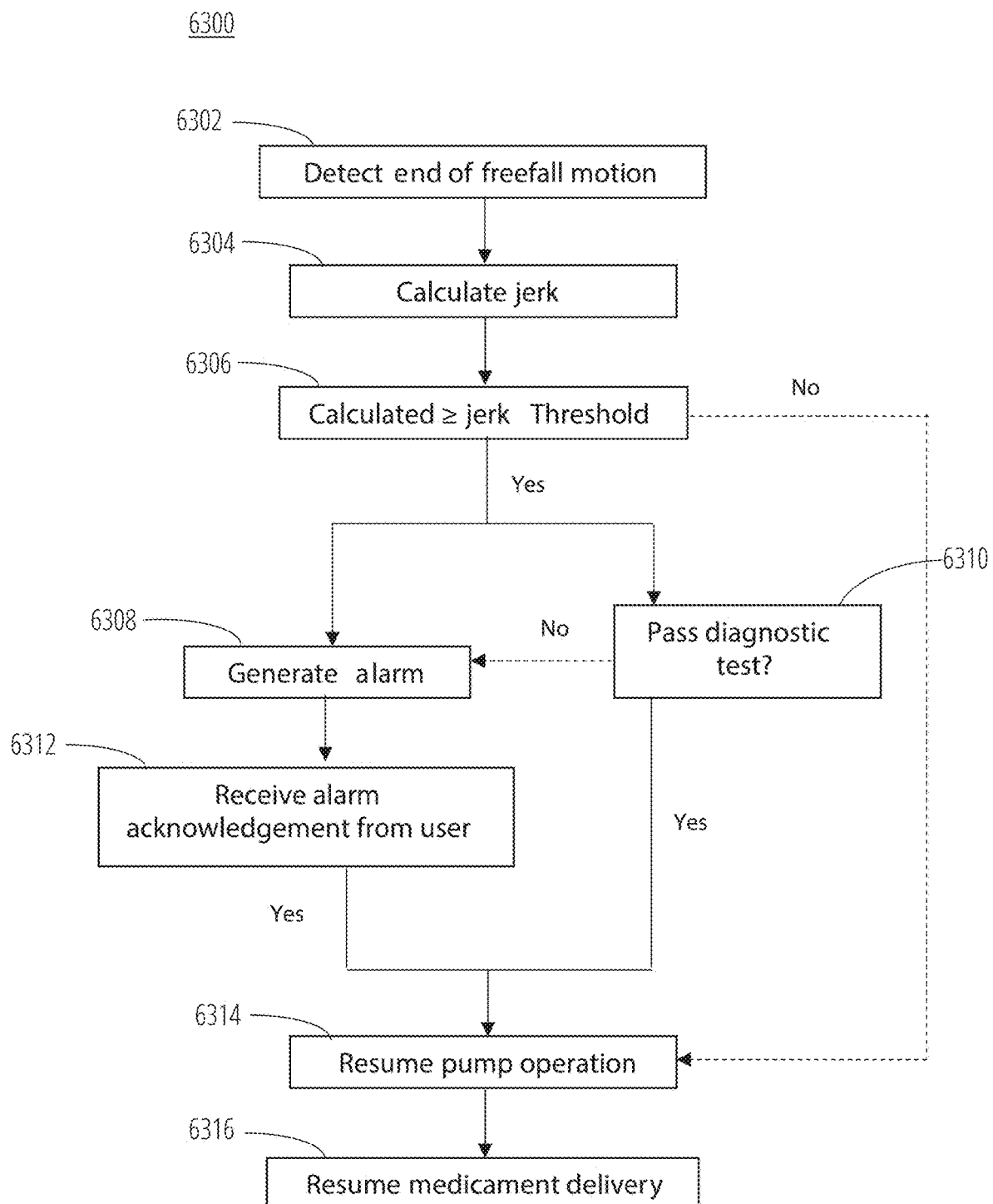
FIG. 63 is a flow diagram illustrating an example procedure to control an operation of an ambulatory medical device pump after freefall motion has ended.

When the AMD has reached the ground, such that the freefall motion is ended, the sensor can also detect and may generate an alarm. FIG. 63 a flow diagram 6300 illustrating an example procedure to control an operation of an ambulatory medical device pump after freefall motion has ended. Once the end of freefall motion is detected at step 6302, the AMD may calculate a jerk at step 6304. The jerk or jolt, corresponding to a rate at which an object's acceleration changes with respect to time. It is a vector quantity (having both magnitude and direction). The jerk or jolt can be associated an impact on the AMD as a result of, for example, contacting the ground or some other object after freefall motion with the impact generating forces or acceleration values on the AMD greater than an alarm and/or diagnostic threshold step 6306. In some cases, the jerk or jolt can occur without freefall motion. For example, the jerk or jolt may be determined because the AMD was hit or bumped against an object that resulted in an impact generating forces or acceleration values on the AMD greater than the alarm and/or diagnostic threshold step 6306.

The AMD then may output an alarm if the calculated jerk is equal to or greater than an alarm and/or diagnostic threshold at step 6308. The alarm and/or diagnostic threshold rate may be used as criteria in determining whether the alarm condition is satisfied by comparing status information (e.g., calculated jerk) to one or more alarm thresholds (e.g., reference jerk that is preset or predetermined jerk threshold) or alarm conditions. The alarm threshold and alarm profile will be further described in detail in the Alarm Condition section.

An alarm can be generated to inform the user 6308 of a malfunction or some other condition of the AMD as result of the jerk. In some cases, the user may be required to acknowledge the alarm 6312. Once the alarm acknowledgement has been received from the user at step 6312, the AMD and/or motor operation may be resumed to continue the delivery of medicament to the subject at steps 6314 and 6316. The alarm acknowledgement will be described in more detail in the Motion-Based Alarm Acknowledgement of User section. If the jerk is on the other hand the alarm less than the alarm and/or diagnostic threshold, the AMD and/or motor operation may be resumed to continue the delivery of medicament to the subject at steps 6314 and 6316 without generating alarms or running a diagnostic test.

In addition or in alternative to generating an alarm, when the calculated jerk is equal to or greater than the alarm and/or diagnostic threshold, a diagnostic test may be performed to check the condition of the pump at step 6310. The diagnostic test can be employed as a standard for determining whether to resume the administration of the medicament to the subject. If the AMD does not pass the diagnostic test, e.g., fails to meet specific requirements set for determining whether to resume the administration of the medicament to the subject based on one or more operating parameters, the AMD or one or more components of the AMD may be considered as being damaged or any of the controllers contained therein may be determined to have a malfunction. In this case, an alarm may be generated informing the user of the damage or the like of the AMD and step 6308 may be performed. On the other hand, if the diagnostic test is passed, the pump operation may be resumed to resume the delivery of medicament to the subject at steps 6314 and 6316.

Alternatively, or in addition to providing the alarm, when the AMD is determined to be malfunctioning (e.g., damaged), the AMD may be reset by restarting the device. The AMD may either automatically restart or direct the user to restart the AMD (e.g., as part of an alarm condition). If restarting the device resolves the malfunction issues caused by the jerk, the AMD may resume pump operation and medicament delivery steps 6314, 6316. In some cases, upon restart, the diagnostic test may be performed and/or the alarm generation process may be performed again. In some cases, if the AMD does not pass a diagnostic test for the second time after restarting, the AMD may generate an alarm 6308 informing the user that the AMD is damaged and needs to be repaired. Such an alarm may be a high severity alarm as discussed herein. In some cases, the AMD may generate other alarms discussed herein while resuming operation 6314, 6316. The other alarms may inform of some malfunction of the AMD that does not require immediate resolution in order for the AMD to resume operation 6314, 6316.

In some cases, the AMD can generate an alarm when the AMD cannot verify the amount of medicament delivered due to the subject. For example, the actual amount of medicament delivered by the AMD may be determined or calculated based on the amount a dispensing screw has been turned by the pump motor to dispense medicament from the cartridge. In some case, the actual amount of medicament delivered by the AMD can be determined based on flow sensors and corresponding outputs indicating the amount of medicament dispensed. In some case, the actual amount of medicament delivered by the AMD can be determined based on the amount of volume remaining or volume change of medicament in the cartridge.

The AMD can also determine how much medicament was supposed or desired to be delivered to the subject based on an algorithm for delivering glucose control therapy as discussed herein. When the AMD determines that the medicament actually delivered does not match or is not the same as the medicament that was supposed or desired to be delivered based on the glucose control therapy protocols, the AMD may generate an alarm as discussed herein. In some cases, the alarm generated because the AMD cannot verify actual versus desired medicament delivery can be part of the generate alarm 6308 and/or diagnostic test 6310 steps as discussed herein. In some cases, the alarm generated because the AMD cannot verify actual versus desired medicament delivery can be part of other alarm generation as discussed herein. For example, the AMD may generate an alarm regarding the error in medicament delivery during operation after resumption of pump operation and medicament delivery 6314, 6316.

The method described herein may be performed by an AMD (e.g., by one or more processors of the AMD) to detect AMD device malfunctions, generate corresponding alerts, and prioritize the alerts to enable the subject or user to quickly and easily determine whether the device malfunction will impact therapy, and should be immediately addressed. In some cases, the method of device malfunction alert prioritization may be used by other systems.

Motion-Based Alarm Acknowledgement

Certain alarms, such as informational alarms, may be dismissible. However, generally the alarm may remain on the alarm list until the condition that caused the alarm is acknowledged and resolved.

A user may be able to acknowledge and/or snooze alarms via a user interface. In some examples, in order to acknowledge and/or snooze alarms, the user may first need to activate the user interface and then provide a gesture to unlock the user interface. For example, the user may use the wake button to activate a touchscreen display and then provide a gesture on the screen to unlock display. In some embodiments, the touchscreen display may be configured to allow the user or subject to navigate directly to the issue or fault for which an alarm is being delivered. This capability provides the user with more direct access to address the fault causing the alarm, so that the fault may be addressed more easily, and the alarm may then be stopped.

Acknowledging the alarm may include an action to respond to the alarm such that the user can resolve the alarm. For example, resolving the alarm may include replacing an insulin cartridge, changing a site where the ambulatory medicament device is connected to the subject, charging a battery of the ambulatory medicament device, providing insulin or a counter-regulatory agent to the subject and/or the ambulatory medicament device, replacing a damaged AMD or motor due to dropping thereof, or any other action that may be performed to address an alarm condition. In some cases, the resolution action may be acknowledging the alarm. For example, if the alarm is informational (e.g., to inform the user that more insulin has been ordered or to inform that the AMD is not functioning properly), acknowledging the alarm may be a sufficient resolution action.

Figure 64:
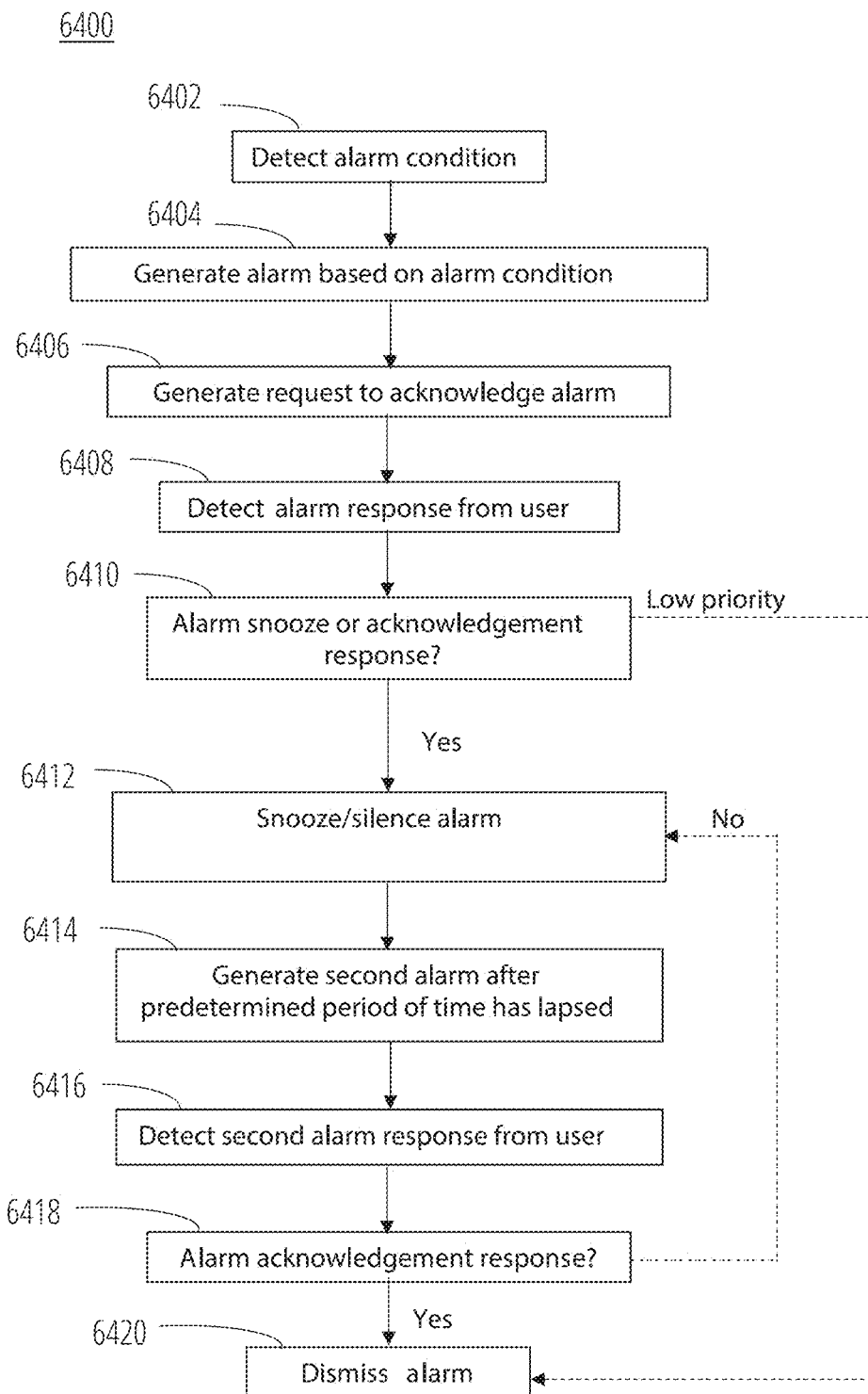
FIG. 64 is a flow diagram illustrating an example procedure to receive an alarm acknowledgement from a user.

Referring to FIG. 64, which is a flow diagram 6400 illustrating an example procedure to receive an alarm acknowledgement from a user, when there is an active alarm detected due to various errors detected such as error in the AMD, error in medicament measurement, etc. In some embodiments, an alarm condition can be detected at step 6402 and an alarm can be generated based on the alarm condition (e.g., severity or urgency level of the alarm as described herein) at step 6404. The alarm can be generated to notify the user of the current situation or operation status of the AMD. The user may be then requested to acknowledge the alarm to make sure that the user is aware of the current alarm and associated operating conditions of the AMD at step 6406. The alarm acknowledgement can be done in various ways, e.g., touching or tapping (one or more taps on one or various locations) on the touchscreen or touching or tapping on the AMD, shaking the AMD, shaking a hand above the touchscreen, swiping on the touchscreen, pressing the wake button or any other implemented button (as a touchscreen or physical button), etc. The alarm acknowledgement will be described in detail later in this section.

Upon receiving a response from the user at step 6408, 6410 to snooze the alarm, the alarm may be snoozed or silenced 6412. In some cases, the alarm may be snoozed for a specified or predetermined period of time at 6412. In some cases, the alarm may be dismissed 6420 when the alarm is acknowledged and the alarm condition is determined to have a low urgency (e.g., level 0-2, including level 1). In some cases, the alarm may be dismissed 6420 when the alarm is not acknowledged or snoozed, but the alarm condition is determined to have a low urgency (e.g., level 1). The low urgency alarm may be generated 6406 and after not detecting an alarm response from the user, the alarm may be dismissed 6420 with low urgency alarms. In some cases, the alarm may be snoozed 6412 when the alarm is acknowledged (and not snoozed by the user when the option to snooze is provided), but the alarm condition is determined to have a higher urgency (e.g., level 2) that merits generating a second alarm 6416 as discussed herein. The AMD can generate user interface screens as discussed herein to provide an option for the user to snooze an alarm and/or acknowledge the alarm. Whether the user can snooze and/or acknowledge the alarm can be determined based on the urgency of the alarm as discussed herein.

When the alarm has been snoozed at step 6412, the AMD may add the alarm condition to a list of alarms as discussed herein. After the alarm has been snoozed 6412, the AMD may start a timer to track the passage of time. After a predetermined period of time has passed, the AMD can generate a second alarm at step 6414 to notify the user that the alarm condition still exists. When the AMD detects 6416 that the user has acknowledged the second alarm, the alarm can be then dismissed at step 6418. Alternatively, if an alarm snooze response is received from the user or the user again does not acknowledge the alarm 6418, the snooze function may be performed again for a predetermined period of time (6412) to generate additional alarms (e.g., second alarms) until the alarm condition is dismissed by the user or resolved as discussed herein.

In some embodiments, the one or more user interface screens configured as a touchscreen may provide a graphical display including information about an alarm when an alarm threshold or condition is reached or exceeded as discussed herein. The one or more user interface screens may be an alarm acknowledgement touch user interface element. The one or more user interface screens may be configured to receive an alarm acknowledgement signal from the user via the touchscreen. Then, the one or more user interface screens may include resumption of administering the medicament to the subject based on the alarm acknowledgement signal.

In some embodiments, when the magnitude of a measured jerk exceeds a threshold, the AMD may be configured to resume operation after the user acknowledges the alarm. The graphical display can be arranged and colored based on an urgency level of the alarm condition. For example, the alarm condition having the highest urgency level may be colored in red and displayed at the top of the screen. The alarm condition having the lowest urgency level may be colored in green at the bottom of the screen for the user to easily discern therebetween. The color and the location herein are merely examples but can be any color and any location (e.g., upper right corner, middle, or the like on the screen).

Further, the graphical display is not limited to the visual display, but could be in the form of sound, by, e.g., a speaker generating audible signals based on the level of the urgency. The audible signal may include one of, e.g., a beep, a series of beeps, a patterned beeping, or a speech output describing the alarm. The volume and the play length of the audible signal may vary based on the level of urgency (e.g., playing for one minute for the highest urgency while playing for 10 seconds for the lowest urgency).

In addition, or alternatively, the ambulatory medicament device may include a haptic motor allowing a haptic alarm signal to be generated therethrough based on an urgency of the alarm condition. The haptic alarm signal may include, e.g., a sustained vibration, a burst vibration, or a vibration pattern. Similarly, the length or intensity of the vibration may vary based on the urgency level of the alarm.

In some embodiments, when a motion is detected, an alarm condition can be detected before generating an alarm. An alarm response from the subject can be detected based on the motion data of the user to determine whether to silence the alarm. The motion data here may include an acceleration of the ambulatory medicament device or touch inputs on touchscreen caused by the alarm response. The alarm response may be a series of taps, e.g., a single tap, a double tap, multi-tap, or a multi-location tap on a body and/or touchscreen of the ambulatory medicament device or a shaking of the ambulatory medicament device (refer to FIG. 64). However, the alarm response is not limited to the taps or shaking. The alarm response may include any other motions or levels of motion (e.g., soft tap, soft shaking, a different number of shakings, etc.) can be implemented. The alarm response may be further determined whether it is an alarm snooze response or an alarm acknowledgement response. Accordingly, when the alarm response is determined to be the alarm snooze response, the alarm may be snoozed for a specific period of time which may vary based on an urgency level of the alarm. For example, a low urgency alarm (e.g., level 1) may be snoozed for a longer predetermined period of time relative to the shorter predetermined period of time of a high or higher urgency alarm (e.g., level 2).

Referring back to FIG. 64, an alarm can be generated based on an urgency level. For instance, when an alarm condition is detected at 6402, the urgency level as described above may be determined and the alarm can be generated based on the determined urgency level 6404. In some examples, for an alarm having a higher urgency level may be generated in red color, a louder sound or a sound in a longer period of time (e.g., 1 minute), higher vibrations, etc., than an alarm having a lower urgency level which may be generated in yellow color, a softer sound, a sound in a shorter period of time (e.g., 10 seconds), softer vibrations, etc., so as to distinguish the alarms. Once the alarm has been generated based on the urgency level, the user may be required to acknowledge if the urgency or priority level is above a certain level. The period of time however can vary based on the urgency level, for example, snoozed for 1 minute for a lower urgent alarm and snoozed for 5 seconds for a higher urgent alarm, at 6412. The user is then again requested to respond to the alarm to confirm that the user is aware of the alarm. In some cases, the user may not be able to snooze the alarm if the alarm is above a certain urgency level (e.g., level 3-5 alarms).

As noted above, a user may be able to acknowledge and/or snooze alarms via a user interface. In some examples, in order to acknowledge and/or snooze alarms, the user may first need to activate the user interface (e.g., by providing a wake action) and then provide a gesture to unlock the user interface. For example, the user may use the wake button or touch input on the AMD to activate a touchscreen display and then provide a gesture on the screen to unlock display. Unlocking the display will be further described below in detail. In some examples, the touchscreen display may be configured to allow the user or subject to navigate directly to the issue or fault for which an alarm is being delivered. This capability provides the user with access to address the fault causing the alarm so that it could be corrected thereby stopping the alarm.

In some cases, a user may be able to acknowledge and/or snooze alarms via motion sensor. As described herein, the AMD may include a motion sensor that detects motion or acceleration of the AMD or on the AMD (e.g., tapping or shaking gestures). The motion sensor can include an accelerometer, gyroscope, and/or other electrical or mechanical motion sensors that convert motion or acceleration into electrical signals. In some examples, the user may tap on the AMD to acknowledge and/or snooze alarms. In some examples, the user may acknowledge and/or snooze alarms via the motion sensor without the AMD activating one or more user interface modules such as the touchscreen display. In some examples, the user may acknowledge and/or snooze alarms via the motion sensor without activating the user interface (e.g., without providing a wake action). The motion sensor may be configured to detect different tap patterns (e.g., a single tap, a double tap, etc.). Each tap pattern may be associated with a different function. In some cases, the AMD can include a user interaction sensor which may include any motion sensor(s) and/or any one of the user interface modules such as the touchscreen or the wake interface. The user interaction sensor can convert electrical or mechanical properties of the user into electrical signals. The electrical signals from the user interaction sensor can be user interaction signals. In some cases, user interaction signals can encompass both user input via a touchscreen and user interaction via a motions sensor as discussed herein.

A user may interact with the alarms generated based on the alarm condition. In some cases, the user can only interact with the alarms when the AMD and/or the user interface is unlocked. In some cases, the user can interact with the alarms to snooze them or to obtain further information, when the AMD is locked. However, the user may not be able to dismiss the alarm without unlocking the ambulatory medicament device. The user may not be able to dismiss the alarm without unlocking the ambulatory medicament device when the alarm is urgent and requires user attention. Interacting with the alarms may include providing information associated with the alarm to a user in response to the user interacting with the alarm, or an indicator representative of the alarm.

In some cases, the AMD can determine that alarm condition requires urgent user attention based on, for example, a severity level of the alarm as discussed. When the alarm condition requires urgent user attention, the AMD can prevent or not allow the alarm to be snoozed via for example taps or other user interactions as discussed herein. In some cases, in response to determining that the alarm requires urgent user attention, the AMD can deactivate or exit a power saving mode into, for example, a wake mode.

In some cases, in response to snoozing the alarm, the AMD may update the alarm condition or alarm information with snoozed status, such as updating the one or more alarm status indicators to indicate that a particular alarm has been snoozed. For example, the alarm status indicators may include or be changed to alarm status icons that indicate an alarm condition has been snoozed.

In some cases, the AMD can move or add the snoozed alarm status indicators to a list of pending alarm conditions. The list of pending alarm conditions can include indications, or the alarm status icons associated with the alarm status indicators that indicate the alarm condition has been snoozed. Adding the snoozed alarm status indicators or alarm status icons to the list of pending alarm conditions can be part of the step of no longer displaying the one or more alarm status indicators on the display in response to the alarm being snoozed. For example, the AMD may not display the list of pending alarm conditions (which can include snoozed or as well as non-snoozed alarms) on an always one screen in a power saving mode of the AMD. The list of pending alarm conditions may then be later access via user input/interaction with AMD or for example, when entering the wake mode. In some cases, an alarm that was dismissed as discussed herein may be added to the list of pending alarm conditions. The dismissed alarm may include a status indicator that indicates that the alarm was dismissed.

In some embodiments, when there is an existing alarm or alarms to be resolved, the touchscreen may not be unlocked until the active alarm is resolved. Once a user acknowledges or resolves the alarm, or the issue can be resolved automatically (e.g., when the AMD was in a freefall motion but there is no error in the medicament delivery after the freefall motion is ended), the user can awake the touchscreen by motion as described above and a home screen can be displayed on the touchscreen. Waking up and unlocking the touchscreen by motion will be described hereinafter.

Motion-Based Wake of AMD

In certain embodiments, referring back to FIG. 32, a user 3226 may wake the AMD from a sleep state or unlock the AMD by interacting with a wake interface 3220. In certain embodiments, the user 3226 may wake the AMD from another state or mode, such as for example a power saving mode or low power mode, the AMD by interacting with a wake interface 3220. When the AMD is in a sleep state or other state/mode, the touchscreen controller may not receive user input or user input signals corresponding to user input (e.g., via a touchscreen display 3222). When the AMD is in a sleep state or other state/mode, the touchscreen controller may not receive user interaction or user interaction signals corresponding to user interaction (e.g., via device sensors 3208, including an accelerometer or other motion sensors).

Waking the AMD may include activating a touchscreen interface or presenting a lock screen to a user. Further, waking the AMD may include waking the touchscreen controller such that it can receive user input or user input signals corresponding to user input. The wake interface 3220 can include one or more of the additional user interfaces mentioned above that are configured to generate and provide a wake input (or wake signal) to the CCM when detecting a pre-set user interaction. Alternatively, or in addition, the wake interface 3220 can be any type of wake interface element of the AMD that a user can interact with to wake at least a feature (e.g., a touchscreen interface) of the AMD. In some cases, the AMD may wake in response to detection of a particular movement or motion. For example, a determination that the ambulatory medicament device is being moved with a particular motion may cause the AMD to awaken or cause the AMD to awake the touchscreen interface of the AMD. In some cases, the AMD may wake in response to detection of a tapping on the AMD, such as a single tap or a double tap. In some embodiments, a single tap or a double tap may activate one or more elements of the user interface module 3218, such as for example the touchscreen display 3222. The touchscreen display can be a touch digitizer that converts analog interactions of the user (e.g., via electrical or mechanical properties of the user) into digital signals communicated to one or more controllers as discussed herein.

The tap control or other gesture control of the AMD may be context sensitive. For example, the AMD's response to gesture controls may depend on whether there are any active alarms. In some cases, when there are no active alarms, a single and/or double can turn on or off (toggle) the touch screen. As another example, in the locked state with an always on screen, a single and/or double can turn on or off (toggle) the backlight.

The context sensitive response of the AMD to user inputs can also be time dependent. For example, when a user snoozes or acknowledges an alarm as discussed herein, if a certain amount of time since snoozing or acknowledging is less than a predetermined context time threshold, the AMD may respond to gesture user inputs (e.g., taps) as discussed herein as if there are no active alarms (even though an alarm may have been recently snoozed and/or acknowledged), such as for example toggling the touchscreen and/or backlight. After more time than the predetermined context time threshold has passed, the AMD may respond to gesture user inputs (e.g., taps) to change and/or display alarm conditions as discussed herein.

When in the wake and/or unlocked state, a user may interact with the touchscreen display 3222, alphanumeric pad, or other types of user interfaces that may be included in the user interface module 3218. The user interface module 3218 may include any combination of one or more of the touchscreen display 3222, alphanumeric pad, or other types of user interfaces.

In some examples, a device sensor 3208 may be a sensor that generates a signal or status value associated with the condition of modules, interfaces, accessories, disposables of the AMD. In some examples, a device sensor 3208 may generate a signal that corresponds to a parameter associated with a component in a module or interface. For example, one device sensor may record the voltage of a battery and another device sensor may record the follow rate of a pump the medicament delivery interface 3214.

In some examples, the alarm system 3202 may implement procedures for allowing the user or subject to change the alarm settings and/or acknowledge an alarm annunciation via the user interface module 3218. In some examples, the user may be able to see one or more alarms annunciated on a user interface (e.g., as a list of alarms), even when the AMD is in a locked state. In these examples, the user may not be able to acknowledge or respond to alarms when the AMD is in the locked state.

In certain embodiments, the user or subject may access an alarm setting screen or acknowledge an alarm annunciation by providing a wake action or a wake action followed by a first gesture via, for example, the touchscreen display 3222. In some cases, the first gesture may be created by shaking the AMD, inputting a swipe gesture on the touchscreen, pinching the AMD, or tapping one or more times on a specific location of the AMD (e.g., a single tap, a double tap, multi-tap, a multi-location tap, sequentially or non-sequentially, on an upper left corner, a lower right corner, or the like of the AMD or the pump). In some cases, touching three corners of the AMD can power on or off the AMD.

In some examples, user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMD. In some embodiments, the visual indication can include animations that suggest or guide user interactions with a touchscreen. For example, the first user interaction can include an arcuate swipe around at least a portion of a generally circular icon or logo. In some examples, the first and/or second user interactions may include a predetermined sequence of numerical and/or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

In some embodiments, a user may be asked to enter a passcode or password to unlock the touchscreen, or, after the touchscreen display has been activated by the wake signal, a passcode may be required to unlock the touchscreen display. The user may enter a security code into the AMD or an intermediary device that the AMD and/or the intermediary device may validate or verify matches the passcode to access certain functions of the AMD. In some examples, the passcode or password can be entered in the form of motion, such as a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. Alternatively, a keypad may be used to enter a passcode for unlocking a user interface.

Figure 65:
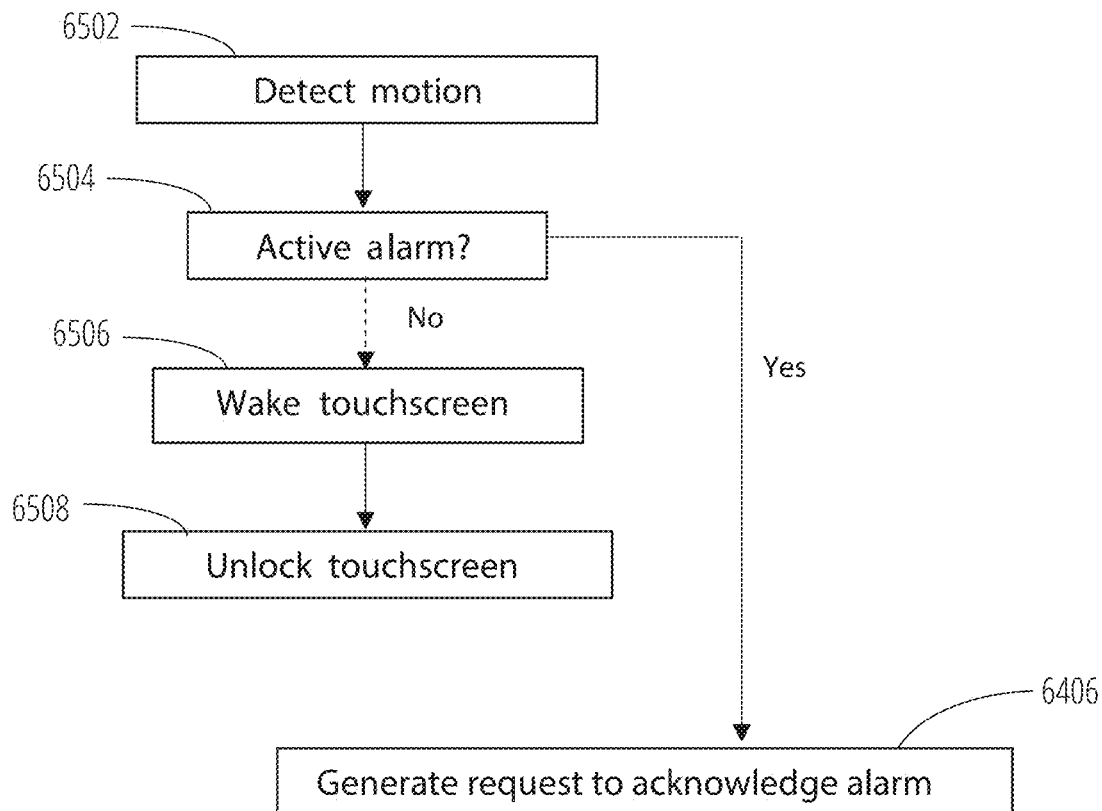
FIG. 65 is a flow diagram illustrating an example procedure to unlock a touchscreen of an ambulatory medical device by motion.

Referring to process 6500 of FIG. 65, when the AMD or a touchscreen of the ambulatory medical device is in a locked state or sleep state, a user can wake up the touchscreen by motion in various forms. When a motion of a user or a motion (e.g., tap on the AMD or movement of the AMD) of the ambulatory medical device is detected at 6502, the ambulatory medical device checks determines whether there is an active alarm to be resolved at 6504. When there is no pending alarm, the touchscreen may become active at 6506. In some cases, where the touchscreen display is off in the locked or sleep state, the AMD may turn on the touchscreen at step 6506. Depending on the gesture or other context sensitive criteria of the AMD operation such as whether it is nighttime, the AMD may turn on the backlight as part of step 6506. The AMD may also unlock the touchscreen 6508 and enter into an active mode in response to the motion detected 6502, depending on for example the type of motion detected, and for example display a home screen. For example, a single tap can turn on step 6506 the touch screen. A double tap can turn on 6506 the touchscreen and unlock the touchscreen 6508. In some cases, where the touchscreen is displaying an always on interface in the locked or sleep state, the AMD may wake 6506 and unlock the touchscreen 6508.

In some cases, if there is an active alarm, a user may be requested to acknowledge the alarm (step 6406 of FIG. 64) or perform an action to resolve the alarm as discussed herein. In some cases, the AMD may display a list of pending alarm conditions as discussed herein. As part of step 6406, the AMD may wake and/or unlock the touchscreen as discussed herein for steps 6506 and/or 6508.

In various embodiments, the AMD can receive a touch input directly from a user via a user interface configured as a touchscreen. The touch input can be made in various ways, for example, a user can tap on the touchscreen, a single tap, a double tap, multi-tap, a multi-location tap, a pinch gesture, or a swipe gesture, or can touch with one or more touches on one or more corners of the touchscreen. The user can touch the touchscreen in the form of any of the above-described touch input or any other touch input to unlock touchscreen. For instance, a computing processor of the AMD may be configured for locking the device, and when a touch input is detected on any portion of the touchscreen, the processor may wake the touchscreen by displaying a home screen. The touch input could be a gesture password for unlocking the touchscreen. The computing processor may include a motion sensor detecting touch gestures performed at any location on the touchscreen. The computing processor may add a distinct input value associated with each identified touch gesture to an input buffer to form a series of input values. The series of input values in the input buffer may then be compared to a series of values corresponding to a predetermined touch gesture passcode sequence. The touchscreen may be unlocked when the series of input values in the input buffer matches the series of values corresponding to the predetermined touch gesture passcode sequence. When the touchscreen does not receive any input for a certain period of time, the touchscreen may enter a locked state until the user attempts a touch input to the touchscreen. In various embodiments, at ouch input may include one or more touches on one or more locations on the AMD (e.g., front, sides, or rear of the AMD).

In certain embodiments, if an incorrect gesture password has been recognized a set number of times, the touchscreen may be locked for a certain period of time or a secondary identification may be required, e.g., an identification code may be sent to a user's phone or via email for security.

When there is no alarm pending, the touchscreen can be unlocked with or without the gesture password check and a home screen may be displayed on the screen. In addition, when the user attempts to unlock the touchscreen, the touchscreen may display a touch user interface element for user to touch.

Figure 66:
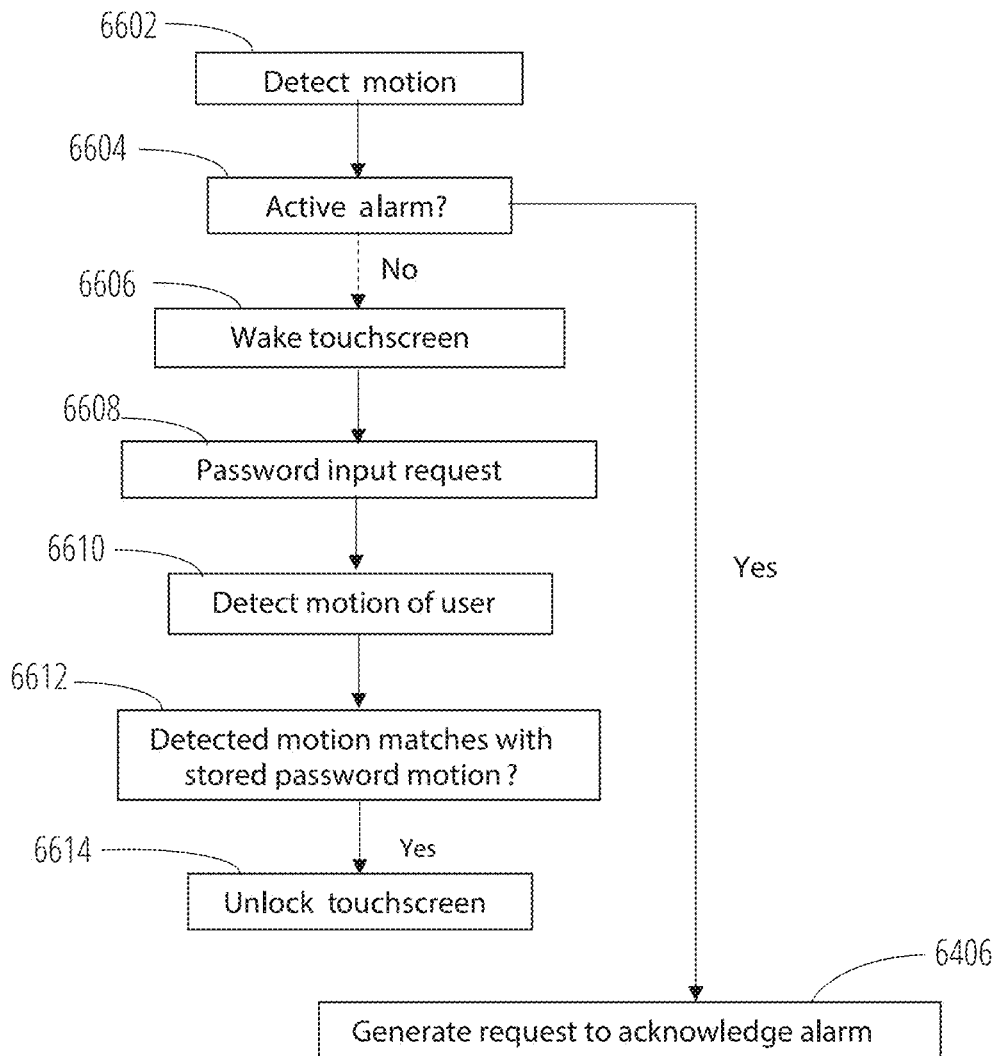
FIG. 66 is a flow diagram illustrating an example procedure to enter a gesture password to unlock a touchscreen of an ambulatory medical device by motion.

For example, referring to the process 6600 of FIG. 66, when a motion is detected (step 6602) while the AMD is in a sleep mode as described above in reference to FIG. 65, the touchscreen can become active upon determining there is no pending alarm at steps 6604, 6606. As part of step 6606, the AMD may perform actions and functions discussed herein in reference to steps 6506 and 6508 discussing FIG. 65.

In some cases, if there is an active alarm, the process may go back to step 6406 of FIG. 64 to request a user to acknowledge the alarm or perform an action to resolve the alarm as discussed herein. In some cases, the AMD may display a list of pending alarm conditions as discussed herein. As part of step 6406, the AMD may wake and/or unlock the touchscreen as discussed herein for steps 6506 and/or 6508 in reference FIG. 65.

In some cases, a password input to unlock the touchscreen may be requested at step 6608 after waking the touchscreen in step 6606. A user can enter a predetermined password in various ways, including user gesture control inputs such as tapping, shaking, etc., as described above, to unlock the touchscreen based on user motion at step 6610. If the motion of the user, as a gesture password input, matches at step 6612 with a stored password that is prestored and authorized, the screen may be unlocked at step 6614. If an incorrect gesture password has been entered, the touchscreen may become locked or return to the sleep or locked state. In some cases, if an incorrect gesture password has been entered more than a set number of times may become locked for a redetermined period of time. In some cases, a further verification may be required to unlock the touchscreen and/or AMD in order to access the AMD. Examples of password generation are disclosed in U.S. Pat. No. 11,103,638, the entire contents of which are incorporated by reference herein and made a part of this specification.

In some examples, a user may be able to acknowledge and/or snooze an alarm via a user interface. In some examples, in order to acknowledge and/or snooze alarms, the user may first need to activate the user interface (e.g., by providing a wake action) and then provide a gesture to unlock the user interface. For example, the user may shake the AMD or pick up the AMD to activate a touchscreen display and then provide a gesture on the screen to unlock the display. In some embodiments, the touchscreen display may be configured to allow the user or subject to navigate directly to the issue, fault, or alarm condition for which an alarm is being delivered. This capability provides the user with more direct access to quickly address the fault causing the alarm so that it may be addressed, thereby increasing the convenience of the user, and simplifying the process whereby the user addresses the cause of the alarm.

In some embodiments, the ambulatory medicament device may receive the touch input via the touchscreen as noted above and determine whether an alarm is active upon receiving the touch input. If it is determined that there is no alarm, the touchscreen may be unlocked to receive the user's touch input command. Here, the touch input can include various forms the user input, e.g., a single tap, a double tap, multi-tap, a multi-location tap, a pinch gesture, a swipe gesture, or the like. In addition, the touch input can be performed on any portion of the touchscreen including one or more corners of the touchscreen. The location of the touch input may be recognized as a different user command, e.g., when an upper right corner is touched, the input may be interpreted as an attempt to, e.g., increase the volume or brightness of the screen. The touch input can further include one or more touches at different locations of the touchscreen. Based on the touch input detected, the touchscreen and the ambulatory medicament device can be unlocked.

Motion-Based Control of Medicament Delivery

In certain embodiments, a user motion input may be used for release of delivery of a bolus medicament dose or other medicament or therapy delivery. As noted above, the motion input can be any form of gesture made to one or more locations on the ambulatory medicament device (e.g., a single tap, a double tap, a triple tap, a multi tap, a multi-location tap, a pinch gesture, or a swipe gesture). The motion can be detected by various sensors such as an accelerometer as described above, a capacitive touch sensor, a resistive touch sensor, an infrared and surface acoustic wave (SAW) touch sensor, etc. as previously described in detail regarding the motion detection.

When a specific motion of a user has been recognized, the user may be asked to confirm the delivery of the medicament dose by requesting a secondary input. The request may be made on the touchscreen or through a speaker, a haptic motor generating a vibration, or any other form that can alert the user. In some embodiments, a blood sugar level of the subject may be continuously monitored in real time to determine whether there is a need for the bolus medicament dose based on the blood sugar level. When the need for the bolus medicament dose is confirmed, the touchscreen may display a menu option for the user to enter a touch input to initiate the medicament bolus dose. Accordingly, it is possible to promptly adjust therapy as desired to secure a sufficient supply of medicament to the subject. In addition, the medicament therapy regimen can be managed quickly without any delay in delivery of an appropriate amount of medicament, for example, by adjusting food intake dose or bolus based on the need.

Figure 67:
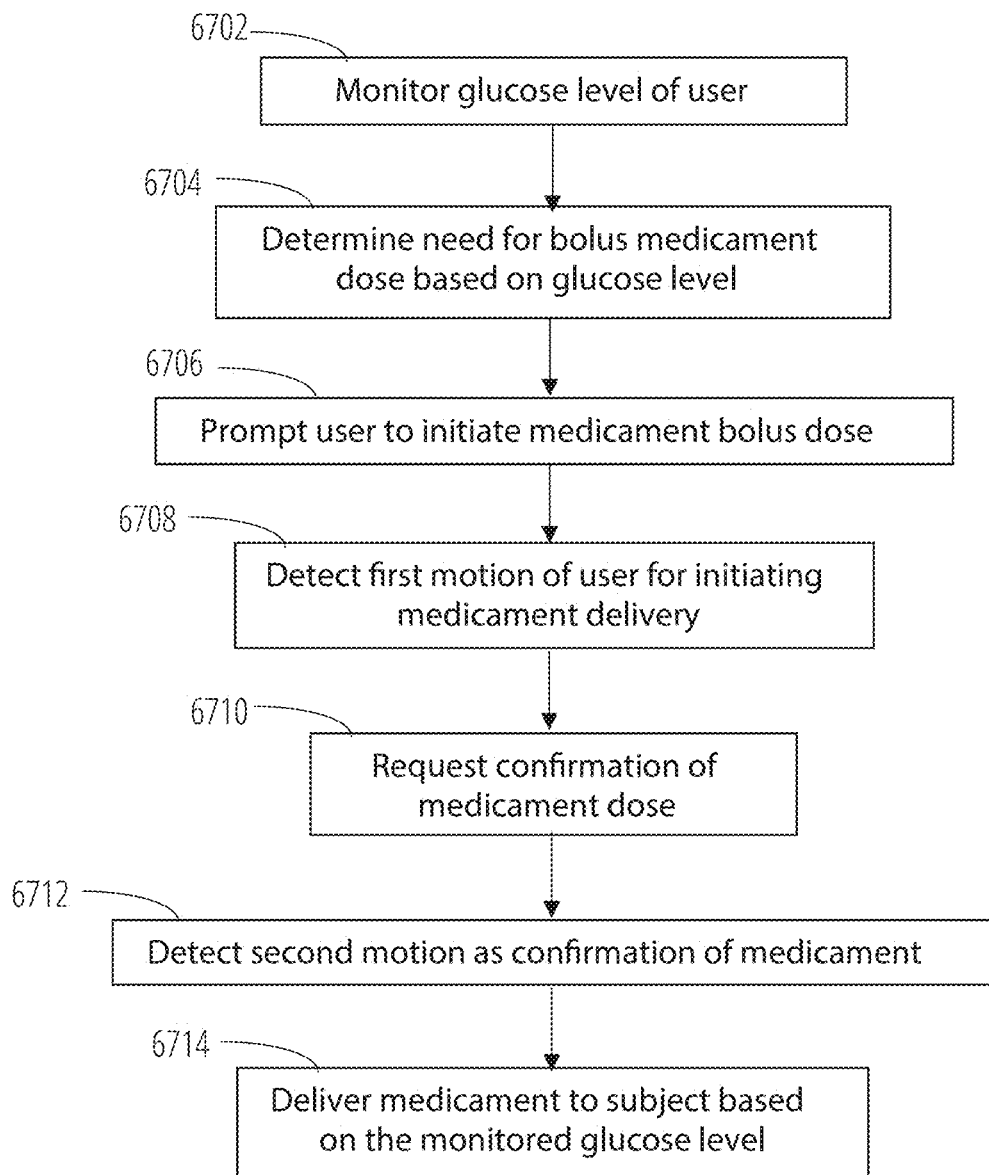
FIG. 67 is a flow diagram illustrating an example procedure to deliver medicament to a subject by motion control.

FIG. 67 is a flow diagram illustrating an example process 6700 to deliver medicament to a subject by motion control. That is, FIG. 67 illustrates alerting a user of medicament delivery need or when change in the medicament delivery is demanded. For instance, the AMD may monitor a glucose level of a user at 6702 in real time. In some examples, the AMD may include a subject sensor 3216 (refer to FIG. 32) that generates a signal or status value associated with one or more physiological indicators (or parameters) of a subject (e.g., heart rate, blood pressure, body temperature, level of blood glucose, serum levels of various hormones or other analytes).

In some such examples, the subject sensor can be a continuous glucose monitoring sensor (CGS). The device and subject monitoring system interface 3210 may continuously receive and analyze signals from device sensors 3208 and subject sensor 3216 to determine the condition of the AMD, the subject, a sensor, and/or other accessories. In some examples, a subject sensor 3216 may be any sensor that generates a signal or status value associated with one or more physiological indicators (or parameters) of a subject (e.g., heart rate, blood pressure, body temperature, level of blood glucose, serum levels of various hormones or other analytes). In some such examples, the subject sensor can be a continuous glucose monitoring sensor (CGS). The device and subject monitoring system interface 3210 may continuously receive and analyze signals from device sensors 3208 and subject sensors 3216 to determine the condition of the AMD, the subject, a sensor, and/or other accessories.

Upon determining that there is a need for a bolus medicament dose or change in bolus medicament dose is desired at step 6704 based on glucose levels of the user or other parameters of the glucose control therapy, the user may be prompted to initiate the medicament dose delivery at step 6706. The user can acknowledge or initiate the medicament dose by providing a specific motion at step 6708 as the user gesture control motion. The motion can include various predetermined motions described herein that correspond to a user gesture control motion for the AMD in the context of bolus delivery. In some cases, when the user motion of medicament delivery initiation has been detected, an additional user input request may be prompted for confirming the medicament delivery at step 6710.

At step 6712, the user may input a second or another motion as user gesture control motion to confirm that the medicament should be delivered. The confirmation of the medicament delivery can be done by the user inputting a specified motion (tap, touch, swiping, etc.). In addition, the tap motion may be a series of taps, e.g., a single tap, a double tap, multi-tap, or a multi-location tap on a body and/or touchscreen of the ambulatory medicament device or a shaking of the ambulatory medicament device.

The confirmation motion input of the user at 6712 may the same as the user gesture control motion input at 6708. In some case, the confirmation motion input of the user at 6710 may be different from the as the user gesture control motion input at 6708. Once the confirmation motion is received at step 6712, the AMD may release the medicament delivery to the subject (e.g., user) at step 6714 based on glucose levels of the user or other parameters of the glucose control therapy.

The user input request discussed herein, including in reference to FIG. 67 for steps 6708 and 6712 may be prompted or requested in various ways. For example, the AMD may include a speaker configured to generate audio prompts. In this case, when a motion or touch input has been detected at step 6708, a sound may be generated via the speaker to alert the user. The sound may be a beep, music, or any other audible signals to alert the user. Such that, a person having a vision problem may be aware of the request to enter an input. However, it is not limited thereto such that the AMD may include a touchscreen controller configured to output display signals configured to generate user interface screens on a touchscreen and to receive user input signals corresponding to user interaction with the touchscreen. In this case, a visual signal may be prompted the user to confirm the medicament dose. The AMD may include a haptic motor configured to generate vibration signals on a body of the subject. In this case, in response to detecting the touch input or motion at step 6708, a vibration signal may be generated to prompt 6710 the subject to confirm the medicament dose at step 6712. When any one of the described requests has been prompted (e.g., sound, vibration, visual, etc.), the user can confirm the medicament dose by providing a touch input or gesture motion as specified at step 6712.

The process 6700 can be applied for various situations, e.g., when a need to initiate the medicament delivery is detected as described above (e.g., high blood glucose level or bolus based on food intake). In some cases, the process 6700 can be used with administration of other medicament such as glucagon, where AMD determines glucagon delivery is desired and prompts the user to initiate and/or confirm delivery of glucagon. In addition, the process 6700 can be applied to a situation when a sudden change in the medicament dose is detected or a change in medicament dose setting is desired. The user can simply accept the change or initiate the medicament dose delivery by providing a specific motion as discussed herein.

In some examples, ambulatory medical devices allow subjects the freedom to treat themselves with an automated blood glucose control system. The automated blood glucose control system may automatically provide insulin and/or a counter-regulatory agent (e.g., glucagon) to a subject to help control the blood glucose level of the subject. Generally, a control algorithm is implemented by an automated blood glucose control system (BGCS) to determine when to deliver one or more glucose control agents and how much agent to provide to the subject. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a sensor, such as a continuous glucose monitoring (CGM) sensor, that obtained automated blood glucose measurements from the subject.

In some cases, the automated blood glucose control system may receive an indication of insulin or medicament to administer to a subject in place of an automatically calculated dose of insulin. For example, the automated blood glucose control system may receive an indication that a subject is consuming or will consume a meal. The indication may include a type of meal to be consumed (e.g., breakfast, lunch, or dinner) and an estimate of the quantity of food or carbohydrates to be consumed (e.g., less than usual, a usual amount, more than usual, 30-40 grams of carbohydrates, 45-60 grams of carbohydrates, etc.). Based on the indication, or meal announcement, the automated blood glucose control system may calculate an amount of insulin to administer to the subject. The calculation may be based on an insulin to carbohydrate ratio provided by a clinician and/or determined by the automated blood glucose control system.

Insulin may be administered subcutaneously into blood of a subject. However, there is often a delay between when the insulin is provided and when the amount of insulin in the subject's blood plasma reaches maximum concentration. This amount of time may vary based on the type of insulin and on the physiology of the particular subject. In addition, when there is an unexpected change in medicament dose has been determined, the user or subject may not be aware of such a case if not looking at the AMD.

In some cases, a subject may receive a manual bolus of insulin or medicament. For example, a user (e.g., healthcare provider, parent, or guardian) or subject may inject a dose of insulin into the subject. As another example, the user or subject may manually direct the automated blood glucose control system to provide a bolus of insulin to the subject.

Accordingly, in some embodiments, the motion activated AMD can make a quick change in medicament delivery. For instance, the process 6700 enables therapy changes efficiently and promptly by a specified gesture motion allowing communication between the user and the AMD. By this, it is possible to reduce several steps, e.g., selecting a menu option on the touchscreen and selecting a submenu option, etc. That is, the one-time motion or touch input can enable to perform various functions of the AMD (e.g., delivery of medicament, change of medicament dose, acknowledging the alarm, etc.). In addition, the user can be informed with a medicament dose change based on real time measurement and make such a change by a simple motion or touch.

In some cases, the indication of an amount of a manual bolus may be received by a user entering a numerical value (e.g., an amount of insulin, a number of carbohydrates, or another calculation) associated with administering insulin, which may be considered a specified gesture interaction required for entry of the manual bolus of medicament. In some cases, a specified gesture interaction required for entry of the manual bolus of medicament may be a sliding action or other movement on a touchscreen to confirm or initiate desired functions as discussed herein. As described above, the automated blood glucose control system may automatically-calculate a meal dose of insulin and present it to a user via a user interface where a user may enter the manual bolus information.

As described herein, the announcement can be made by generating a sound or vibration without the user having to manipulate the AMD to find out. The user can initiate the medicament delivery by a touch input and accept any modification in the medicament dose by a touch input as well. The touch input is not limited such that the user can make a single tap, double taps, or triple taps on the touch screen or on any portion of the AMD. For example, one touch may indicate initiating the medicament delivery, double tap may indicate confirmation of the delivery, and triple tap may indicate verification of change in medicament dose determined based on detected blood sugar level. Thus, the motion-enabled medicament delivery efficiently and quickly change the medicament delivery to the user in a simplified way.

EXAMPLE EMBODIMENTS

Further embodiments of glucose level control systems that can be combined with the features disclosed herein can be found in: U.S. Pat. App. No. 63/169,112 filed on Mar. 31, 2021; PCT. Pub. No. WO 2021/067856 filed on Oct. 2, 2020; U.S. Pat. Pub. No. 2021/0213200 filed on Mar. 25, 2021; and PCT Pub. No. WO 2021/067767 filed on Oct. 2, 2020, which are all hereby incorporated by reference in their entireties herein for all purposes.

Some additional nonlimiting examples of embodiments discussed above are provided below. These should not be read as limiting the breadth of the disclosure in any way.

In a 1st example, an ambulatory medicament pump configured to maintain delivery of therapy to a subject after determining that a possible occlusion exists in a medicament delivery system, the ambulatory medicament pump comprising: a medicament reservoir configured to store medicament to be delivered as therapy to the subject; a medicament delivery interface configured to couple to a medicament passageway connecting the medicament reservoir to a subcutaneous depot of the subject through the skin of the subject when the ambulatory medicament pump is operatively connected to the subject; a pump motor configured to deliver the medicament from the medicament reservoir through the medicament delivery interface; a non-transitory memory configured to store specific computer-executable instructions; and a hardware processor in communication with the non-transitory memory and configured to execute the specific computer-executable instructions to at least: detect a fluid delivery parameter associated with the medicament delivery system; determine that the fluid delivery parameter satisfies an initial occlusion condition, wherein the initial occlusion condition indicates that a possible occlusion exists that interferes with delivery via the medicament delivery system; in response to the determination that the fluid delivery parameter satisfies the initial occlusion condition, maintain delivery of therapy to the subject; receive a verification parameter associated with the possible occlusion; determine that the verification parameter satisfies a final occlusion condition, wherein the final occlusion condition indicates that a probable occlusion exists in the medicament delivery system; and in response to the determination that the verification parameter satisfies the final occlusion condition, modify delivery of therapy to the subject.

In a 2nd example, the ambulatory medicament pump of example 1, wherein the hardware processor is further configured to execute the specific computer-executable instructions to at least: generate a user alert based at least in part on the determination that the fluid delivery parameter satisfies the initial occlusion condition.

In a 3rd example, the ambulatory medicament pump of any of examples 1-2, wherein the hardware processor is further configured to execute the specific computer-executable instructions to at least: generate a user alert based at least in part on the determination that the verification parameter satisfies the final occlusion condition.

In a 4th example, the ambulatory medicament pump of any of examples 1-3, wherein the medicament passageway comprises a delivery tube operatively coupled between the medicament reservoir and an infusion site configured to deliver the medicament through the skin of the subject.

In a 5th example, the ambulatory medicament pump of any of examples 1-4, wherein the fluid delivery parameter comprises a current supplied to the pump motor.

In a 6th example, the ambulatory medicament pump of any of examples 1-5, wherein modifying delivery of therapy to the subject comprises stopping delivery of therapy.

In a 7th example, the ambulatory medicament pump of any of examples 1-6, wherein the verification parameter comprises a glucose level signal received from a sensor configured to detect a glucose level of the subject.

In an 8th example, the ambulatory medicament pump of example 7, wherein the final occlusion condition comprises a glucose level indicating a threshold value of at least 150 mg/dL of blood glucose concentration.

In a 9th example, the ambulatory medicament pump of any of examples 1-8, wherein the hardware processor is further configured to execute the specific computer-executable instructions to at least: in response to the determination that the fluid delivery parameter satisfies the initial occlusion condition, pause delivery of therapy for at least 3 seconds.

In a 10th example, the ambulatory medicament pump of any of examples 1-9, wherein the hardware processor is further configured to execute the specific computer-executable instructions to at least: in response to the determination that the verification parameter satisfies the final occlusion condition, increase delivery of therapy to the subject after a passage of an amount of time.

In a 11th example, the ambulatory medicament pump of any of examples 1-10, wherein the hardware processor is further configured to execute the specific computer-executable instructions to at least: in response to the determination that the fluid delivery parameter satisfies the initial occlusion condition, modify an attribute of the delivery of therapy while maintaining delivery of the therapy to the subject.

In a 12th example, the ambulatory medicament pump of any of examples 1-11, wherein the hardware processor is further configured to execute the specific computer-executable instructions to at least: determine that the fluid delivery parameter satisfies an intermediate occlusion condition, wherein the intermediate occlusion condition indicates that the possible occlusion persists; and in response to the determination that the fluid delivery parameter satisfies the intermediate occlusion condition, modify an attribute of the delivery of therapy.

In a 13th example, the ambulatory medicament pump of any of examples 1-12, wherein attribute of the delivery of therapy comprises one or more of a rate of delivery or a size of a bolus of therapy.

In a 14th example, an occlusion detection system comprising: a non-transitory memory configured to store specific computer-executable instructions; and a hardware processor in communication with the non-transitory memory and configured to execute the specific computer-executable instructions to at least: receive a fluid delivery parameter associated with a medicament delivery system; determine that the fluid delivery parameter satisfies an initial occlusion condition, wherein the initial occlusion condition indicates that a possible occlusion exists in the medicament delivery system; in response to the determination that the fluid delivery parameter satisfies the initial occlusion condition, send an instruction to the medicament delivery system to maintain delivery of therapy to a subject; receive a verification parameter associated with the possible occlusion; determine that the verification parameter satisfies a final occlusion condition, wherein the final occlusion condition indicates that a probable occlusion exists in the medicament delivery system; and in response to the determination that the verification parameter satisfies the final occlusion condition, send an instruction to the medicament delivery system to modify delivery of therapy to the subject.

In a 15th example, the occlusion detection system of example 14, wherein the hardware processor is further configured to execute the specific computer-executable instructions to at least: generate a user alert based at least in part on the determination that the fluid delivery parameter satisfies the initial occlusion condition.

In a 16th example, the occlusion detection system of any of examples 14-15, wherein the hardware processor is further configured to execute the specific computer-executable instructions to at least: generate a user alert based at least in part on the determination that the verification parameter satisfies the final occlusion condition.

In a 17th example, the occlusion detection system of any of examples 14-16, wherein the fluid delivery parameter comprises a current supplied to a pump motor in communication with the occlusion detection system.

In a 18th example, the occlusion detection system of any of examples 14-17, wherein the fluid delivery parameter comprises a pressure obtained by a pressure sensor in communication with the occlusion detection system.

In a 19th example, the occlusion detection system of any of examples 14-18, wherein sending an instruction to the medicament delivery system to modify delivery of therapy to the subject comprises sending an instruction to the medicament delivery system to halt delivery of therapy.

In a 20th example, the occlusion detection system of any of examples 14-19, wherein the verification parameter comprises a glucose level signal received from a sensor configured to detect a glucose level of the subject.

In a 21st example, the occlusion detection system of example 20, wherein the final occlusion condition comprises a glucose level indicating a threshold value of at least 150 mg/dL of blood glucose concentration.

In a 22nd example, the occlusion detection system of any of examples 14-21, wherein the hardware processor is further configured to execute the specific computer-executable instructions to at least: in response to the determination that the fluid delivery parameter satisfies the initial occlusion condition, send an instruction to pause delivery of therapy for at least 3 seconds.

In a 23rd example, the occlusion detection system of any of examples 14-22, wherein the hardware processor is further configured to execute the specific computer-executable instructions to at least: in response to the determination that the verification parameter satisfies the final occlusion condition, send an instruction to increase delivery of therapy to the subject after a passage of an amount of time.

In a 24th example, an ambulatory medicament device configured to maintain indications of alarm conditions on a list of pending alarm conditions without auditory or haptic annunciation of at least some of the alarm conditions while a do not disturb mode is active, the ambulatory medicament device comprising: a monitoring system interface configured to receive status information, wherein the status information comprises at least one of device information pertaining to a condition of the ambulatory medicament device or subject information pertaining to a condition of a subject; a memory configured to store specific computer-executable instructions and the list of pending alarm conditions; and a hardware processor in communication with the memory and configured to execute the specific computer-executable instructions to at least: receive alarm muting instructions via user interaction with an alarm muting control interface; in response to determining that alarm annunciation should be muted in accordance with the alarm muting instructions, activate the do not disturb mode of the ambulatory medicament device, wherein at least some alarm annunciation patterns are not aurally or haptically annunciated while the ambulatory medicament device is in the do not disturb mode; detect, via the monitoring system interface, that the status information or the subject information indicates at least one of a first alarm condition, a second alarm condition, or a third alarm condition; determine that the first alarm condition requires urgent user attention; in response to determining that the first alarm condition requires urgent user attention, annunciate the first alarm condition, without deactivating the do not disturb mode, using a first alarm condition annunciation pattern comprising at least one of auditory or haptic annunciation; maintain an indication of the first alarm condition on the list of pending alarm conditions until the first alarm condition is resolved; determine that the second alarm condition does not require urgent user attention; in response to determining that the second alarm condition does not require urgent user attention, maintain an indication of the second alarm condition on the list of pending alarm conditions until the second alarm condition is resolved without auditory or haptic annunciation of the second alarm condition while the do not disturb mode is active; determine that the third alarm condition does not require urgent user attention and that the third alarm condition has lower priority than the second alarm condition; and upon deactivation of the do not disturb mode, annunciate the second alarm condition without auditory or haptic annunciation of the third alarm condition.

In a 25th example, the ambulatory medicament device of example 24, wherein the hardware processor is configured to execute further computer-executable instructions to, in response to determining that the first alarm condition requires urgent user attention, deactivate the do not disturb mode.

In a 26th example, the ambulatory medicament device of any of examples 24-25, wherein determining that the first alarm condition requires urgent user attention comprises: determining a severity level of the first alarm condition; and determining that the severity level of the first alarm condition exceeds a threshold severity level.

In a 27th example, the ambulatory medicament device of any of examples 24-26, wherein the alarm muting control interface comprises a touchscreen controller configured to output display signals configured to generate user interface screens on a touchscreen and to receive user input signals corresponding to user interaction with the touchscreen.

In a 28th example, the ambulatory medicament device of any of examples 24-27, wherein the alarm muting instructions comprise a recurring time interval, wherein the hardware processor is configured to execute further computer-executable instructions to activate the do not disturb mode during the recurring time interval.

In a 29th example, the ambulatory medicament device of example 28, wherein the recurring time interval comprises a time interval occurring every day between 18:00 and 07:00.

In a 30th example, the ambulatory medicament device of any of examples 24-29, wherein the alarm muting control interface is part of a remote device that is separate from the ambulatory medicament device.

In a 31st example, the ambulatory medicament device of any of examples 24-30, wherein the list of pending alarm conditions is sorted according to severity levels of alarm conditions included on the list of pending alarm conditions.

In a 32nd example, the ambulatory medicament device of any of examples 24-31, wherein the list of pending alarm conditions is displayed on a user interface of the ambulatory medicament device.

In a 33rd example, the ambulatory medicament device of example 32, wherein the list of pending alarm conditions comprises alarm status indicators, wherein the alarm status indicators indicate whether pending alarm conditions in the list of pending alarm conditions were annunciated or muted.

In a 34th example, the ambulatory medicament device of any of examples 24-33, wherein the alarm muting instructions comprise a time period during which the do not disturb mode is to remain active, wherein the hardware processor is configured to execute further computer-executable instructions to deactivate the do not disturb mode after the time period has passed.

In a 35th example, the ambulatory medicament device of example 34, wherein the hardware processor is configured to execute further computer-executable instructions to: receive via user interaction with the alarm muting control interface, prior to termination of the time period, instructions to deactivate the do not disturb mode; and deactivate the do not disturb mode.

In a 36th example, the ambulatory medicament device of any of examples 24-35, wherein the hardware processor is configured to execute further computer-executable instructions to: determine the second alarm condition has not been resolved for a threshold amount of time; escalate the second alarm condition such that the second alarm condition requires urgent user attention; and in response to determining that the second alarm condition requires urgent user attention, annunciate the second alarm condition using a second alarm condition annunciation pattern comprising at least one of auditory or haptic annunciation.

In a 37th example, the ambulatory medicament device of any of examples 24-36 wherein resolving alarm conditions comprises at least one of: correcting the alarm conditions, acknowledging the alarm conditions, or snoozing the alarm conditions.

In a 38th example, the ambulatory medicament device of example 37, wherein correcting the alarm conditions comprises one or more actions taken by a user that address a condition which caused an alarm to be generated.

In a 39th example, the ambulatory medicament device of any of examples 24-38, wherein the first alarm condition is resolved automatically when the status information or the subject information no longer indicates the first alarm condition.

In a 40th example, the ambulatory medicament device of any of examples 24-39, wherein the hardware processor is configured to execute further computer-executable instructions to maintain an indication of the third alarm condition on the list of pending alarm conditions until the third alarm condition is resolved without auditory or haptic annunciation of the third alarm condition.

In a 41st example, a glucose control system comprising: a monitoring system interface configured to receive status information, wherein the status information comprises at least one of device information pertaining to a condition of the glucose control system or subject information pertaining to a condition of a subject; a memory configured to store specific computer-executable instructions and a list of pending alarm conditions; and a hardware processor in communication with the memory and configured to execute the specific computer-executable instructions to at least: receive alarm muting instructions via user interaction with an alarm muting control interface; in response to determining that alarm annunciation should be muted in accordance with the alarm muting instructions, activate a do not disturb mode of the glucose control system, wherein at least some alarm annunciation patterns are muted while the glucose control system is in the do not disturb mode; detect, via the monitoring system interface, that the status information or the subject information indicates an alarm condition; determine that the alarm condition does not require urgent user attention; and in response to determining that the alarm condition does not require urgent user attention, maintain an indication of the alarm condition on the list of pending alarm conditions until the alarm condition is resolved without auditory or haptic annunciation of the alarm condition while the do not disturb mode is active.

In a 42nd example, the glucose control system of example 41, wherein the list of pending alarm conditions is sorted according to severity levels of alarm conditions included on the list of pending alarm conditions.

In a 43rd example, the glucose control system of example 42, wherein the hardware processor is configured to execute further computer-executable instructions to, upon deactivation of the do not disturb mode, annunciate a most severe alarm condition, based on the severity levels of the alarm conditions included on the list of pending alarm conditions.

In a 44th example, the glucose control system of any of examples 41-43, wherein the hardware processor is configured to execute further computer-executable instructions to: detect, via the monitoring system interface, a second alarm condition; determine that the second alarm condition requires urgent user attention; and in response to determining that the second alarm condition requires urgent user attention, deactivate the do not disturb mode.

In a 45th example, the glucose control system of any of examples 41-44, wherein the hardware processor is configured to execute further computer-executable instructions to: detect, via the monitoring system interface, a second alarm condition; determine that the second alarm condition requires urgent user attention; and in response to determining that the second alarm condition requires urgent user attention, annunciate the second alarm condition without deactivating the do not disturb mode, using a second alarm condition annunciation pattern comprising at least one of auditory or haptic annunciation.

In a 46th example, the glucose control system of any of examples 41-45, wherein the list of pending alarm conditions comprises alarm status indicators, wherein the alarm status indicators indicate whether pending alarm conditions in the list of pending alarm conditions were annunciated or muted.

In a 47th example, the glucose control system of any of examples 41-46, wherein the alarm muting control interface comprises a touchscreen controller configured to output display signals configured to generate user interface screens on a touchscreen and to receive user input signals corresponding to user interaction with the touchscreen.

In a 48th example, a method of annunciating alarms associated with a glucose control system, the method comprising: receiving alarm muting instructions via user interaction with an alarm muting control interface; in response to determining that alarm annunciation should be muted in accordance with the alarm muting instructions, activating a do not disturb mode of the glucose control system, wherein at least some alarm annunciation patterns are muted while the glucose control system is in the do not disturb mode; detecting that an alarm condition exists; determining that the alarm condition does not require urgent user attention; and in response to determining that the alarm condition does not require urgent user attention, maintain an indication of the alarm condition on a list of pending alarm conditions until the alarm condition is resolved without auditory or haptic annunciation of the alarm condition while the do not disturb mode is active.

In a 49th example, the method of example 48, wherein detecting that an alarm condition exists comprises detecting that at least one of device information pertaining to a condition of the glucose control system or subject information pertaining to a condition of a subject indicates an alarm condition.

In a 50th example, the method of any of examples 48-49, wherein receiving the alarm muting instructions comprises receiving, via user interaction with the alarm muting control interface, a time period during which the do not disturb mode is to remain active.

In a 51st example, the method of example 50, further comprising: receiving, via user interaction with the alarm muting control interface, prior to termination of the time period, instructions to deactivate the do not disturb mode; and deactivating the do not disturb mode.

In a 52nd example, the method of any of examples 48-51, further comprising: detecting a second alarm condition; determining that the second alarm condition requires urgent user attention; and in response to determining that the second alarm condition requires urgent user attention, deactivating the do not disturb mode.

In a 53rd example, the method of any of examples 48-52, further comprising: detecting a second alarm condition; determining that the second alarm condition requires urgent user attention; and in response to determining that the second alarm condition requires urgent user attention, annunciating the second alarm condition without deactivating the do not disturb mode, using a second alarm condition annunciation pattern comprising at least one of auditory or haptic annunciation.

In a 54th example, an ambulatory medicament device configured to display critical status information in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a touchscreen controller configured to output display signals configured to generate user interface screens on a touchscreen and to receive user input signals corresponding to user input on the touchscreen, wherein the touchscreen is configured to be illuminated by a backlight; an accelerometer configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user input signals via the touchscreen controller; receive the user interaction signals via the accelerometer; activate a power saving mode of the ambulatory medicament device after a period of inactivity or in response to a request to activate the power saving mode, wherein the period of inactivity comprises the hardware processor not receiving a user input signal or a user interaction signal for a predetermined period of time, wherein the touchscreen controller is configured to not receive the user input signals when the ambulatory medicament device is in the power saving mode; turn off the backlight; receive the status information via the monitoring system interface; determine critical status information from the status information; generate a display of a critical status information interface screen on the touchscreen; and display on the critical status information interface screen at least one critical status indicator selected from a plurality of critical status indicators corresponding to the critical status information, wherein the plurality of critical status indicators comprises: a glucose level indicator of the subject, a battery level indicator of the ambulatory medicament device, a therapy status indicator, a remaining medicament level indicator, and an alarm status indicator.

In a 55th example, the ambulatory medicament device of example 54, wherein the hardware processor is configured to execute further computer-executable instructions to determine that a power level of a battery of the ambulatory medicament device is below a predetermined power level threshold and in response to determining that the power level of the battery of the ambulatory medicament device is below the predetermined power level threshold, the hardware processor is configured to execute further computer-executable instructions to: generate a display of a battery status interface; and display on the battery status interface a battery charging indicator to prioritize displaying the status information corresponding to the power level being below the predetermined power level threshold.

In a 56th example, the ambulatory medicament device of example 55, wherein the battery charging indicator comprises an image of a battery charger for a battery of the ambulatory medicament device.

In a 57th example, the ambulatory medicament device of any of examples 54-56, wherein the hardware processor is configured to execute further computer-executable instructions to determine whether a glucose level of the subject is within a predetermined glucose range and in response to determining that the glucose level is not within the predetermined glucose range, the hardware processor is configured to execute further computer-executable instructions to: generate a display of a glucose interface screen; and display on the glucose interface screen the glucose level indicator to prioritize displaying the status information corresponding to the glucose level not being within the predetermined glucose range.

In a 58th example, the ambulatory medicament device of any of examples 54-57, wherein the hardware processor is further configured to execute the computer-executable instructions to display on the critical status information interface screen an alarm state icon comprising a visual indication of a count of alarm conditions.

In a 59th example, the ambulatory medicament device of any of examples 54-58, wherein the hardware processor is configured to execute further computer-executable instructions to: activate a privacy mode in response to a request to activate the privacy mode; generate a display of a privacy mode interface screen; and display on the privacy mode interface screen one or more status indicators corresponding to the status information without displaying at least one of the plurality of critical status indicators.

In a 60th example, the ambulatory medicament device of example 59, wherein the at least one of the plurality of critical status indicators not displayed comprises at least one of the glucose level indicator of the subject or the therapy status indicator.

In a 61st example, the ambulatory medicament device of example 60, wherein none of the plurality of critical status indicators are displayed on the privacy mode interface screen.

In a 62nd example, the ambulatory medicament device of any of examples 59-61, wherein the hardware processor is configured to execute further computer-executable instructions to turn off the touchscreen while in off the privacy mode.

In a 63rd example, the ambulatory medicament device of any of examples 59-62, wherein the hardware processor is configured to execute further computer-executable instructions to activate the privacy mode while activating the power saving mode.

In a 64th example, the ambulatory medicament device of any of examples 59-63, wherein the hardware processor is configured to execute further computer-executable instructions to receive the request to activate the privacy mode interface screen while in the power saving mode.

In a 65th example, the ambulatory medicament device of any of examples 59-64, wherein the hardware processor is configured to execute further computer-executable instructions to receive the request to activate the privacy mode interface screen while not in the power saving mode.

In a 66th example, the ambulatory medicament device of any of examples 59-65, wherein the touchscreen comprises a filter configured to have a predetermined viewing angle range relative to the touchscreen such that information cannot be seen on the touchscreen when viewed from an angle outside of the predetermined viewing angle range.

In a 67th example, the ambulatory medicament device of any of examples 59-66, wherein in the power saving mode, the ambulatory medicament device displays the critical status information interface screen by using 5-10% additional electric current relative to electric current used with the touchscreen turned off while the ambulatory medicament device is operating.

In a 68th example, the ambulatory medicament device of any of examples 54-67, wherein the hardware processor is configured to execute further computer-executable instructions to: determine that the user interaction signals correspond to a single tap on the ambulatory medicament device; and in response to determining that the user interaction corresponds to the single tap on the ambulatory medicament device, turn off a touchscreen display.

In a 69th example, the ambulatory medicament device of example 68, wherein the hardware processor is configured to execute further computer-executable instructions to: determine that the user interaction signals correspond to an other single tap on the ambulatory medicament device; and in response to determining that the user interaction corresponds to the other single tap on the ambulatory medicament device, turn on the touchscreen while remaining in the power saving mode.

In a 70th example, the ambulatory medicament device of any of examples 54-69, wherein the hardware processor is configured to execute further computer-executable instructions to: determine that the user interaction signals correspond to a double tap on the ambulatory medicament device; and in response to determining that the user interaction corresponds to the double tap on the ambulatory medicament device, turn on the backlight while remaining in the power saving mode.

In a 71st example, the ambulatory medicament device of example 70, wherein the hardware processor is configured to execute further computer-executable instructions to: determine that the user interaction signals correspond to an other double tap on the ambulatory medicament device; and in response to determining that the user interaction corresponds to the other double tap on the ambulatory medicament device, turn off the backlight while remaining in the power saving mode.

In a 72nd example, the ambulatory medicament device of any of examples 54-71, wherein the hardware processor is configured to execute further computer-executable instructions to: determine that the user interaction signals correspond to a single tap or a double tap on the ambulatory medicament device; and in response to determining that the user interaction corresponds to the single tap or the double tap on the ambulatory medicament device, deactivate the power saving mode.

In a 73rd example, the ambulatory medicament device of any of examples 54-72, wherein the hardware processor is configured to execute further computer-executable instructions to update the critical status information interface screen in the power saving mode less frequently than updating the user interface screens in a wake mode of the ambulatory medicament device.

In a 74th example, the ambulatory medicament device of any of examples 54-73, wherein the hardware processor is configured to execute further computer-executable instructions to: receive a request to activate a wake mode of the ambulatory medicament device; and in response to receiving the request to activate the wake mode, deactivate the power saving mode.

In a 75th example, the ambulatory medicament device of example 74, wherein in response to receiving the request to activate the wake mode, the hardware processor is configured to execute further computer-executable instructions to: determine that the request to activate the wake mode was received during a predefined period of time; and in response to determining that the request was received during the predefined period of time, turn on the backlight.

In a 76th example, the ambulatory medicament device of example 75, wherein the predefined period of time is between 8:00 PM and 7:00 AM of a day.

In a 77th example, the ambulatory medicament device of any of examples 74-76, wherein the hardware processor is configured to execute further computer-executable instructions to receive a wake request signal corresponding to user request on a wake interface of the ambulatory medicament device to active the wake mode.

In a 78th example, the ambulatory medicament device of example 77, wherein the wake interface comprises a physical button, a capacitive sensor, or an inductive sensor.

In a 79th example, the ambulatory medicament device of any of examples 77-78, wherein the hardware processor is configured to execute further computer-executable instructions to: generate a display of a power saving interface screen on the touchscreen; and display on the power saving interface screen one or more wake mode indicators corresponding to a location of the wake interface, a message to interact with the wake interface to activate the wake mode, or both.

In an 80th example, the ambulatory medicament device of example 79, wherein the hardware processor is configured to execute further computer-executable instructions to not display the one or more wake mode indicators in the wake mode.

In a 81st example, the ambulatory medicament device of any of examples 77-80, wherein in response to receiving the wake request signal, the hardware processor is configured to execute further computer-executable instructions to: determine that the wake request signal was received for a first predetermined time length; and in response to determining that the wake request signal was received for the first predetermined time length, turn on the backlight to 40-60% brightness relative to a maximum brightness of the backlight.

In a 82nd example, the ambulatory medicament device of example 81, wherein the hardware processor is configured to execute further computer-executable instructions to: determine that the wake request signal was received for a second predetermined time length, the second predetermined time length being longer than the first predetermined time length; and in response to determining that the wake request signal was received for the second predetermined time length, turn on the backlight to the maximum brightness of the backlight.

In an 83rd example, the ambulatory medicament device of any of examples 54-82, wherein the hardware processor is configured to execute further computer-executable instructions to lower a refresh rate of the touchscreen to a lower refresh level relative to a maximum refresh rate of touchscreen.

In an 84th example, the ambulatory medicament device of example 83, wherein the lower refresh rate of the touchscreen is 1 hertz.

In an 85th example, the ambulatory medicament device of any of examples 83-84, wherein the maximum refresh rate of the touchscreen is 60 hertz.

In an 86th example, the ambulatory medicament device of any of examples 54-85, wherein the hardware processor is configured to execute further computer-executable instructions to lower brightness of the touchscreen of the ambulatory medicament device to a lower brightness level relative to a full brightness level of the touchscreen.

In an 87th example, the ambulatory medicament device of any of examples 54-86, wherein the ambulatory medicament device comprises a bi-hormonal pump capable of administering insulin and a counter-regulatory agent.

In an 88th example, the ambulatory medicament device of any of examples 54-87, wherein the status information is received from a sensor that measures at least one of a characteristic of the ambulatory medicament device or a physiological parameter of the subject.

In a 89th example, an ambulatory medicament device configured to display critical status information in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the motion sensor; activate a power saving mode of the ambulatory medicament device after a period of inactivity or in response to a request to activate the power saving mode, wherein the period of inactivity comprises the hardware processor not receiving a user interaction signal for a predetermined period of time; turn off a backlight of the ambulatory medicament device configured to illuminate a touchscreen of the ambulatory medicament device; receive the status information via the monitoring system interface; determine critical status information from the status information; generate a display of a critical status information interface screen on the touchscreen; and display on the critical status information interface screen at least one of a plurality of critical status indicators corresponding to the critical status information, wherein the plurality of critical status indicators comprises: a medicament device status indicator, and a subject status indicator.

In a 90th example, the ambulatory medicament device of example 89, further comprising any one or more features of example 54 to example 88.

In a 91st example, an ambulatory medicament device configured to display critical status information in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a memory configured to store computer-executable instructions; and a hardware processor in communication with the memory and configured to execute the computer-executable instructions to at least: activate a power saving mode of the ambulatory medicament device after a period of inactivity or in response to a request to activate the power saving mode, wherein the period of inactivity comprises the hardware processor not receiving user input for a predetermined period of time; turn off a backlight of the ambulatory medicament device configured to illuminate a touchscreen of the ambulatory medicament device; receive the status information via the monitoring system interface; determine critical status information from the status information; generate a display of a critical status information interface screen on the touchscreen; and display on the critical status information interface screen at least one of a plurality of critical status indicators corresponding to the critical status information, wherein the plurality of critical status indicators comprises: a medicament device status indicator, and a subject status indicator.

In a 92nd example, the ambulatory medicament device of example 91, further comprising any one or more features of example 54 to example 88.

In a 93rd example, an ambulatory medicament device configured to display critical status information in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a memory configured to store computer-executable instructions; and a hardware processor in communication with the memory and configured to execute the computer-executable instructions to at least: activate a power saving mode of the ambulatory medicament device after a period of inactivity or in response to a request to activate the power saving mode, wherein the period of inactivity comprises the hardware processor not receiving user input for a predetermined period of time; receive the status information via the monitoring system interface; determine critical status information from the status information; generate a display of a critical status information interface screen on a touchscreen of the ambulatory medicament device; and display on the critical status information interface screen at least one of a plurality of critical status indicators corresponding to the critical status information, wherein the plurality of critical status indicators comprises: a medicament device status indicator, and a subject status indicator.

In a 94th example, the ambulatory medicament device of example 93, further comprising any one or more features of example 54 to example 88.

In a 95th example, the ambulatory medicament device of any of examples 93-94, wherein the hardware processor is configured to execute further computer-executable instructions to dim a backlight of the ambulatory medicament device to a lower illumination level relative to a maximum illumination level of the backlight, the backlight configured to illuminate the touchscreen.

In a 96th example, the ambulatory medicament device of example 95, wherein the lower illumination level of the backlight is 40-60% of the maximum illumination level of the backlight.

In a 97th example, an ambulatory medicament device configured to respond to user input or interaction in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a touchscreen controller configured to output display signals configured to generate user interface screens on a touchscreen and to receive user input signals corresponding to user input on the touchscreen, wherein the touchscreen is configured to be illuminated by a backlight; an accelerometer configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user input signals via the touchscreen controller; receive the user interaction signals via the accelerometer; activate a power saving mode of the ambulatory medicament device after a period of inactivity or in response to a request to activate the power saving mode, wherein the period of inactivity comprises the hardware processor not receiving a user input signal or a user interaction signal for a predetermined period of time; in response to activating the power saving mode, cause the touchscreen controller to not receive the user input signals; receive the status information via the monitoring system interface; determine that the status information satisfies an alarm condition for the ambulatory medicament device or for the subject; in response to determining that the status information satisfies the alarm condition: generate a display of an alarm interface screen on the touchscreen; display on the alarm interface screen one or more alarm status indicators corresponding to the alarm condition; determine that the user interaction signals correspond to the double tap on the ambulatory medicament device; and in response to determining that the user interaction corresponds to the double tap on the ambulatory medicament device: snooze the alarm condition; and update the one or more alarm status indicators to indicate that the alarm condition was snoozed; determine that the status information does not satisfy an alarm condition for the ambulatory medicament device or for the subject; and in response to determining that the status information does not satisfy the alarm condition: determine that the user interaction signals correspond to the single tap on the ambulatory medicament device or the double tap on the ambulatory medicament device; in response to determining that the user interaction corresponds to the single tap on the ambulatory medicament device: generate a display of the user interface screens on the touchscreen; and display on the user interface screens one or more status information indicators corresponding to the status information; and in response to determining that the user interaction corresponds to the double tap on the ambulatory medicament device, generate the display of the user interface screens on the touchscreen; display on the user interface screens the one or more status information indicators corresponding to the status information; and turn on the backlight to illuminate the touchscreen.

In a 98th example, the ambulatory medicament device of example 97, wherein in response to determining that the status information satisfies the alarm condition, the hardware processor is configured to execute further computer-executable instructions to annunciate the alarm condition using an alarm annunciation pattern comprising at least one of audio or haptic annunciation.

In a 99th example, the ambulatory medicament device of any of examples 97-98, wherein in response to determining that the status information satisfies the alarm condition, the hardware processor is configured to execute further computer-executable instructions to: determine that the alarm condition requires urgent user attention; and in response to determining that the alarm condition requires urgent user attention, display on the alarm interface screen the one or more alarm status indicators without snoozing the alarm condition in response to the double tap on the ambulatory medicament device.

In a 100th example, the ambulatory medicament device of example 99, in response to determining that the alarm condition requires urgent user attention, the hardware processor is configured to execute further computer-executable instructions to deactivate the power saving mode.

In a 101st example, the ambulatory medicament device of any of examples 99-100, wherein the hardware processor is configured to execute further computer-executable instructions to: determine that the alarm condition does not require urgent user attention; and in response to determining that the alarm condition does not require urgent user attention, allow the alarm condition to be snoozed.

In a 102nd example, the ambulatory medicament device of any of examples 97-101, wherein in response to snoozing the alarm condition, the hardware processor is configured to execute further computer-executable instructions to maintain the one or more alarm status indicators on a list of pending alarm conditions.

In a 103rd example, the ambulatory medicament device of example 102, wherein the list of pending alarm conditions is not displayed on the user interface screens with the power saving mode active.

In a 104th example, the ambulatory medicament device of any of examples 102-103, wherein the list of pending alarm conditions comprises alarm status icons, wherein the alarm status icons indicate whether the alarm condition was snoozed.

In a 105th example, the ambulatory medicament device of any of examples 97-104, wherein in response to displaying on the alarm interface screen that the alarm condition was snoozed, the hardware processor is configured to execute further computer-executable instructions to not display the one or more alarm status indicators after the predetermined period of time or an other predetermined period of time.

In a 106th example, the ambulatory medicament device of any of examples 97-105, wherein activating the power saving mode comprises turning off the backlight.

In a 107th example, the ambulatory medicament device of any of examples 97-106, wherein activating the power saving mode comprises turning off the touchscreen.

In 108th example, the ambulatory medicament device of example 107, wherein in response to determining that the status information satisfies the alarm condition, the hardware processor is configured to execute further computer-executable instructions to turn on the touchscreen.

In a 109th example, the ambulatory medicament device of any of examples 107-108, wherein in response to determining that the status information does not satisfy the alarm condition and that the user interaction signals correspond to the single tap or the double tap on the ambulatory medicament device, the hardware processor is configured to execute further computer-executable instructions to turn on the touchscreen.

In a 110th example, the ambulatory medicament device of any of examples 107-109, wherein in response to determining that the status information does not satisfy the alarm condition and that the user interaction signals correspond to the double tap on the ambulatory medicament device, the hardware processor is configured to execute further computer-executable instructions to turn on the touchscreen and turn on the backlight.

In a 111th example, the ambulatory medicament device of any of examples 97-110, wherein the hardware processor is configured to execute further computer-executable instructions to: determine that the user interaction signals correspond to an other single tap on the ambulatory medicament device; and in response to determining that the user interaction corresponds to the other single tap on the ambulatory medicament device, turn off the touchscreen.

In a 112th example, the ambulatory medicament device of any of examples 97-111, wherein the hardware processor is configured to execute further computer-executable instructions to: determine that the user interaction signals correspond to an other double tap on the ambulatory medicament device; and in response to determining that the user interaction corresponds to the other double tap on the ambulatory medicament device, turn off the backlight.

In a 113th example, the ambulatory medicament device of any of examples 97-112, wherein in response to determining that the status information satisfies the alarm condition, the hardware processor is configured to execute further computer-executable instructions to deactivate the power saving mode.

In a 114th example, the ambulatory medicament device of example 113, wherein in response to displaying on the alarm interface screen that the alarm condition was snoozed, the hardware processor is configured to execute further computer-executable instructions to activate the power saving mode of the ambulatory medicament device after the period of inactivity.

In a 115th example, the ambulatory medicament device of any of examples 97-114, wherein in response to determining that the status information does not satisfy the alarm condition and that the user interaction signals correspond to the single tap or the double tap on the ambulatory medicament device, the hardware processor is configured to execute further computer-executable instructions to deactivate the power saving mode.

In a 116th example, the ambulatory medicament device of example 115, wherein the hardware processor is configured to execute further computer-executable instructions to: determine that the user interaction signals correspond to an other single tap on the ambulatory medicament device; and in response to determining that the user interaction corresponds to the other single tap on the ambulatory medicament device, activate the power saving mode of the ambulatory medicament device.

In a 117th example, the ambulatory medicament device of any of examples 97-116, wherein in response to determining that the status information does not satisfy the alarm condition and that the user interaction corresponds to the single tap on the ambulatory medicament device, the hardware processor is configured to execute further computer-executable instructions to: generate the display of the alarm interface screen; and display on the alarm screen interface that one or more alarm conditions were previously snoozed.

In a 118th example, the ambulatory medicament device of any of examples 97-117, wherein in response to activating the power saving mode, the hardware processor is configured to execute further computer-executable instructions to: determine critical status information from the status information; generate a display of a critical status information interface screen; and display on the critical status information interface screen at least one of a plurality of critical status indicators corresponding to the critical status information.

In a 119th example, the ambulatory medicament device of example 118, wherein in response to activating the power saving mode, the hardware processor is configured to execute further computer-executable instructions to turn off the backlight.

In a 120th example, the ambulatory medicament device of any of examples 118-119, wherein the plurality of critical status indicators comprises a glucose level indicator of the subject, a battery level indicator of the ambulatory medicament device, an alert status indicator, a therapy status indicator, a remaining medicament level indicator, and the one or more alarm status indicators.

In a 121st example, the ambulatory medicament device of any of examples 118-120, wherein the hardware processor is configured to execute further computer-executable instructions to update the critical status information interface screen in the power saving mode less frequently than the user interface screens in a wake mode of the ambulatory medicament device.

In a 122nd example, the ambulatory medicament device of any of examples 97-120, wherein the hardware processor is configured to execute further computer-executable instructions to: receive a request to activate a wake mode of the ambulatory medicament device; and in response to receiving the request to activate the wake mode, deactivate the power saving mode.

In a 123rd example, the ambulatory medicament device of example 122, wherein the request to activate the wake mode comprises the single tap or the double tap.

In a 124th example, the ambulatory medicament device of any of examples 122-123, wherein in response to receiving the request to activate the wake mode, the hardware processor is configured to execute further computer-executable instructions to: determine whether the request to active the wake mode was received during a predefined period of time; and in response to determining that the request was received during the predefined period of time, turn on the backlight.

In a 125th example, the ambulatory medicament device of example 124, wherein the predefined period of time is between 8:00 PM and 7:00 AM of a day.

In a 126th example, the ambulatory medicament device of any of examples 122-125, wherein the hardware processor is configured to execute further computer-executable instructions to receive a wake request signal corresponding to user request on a wake interface of the ambulatory medicament device to active the wake mode.

In a 127th example, the ambulatory medicament device of example 126, wherein the wake interface comprises a comprises a physical button, a capacitive sensor, or an inductive sensor.

In a 128th example, the ambulatory medicament device of any of examples 126-127, wherein the request to active the power saving mode is received via the wake interface of the ambulatory medicament device.

In a 129th example, the ambulatory medicament device of any of examples 97-128, wherein, in response to updating the one or more alarm status indicators to indicate that the alarm condition was snoozed, the hardware processor is configured to execute further computer-executable instructions to display on the alarm interface screen that the alarm condition was snoozed.

In a 130th example, the ambulatory medicament device of any of examples 97-129, wherein in response to determining that the status information satisfies the alarm condition, the hardware processor is configured to execute further computer-executable instructions to annunciate the alarm condition using at least one of an auditory annunciation pattern or a haptic annunciation pattern.

In a 131st example, the ambulatory medicament device of any of examples 97-130, wherein the ambulatory medicament device comprises a bi-hormonal pump capable of administering insulin and a counter-regulatory agent.

In a 132nd example, the ambulatory medicament device of any of examples 97-131, wherein the status information is received from a sensor that measures at least one of a characteristic of the ambulatory medicament device or a physiological parameter of the subject.

In a 133rd example, an ambulatory medicament device configured to respond to user interaction in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the motion sensor; activate a power saving mode of the ambulatory medicament device after a period of inactivity or in response to a request to activate the power saving mode, wherein the period of inactivity comprises the hardware processor not receiving a user interaction signal for a predetermined period of time; receive the status information via the monitoring system interface; determine that the status information satisfies an alarm condition for the ambulatory medicament device or for the subject; in response to determining that the status information satisfies the alarm condition: generate a display of an alarm interface screen on a touchscreen of the ambulatory medicament device; display on the alarm interface screen one or more alarm status indicators corresponding to the alarm condition; determine that the user interaction signals correspond to the double tap on the ambulatory medicament device; and in response to determining that the user interaction corresponds to the double tap on the ambulatory medicament device, snooze the alarm condition.

In a 134th example, the ambulatory medicament device of example 133, wherein the motion sensor comprises at least one of an accelerometer or a gyroscope.

In a 135th example, the ambulatory medicament device of any of examples 133-134, further comprising a touchscreen controller configured to output display signals configured to generate user interface screens on the touchscreen and to receive user input signals corresponding to user input on the touchscreen, the hardware processor is configured to execute further computer-executable instructions to receive the user input signals via the touchscreen controller, wherein the period of inactivity for activating the power saving mode comprises the hardware processor not receiving a user input signal for the predetermined period of time.

In a 136th example, the ambulatory medicament device of example 135, wherein the hardware processor is configured to execute further computer-executable instructions to: determine that the user interaction signals correspond to the single tap on the ambulatory medicament device or the double tap on the ambulatory medicament device; in response to determining that the user interaction corresponds to the single tap on the ambulatory medicament device: cause the touchscreen controller to receive the user input signals; and in response to determining that the user interaction corresponds to the double tap on the ambulatory medicament device, cause the touchscreen controller to receive the user input signals; and turn on a backlight of the ambulatory medicament device to illuminate the touchscreen.

In a 137th example, the ambulatory medicament device of any of examples 133-136, wherein the hardware processor is configured to execute further computer-executable instructions to display on the alarm interface screen that the alarm condition was snoozed.

In a 138th example, the ambulatory medicament device of any of examples 133-137, wherein the hardware processor is configured to execute further computer-executable instructions to: determine that the user interaction signals correspond to the single tap on the ambulatory medicament device or the double tap on the ambulatory medicament device; in response to determining that the user interaction corresponds to the single tap on the ambulatory medicament device: generate a display of the user interface screens on the touchscreen of the ambulatory medicament device; and display on the user interface screens one or more status information indicators corresponding to the status information; and in response to determining that the user interaction corresponds to the double tap on the ambulatory medicament device: generate the display of the user interface screens on the touchscreen; display on the user interface screens the one or more status information indicators corresponding to the status information; and turn on a backlight of the ambulatory medicament device to illuminate the touchscreen.

In a 139th example, the ambulatory medicament device of any of examples 133-138, wherein the hardware processor is configured to execute further computer-executable instructions to: determine that the user interaction signals correspond to the single tap on the ambulatory medicament device or the double tap on the ambulatory medicament device; in response to determining that the user interaction corresponds to the single tap on the ambulatory medicament device: turn on a touchscreen of the ambulatory medicament device; and in response to determining that the user interaction corresponds to the double tap on the ambulatory medicament device: turn on the touchscreen; and turn on a backlight of the ambulatory medicament device to illuminate the touchscreen.

In a 140th example, the ambulatory medicament device of any of examples 133-139, wherein the touchscreen is configured to be illuminated by a backlight.

In a 141st example, the ambulatory medicament device of any of examples 133-140, further comprising any one or more features of example 98 to example 132.

In a 142nd example, an ambulatory medicament device configured to respond to user interaction, the ambulatory medicament device comprising: a monitoring system interface configured to receive status information, wherein the status information comprises at least one of device information pertaining to a condition of the ambulatory medicament device or subject information pertaining to a condition of a subject; a user interaction sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the user interaction sensor; activate a power saving mode of the ambulatory medicament device after a period of inactivity or in response to a request to activate the power saving mode, wherein the period of inactivity comprises the hardware processor not receiving a user interaction signal for a predetermined period of time; receive the status information via the monitoring system interface; determine that the status information satisfies an alarm condition for the ambulatory medicament device or for the subject; in response to determining that the status information satisfies the alarm condition: generate a display of an alarm interface screen on a touchscreen of the ambulatory medicament device; display on the alarm interface screen one or more alarm status indicators corresponding to the alarm condition; determine that the user interaction signals correspond to the double tap on the ambulatory medicament device; and in response to determining that the user interaction corresponds to the double tap on the ambulatory medicament device, snooze the alarm condition.

In a 143rd example, the ambulatory medicament device of example 142, wherein the user interaction sensor comprises at least one of a motion sensor or a touchscreen.

In a 144th example, the ambulatory medicament device of any of examples 142-143, wherein the hardware processor is configured to execute further computer-executable instructions to activate a power saving mode of the ambulatory medicament device after a period of inactivity or in response to a request to activate the power saving mode, wherein the period of inactivity comprises the hardware processor not receiving a user interaction signal for a predetermined period of time.

In a 145th example, the ambulatory medicament device of any of examples 142-144, further comprising any one or more features of example 98 to example 132 and example 134 to example 141.

In a 146th example, an ambulatory medicament device configured to respond to user input or interaction in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a touchscreen controller configured to output display signals configured to generate user interface screens on a touchscreen and to receive user input signals corresponding to user input on the touchscreen, wherein the touchscreen is configured to be illuminated by a backlight; a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the motion sensor; activate a power saving mode of the ambulatory medicament device after a period of inactivity or in response to a request to activate the power saving mode, wherein the period of inactivity comprises the hardware processor not receiving a user interaction signal for a predetermined period of time; in response to activating the power saving mode, cause the touchscreen controller to not receive the user input signals; receive the status information via the monitoring system interface; determine that the status information satisfies an alarm condition for the ambulatory medicament device or for the subject; in response to determining that the status information satisfies the alarm condition: cause the touchscreen controller to receive the user input signals; determine that the user interaction signals correspond to the double tap on the ambulatory medicament device; and in response to determining that the user interaction corresponds to the double tap on the ambulatory medicament device, snooze the alarm condition.

In a 147th example, the ambulatory medicament device of example 146, further comprising any one or more features of example 97 to example 144.

In a 148th example, an ambulatory medicament device configured to respond to user interaction in a power saving mode, the ambulatory medicament device comprising: a monitoring system interface configured to receive status information, wherein the status information comprises at least one of device information pertaining to a condition of the ambulatory medicament device or subject information pertaining to a condition of a subject; a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the motion sensor; activate a power saving mode of the ambulatory medicament device after a period of inactivity or in response to a request to activate the power saving mode, wherein the period of inactivity comprises the hardware processor not receiving a user interaction signal for a predetermined period of time; receive the status information via the monitoring system interface; determine that the user interaction signals correspond to the single tap on the ambulatory medicament device or the double tap on the ambulatory medicament device; in response to determining that the user interaction corresponds to the single tap on the ambulatory medicament device: generate a display of the user interface screens on a touchscreen of the ambulatory medicament device; and display on the user interface screens one or more status information indicators corresponding to the status information; and in response to determining that the user interaction corresponds to the double tap on the ambulatory medicament device, generate the display of the user interface screens on the touchscreen; display on the user interface screens the one or more status information indicators corresponding to the status information; and turn on a backlight of the ambulatory medicament device to illuminate the touchscreen.

In a 149th example, the ambulatory medicament device of example 148, further comprising any one or more features of example 97 to example 144.

In a 150th example, in ambulatory medicament device configured to respond to user interaction in a power saving mode, the ambulatory medicament device comprising: a user interaction sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user interaction signals via the user interaction sensor; activate a power saving mode of the ambulatory medicament device after a period of inactivity or in response to a request to activate the power saving mode, wherein the period of inactivity comprises the hardware processor not receiving a user interaction signal for a predetermined period of time; determine that the user interaction signals correspond to the single tap on the ambulatory medicament device or the double tap on the ambulatory medicament device; in response to determining that the user interaction corresponds to the single tap on the ambulatory medicament device: turn on a touchscreen of the ambulatory medicament device; and in response to determining that the user interaction corresponds to the double tap on the ambulatory medicament device, turn on the touchscreen; and turn on a backlight of the ambulatory medicament device to illuminate the touchscreen.

In a 151st example, the ambulatory medicament device of example 150, further comprising any one or more features of example 97 to example 144.

In a 152nd example, an ambulatory medicament device configured to respond to user input or interaction in a power saving mode, the ambulatory medicament device comprising: a touchscreen controller configured to output display signals configured to generate user interface screens on a touchscreen and to receive user input signals corresponding to user input on the touchscreen, wherein the touchscreen is configured to be illuminated by a backlight; a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device; a memory configured to store computer-executable instructions; and a hardware processor in communication with the memory and configured to execute the computer-executable instructions to at least: receive the user input signals via the touchscreen controller; receive the user interaction signals via the motion sensor; activate a power saving mode of the ambulatory medicament device after a period of inactivity or in response to a request to activate the power saving mode, wherein the period of inactivity comprises the hardware processor not receiving a user input signal for a predetermined period of time; in response to activating the power saving mode, cause the touchscreen controller to not receive the user input signals; determine that the user interaction signals correspond to the single tap on the ambulatory medicament device or the double tap on the ambulatory medicament device; in response to determining that the user interaction corresponds to the single tap on the ambulatory medicament device: cause the touchscreen controller to receive the user input signals; and in response to determining that the user interaction corresponds to the double tap on the ambulatory medicament device, cause the touchscreen controller to receive the user input signals; and turn on the backlight to illuminate the touchscreen.

In a 153rd example, the ambulatory medicament device of example 152, further comprising any one or more features of example 97 to example 144.

In a 154th example, an ambulatory medicament device configured to manage a medicament therapy regimen based on motion data associated with movement of the ambulatory medicament device, the ambulatory medicament device comprising: a medicament reservoir configured to store a medicament; an ambulatory medicament pump configured to deliver the medicament from the medicament reservoir to a subject; a motion sensor configured to collect the motion data; a memory configured to store specific computer-executable instructions; and a hardware processor in communication with the memory and configured to execute the specific computer-executable instructions to at least: receive the motion data from the motion sensor; detect a freefall motion of the ambulatory medicament device based on the motion data; and in response to detecting the freefall motion, halt operation of the ambulatory medicament pump.

In a 155th example, the ambulatory medicament device of example 154, wherein the halt operation of the ambulatory medicament pump comprises pausing delivery of the medicament, wherein the hardware processor is further configured to execute the specific computer-executable instructions to at least: pause the delivery of the medicament by ceasing rotation of a motor of the ambulatory medicament pump.

In a 156th example, the ambulatory medicament device of any of examples 154-155, wherein the hardware processor is further configured to execute the specific computer-executable instructions to at least: pause the delivery of the medicament by cutting power supply to the ambulatory medicament pump.

In a 157th example, the ambulatory medicament device of any of examples 154-156, wherein the hardware processor is further configured to execute the specific computer-executable instructions to at least: record an amount of medicament administered to the subject; and in response to detecting the freefall motion: determine an amount of medicament administered between a time the freefall motion was detected and a time delivery of the medicament was paused, and record the amount of medicament administered between the time the freefall motion was detected and the time delivery of the medicament was paused.

In a 158th example, the ambulatory medicament device of example 157, wherein the hardware processor is configured to execute the specific computer-executable instructions to at least: determine the amount of medicament administered to the subject based on a number of cycles completed by the ambulatory medicament pump between the time the freefall motion was detected and the time delivery of the medicament was paused.

In a 159th example, the ambulatory medicament device of any of examples 154-158, wherein the ambulatory medicament pump is a peristaltic pump.

In a 160th example, the ambulatory medicament device of any of examples 154-159, wherein the hardware processor is further configured to execute the computer-specific executable instructions to at least: detect an end of the freefall motion.

In a 161st example, the ambulatory medicament device of example 160, wherein the hardware processor is further configured to execute the computer-executable instructions to at least: in response to detecting the end of the freefall motion, resume administering the medicament to the subject.

In a 162nd example, the ambulatory medicament device of example 161, wherein the hardware processor is further configured to execute the computer-executable instructions to at least: in response to detecting the end of the freefall motion, notify the subject of the resumption of administering the medicament to the subject.

In a 163rd example, the ambulatory medicament device of example 162, wherein the resumption of administering the medicament to the subject is notified via a user interface of the ambulatory medicament device.

In a 164th example, the ambulatory medicament device of any of examples 162-163, wherein the hardware processor is further configured to execute the computer-executable instructions to at least: in response to detecting the end of the freefall motion, request the subject to accept the resumption of administering the medicament to the subject via a user interface.

In a 165th example, the ambulatory medicament device of example 164, wherein the hardware processor is further configured to execute the computer-executable instructions to at least: in response to receiving a user's input, resume administering the medicament to the subject.

In a 166th example, the ambulatory medicament device of any of examples 160-165, wherein the hardware processor is further configured to execute the computer-executable instructions to at least: in response to detecting the end of the freefall motion, retrieve the motion data from the motion sensor, wherein the motion data includes an acceleration of the ambulatory medicament device; calculate a jerk of the ambulatory medicament device during or following the freefall motion based on the acceleration; determine whether the jerk exceeds a threshold value; and in response to determining that the jerk is less than the threshold value, resume administering the medicament to the subject.

In a 167th example, the ambulatory medicament device of example 166, wherein the hardware processor is further configured to execute the specific computer-executable instructions to at least: in response to determining that the jerk exceeds the threshold value, generate an alarm; and receive an alarm response signal from the subject.

In a 168th example, the ambulatory medicament device of example 167, wherein the alarm comprises an urgency level based on the calculated jerk.

In a 169th example, the ambulatory medicament device of any of examples 167-168, wherein the alarm response signal is one of: an alarm snooze signal configured to snooze the alarm or an alarm acknowledgement signal configured to dismiss the alarm.

In a 170th example, the ambulatory medicament device of example 169, wherein the hardware processor is further configured to execute the specific computer-executable instructions to at least: receive an alarm acknowledgement signal from the subject; and in response to receiving the alarm acknowledgement signal, resume administering the medicament to the subject.

In a 171st example, the ambulatory medicament device of example 170, wherein the alarm acknowledgement signal is configured to be detected by the motion sensor and is one of: a gesture input or a touch input.

In a 172nd example, the ambulatory medicament device of any of examples 167-171 further comprising a touchscreen controller configured to output display signals configured to generate user interface screens on a touchscreen and to receive user input signals corresponding to user interaction with the touchscreen, and wherein the hardware processor is further configured to execute the specific computer-executable instructions to at least: generate a graphical display of the alarm on the touchscreen, the graphical display including information about the alarm and an alarm acknowledgement touch user interface element; receive an alarm acknowledgement signal from the user via the touchscreen; and in response to receiving the alarm acknowledgement signal, resume administering the medicament to the subject.

In a 173rd example, the ambulatory medicament device of example 166, wherein the hardware processor is further configured to execute the specific computer-executable instructions to at least: in response to determining that the jerk exceeds the threshold value, restart the ambulatory medicament device.

In a 174th example, the ambulatory medicament device of any of examples 166-173, wherein the hardware processor is further configured to execute the specific computer-executable instructions to at least: in response to determining that the jerk exceeds the threshold value, perform a diagnostic test on the ambulatory medicament pump; and in response to the ambulatory medicament pump passing the diagnostic test, resume administering the medicament to the subject.

In a 175th example, the ambulatory medicament device of example 174, wherein the hardware processor is further configured to execute the specific computer-executable instructions to at least: in response to the ambulatory medicament pump failing the diagnostic test, generate an alarm indicating that the pump is damaged.

In a 176th example, the ambulatory medicament device of any of examples 174-175, wherein the hardware processor is further configured to execute the specific computer-executable instructions to at least: in response to the ambulatory medicament pump failing the diagnostic test, restart the ambulatory medicament device.

In a 177th example, the ambulatory medicament device of any of examples 154-176, wherein the motion sensor comprises an accelerometer.

In a 178th example, the ambulatory medicament device of example 177, wherein the hardware processor is configured to detect the freefall motion of the ambulatory medicament device by: detecting a zero output from the accelerometer.

In a 179th example, the ambulatory medicament device of any of examples 177-178, wherein the hardware processor is further configured to execute the specific computer-executable instructions to at least: in response to detecting the freefall motion, detect an end to the freefall motion by receiving a baseline output from the accelerometer.

In a 180th example, the ambulatory medicament device of example 179, wherein the baseline output is equal to the acceleration of gravity.

In a 181st example, the ambulatory medicament device of any of examples 179-180, wherein the baseline output is within a range of acceleration values surrounding the acceleration of gravity, wherein the range of acceleration values encompasses accelerations felt by the ambulatory medicament device while attached to the subject.

In a 182nd example, the ambulatory medicament device of any of examples 154-181, wherein the hardware processor is further configured to execute the specific computer-executable instructions to at least: pause delivery of the medicament for a period of time.

In a 183rd example, the ambulatory medicament device of example 182, wherein the period of time is one of: one minute, five minutes, ten minutes, thirty minutes, an hour, or an amount of time defined by the subject.

In a 184th example, the ambulatory medicament device of any of examples 154-183, wherein the hardware processor is configured to execute the specific computer-executable instructions to at least: in response to detecting the freefall motion, pause delivery of the medicament until one of: an end of the freefall motion is detected, an alarm confirmation signal is received from the subject, or the ambulatory medicament pump passes a diagnostic test.

In a 185th example, an ambulatory medicament device configured to manage a medicament therapy regimen based on motion data associated with movement of the ambulatory medicament device, the ambulatory medicament device comprising: a medicament reservoir configured to store a medicament; an ambulatory medicament pump configured to deliver the medicament from the medicament reservoir to a subject; a motion sensor configured to collect the motion data; a memory configured to store specific computer-executable instructions; and a hardware processor in communication with the memory and configured to execute the specific computer-executable instructions to at least: detect an alarm condition; generate an alarm; detect an alarm response from the subject based on the motion data; and silence the alarm based on the alarm response received from the subject.

In a 186th example, the ambulatory medicament device of example 185, wherein the motion sensor is an accelerometer configured to record the motion data, the motion data including an acceleration of the ambulatory medicament device caused by the alarm response.

In a 187th example, the ambulatory medicament device of any of examples 185-186, wherein the alarm response is one of: a single tap, a double tap, multi-tap, or a multi-location tap on a body of the ambulatory medicament device or a shaking of the ambulatory medicament device.

In a 188th example, the ambulatory medicament device of any of examples 185-187, wherein the hardware processor is further configured to determine whether the alarm response is an alarm snooze response or an alarm acknowledgement response.

In a 189th example, the ambulatory medicament device of any of examples 185-188, wherein the alarm response is an alarm snooze response, and wherein the hardware processor is further configured to execute the specific computer-executable instructions to at least: snooze the alarm for a period of time, wherein the period of time is determined based on an urgency level of the alarm.

In a 190th example, the ambulatory medicament device of example 189, wherein the hardware processor is further configured to execute the specific computer-executable instructions to at least: generate a second alarm after the period of time has elapsed; receive an alarm acknowledgement response; and dismiss the alarm.

In a 191st example, the ambulatory medicament device of any of examples 185-190, wherein the alarm response is an alarm acknowledgement response, and wherein the hardware processor is further configured to execute the specific computer-executable instructions to at least: dismiss the alarm.

In a 192nd example, the ambulatory medicament device of any of examples 185-191, wherein the alarm is one of: a low-level alarm, a medium-level alarm, or a high-level alarm, wherein a level of the alarm is determined based on the alarm condition.

In a 193rd example, the ambulatory medicament device of any of examples 185-192, wherein the alarm has an urgency level between 0 and 5, wherein the urgency level is determined based on the alarm condition.

In a 194th example, the ambulatory medicament device of any of examples 185-193, wherein the hardware processor is further configured to execute the specific computer-executable instructions to at least: generate the alarm based on an urgency level associated with the alarm condition.

In a 195th example, the ambulatory medicament device of any of examples 185-194 further comprising a touchscreen controller configured to output display signals configured to generate user interface screens on a touchscreen and to receive user input signals corresponding to user interaction with the touchscreen, wherein the hardware processor is further configured to execute the specific computer-executable instructions to at least: generate a graphical display of the alarm on the touchscreen; and receive the alarm response through a touch user interface implemented on the touchscreen.

In a 196th example, the ambulatory medicament device of example 195, wherein the graphical display includes alarm information, an alarm snooze touch user interface element, and an alarm acknowledgement touch user interface element.

In a 197th example, the ambulatory medicament device of any of examples 195-196, wherein the graphical display is arranged and colored based on an urgency level of the alarm condition.

In a 198th example, the ambulatory medicament device of any of examples 185-197 further comprising a speaker, and wherein the hardware processor is further configured to execute the specific computer-executable instructions to at least: generate an audible signal through the speaker based on an urgency of the alarm condition.

In a 199th example, the ambulatory medicament device of example 198, wherein the audible signal comprises one of: a beep, a series of beeps, a patterned beeping, or a speech output describing the alarm.

In a 200th example, the ambulatory medicament device of any of examples 185-199 further comprising a haptic motor, wherein the hardware processor is further configured to execute the specific computer-executable instructions to at least: generate a haptic alarm signal through the haptic motor based on an urgency of the alarm condition.

In a 201st example, the ambulatory medicament device of example 200, wherein the haptic signal comprises one of: a sustained vibration, a burst vibration, or a vibration pattern.

In a 202nd example, an ambulatory medicament device configured to manage a medicament therapy regimen based on motion data associated with movement of the ambulatory medicament device, the ambulatory medicament device comprising: a touchscreen controller configured to output display signals configured to generate user interface screens on a touchscreen and to receive user input signals corresponding to user interaction with the touchscreen; a motion sensor configured to collect the motion data; a memory configured to store specific computer-executable instructions; and a hardware processor in communication with the memory and configured to execute the specific computer-executable instructions to at least: receive a touch input from a subject; determine whether an alarm is active; and in response to determining there are no alarms pending, wake the touchscreen.

In a 203rd example, the ambulatory medicament device of example 202, wherein the touch input is received through the touchscreen.

In a 204th example, the ambulatory medicament device of any of examples 202-203, wherein the motion sensor comprises an accelerometer, and wherein the motion data includes an acceleration of the ambulatory medicament device.

In a 205th example, the ambulatory medicament device of example 204, wherein the hardware processor is further configured to execute the specific computer executable instructions to at least: receive the touch input by detecting an acceleration of the ambulatory medicament device caused by the touch input.

In a 206th example, the ambulatory medicament device of any of examples 202-205, wherein the touch input comprises one or more of: a single tap, a double tap, multi-tap, a multi-location tap, a pinch gesture, or a swipe gesture.

In a 207th example, the ambulatory medicament device of any of examples 202-206, wherein the touch input comprises one or more touches on one or more corners of the touchscreen.

In a 208th example, the ambulatory medicament device of example 207, wherein the touch input comprises a first touch on a first corner of the touchscreen, a second touch on a second corner of the touchscreen, and a third touch on a third corner of the touchscreen.

In a 209th example, the ambulatory medicament device of any of examples 202-208, wherein the touch input comprises one or more touches on the ambulatory medicament device.

In a 210th example, the ambulatory medicament device of any of examples 202-209, wherein the hardware processor is further configured to execute the specific computer-executable instructions to at least: unlock the touchscreen and the ambulatory medicament device based on the touch input.

In a 211th example, the ambulatory medicament device of example 210, wherein the touch input comprises a gesture password, and wherein the hardware processor is further configured to execute the specific computer-executable instructions to at least: determine whether the gesture password matches a stored password; and in response to determining that the gesture password matches a stored password, unlock the touchscreen and the ambulatory medicament device.

In a 212th example, the ambulatory medicament device of any of examples 202-211, wherein the hardware processor is further configured to execute the specific computer-executable instructions to at least: in response to determining that there are no alarms pending, wake the touchscreen by: displaying a home screen.

In a 213th example, the ambulatory medicament device of any of examples 202-212, wherein the hardware processor is further configured to execute the specific computer-executable instructions to at least: in response to determining that there are no alarms pending, wake the touchscreen by: displaying an unlock display on the touchscreen, the unlock display comprising a touch user interface element configured to unlock the device.

In a 214th example, the ambulatory medicament device of any of examples 202-213, wherein the hardware processor is further configured to execute the specific computer-executable instructions to at least: receive, via the touchscreen, a second touch input comprising a gesture password; determine whether the gesture password matches a stored password; and in response to determining that the gesture password matches a stored password, unlock the touchscreen.

In a 215th example, an ambulatory medicament device configured to administer a medicament therapy dose based on motion data associated with movement of the ambulatory medicament device, the ambulatory medicament device comprising: a medicament reservoir configured to store a medicament; an ambulatory medicament pump configured to deliver the medicament from the medicament reservoir to a subject; a motion sensor configured to collect the motion data; a memory configured to store specific computer-executable instructions; and a hardware processor in communication with the memory and configured to execute the specific computer-executable instructions to at least: detect a touch input based on the motion data; and in response to detecting the touch input, deliver a medicament dose.

In a 216th example, the ambulatory medicament device of example 215, wherein the medicament is one of: insulin or glucagon.

In a 217th example, the ambulatory medicament device of any of examples 215-216, wherein the motion sensor comprises an accelerometer, and wherein the motion data includes an acceleration of the ambulatory medicament device.

In a 218th example, the ambulatory medicament device of example 217, wherein the hardware processor is further configured to execute the specific computer-executable instructions to at least: detect the touch input based on an acceleration of the ambulatory medicament device caused by the touch input.

In a 219th example, the ambulatory medicament device of any of examples 215-218, wherein the touch input comprises one or more of: a single tap, a double tap, a triple tap, a multi tap, a multi-location tap, a pinch gesture, or a swipe gesture.

In a 220th example, the ambulatory medicament device of any of examples 215-219, wherein the touch input comprises one or more touches on one or more corners of the device.

In a 221st example, the ambulatory medicament device of example 220, wherein the touch input comprises a first touch on a first corner of the device, a second touch on a second corner of the device, and a third touch on a third corner of the device.

In a 222nd example, the ambulatory medicament device of any of examples 215-221, wherein the touch input comprises a sequence of one or more touches on one or more locations on the ambulatory medicament device.

In a 223rd example, the ambulatory medicament device of example 222, wherein the one or more locations comprises: a front of the device, one or more sides of the device, and a rear of the device.

In a 224th example, the ambulatory medicament device of any of examples 215-223, wherein the hardware processor is further configured to execute the specific computer-executable instructions to at least: in response to detecting the touch input, prompt the subject to confirm the medicament dose; detect a second touch input based on the motion data, the second touch input configured to confirm the medicament dose; and in response to detecting the second touch input from the subject, deliver the medicament dose.

In a 225th example, the ambulatory medicament device of any of examples 215-224 further comprising a touchscreen controller configured to output display signals configured to generate user interface screens on a touchscreen and to receive user input signals corresponding to user interaction with the touchscreen, wherein the hardware processor is further configured to execute the specific computer-executable instructions to at least: in response to detecting the touch input, prompt the subject, via the touchscreen, to confirm the medicament dose; detect a second touch input based on the motion data, the second touch input configured to confirm the medicament dose; and in response to detecting the second touch input from the subject, deliver the medicament dose.

In a 226th example, the ambulatory medicament device of any of examples 215-225 further comprising a speaker configured to generate audio prompts, wherein the hardware processor is further configured to execute the specific computer-executable instructions to at least: in response to detecting the touch input, prompt the subject, via the speaker, to confirm the medicament dose; detect a second touch input based on the motion data, the second touch input configured to confirm the medicament dose; and in response to detecting the second touch input from the subject, deliver the medicament dose.

In a 227th example, the ambulatory medicament device of any of examples 215-226 further comprising a haptic motor configured to generate vibration signals on a body of the subject, wherein the hardware processor is further configured to execute the specific computer-executable instructions to at least: in response to detecting the touch input, generate a vibration signal to prompt the subject to confirm the medicament dose; detect a second touch input based on the motion data, the second touch input configured to confirm the medicament dose; and in response to detecting the second touch input from the subject, deliver the medicament dose.

In a 228th example, the ambulatory medicament device of any of examples 215-227, wherein the hardware processor is further configured to execute the specific computer-executable instructions to at least: monitor a blood sugar level of the subject; determine a need for a bolus medicament dose based on the blood sugar level of the subject; and in response to determining a need for the bolus medicament dose, prompt the subject to initiate the medicament bolus dose by entering the touch input.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware. Further, the computing system may include, be implemented as part of, or communicate with an automated blood glucose system, an ambulatory medicament system, or an ambulatory medical device.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Many variations and modifications may be made to the above-described embodiments, the elements of which are to be understood as being among other acceptable examples. All such modifications and variations are intended to be included herein within the scope of this disclosure.

What is claimed is:

1. An ambulatory medicament device configured to display critical status information in a power saving mode, the ambulatory medicament device comprising:
    a monitoring system interface configured to receive status information, wherein the status information comprises at least one of device information pertaining to a condition of the ambulatory medicament device or subject information pertaining to a condition of a subject;
    a touchscreen controller configured to output display signals configured to generate user interface screens on a touchscreen and to receive user input signals corresponding to user input on the touchscreen, wherein the touchscreen is configured to be illuminated by a backlight;
    an accelerometer configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device;
    a memory configured to store specific computer-executable instructions; and
    a hardware processor in communication with the memory and configured to execute the specific computer-executable instructions to at least:
        receive the user input signals via the touchscreen controller;
        receive the user interaction signals via the accelerometer;
        activate a power saving mode of the ambulatory medicament device after a period of inactivity or in response to a request to activate the power saving mode, wherein the period of inactivity comprises the hardware processor not receiving a user input signal or a user interaction signal for a predetermined period of time, wherein the touchscreen controller is configured to not receive the user input signals when the ambulatory medicament device is in the power saving mode;

turn off the backlight;

receive the status information via the monitoring system interface;

determine critical status information from the status information;

generate a display of a critical status information interface screen on the touchscreen; and display on the critical status information interface screen at least one critical status indicator selected from a plurality of critical status indicators corresponding to the critical status information, wherein the plurality of critical status indicators comprises:

a glucose level indicator of the subject, a battery level indicator of the ambulatory medicament device, a therapy status indicator, a remaining medicament level indicator, and an alarm status indicator.

2. The ambulatory medicament device of claim 1, wherein the hardware processor is further configured to execute the specific computer-executable instructions to determine that a power level of a battery of the ambulatory medicament device is below a predetermined power level threshold and in response to determining that the power level of the battery of the ambulatory medicament device is below the predetermined power level threshold, the hardware processor is further configured to execute the specific computer-executable instructions to:

generate a display of a battery status interface screen; and display on the battery status interface screen a battery charging indicator to prioritize displaying the status information corresponding to the power level being below the predetermined power level threshold.

3. The ambulatory medicament device of claim 1, wherein the hardware processor is further configured to execute the specific computer-executable instructions to determine whether a glucose level of the subject is within a predetermined glucose range and in response to determining that the glucose level is not within the predetermined glucose range, the hardware processor is further configured to execute the specific computer-executable instructions to:

generate a display of a glucose interface screen; and display on the glucose interface screen the glucose level indicator to prioritize displaying the status information corresponding to the glucose level not being within the predetermined glucose range.

4. The ambulatory medicament device of claim 1, wherein the hardware processor is further configured to execute the specific computer-executable instructions to display on the critical status information interface screen an alarm state icon comprising a visual indication of a count of alarm conditions.

5. The ambulatory medicament device of claim 1, wherein the hardware processor is further configured to execute the specific computer-executable instructions to:

activate a privacy mode in response to a request to activate the privacy mode;

generate a display of a privacy mode interface screen; and display on the privacy mode interface screen one or more status indicators corresponding to the status information without displaying at least one of the plurality of critical status indicators.

6. The ambulatory medicament device of claim 5, wherein the at least one of the plurality of critical status indicators not displayed comprises at least one of the glucose level indicator of the subject or the therapy status indicator.

7. The ambulatory medicament device of claim 5, wherein the hardware processor is further configured to execute the specific computer-executable instructions to turn off the touchscreen while in the privacy mode.

8. The ambulatory medicament device of claim 5, wherein the hardware processor is further configured to execute the specific computer-executable instructions to activate the privacy mode while activating the power saving mode.

9. The ambulatory medicament device of claim 5, wherein the hardware processor is further configured to execute the specific computer-executable instructions to receive the request to activate the privacy mode interface screen while in the power saving mode.

10. The ambulatory medicament device of claim 5, wherein the hardware processor is further configured to execute the specific computer-executable instructions to receive the request to activate the privacy mode interface screen while not in the power saving mode.

11. The ambulatory medicament device of any of claim 1, wherein the hardware processor is further configured to execute the specific computer-executable instructions to:

determine that the user interaction signals correspond to a single tap on the ambulatory medicament device; and in response to determining that the user interaction corresponds to the single tap on the ambulatory medicament device, turn off the touchscreen.

12. The ambulatory medicament device of claim 11, wherein the hardware processor is further configured to execute the specific computer-executable instructions to:

determine that the user interaction signals correspond to an other single tap on the ambulatory medicament device; and in response to determining that the user interaction corresponds to the other single tap on the ambulatory medicament device, turn on the touchscreen while remaining in the power saving mode.

13. The ambulatory medicament device of any of claim 1, wherein the hardware processor is further configured to execute the specific computer-executable instructions to:

determine that the user interaction signals correspond to a double tap on the ambulatory medicament device; and in response to determining that the user interaction corresponds to the double tap on the ambulatory medicament device, turn on the backlight while remaining in the power saving mode.

14. The ambulatory medicament device of claim 13, wherein the hardware processor is further configured to execute the specific computer-executable instructions to:

determine that the user interaction signals correspond to an other double tap on the ambulatory medicament device; and in response to determining that the user interaction corresponds to the other double tap on the ambulatory medicament device, turn off the backlight while remaining in the power saving mode.

15. The ambulatory medicament device of claim 1, wherein the hardware processor is further configured to execute the specific computer-executable instructions to:

determine that the user interaction signals correspond to a single tap or a double tap on the ambulatory medicament device; and in response to determining that the user interaction corresponds to the single tap or the double tap on the ambulatory medicament device, deactivate the power saving mode.

16. The ambulatory medicament device of claim 1, wherein the hardware processor further is configured to execute the specific computer-executable instructions to update the critical status information interface screen in the power saving mode less frequently than updating the user interface screens in a wake mode of the ambulatory medicament device.

17. The ambulatory medicament device of claim 1, wherein the hardware processor is further configured to execute the specific computer-executable instructions to:
receive a request to activate a wake mode of the ambulatory medicament device; and
in response to receiving the request to activate the wake mode, deactivate the power saving mode.

18. The ambulatory medicament device of claim 17, wherein in response to receiving the request to activate the wake mode, the hardware processor is further configured to execute the specific computer-executable instructions to:
determine that the request to activate the wake mode was received during a predefined period of time; and
in response to determining that the request was received during the predefined period of time, turn on the backlight.

19. The ambulatory medicament device of claim 17, wherein the hardware processor is further configured to execute the specific computer-executable instructions to receive a wake request signal corresponding to user request on a wake interface of the ambulatory medicament device to active the wake mode.

20. The ambulatory medicament device of claim 1, wherein the hardware processor is further configured to execute the specific computer-executable instructions to lower a refresh rate of the touchscreen to a lower refresh rate relative to a maximum refresh rate of touchscreen.

21. The ambulatory medicament device of claim 1, wherein the status information is received from a sensor that measures at least one of a characteristic of the ambulatory medicament device or a physiological parameter of the subject.

22. The ambulatory medicament device of claim 21 further comprising a touchscreen controller configured to output display signals configured to generate user interface screens on the touchscreen and to receive user input signals corresponding to user input on the touchscreen, wherein the touchscreen is configured to be illuminated by the backlight;
wherein the period of inactivity comprises the hardware processor not receiving a user input signal for the predetermined period of time, and wherein the touchscreen controller is configured to not receive the user input signals when the ambulatory medicament device is in the power saving mode.

23. The ambulatory medicament device of claim 21, wherein the hardware processor is further configured to execute the specific computer-executable instructions to:
activate a privacy mode in response to a request to activate the privacy mode;
generate a display of a privacy mode interface screen; and
display on the privacy mode interface screen one or more status indicators corresponding to the status information without displaying at least one of the plurality of critical status indicators.

24. The ambulatory medicament device of claim 21, wherein the hardware processor is further configured to execute the specific computer-executable instructions to:
receive a request to activate a wake mode of the ambulatory medicament device; and
in response to receiving the request to activate the wake mode, deactivate the power saving mode.

25. The ambulatory medicament device of claim 21, wherein the hardware processor is further configured to execute the specific computer-executable instructions to display on the critical status information interface screen an alarm state icon comprising a visual indication of a count of alarm conditions.

26. The ambulatory medicament device of claim 1, wherein the hardware processor is configured to execute further computer-executable instructions to lower brightness of the touchscreen of the ambulatory medicament device to a lower brightness level relative to a full brightness level of the touchscreen.

27. The ambulatory medicament device of claim 1, wherein the ambulatory medicament device comprises a bi-hormonal pump capable of administering insulin and a counter-regulatory agent.

28. The ambulatory medicament device of claim 5, wherein the touchscreen comprises a filter configured to have a predetermined viewing angle range relative to the touchscreen such that information cannot be seen on the touchscreen when viewed from an angle outside of the predetermined viewing angle range.

29. The ambulatory medicament device of claim 5, wherein in the power saving mode, the ambulatory medicament device displays the critical status information interface screen by using 5-10% additional electric current relative to electric current used with the touchscreen turned off while the ambulatory medicament device is operating.

30. An ambulatory medicament device configured to display critical status information in a power saving mode, the ambulatory medicament device comprising:
a monitoring system interface configured to receive status information, wherein the status information comprises at least one of device information pertaining to a condition of the ambulatory medicament device or subject information pertaining to a condition of a subject;
a motion sensor configured to detect user interaction with the ambulatory medicament device and output user interaction signals corresponding to the user interaction with the ambulatory medicament device, wherein user interaction with the ambulatory medicament device comprises a single tap or a double tap on the ambulatory medicament device;
a memory configured to store specific computer-executable instructions; and
a hardware processor in communication with the memory and configured to execute the specific computer-executable instructions to at least:
receive the user interaction signals via the motion sensor;
activate a power saving mode of the ambulatory medicament device after a period of inactivity or in response to a request to activate the power saving mode, wherein the period of inactivity comprises the hardware processor not receiving a user interaction signal for a predetermined period of time;
turn off a backlight of the ambulatory medicament device configured to illuminate a touchscreen of the ambulatory medicament device;

receive the status information via the monitoring system interface;
determine critical status information from the status information;
generate a display of a critical status information interface screen on the touchscreen; and
display on the critical status information interface screen at least one of a plurality of critical status indicators corresponding to the critical status information, wherein the plurality of critical status indicators comprises:
a medicament device status indicator, and
a subject status indicator.

\* \* \* \* \*